United States Patent
Coyne et al.

(10) Patent No.: US 10,365,322 B2
(45) Date of Patent: Jul. 30, 2019

(54) WEAR-OUT MONITOR DEVICE

(71) Applicant: Analog Devices Global, Hamilton (BM)

(72) Inventors: Edward John Coyne, Athenry (IE); Alan J. O'Donnell, Castletroy (IE); Shaun Bradley, Murroe (IE); David Aherne, Limerick (IE); David Boland, Limerick (IE); Thomas G. O'Dwyer, Arlington, MA (US); Colm Patrick Heffernan, Annacotty (IE); Kevin B. Manning, Andover, MA (US); Mark Forde, Nenagh (IE); David J. Clarke, Patrickswell (IE); Michael A. Looby, Ballysheedy (IE)

(73) Assignee: ANALOG DEVICES GLOBAL, Hamilton (BM)

( * ) Notice: Subject to any disclaimer, the term of this patent is extended or adjusted under 35 U.S.C. 154(b) by 0 days.

(21) Appl. No.: 15/490,584

(22) Filed: Apr. 18, 2017

(65) Prior Publication Data
US 2017/0299650 A1 Oct. 19, 2017

Related U.S. Application Data

(63) Continuation-in-part of application No. 15/291,742, filed on Oct. 12, 2016.
(Continued)

(51) Int. Cl.
*G01R 31/28* (2006.01)

(52) U.S. Cl.
CPC ..... *G01R 31/2879* (2013.01); *G01R 31/2874* (2013.01)

(58) Field of Classification Search
CPC .......................... G01R 31/2872; G01N 27/041
(Continued)

(56) References Cited

U.S. PATENT DOCUMENTS 4,345,477 A * 8/1982 Johnson ............... G01L 1/2281
257/419
5,666,127 A 9/1997 Kochiyama et al.
(Continued)

FOREIGN PATENT DOCUMENTS

CN 102576774 7/2012
CN 103490493 1/2014
(Continued)

OTHER PUBLICATIONS

Haus, Hermann A. and James R. Melcher, Electromagnetic Fields and Energy, Chapter 6 (Massachusetts Institute of Technology: MIT OpenCourseWare). Available at: http://ocw.mit.edu.resources/res-6-001-electromagnetic-fields-and-energy-spring-2008/chapter-6/06.pdf (accessed Jul. 27, 2015). License: Creative Commons Attribution-NonCommercial-Share Alike. Also available from Prentice-Hall: Englewood Cliffs, NJ, 1989, ISBN: 9780132490207.
(Continued)

*Primary Examiner* — Farhana A Hoque
(74) *Attorney, Agent, or Firm* — Knobbe, Martens, Olson & Bear LLP

(57) ABSTRACT

The disclosed technology generally relates to integrated circuit devices with wear out monitoring capability. An integrated circuit device includes a wear-out monitor device configured to record an indication of wear-out of a core circuit separated from the wear-out monitor device, wherein the indication is associated with localized diffusion of a diffusant within the wear-out monitor device in response to a wear-out stress that causes the wear-out of the core circuit.

43 Claims, 96 Drawing Sheets

Related U.S. Application Data

(60) Provisional application No. 62/455,481, filed on Feb. 6, 2017, provisional application No. 62/447,824, filed on Jan. 18, 2017, provisional application No. 62/324,828, filed on Apr. 19, 2016.

(58) Field of Classification Search
USPC .................. 324/762.01; 438/14; 361/18
See application file for complete search history.

(56) References Cited

U.S. PATENT DOCUMENTS

| | | |
|---|---|---|
| 5,784,242 A | 7/1998 | Watt |
| 5,946,175 A | 8/1999 | Yu |
| 6,236,087 B1 | 5/2001 | Daly et al. |
| 6,249,410 B1 | 6/2001 | Ker et al. |
| 6,411,544 B1 | 6/2002 | Devin |
| 6,645,309 B1 | 11/2003 | Myers |
| 6,819,539 B1 | 11/2004 | Wright et al. |
| 6,898,061 B1 | 5/2005 | Kimber et al. |
| 6,920,026 B2 | 7/2005 | Chen et al. |
| 7,142,400 B1 | 11/2006 | Williams et al. |
| 7,268,517 B2 | 9/2007 | Rahmel et al. |
| 7,274,545 B2 | 9/2007 | Marum et al. |
| 7,411,767 B2 | 8/2008 | Huang et al. |
| 7,514,804 B2 | 4/2009 | Wang |
| 7,570,468 B2 | 8/2009 | Bernard et al. |
| 7,593,202 B2 | 9/2009 | Khazhinsky et al. |
| 7,630,184 B2 | 12/2009 | Crain et al. |
| 7,791,481 B2 | 9/2010 | Landt et al. |
| 7,989,936 B2 | 8/2011 | McCain |
| 8,000,067 B1 | 8/2011 | Jin et al. |
| 8,068,319 B1 | 11/2011 | Chan et al. |
| 8,112,138 B2 | 2/2012 | Reggiardo |
| 8,164,113 B2 | 4/2012 | Lin et al. |
| 8,169,760 B2 | 5/2012 | Chang et al. |
| 8,238,068 B2 | 8/2012 | Shannon |
| 8,354,300 B2 | 1/2013 | Henderson et al. |
| 8,373,559 B2 | 2/2013 | McCain |
| 8,400,743 B2 | 3/2013 | Kosonocky et al. |
| 8,520,351 B2 | 8/2013 | Hong |
| 8,582,261 B2 | 11/2013 | Salcedo et al. |
| 8,630,072 B2 | 1/2014 | Smith |
| 8,755,195 B2 | 6/2014 | Savory et al. |
| 8,796,729 B2 | 8/2014 | Clarke et al. |
| 8,853,799 B2 | 10/2014 | O'Donnell |
| 8,957,488 B2 | 2/2015 | Keysar et al. |
| 9,311,807 B2 | 4/2016 | Schultz et al. |
| 9,380,949 B2 | 7/2016 | Schuessler |
| 9,389,681 B2 | 7/2016 | Sankar et al. |
| 9,871,373 B2 | 1/2018 | O'Donnell et al. |
| 10,032,683 B2 | 7/2018 | Davis et al. |
| 10,263,596 B2 | 4/2019 | Doll et al. |
| 2002/0076840 A1* | 6/2002 | Englisch .......... G03F 1/40 438/14 |
| 2004/0027159 A1 | 2/2004 | Oertle et al. |
| 2005/0054197 A1* | 3/2005 | Sato ............ G06F 17/5018 438/689 |
| 2005/0127953 A1 | 6/2005 | Oertle et al. |
| 2006/0274799 A1 | 12/2006 | Collins et al. |
| 2006/0284302 A1 | 12/2006 | Kim et al. |
| 2007/0174011 A1 | 7/2007 | Enta |
| 2007/0230073 A1 | 10/2007 | Ker et al. |
| 2007/0297105 A1 | 12/2007 | Brennan et al. |
| 2008/0036487 A1 | 2/2008 | Bradley et al. |
| 2008/0074817 A1 | 3/2008 | Crain et al. |
| 2008/0129523 A1 | 6/2008 | Assimos |
| 2008/0266730 A1 | 10/2008 | Viborg et al. |
| 2008/0297939 A1 | 12/2008 | Amemiya |
| 2009/0287435 A1 | 11/2009 | Ker |
| 2010/0141094 A1 | 6/2010 | Lee et al. |
| 2010/0271742 A1 | 10/2010 | Shannon et al. |
| 2011/0209744 A1 | 9/2011 | Hu |
| 2011/0261489 A1 | 10/2011 | Zupcau et al. |
| 2012/0001163 A1 | 1/2012 | Kobayashi et al. |
| 2012/0006122 A1* | 1/2012 | Aitken ............. H01L 22/12 73/763 |
| 2012/0017962 A1 | 1/2012 | Skotnicki et al. |
| 2012/0077291 A1 | 3/2012 | Pasveer et al. |
| 2012/0153437 A1 | 6/2012 | Chen et al. |
| 2012/0162849 A1 | 6/2012 | Tang |
| 2012/0174582 A1 | 7/2012 | Moussavi |
| 2013/0057111 A1 | 3/2013 | Mukter-Uz-Zaman et al. |
| 2014/0062381 A1 | 3/2014 | Teggatz et al. |
| 2014/0125366 A1 | 5/2014 | Thøgersen et al. |
| 2014/0246066 A1 | 9/2014 | Chen et al. |
| 2014/0362481 A1 | 12/2014 | Prabhu et al. |
| 2015/0040677 A1 | 2/2015 | Hammerschmidt |
| 2015/0270178 A1* | 9/2015 | Alptekin ......... H01L 21/28512 257/288 |
| 2016/0009547 A1 | 1/2016 | Mason et al. |
| 2016/0116924 A1 | 4/2016 | Meijer et al. |
| 2016/0172849 A1 | 6/2016 | Dibra |
| 2016/0178694 A1 | 6/2016 | Fry et al. |
| 2016/0285255 A1 | 9/2016 | O'Donnell et al. |
| 2017/0126229 A1 | 5/2017 | Tan et al. |
| 2017/0160338 A1 | 6/2017 | Connor et al. |
| 2017/0242068 A1 | 8/2017 | Le et al. |
| 2017/0255507 A1 | 9/2017 | Milor et al. |
| 2018/0115155 A1 | 4/2018 | Kuo |
| 2018/0143242 A1 | 5/2018 | Connor et al. |
| 2018/0285562 A1 | 10/2018 | Radhakrishnan et al. |

FOREIGN PATENT DOCUMENTS

| | | |
|---|---|---|
| DE | 41 26 376 A1 | 2/1993 |
| DE | 4126376 * | 2/1993 |
| EP | 2 280 458 | 2/2011 |
| EP | 2 333 925 | 6/2011 |
| JP | H04-152664 | 5/1992 |
| JP | 2000-223685 | 8/2000 |
| JP | 2002-111041 | 4/2002 |
| JP | 2002-246514 | 8/2002 |
| JP | 2005-283389 | 10/2005 |
| JP | 2006-352136 | 12/2006 |
| JP | 2008-173462 | 7/2008 |
| JP | 2009-081160 | 4/2009 |
| JP | 2009-200189 | 9/2009 |
| TW | 200912555 | 3/2009 |
| TW | 201222830 | 6/2012 |
| TW | 201234138 | 8/2012 |
| TW | 201317559 | 5/2013 |
| TW | 201347002 | 11/2013 |
| TW | 201517213 | 5/2015 |
| WO | WO 2010/053997 | 5/2010 |
| WO | WO 2010/100929 | 9/2010 |
| WO | WO 2010/136919 | 12/2010 |

OTHER PUBLICATIONS

Huang, Gregory T., "Electroactive Polymers", MIT Technology Review, Dec. 1, 2002. Available at: http://www.technologyreview.com/article/401750/electroactive-polymers/ (accessed Jul. 27, 2015).

International Search Report and Writing Opinion dated Aug. 8, 2017 in PCT Application No. PCT/US2017/027988.

Jones, Scotten W., "Diffusion in Silicon", IC Knowledge LLC, 2000, 71 pgs.

Lee, Sanghyo, et al. "Triboelectric Energy Harvester Based on Wearable Textile Platforms Employing Various Surface Morphologies", Nano Energy, Mar. 2015, vol. 12, pp. 410-418.

Mhira, S., et al. "Mission Profile Recorder: An Aging Monitor for Hard Events",Reliability Physics Symposium (RPS), 2016 IEEE International, IEEE, 2016, pp. 4C-3-1-4C-3-5.

Suzuki, Yuji, "Development of a Mems Energy Harvester With High-Performance Polymer Electrets." Department of Mechanical Engineering, The University of Tokyo, Bunkyo-ku, Japan, Jan. 2010, 6 pages. Available at: http://blog.nus.edu.sg/a0066807/files/2011/03/047_Suzuki_9922.pdf (accessed Jul. 27, 2015).

Tasca, Dante M., "Pulse Power Failure Modes in Semiconductors", IEEE Transactions on Nuclear Science, vol. 17. Issue 6, Dec. 1970, pp. 364-372.

(56) References Cited

OTHER PUBLICATIONS

Wang, Xiaofei et al. "Silicon Odometers: Compact In Situ Aging Sensors for Robust System Design", IEE Micro, vol. 34, No. 6, Nov./Dec. 2014, pp. 74-86.

Wunsch, D.C., et al., "Determination of Threshold Failure Levels of Semiconductor Diodes and Transistors Due to Pulse Voltages,"IEEE Transactions on Nuclear Science, vol. 15, Issue 6, Dec. 1968, pp. 244-259.

"ESD Patent Report—Additional Search for Concepts in 3 US Patents and Ideas in Alan's May 5, 2014 email", Innography, 2013, 9 pages.

European Search Report dated Aug. 5, 2016 for European Patent Application No. 16160442.6 filed Mar. 15, 2016, 7 pages.

"Improvements to ESD Structures—Alternate Uses of ESD-Patent Report", Innography, 2013, 16 pgs.

U.S. Department of Transportation, Federal Highway Administration Research and Technology, "Chapter 2, Traffic Detector Handbook: Third Edition—vol. 1", May 2006. Available at: http:www.fhwa.dot.gov/publications/research/operations/its/06108/02a.cfm (accessed Jul. 27, 2015).

Search Report issued in Taiwan application No. 106113115 dated Oct. 19, 2017.

Bailey, Brian, "Minimizing Chip Aging Effects," Sep. 13, 2018 downloaded from https://semiengineering.com/minimizing-chip-aging-effects/ on Sep. 19, 2018, 24 pgs.

Bailey, Brian, "Chip Aging Becomes Design Problem," Aug. 9, 2018 downloaded from https://semiengineering.com/chip-aging-becomes-design-problem/ on Sep. 19, 2018, 30 pgs.

Mutschler, Ann Steffora, "Ensuring Chip Reliability from the Inside," May 31, 2018, downloaded from https://semiengineering.com/ensuring-chip-reliability-from-the-inside/ on Sep. 19, 2018, 22 pgs.

Mutschler, Ann Steffora, "Aging in Advanced Nodes," Sep. 17, 2018, downloaded from https://semiengineering.com/a-turning-point-for-aging/ on Sep. 19, 2018, 25 pgs.

Haghbayan et al., "Can dark silicon be exploited to prolong system lifetime?" ResearchGate, Article in IEEE Design and Test—Nov. 2016; IEEE CEDA, IEEE CASS, IEEE SSCS, and TTTC; Mar./Apr. 2016 2017; 10 pages.

* cited by examiner

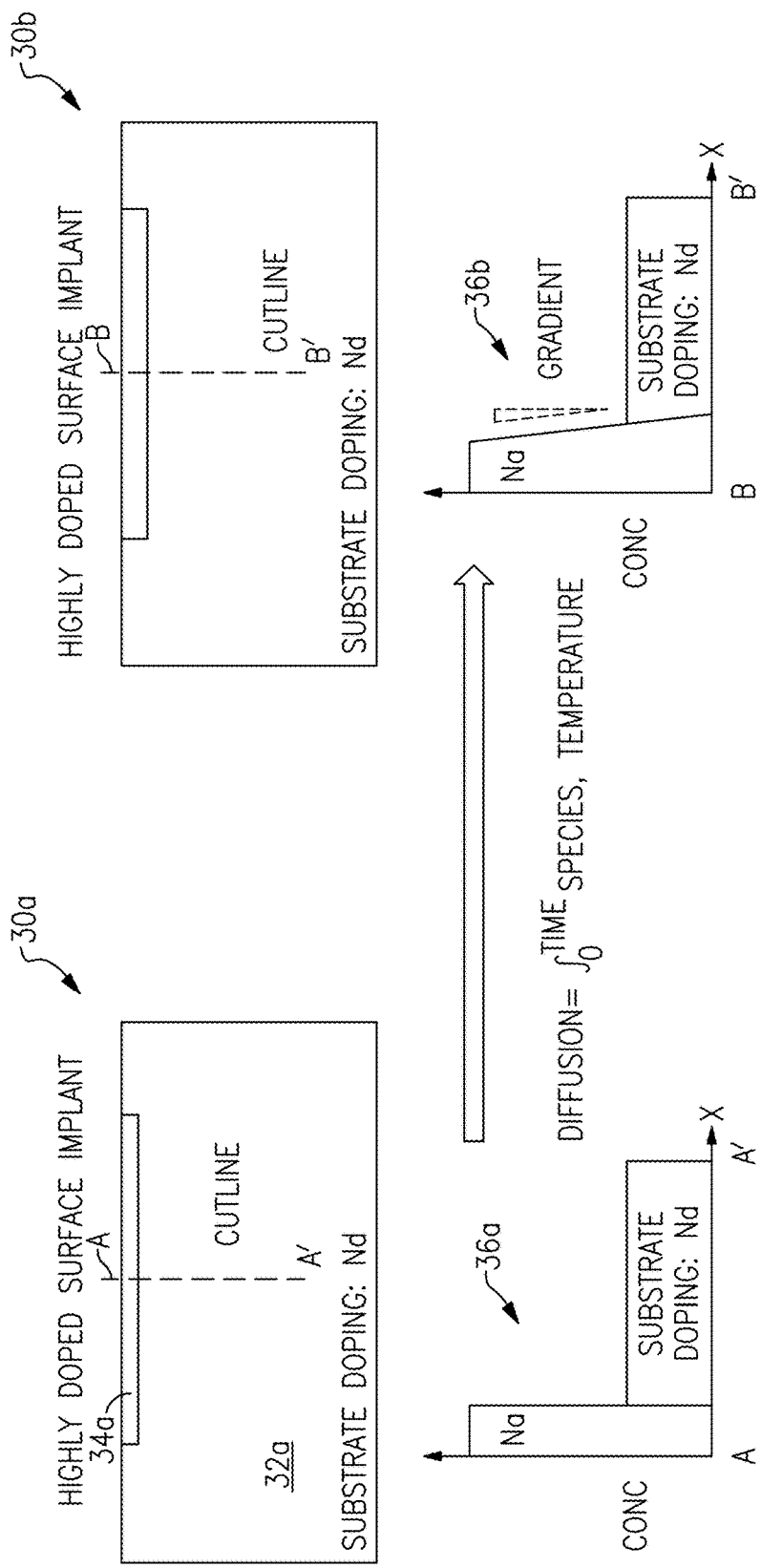

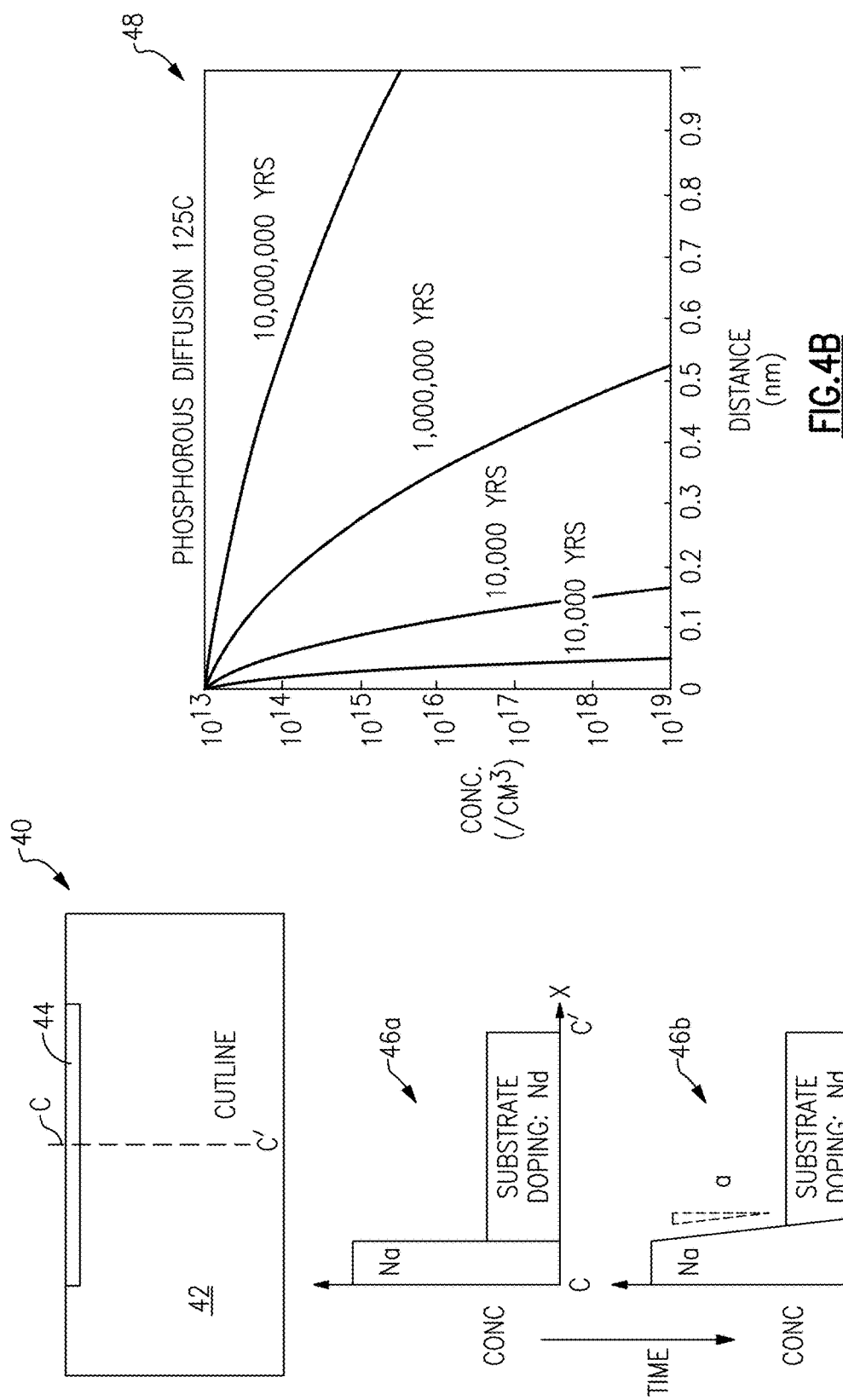

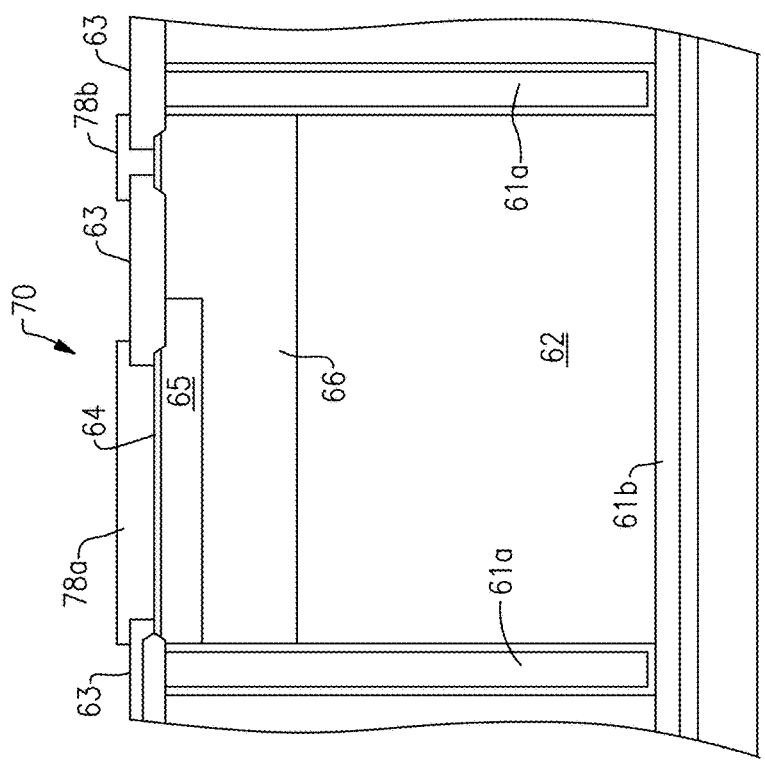
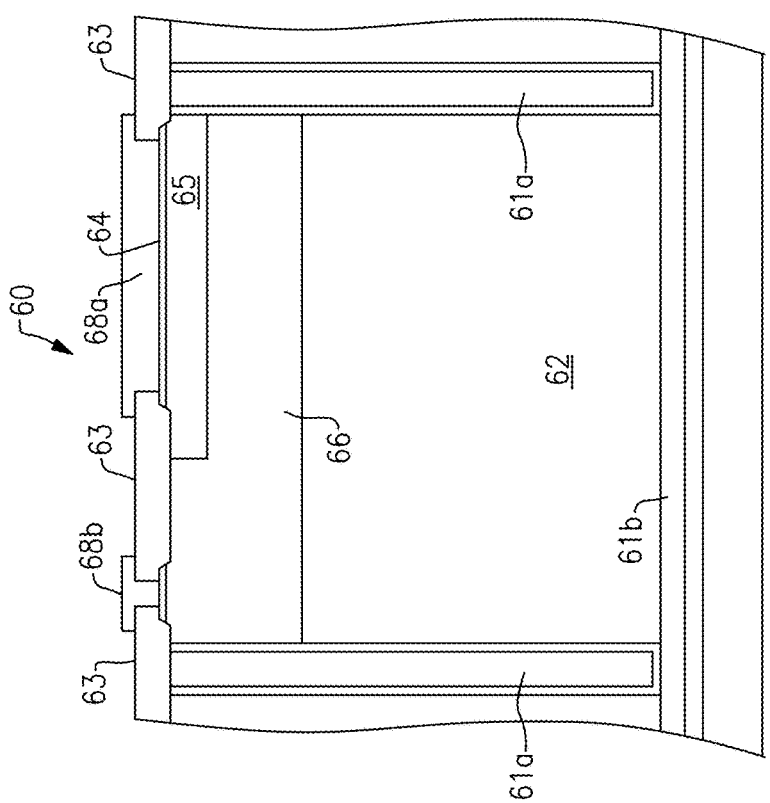

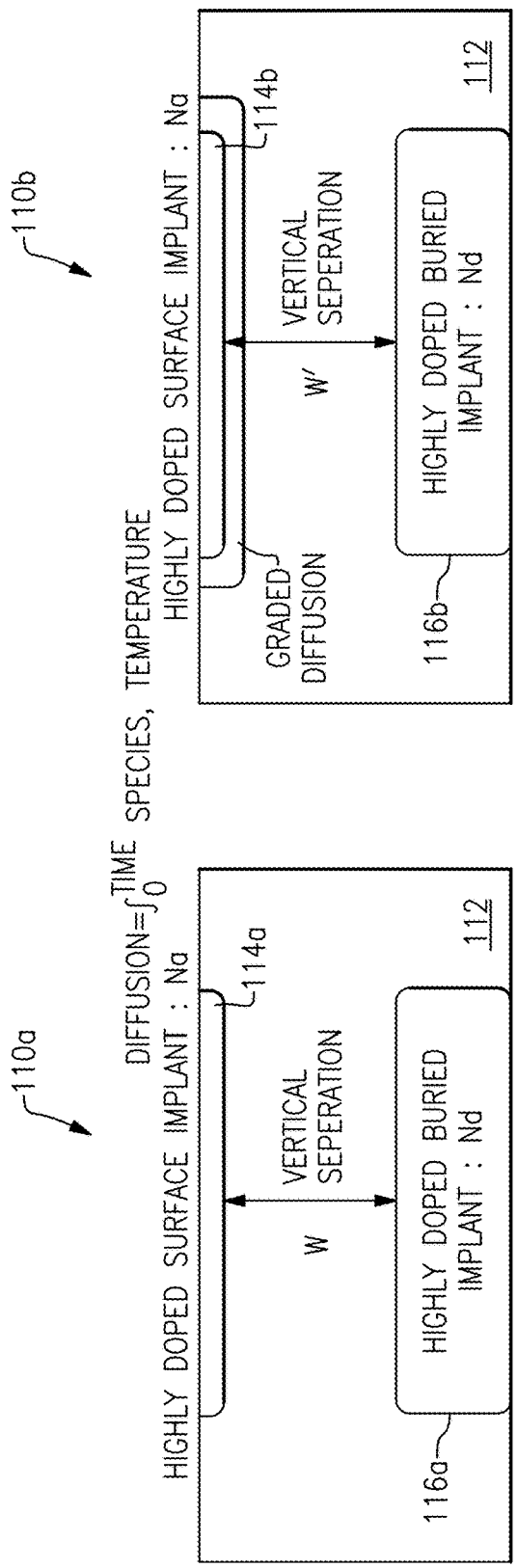

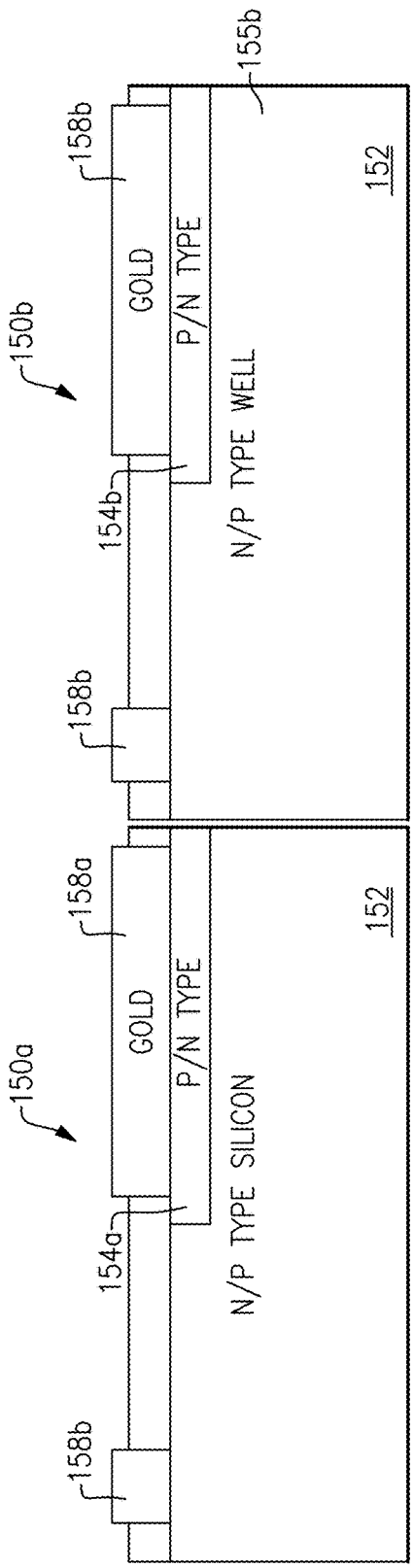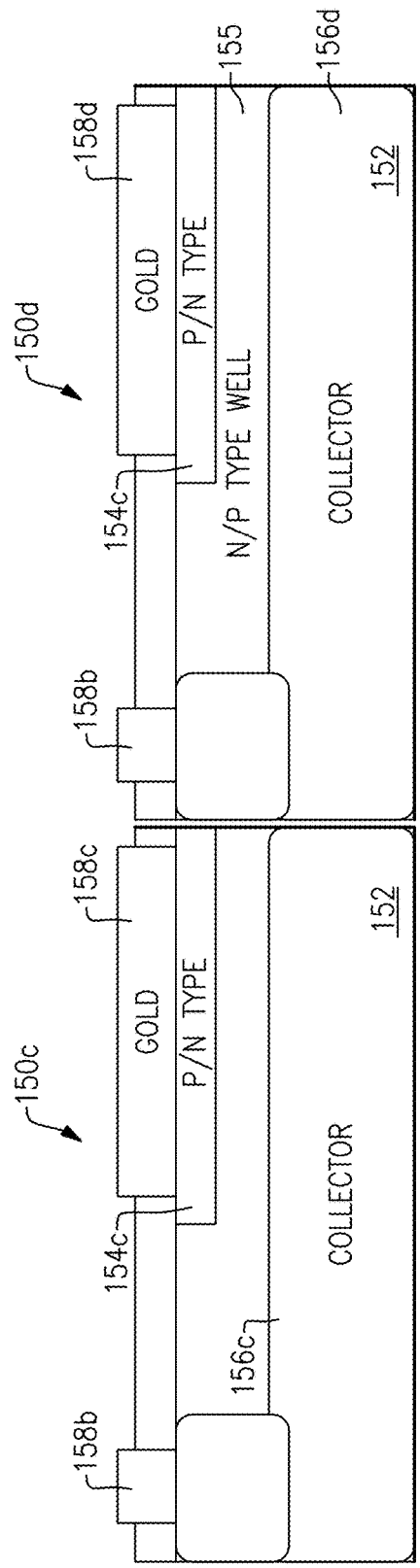

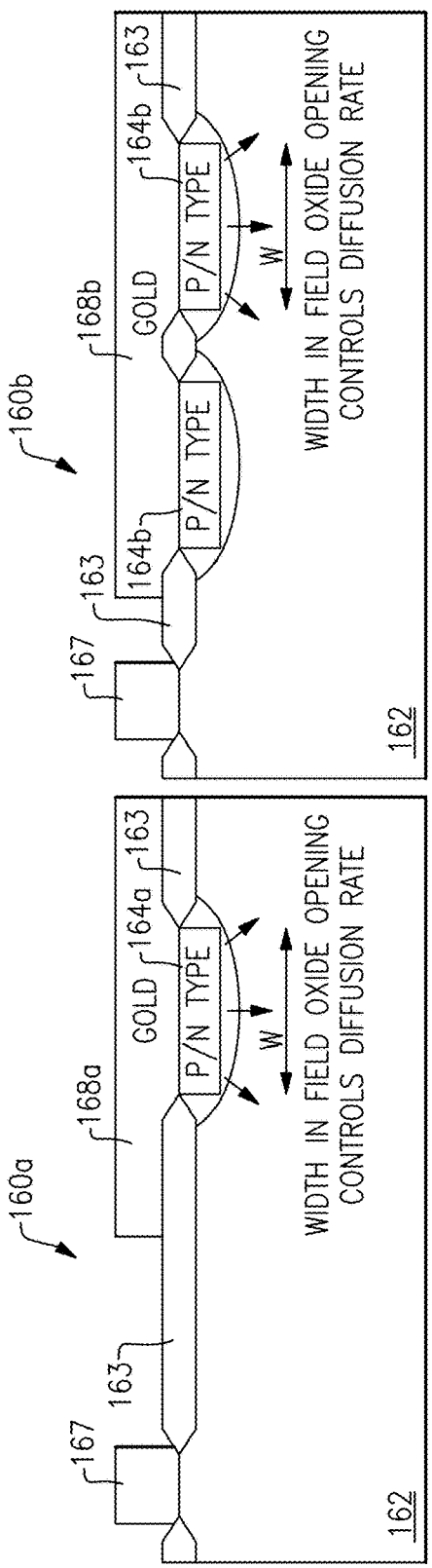
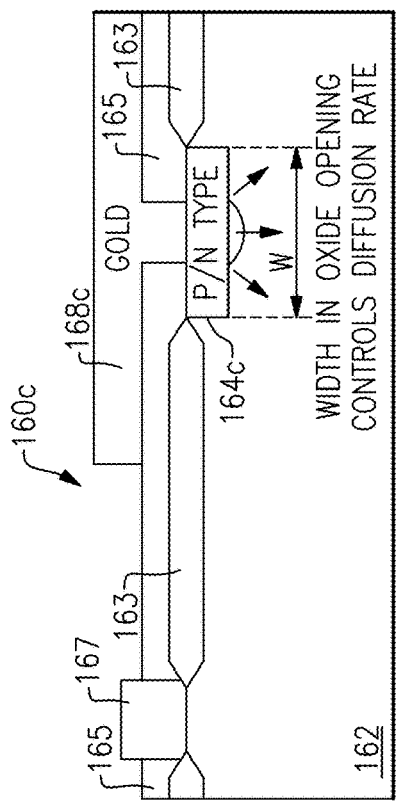
FIG.16A
FIG.16B
FIG.16C

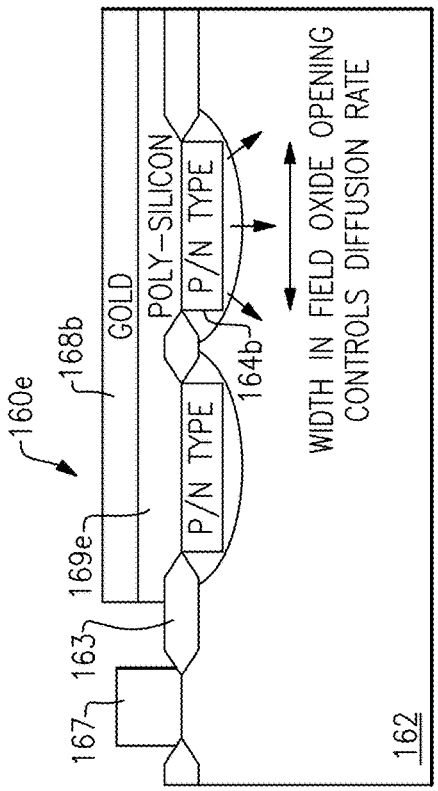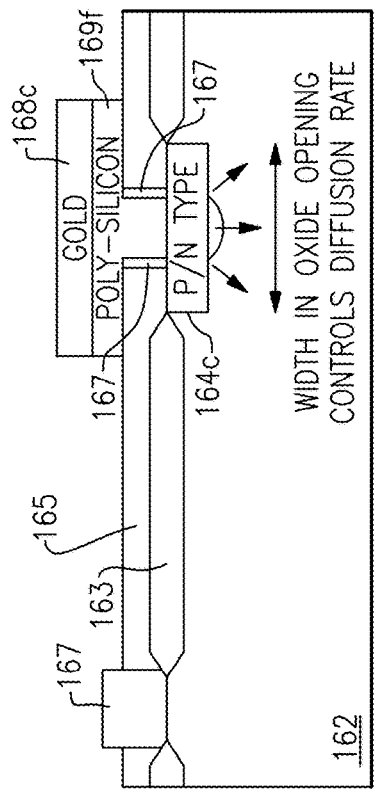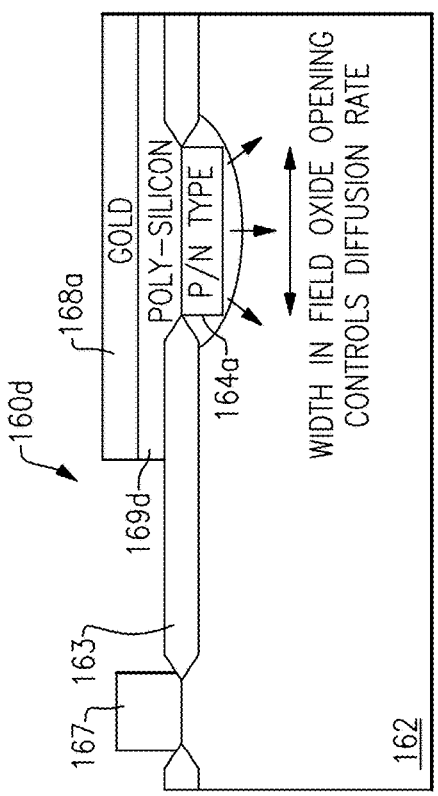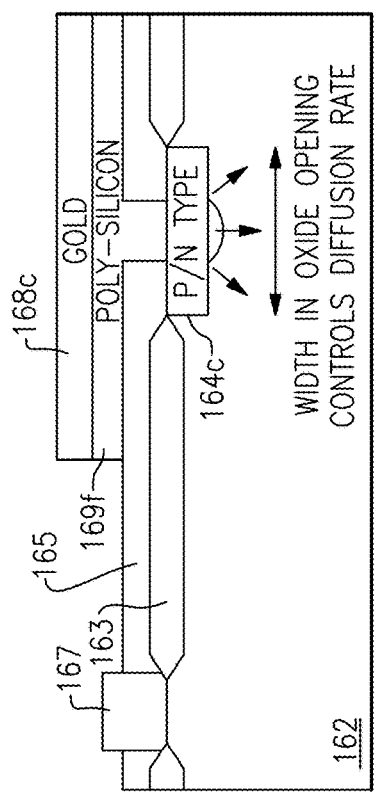

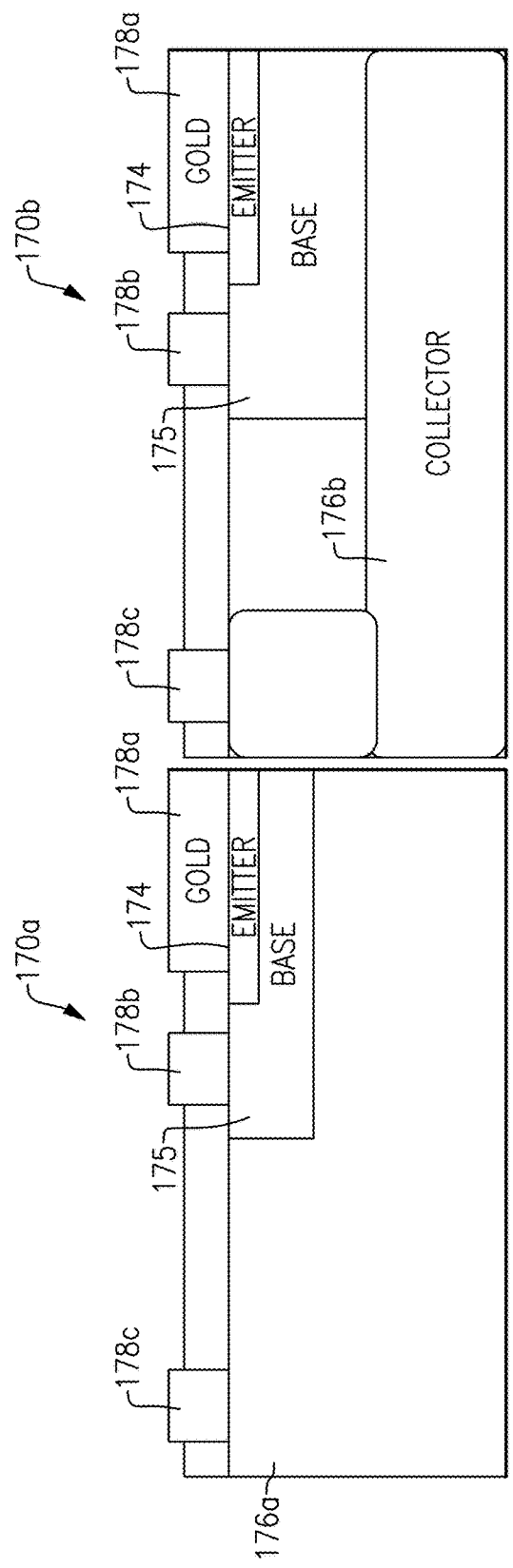

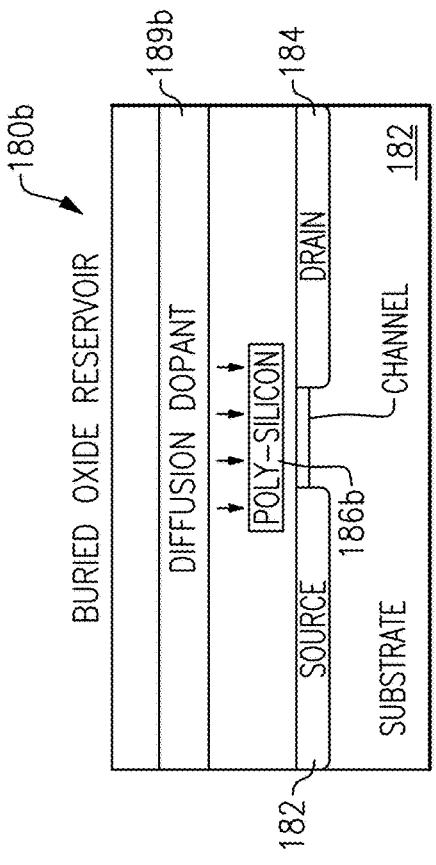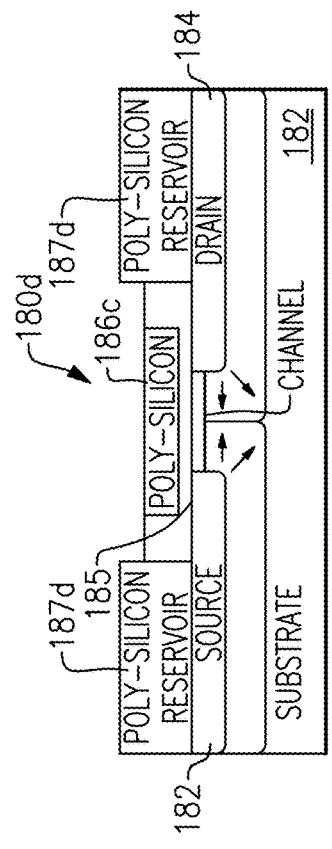
FIG.18A    FIG.18B
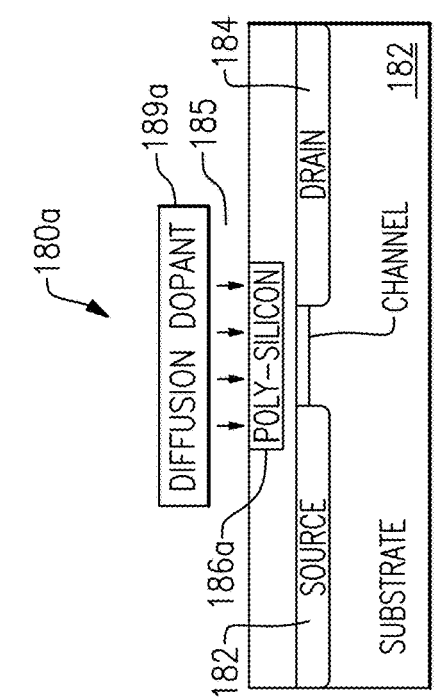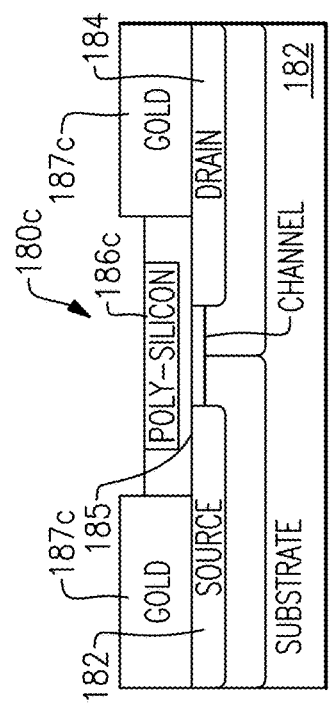
FIG.18C    FIG.18D

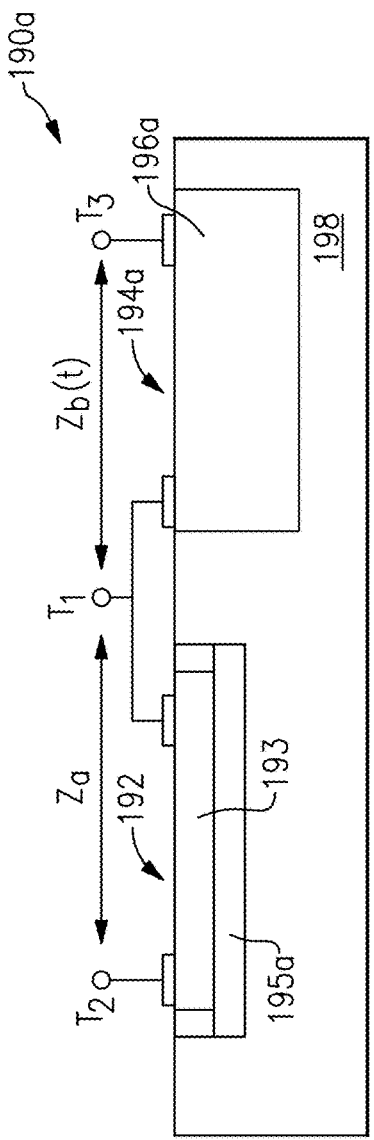
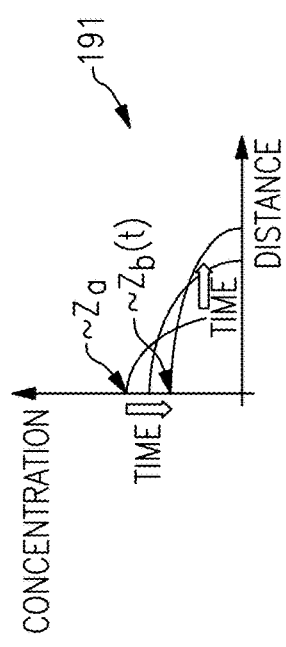
FIG.19A
FIG.19B

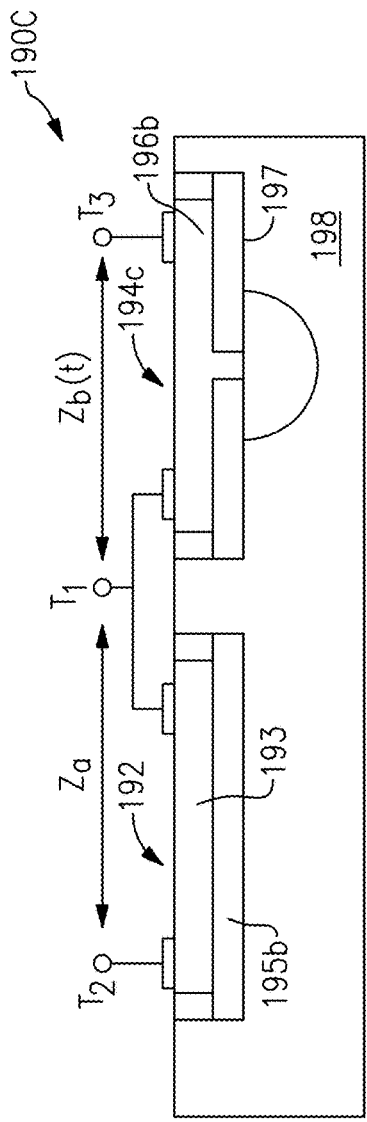
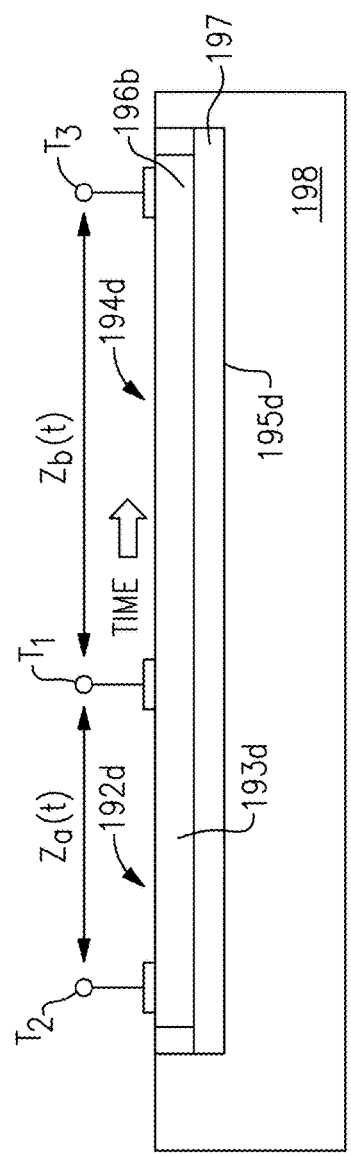
FIG.19C
FIG.19D

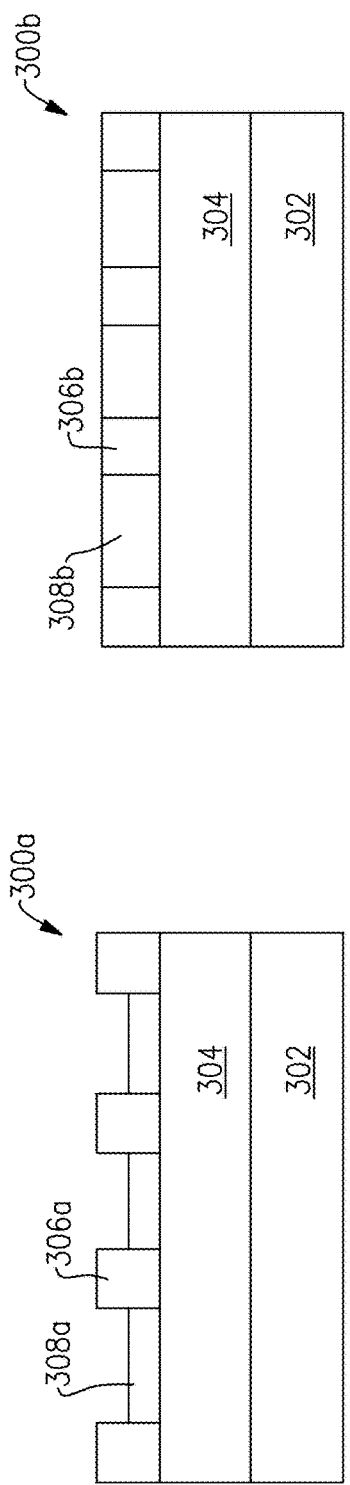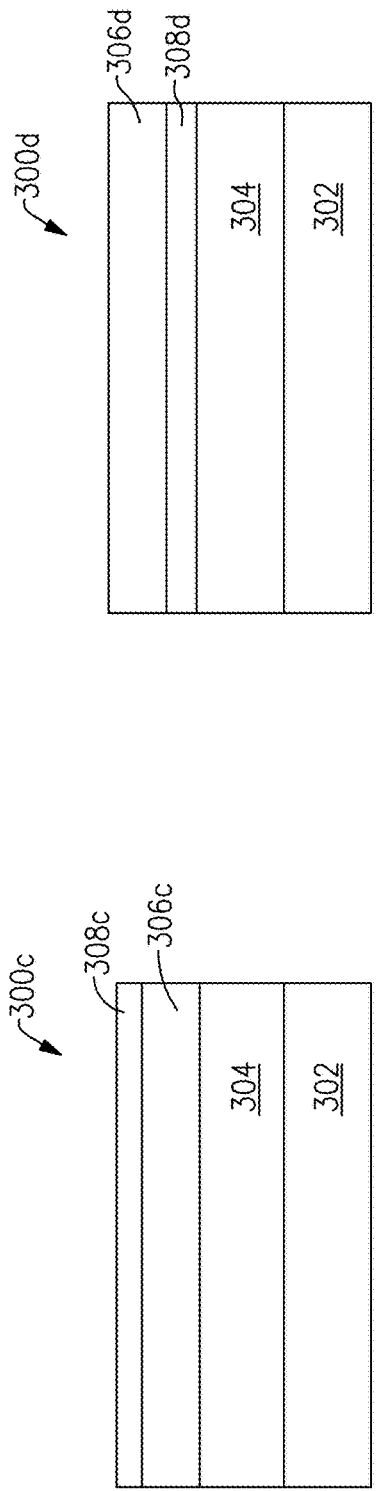

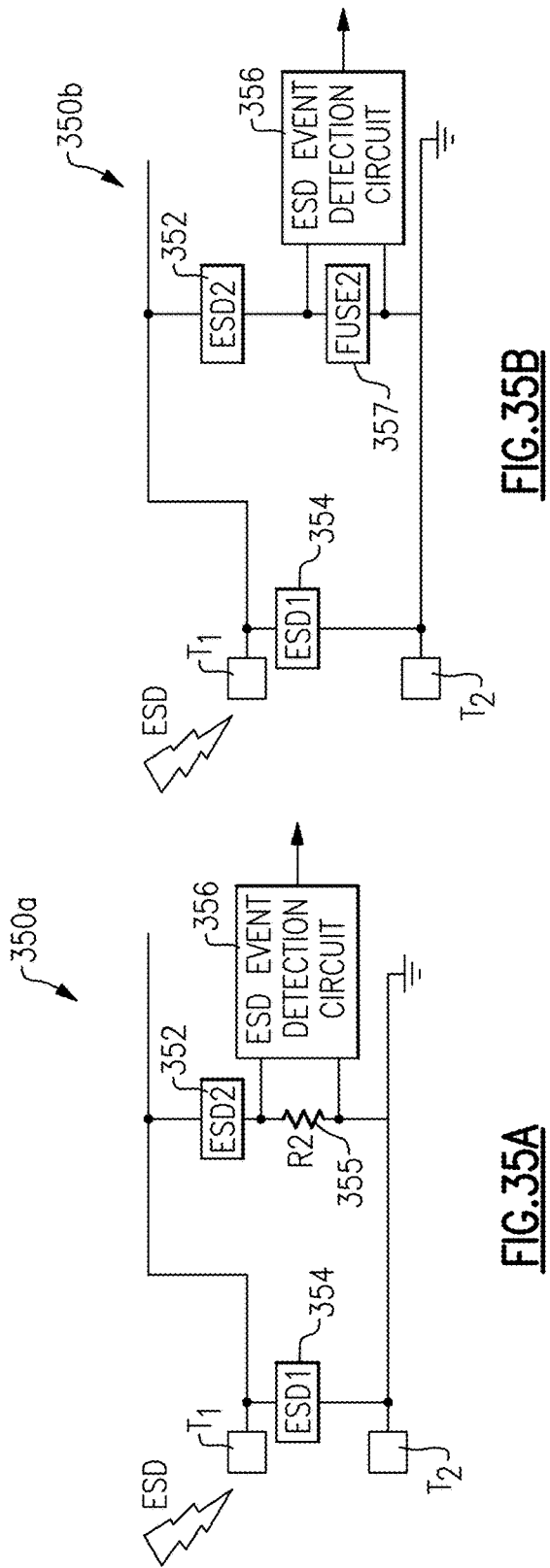

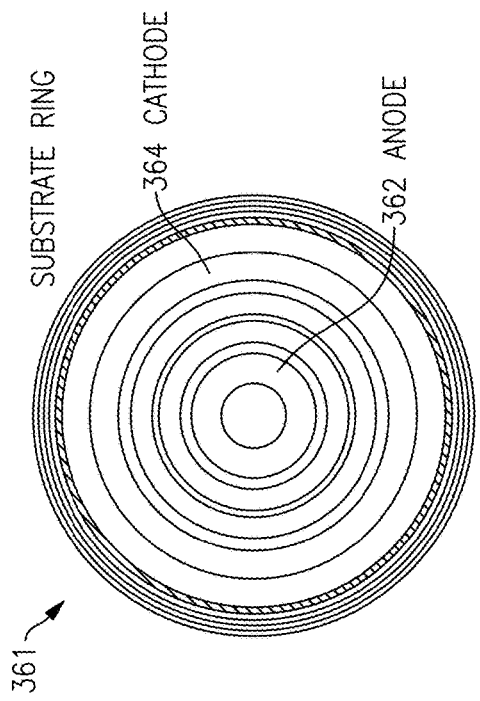
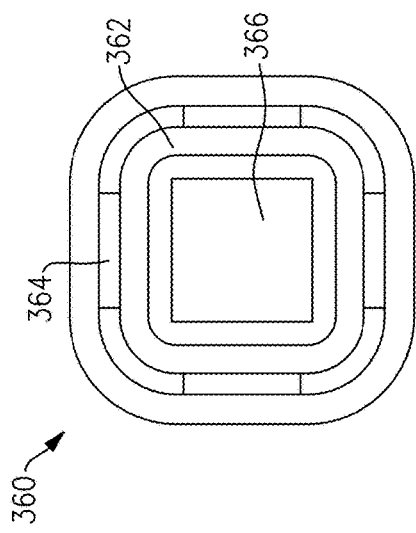
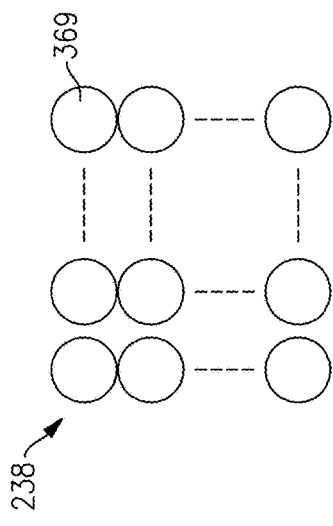
FIG.36B
FIG.36A
FIG.36C

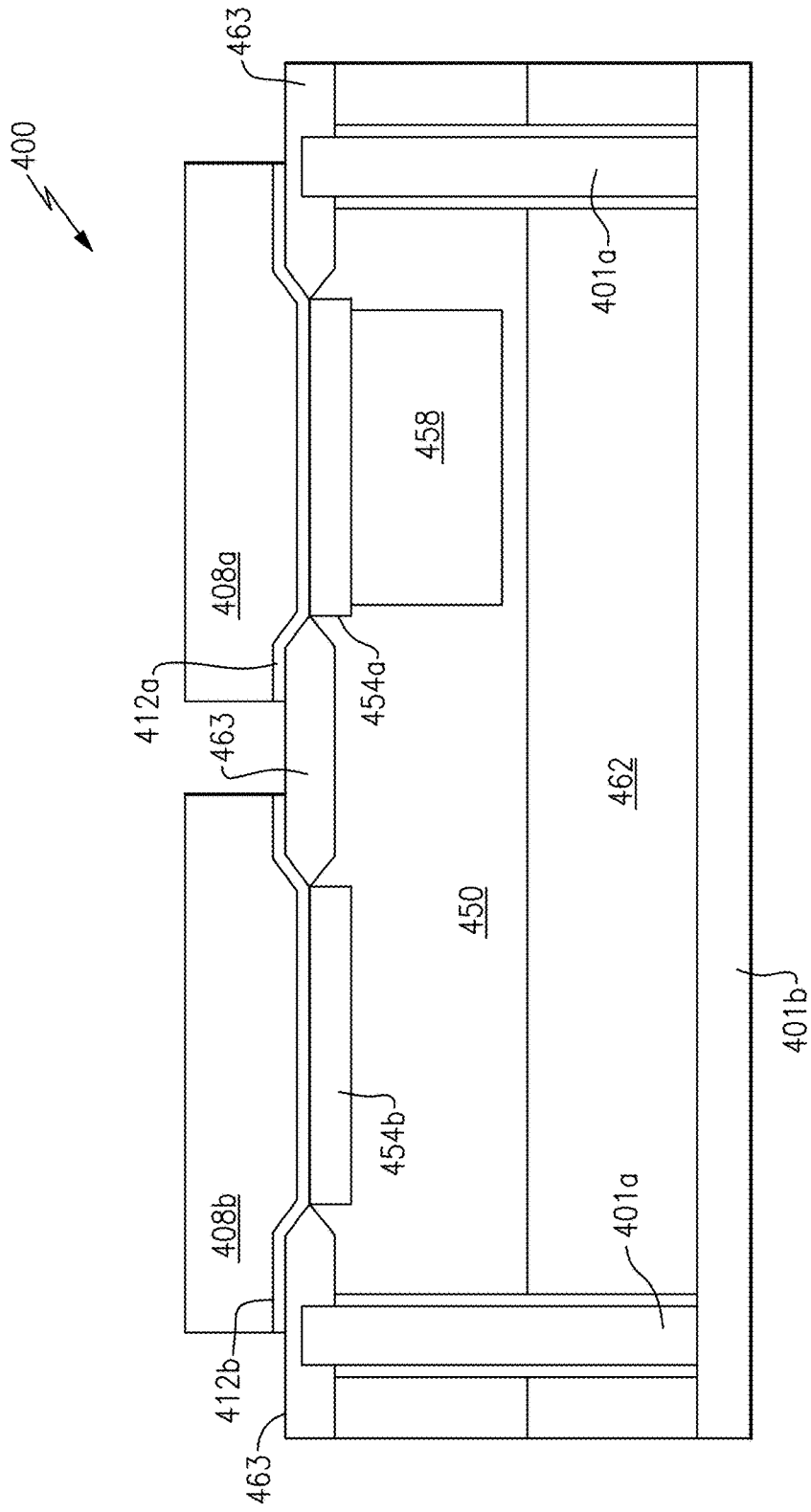

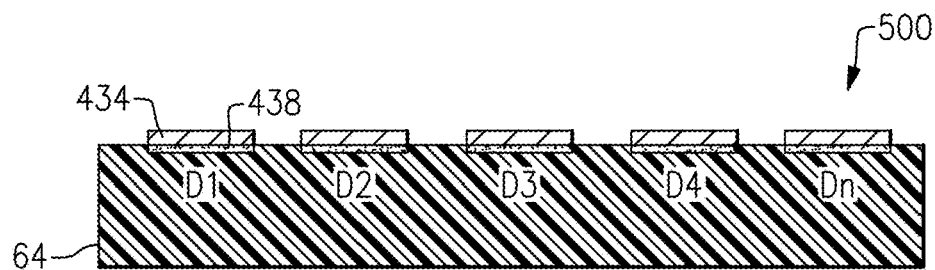
FIG.50A
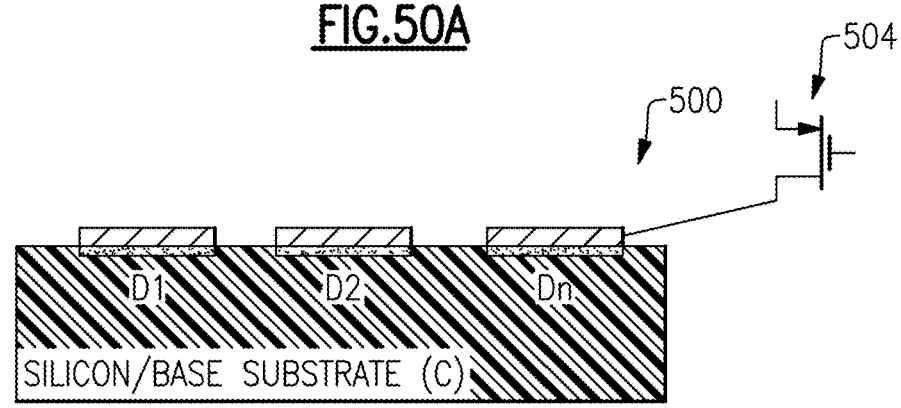
FIG.50B
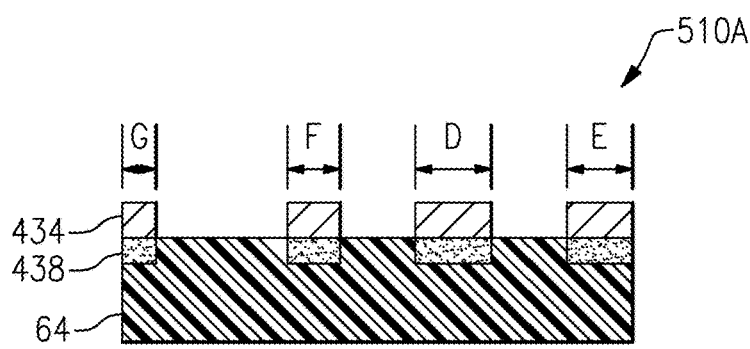
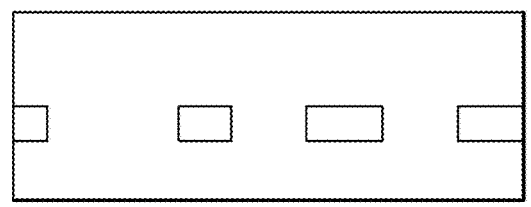
FIG.51A

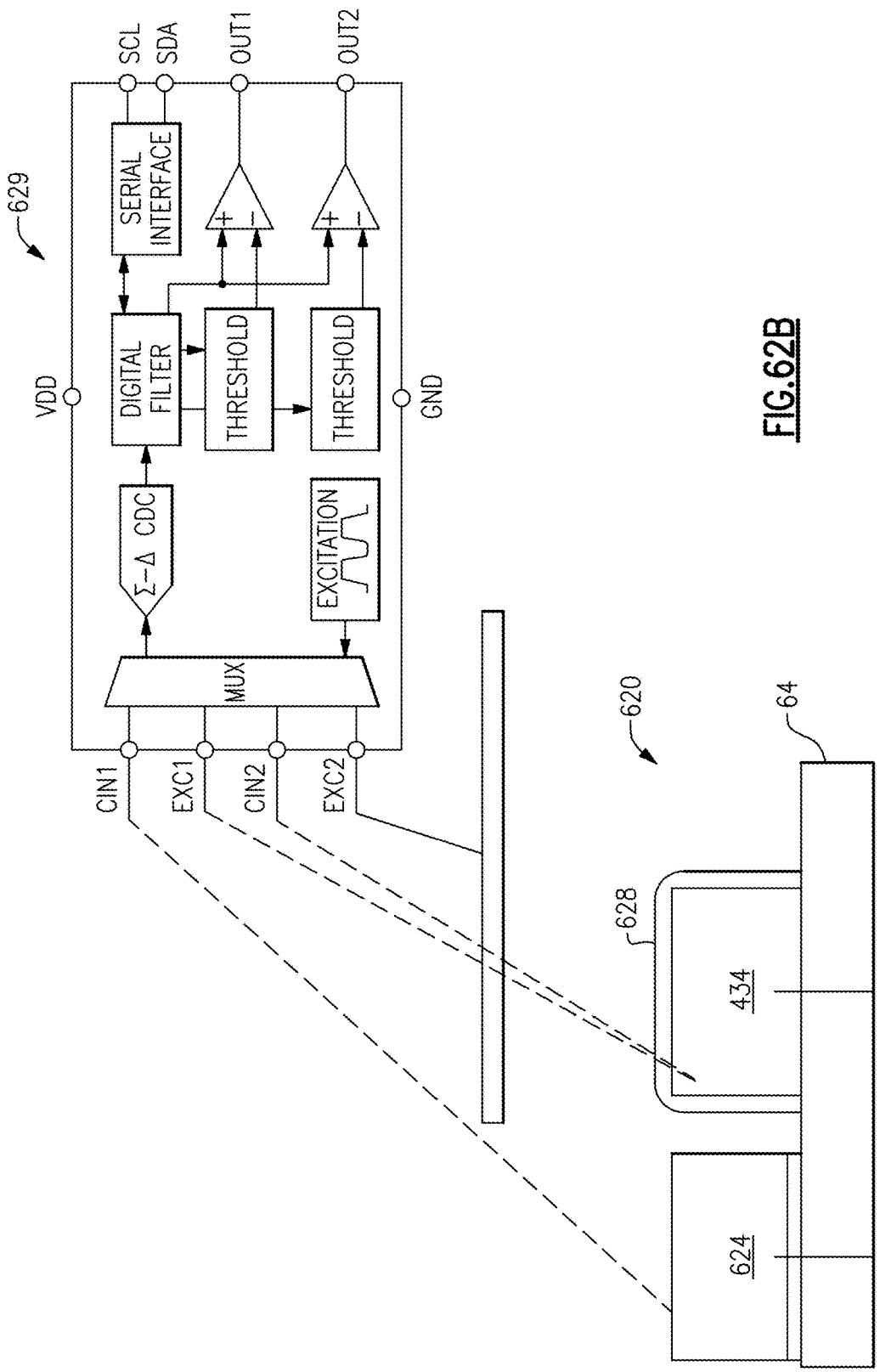

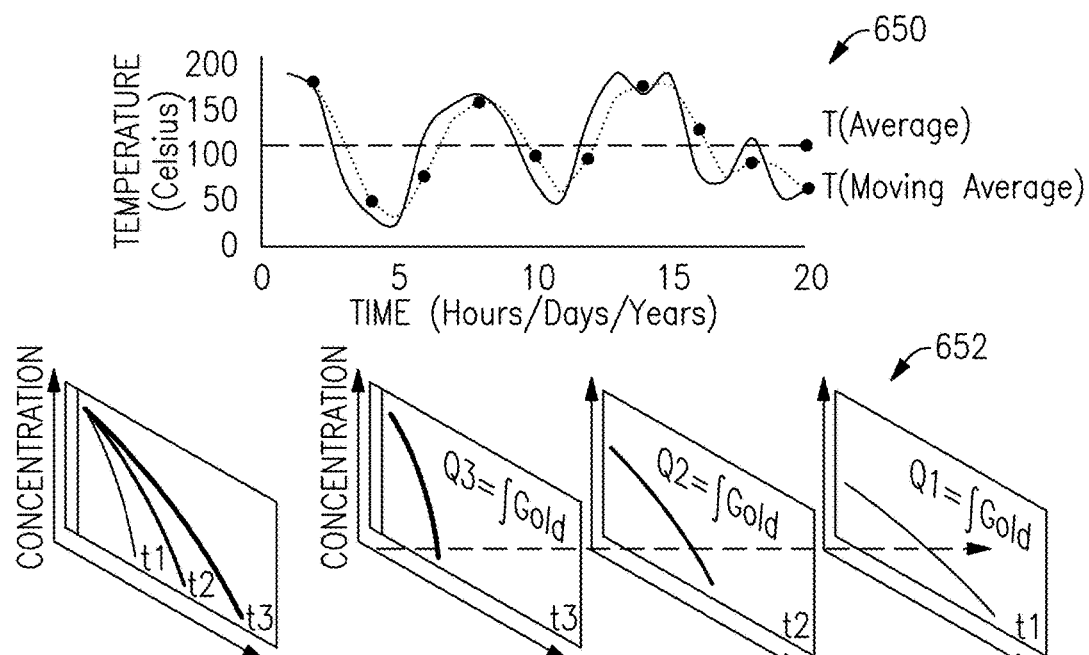
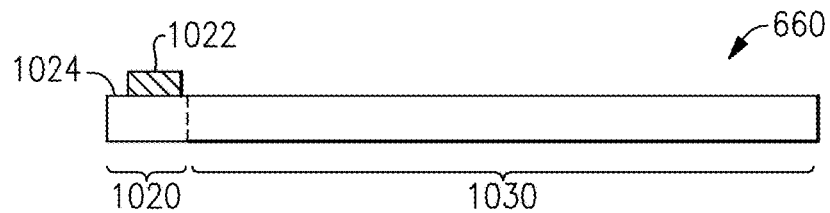
FIG.66A

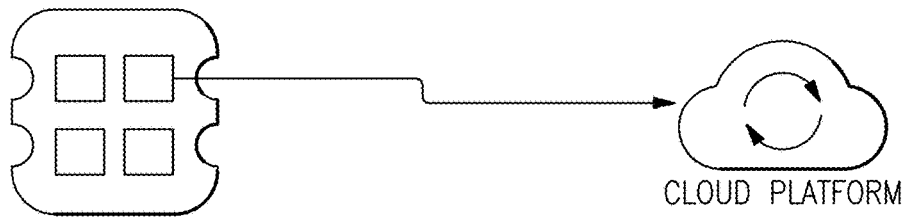
MODULE WITH WOS AND COMPONENTS TO TALK DIRECTLY TO THE
CLOUD PLATFORM
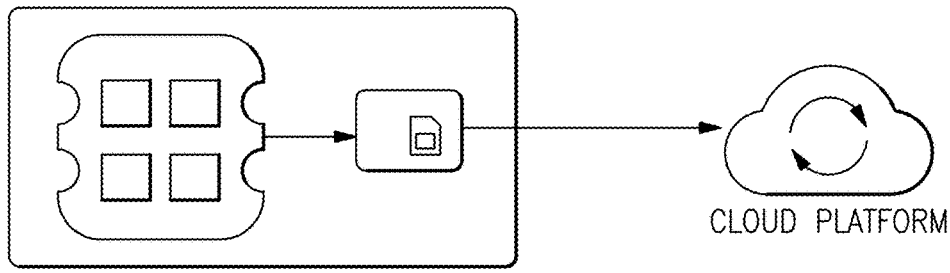
MODULE WITH WOS AND LOCAL COMPONENT THAT TALK TO AN ADDITIONAL
LOCAL COMPONENT THAT TALKS DIRECTLY TO THE CLOUD PLATFORM
FIG.105
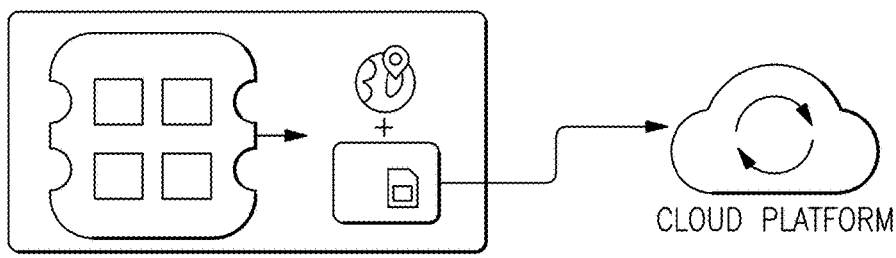
FIG.106

WEAR-OUT MONITOR DEVICE

INCORPORATION BY REFERENCE

This application claims the benefit of priority of and incorporates by reference the entirety of each of the following provisional patent applications: U.S. Provisional Application No. 62/324,828, filed Apr. 19, 2016; U.S. Provisional Application No. 62/447,824, filed Jan. 18, 2017; and U.S. Provisional Application No. 62/455,481, filed Feb. 6, 2017. This application is a continuation-in-part of U.S. application Ser. No. 15/291,742, filed Oct. 12, 2016, the entire disclosure of which is hereby incorporated by reference in its entirety herein.

FIELD OF THE DISCLOSURE

The disclosed technology generally relates to wear-out monitor devices for integrated circuit devices.

BACKGROUND

Mission lifetimes of some integrated circuit (IC) devices can be predicted based on, e.g., theoretical, empirical or semi-empirical models of failure mechanisms. Failure mechanisms, in turn, depend on the type(s) of wear-out stress(es) that cause failure of the IC devices. Stresses that cause wear-out of the IC devices include thermal stress, voltage (or electromagnetic field) stress, current stress, and mechanical stress, among other types of stresses. Some failures are caused by acute stresses, e.g., an electrical overstress (EOS) or an electrostatic discharge (ESD) event, while other failures are caused by cumulative stresses, e.g., thermal, voltage or current stresses during operation. The IC devices that are subjected to these wear-out stresses beyond their predicted mission lifetimes can be subject to increased probability of reliability failures, which can be sudden and catastrophic. For example, certain thermally activated failure mechanisms, e.g., data retention of memory devices, have predictable time-to-fail at a given temperature. However, the stresses that cause wear-out can be intermittent and variable. As a result, it can be difficult to predict a time-to-fail even when the failure mechanisms are relatively well-known. Therefore, it is desirable to monitor cumulative stresses real-time, such that a user can monitor, e.g., automatically, how close to the end of the mission lifetime the IC device actually is, to avoid sudden failures.

One approach to monitor wear-out stresses may be to implement a sensor system. The sensor system can include one or more sensors, e.g., a temperature sensor and a current sensor, for measuring the stresses and the associated circuitry for converting the measured stresses. The measured values associated with the stresses can then be recorded and tracked for possible excursions outside a prescribed limit. Such monitoring can be performed over a lifetime of a product to alert the user of a predicted failure. However, there can be a number of restrictions for such a system. For example, the sensor system may include a power supply for continuous sensing over the lifetime of the product. In addition, the sensed signal, e.g., voltage or current signal, may be volatile and be lost if not stored. A wear-out level of a component being monitored may then be calculated from the stored information. As a result, a built-in memory and/or an ability to transmit information to an external memory may be implemented. Furthermore, the range of monitored conditions may be limited by the sensors themselves. For example, if the sensor is a semiconductor-based device, the range of temperature, voltage and/or current that can be monitored for the monitored component may be limited by the operating parameters of the semiconductor-based device. Outside of the range, excursions may not be monitored and recorded because of possible failures of the sensor system itself. Thus, there is a desire for improved wear-out monitor devices.

SUMMARY OF SOME ASPECTS OF THE DISCLOSURE

The innovations described in the claims each have several aspects, no single one of which is solely responsible for its desirable attributes. Without limiting the scope of the claims, some prominent features of this disclosure will now be briefly described.

In one aspect, an integrated circuit device with wear out monitoring includes a core circuit and a wear-out monitor device. The wear-out monitor device is configured to adjust an indication of wear out of the core circuit regardless of whether the core circuit is activated. The integrated circuit device additionally includes a sensing circuit configured to detect an electrical property associated with the wear-out monitor device, wherein the electrical property is indicative of the wear out of the core circuit.

In some embodiments, the wear-out monitor device comprises a substrate and monitor atoms configured to diffuse in the substrate, wherein a doping profile of the monitor atoms in the substrate is indicative of wear out of the core circuit.

In some embodiments, the monitor atoms have a diffusion activation energy between 0.75 eV and 2.5 eV in the substrate.

In some embodiments, the monitor atoms includes one or more elements selected from the group consisting of aluminum (Al), cobalt (Co), platinum (Pt), sulfur (S), nickel (Ni), silver (Ag), zinc (Zn), gold (Au), chromium (Cr), copper (Cu), iron (Fe), sodium (Na), and potassium (K).

In some embodiments, the core circuit and the wear-out monitor device are formed in the substrate that is a common substrate formed of a semiconductor material and configured such that the monitor atoms remain in the wear-out monitor device under a wear-out stress without diffusing into the core circuit.

In some embodiments, the wear-out monitor device includes a reservoir of the monitor atoms formed on a surface of the substrate, wherein the reservoir serves as a first electrode of the wear-out monitor device, and wherein the wear-out monitor device further comprises a second electrode on the surface formed of a different material than the first electrode.

In some embodiments, the substrate includes a semiconductor material as a diffusing medium for the monitor atoms.

In some embodiments, the monitor device includes a PN junction, wherein the reservoir physically contacts one of a p-doped region or an n-doped region of the PN junction, and wherein the second electrode electrically contacts the other of the p-doped region or the n-doped region.

In some embodiments, the electrical property includes a reverse bias current of the PN junction.

In some embodiments, the monitor device comprises a first doped region and a second doped region that are separated from each other and configured to punch-through under a bias between the first doped region and the second doped region, wherein the first doped region and the second doped region have opposite conductivity types, and wherein the monitor atoms are configured to diffuse from the first doped region towards the second doped region under the bias.

In some embodiments, the second doped region is a buried region that is vertically separated from the first doped region that is formed at a surface of the semiconductor material.

In some embodiments, the first doped region and the second doped region are formed at a surface region of the semiconductor material and are laterally separated from each other.

In some embodiments, the monitor device includes a field effect transistor comprising a source region and a drain region that are separated from each other by a channel region, and wherein, under a bias, the monitor atoms are configured to diffuse from one of the source region or the drain region into the channel towards the other of the source region or the drain region.

In some embodiments, the integrated circuit device further includes a reference device coupled to the sensing circuit, wherein the sensing circuit is configured to provide an indication of wear-out based on a comparison of the electrical property of the wear-out monitor device with a corresponding electrical property of the reference device.

In some embodiments, the reference device includes the same type of device as the wear-out monitor device while having at least one electrode formed of a material different than a corresponding electrode of the wear-out monitor device having the monitor atoms.

In some embodiments, the indication of wear-out is indicative of one or more of a thermal stress, a voltage stress, or a current stress.

In some embodiments, the monitor atoms are configured such that a wear-out stress causes a change in a rate at which the monitor atoms diffuse in the substrate.

In some embodiments, the wear-out monitor device includes a p-doped region and an n-doped region, wherein the p-doped region comprises a p-type dopant different from the diffusing material and the n-doped region comprises an n-type dopant different from the diffusing material.

In another aspect, a method of monitoring a wear-out of an integrated circuit device including a core circuit and a wear-out monitor device includes detecting an electrical property of a wear-out monitor device, wherein the wear-out monitor device includes a semiconductor material and monitor atoms configured to diffuse into the semiconductor material, and wherein the electrical property corresponds to a concentration profile of the monitor atoms in the semiconductor material that is indicative of wear-out of the core circuit. The method additionally includes reporting the electrical property of the wear-out monitor device.

In some embodiments, prior to detecting, the method includes subjecting the integrated circuit device to a stress condition that causes the monitor atoms diffuse in the semiconductor material.

In some embodiments, the method further includes determining whether the wear-out of the core circuit has reached a predetermined level based on the detected electrical property of the wear-out device.

In some embodiments, the monitor device comprises a plurality of doped regions and a reservoir of the monitor atoms physically contacting one of the doped regions and serving as an electrode, and detecting the electrical property includes measuring a current or a voltage using the electrode.

In some embodiments, the stress condition comprises one or more of a thermal stress condition, a voltage stress condition, or a current stress condition.

In another aspect, an integrated circuit device with wear-out monitoring includes a core circuit and means for recording wear-out of the core circuit as a doping profile of a diffusing material in a substrate. The integrated circuit device additionally includes means for detecting an indication of wear-out of the core circuit, the means for recording wear-out being in communication with the means for recording the indication of wear-out.

In some embodiments, the diffusing material has a diffusion activation energy in the substrate between 0.75 eV and 2.5 eV.

In some embodiments, the substrate is a semiconductor substrate.

In some embodiments, the means for recording includes a first doped region doped with a first dopant of a first type and a second doped region doped region doped with a second dopant of a second type.

In some embodiments, the means for recording further includes a reservoir comprising atoms of the diffusing material, wherein the reservoir contacts one of the first doped region or the second doped region.

In some embodiments, the means for recording includes a PN junction having a p-doped region and an n-doped region, wherein the p-doped region comprises a p-type dopant different from the dopant and the n-doped region comprises an n-type dopant different from the diffusing material.

In some embodiments, the means for recording includes a metal-oxide-silicon transistor having a source region and a drain region, wherein the source region and the drain region are doped with an n-type dopant or a p-type dopant different from the diffusing dopant.

In some embodiments, the means for recording comprises a monitoring region and a reference region formed in the substrate, wherein each of the monitoring region and the reference region comprises the diffusing material and at least the reference region comprises a barrier configured to restrict diffusion of the diffusing material into the substrate.

In some embodiments, the means for detecting is configured to measure impedance values from each of the monitoring region and the reference region and to determine the wear-out of the core circuit based on a comparison of the measured impedance values.

In another aspect, an integrated circuit device comprises a wear-out monitor device configured to record an indication of wear-out of a core circuit separated from the wear-out monitor device, wherein the indication is associated with localized diffusion of a diffusant within the wear-out monitor device in response to a wear-out stress that causes the wear-out of the core circuit.

In some embodiments, the wear-out monitor device comprises a reservoir comprising the diffusant and a diffusion region in communication with the reservoir, such that the wear-out stress causes the diffusant to diffuse from the reservoir into the diffusion region.

In some embodiments, the diffusion region comprises a semiconductor material.

In some embodiments, the indication of wear-out is associated with a concentration of the diffusant in the diffusion region.

In some embodiments, the diffusant has a diffusion activation energy between 0.75 eV and 2.5 eV in the diffusion region.

In some embodiments, the diffusant includes one or more elements selected from the group consisting of aluminum (Al), cobalt (Co), platinum (Pt), sulfur (S), nickel (Ni), silver (Ag), zinc (Zn), gold (Au), chromium (Cr), copper (Cu), iron (Fe), sodium (Na), and potassium (K).

In some embodiments, the reservoir is formed at a surface of a substrate, wherein the reservoir serves as a first electrode of the wear-out monitor device, and wherein the wear-out monitor device further comprises a second electrode formed at the surface and formed of a material different from the reservoir.

In some embodiments, the core circuit and the wear-out monitor device are formed in a common substrate formed of a semiconductor material and configured such that the diffusant remains in the wear-out monitor device under a wear-out stress without diffusing into the core circuit.

In some embodiments, the integrated circuit device further comprises a sensing circuit electrically connected to the wear-out monitor device and configured to detect an electrical property that changes in response to the localized diffusion of the diffusant into the diffusion region.

In some embodiments, the integrated circuit device comprises the core circuit that is physically separated from the wear-out monitor device such that the diffusant does not diffuse into the core circuit from the wear-out monitor device.

In some embodiments, the wear-out monitor device is configured to be activated by a stimulus prior to recording the indication of wear-out.

In some embodiments, the integrated circuit device further comprises a control circuit connected to the wear-out monitor device and configured to supply the stimulus, wherein the stimulus comprises at least one of a voltage stimulus or a current stimulus.

In some embodiments, the stimulus comprises an optical stimulus.

In some embodiments, a physical barrier having an energy barrier for diffusion of the diffusant is disposed between the reservoir and the diffusion region, wherein the physical barrier is configured such that the energy barrier is reduced in response to the stimulus to activate the wear-out monitor device.

In some embodiments, the wear-out monitor device is configured such that the stimulus provides sufficient thermal energy to the barrier to reduce the energy barrier.

In some embodiments, the diffusion region and the reservoir have different compositions such that the region has an energy barrier for diffusion of the diffusant relative to the reservoir, wherein the energy barrier is such that the stimulus imparts sufficient energy to the diffusant to activate the wear-out monitor device.

In some embodiments, the energy barrier is greater than an average thermal energy of the diffusant in the reservoir at room temperature.

In some embodiments, the wear-out monitor device comprises a plurality of monitor structures each configured to record an indication of wear-out of the core circuit.

In some embodiments, different ones of the monitor structures are configured to be activated by different stimuli prior to recording indications of wear-out of the core circuit.

In some embodiments, the different ones of the monitor structures have different physical barriers formed between the respective reservoirs and the respective diffusion regions.

In some embodiments, different ones of the monitor structures have diffusion regions that are configured differently.

In some embodiments, the differently configured diffusion regions have different compositions.

In some embodiments, different ones of the monitor structures have reservoirs that are configured differently.

In some embodiments, differently configured reservoirs have different compositions.

In some embodiments each of the monitor structures has a plurality electrodes formed thereon.

In some embodiments, electrodes of the plurality electrodes are regularly spaced apart from each other.

In some embodiments, the monitor structures are arranged laterally on a common substrate.

In some embodiments, adjacent monitor structures are formed at regular intervals.

In some embodiments, the reservoir and the diffusion region are disposed laterally relative to each other on a common substrate such that the indication of wear-out is based on the localized diffusion of diffusant having a net direction of diffusion in a lateral direction parallel to a major surface of the substrate.

In some embodiments, the net direction of diffusion is a radially inward direction towards a centrally located diffusion region from a reservoir region incorporating the diffusant that surrounds the diffusion region.

In some embodiments, the indication of wear-out is based on the diffusion of diffusant having a net direction of diffusion that is a radially outward direction from a centrally located reservoir region incorporating the diffusant towards a diffusion region surrounding the reservoir region.

In some embodiments, the monitor structures are arranged vertically on a common substrate.

In some embodiments, atoms of a substrate serves as the diffusant, such that the wear-out stress causes atoms of the substrate to diffuse from the substrate into the diffusion region.

In some embodiments, the wear-out stress causes formation of an oxide comprising the atoms of the substrate a surface of the reservoir.

In some embodiments, the integrated circuit device further comprises a sensing circuit electrically connected to the wear-out monitor device and configured to detect an electrical property that changes in response to the localized diffusion of atoms of the substrate into the diffusion region.

In some embodiments, the sensing circuit is configured to measure a resistivity of the diffusion region.

In some embodiments, the wear-out monitor device further includes a reference electrode, wherein the sensing circuit is configured to measure a capacitance between the reference electrode and the diffusion region.

In some embodiments, the wear-out monitor device is configured to apply an electric field to the diffusion region in a first direction, and wherein the diffusant has a charge state when diffused in the diffusion region such that, when the electric field is applied to the diffusion region having the diffusant diffused therein, the electric field causes the diffusant to further diffuse in the diffusion region in the first direction.

In some embodiments, the diffusion region and the reservoir are adjacently disposed in a second direction different than the first direction and configured such that the wear-out stress causes the diffusant to diffuse in the second direction.

In some embodiments, the diffusion region is disposed in a semiconductor substrate and the reservoir is formed on a surface of the semiconductor substrate such that the wear-out stress causes the diffusant to diffuse in a direction normal to the semiconductor substrate surface, and the electric field causes the diffusant to diffuse in a direction parallel to the semiconductor substrate surface.

In some embodiments, a plurality of conductive structures are formed on a surface of the diffusion region along the first direction and provide electrical access to the diffusion region at a plurality of locations.

In some embodiments, the wear-out monitor device is configured to apply the electric field by applying a voltage on one or more of the conductive structures.

In some embodiments, the diffusion region comprises a semiconductor material doped with a dopant having a concentration that is graded in the first direction, such that the electric field varies in magnitude across the diffusion region in the first direction.

In some embodiments, the wear-out monitor has oppositely doped semiconductor regions in the diffusion region such that the electric field is a built-in electric field in the diffusion region.

In some embodiments, the wear-out monitor device is configured such that the wear-out stress causes the diffusant to diffuse away from the reservoir and into the diffusion region, wherein the diffusant have a charge state when diffused into the diffusion region, and wherein the wear-out monitor device is further configured to apply an electric field to the diffusion region such that, when the electric field is applied to the diffusion region having the diffusant diffused therein, the electric field causes the diffusant to diffuse toward the reservoir.

In some embodiments, the wear-out monitor device is configured to apply the electric field having a magnitude such that, when the electric field is applied to the diffusion region having the diffusant diffused therein, the electric field causes the diffusant to diffuse in a direction of increasing concentration gradient.

In some embodiments, the wear-out monitor device is configured to activate diffusion of the diffusant in response to a stimulus.

In some embodiments, the stimulus comprises at least one of a voltage, a current, light, or heat.

In some embodiments, the integrated circuit device further comprises a control circuit configured to apply the stimulus to the wear-out device.

In some embodiments, the integrated circuit device further comprises a sensing circuit electrically connected to the wear-out monitor device and configured to provide an indication of a diffusion profile over time.

In some embodiments, the integrated circuit device further comprises a sensing circuit electrically connected to the wear-out monitor device and configured to provide an indication of wear-out in situ.

In some embodiments, the wear-out monitor device comprises a semiconductor substrate and the diffusant is configured to diffuse into the semiconductor substrate.

In some embodiments, the integrated circuit device further comprises a sensing circuit electrically connected to the wear-out monitor device and configured to detect an electrical property that changes in response to the localized diffusion of diffusant into the semiconductor substrate.

In some embodiments, the integrated circuit device further comprises a sensing circuit electrically connected to the wear-out monitor device and configured to detect an electrical property that changes in response to localized diffusion of a semiconductor material of the wear-out monitor device into a diffusion region.

In some embodiments, the wear-out monitor device is configured to enable a stimulus to be applied that causes a direction of the localized diffusion to change in response to the stimulus.

In another aspect, a method of monitoring wear-out of a core circuit of an integrated circuit device uses a wear-out monitor device separated from the core circuit. The method comprises recording an indication of wear-out of the core circuit, wherein the indication is associated with localized diffusion of a diffusant within the wear-out monitor device in response to a wear-out stress that causes the wear-out of the core circuit. The method additionally includes detecting an electrical property that changes in response to the localized diffusion of the diffusant. The method further includes reporting the electrical property of the wear-out monitor device.

In some embodiments, the method further comprises, prior to recording, subjecting the wear-out monitor device to the wear-out stress that causes the localized diffusion from a reservoir comprising the diffusant into a diffusion region.

In some embodiments, the method further comprises, prior to subjecting the wear-out monitor device to the wear-out stress, activating the monitor device by applying a stimulus to overcome an energy barrier.

In some embodiments, applying the stimulus alters a physical barrier having the energy barrier and reduces the energy barrier.

In some embodiments, the method further comprises, after subjecting the wear-out monitor device to the wear-out stress, applying an electric field to the diffusion region having the diffusant diffused therein in a first direction such that the electric field causes the diffusant to further diffuse in the first direction.

In some embodiments, the method further comprises, after subjecting the wear-out monitor device to the wear-out stress which causes the diffusant to diffuse away from the reservoir and into the diffusion region, applying an electric field to the diffusion region having the diffusant diffused therein, such that the electric field causes the diffusant to diffuse toward the reservoir.

In another aspect, an integrated circuit device has wear-out monitoring capability of a core circuit in the integrated circuit device. The integrated circuit device comprises means for recording an indication of wear-out of a core circuit, wherein the indication is associated with localized diffusion of a diffusant within the means for recording in response to a wear-out stress that causes the wear-out of the core circuit. The integrated circuit device additionally comprises means for detecting the indication of wear-out of the core circuit, the means for detecting the indication of wear-out being in communication with the means for recording the indication of wear-out.

In some embodiments, the means for recording comprises a reservoir comprising the diffusant and a diffusion region in communication with the reservoir such that the wear-out stress causes the diffusant to diffuse from the reservoir into the diffusion region.

In some embodiments, the means for recording is configured to activate in response to a stimulus prior to causing the diffusant to diffuse from the reservoir into the diffusion region.

In some embodiments, the integrated circuit device further comprises means for applying an electric field to the diffusion region in a first direction, and wherein the diffusant has a charge state when diffused in the diffusing region such that, when the electric field is applied to the diffusing region having the diffusant diffused therein, the electric field causes the diffusant to further diffuse in the diffusing region in the first direction.

In some embodiments, the means for recording is configured such that the wear-out stress causes the diffusant to diffuse away from the reservoir and into the diffusion region, wherein the diffusant have a charge state when diffused into the diffusion region, and wherein the recording means is further configured to apply an electric field to the diffusion region such that, when the electric field is applied to the diffusion region having the diffusant diffused therein, the electric field causes the diffusant to diffuse toward the reservoir.

In another aspect, a sensor includes an integrated data recording structure. The sensor includes a first region adapted to be exposed to a material which serves as a solute within a body of the sensor. The sensor additionally includes a second region contacting the first region and adapted to migrate the solute away from the first region such that the concentration of the solute as a function of time becomes encoded as a spatial distribution of the solute within the body of the sensor.

In some embodiments, the second region is configured to migrate the solute in a first direction under an electric field (E-field).

In some embodiments, the E-field is an intrinsic E-field provided by a spatially graded doping profile within a material forming the second region.

In some embodiments, the E-field is provided by a voltage difference applied across the second region.

In some embodiments, the sensor further includes a read structure extending along the second region for reading electrical properties of the second region as a function of position along the second region.

In some embodiments, the read structure comprises a plurality of electrodes disposed along the second region.

In some embodiments, the read structure comprises a plurality of transistors disposed along the second region, where the transistors comprise bipolar junction transistors and the second region serves as a base region for respective ones of the bipolar transistors; and/or where the transistors comprise are field effect transistors and the second region acts as a gate or channel region for respective ones of the field effect transistors.

In some embodiments, the read structure comprises a plurality of diodes.

In some embodiments, the sensor further includes a reference channel, where the reference channel comprises a third region corresponding to the second region of the sensor, but not contacting the first region.

In some embodiments, a temperature comprises the sensor which includes the integrated data recording structure described above. The first region of the sensor is in contact with or doped with the material serving as the solute, where the material has an activation energy with respect to a material of the body of the sensor of less than 3 electron volts (eV).

In some embodiments, the material serving as the solute in the temperature sensor is selected to have an activation energy less than 2 eV and greater than 0.7 eV.

In some embodiments, the material in the temperature sensor is selected from a group consisting of silver, gold and copper.

In some embodiments a concentration sensor comprises the temperature sensor described above. In addition, the concentration sensor further comprises a third region exposed to a reagent which serves as a second solute; and a fourth region in contact with the third region and adapted to migrate the second solute along the fourth region.

In some embodiments, the sensor further includes a structure for controlling contact between the material serving as the solute and the first region.

In some embodiments, the structure for controlling contact is responsive to one or more of temperature, pressure and electrical control.

In some embodiments, the sensor further includes a read circuit.

In some embodiments, a die carries the sensor described above.

In some embodiments, a chip scale package comprises the die described above that is co-packaged with at least one other die.

In another aspect, a temperature sensor operable to record temperature in an unpowered state comprises a solute material placed in contact with a memory region of a semiconductor. The memory region of the semiconductor is doped such that an intrinsic electric field exists therein so as to migrate the solute along the memory region such that temperature as a function of time becomes encoded as a spatial distribution of solute within the memory region.

In another aspect, a method of manufacturing a temperature sensor comprises adapting a region of a semiconductor such that an electric field gradient exists across the region. The method additionally includes forming a plurality of read structures within the region of the semiconductor configured such that electrical properties as a function of position within the region can be determined. The method further includes exposing a portion of the region of semiconductor to a source of impurities, whereby the impurities modify the electrical properties of the semiconductor.

For purposes of summarizing the disclosure, certain aspects, advantages and novel features of the innovations have been described herein. It is to be understood that not necessarily all such advantages may be achieved in accordance with any particular embodiment. Thus, the innovations may be embodied or carried out in a manner that achieves or optimizes one advantage or group of advantages as taught herein without necessarily achieving other advantages as may be taught or suggested herein.

BRIEF DESCRIPTION OF THE DRAWINGS

Embodiments of this disclosure will now be described, by way of non-limiting example, with reference to the accompanying drawings.

FIGS. 3A and 3B illustrate a wear-out monitor device having monitor atoms whose rate of diffusion changes in response to a wear-out stress, according to embodiments.

FIG. 4A illustrates a wear-out monitor device having phosphorus as monitor atoms, according to embodiments.

FIG. 4B is a graph illustrating calculated concentration profiles of phosphorus in silicon substrate of the wear-out monitor device in FIG. 4A, after diffusing at 125° C. for various times.

FIG. 7A is an illustration of a wear-out monitor device comprising monitor atoms configured to diffuse in a semiconductor material, according to embodiments.

FIG. 7B is an illustration of a reference device configured to provide reference measurement for the monitor device of FIG. 7A, according to embodiments.

FIGS. 11A and 11B are illustrations of a wear-out monitor device configured as a vertical punch-through wear-out monitor device, according to embodiments.

FIGS. 15A-15D illustrate various configurations of wear-out monitor devices comprising a PN junction and a layer of monitor atoms configured to diffuse into the PN junction, according to embodiments.

FIGS. 16A-16G illustrate various configurations of wear-out monitor devices for controlling diffusion rate of monitor atoms into the underlying substrate, according to embodiments.

FIGS. 17A and 17B illustrate wear-out monitor devices configured as bipolar junction transistors (BJTs), according to embodiments.

FIGS. 18A-18D illustrate wear-out monitor devices configured as metal oxide semiconductor (MOS) transistors, according embodiments.

FIGS. 19A and 19C-19D illustrate wear-out monitor devices configured as impedance measurement devices, according to embodiments.

FIG. 19B schematically illustrate time evolution of concentration profile of wear-out monitor devices of FIGS. 19A and 19C-19D.

FIGS. 30A-30D illustrate various embodiments of wear-out monitor devices having structures configured to oxidize or corrode for determining cumulative wear-out stresses, according to embodiments.

FIGS. 35A and 35B illustrate schematic diagrams ESD event detection circuits configured as wear-out monitor devices, respectively, according to embodiments.

FIGS. 36A-36C illustrate example physical layouts of an ESD protection devices configured as wear-out monitor devices, according to embodiments.

FIG. 40 is an illustration of a wear-out monitor device comprising monitor atoms configured to diffuse in a semiconductor material, according to embodiments.

FIG. 50A illustrates a cross-sectional view of a wear-out monitor device configured to record an indication of wear out of a core circuit based on localized atomic diffusion of monitor atoms, where the wear-out monitor device includes a plurality of monitor structures, according to embodiments.

FIG. 50B illustrates an example control circuit having a current supply transistor electrically connected to and configured to supply the electrical stimulus to the wear-out monitor device illustrated in FIG. 50A, according to embodiments.

FIG. 51A illustrates a cross-sectional view (upper drawing) and a top-down plan-view (lower drawing) of a wear-out monitor device configured to record an indication of wear out of a core circuit based on localized atomic diffusion of monitor atoms, according to embodiments.

FIG. 62B illustrates a close-up view of the wear-out monitor device illustrated in FIG. 62A electrically connected to a sensing circuit configured to detect electrical signatures associated with the structural modifications to the reservoir resulting from interdiffusion of atoms, according to embodiments.

FIG. 65 is a graph comparing temperature fluctuations against an average temperature and against a moving average temperature FIGS. 66A-66C is a schematic diagram of a temperature sensor according to some embodiments.

FIG. 70B schematically illustrates an electric field as a function of distance corresponding to the doping concentration profile of FIG. 14a;

FIG. 70C schematically illustrates an electric potential corresponding to the doping concentration profile of FIG. 14a;

FIG. 92 illustrates wear-out monitor comprising a substrate having formed thereon a reservoir of monitor atoms and a plurality of electrodes for time-resolved monitoring, where a plurality of monitor MOS transistors whose gates serve as the electrodes, according to embodiments.

FIG. 93 illustrates wear-out monitor comprising a substrate having formed thereon a reservoir of monitor atoms and a plurality of electrodes for time-resolved monitoring, where a plurality of monitor MOS transistors whose gates serve as the electrodes, according to embodiments.

FIG. 94 illustrates the electrodes being connected to a reverse bias leakage multiplexed measurement circuitry comprising a reference structure for differential measurements, where the measurement circuitry is configured to measure reverse bias recovery current, according to embodiments.

FIG. 95A illustrates a sensing circuit configured to measure reverse bias recovery current and comprising a monitor diode for monitoring wear-out of a core circuit, according to embodiments.

FIG. 95B illustrates the measured current as the monitor diode is switched from a forward biased configuration to a reverse biased configuration, using the sensing circuit illustrated in FIG. 96A.

FIG. 96A illustrates a sensing circuit comprising a reference diode, which does not have impurities diffused therein.

FIG. 96B illustrates the measured current as the reference diode of FIG. 96A is switched from a forward biased configuration to a reverse biased configuration, using the sensing circuit illustrated in FIG. 96A.

Figure 97:
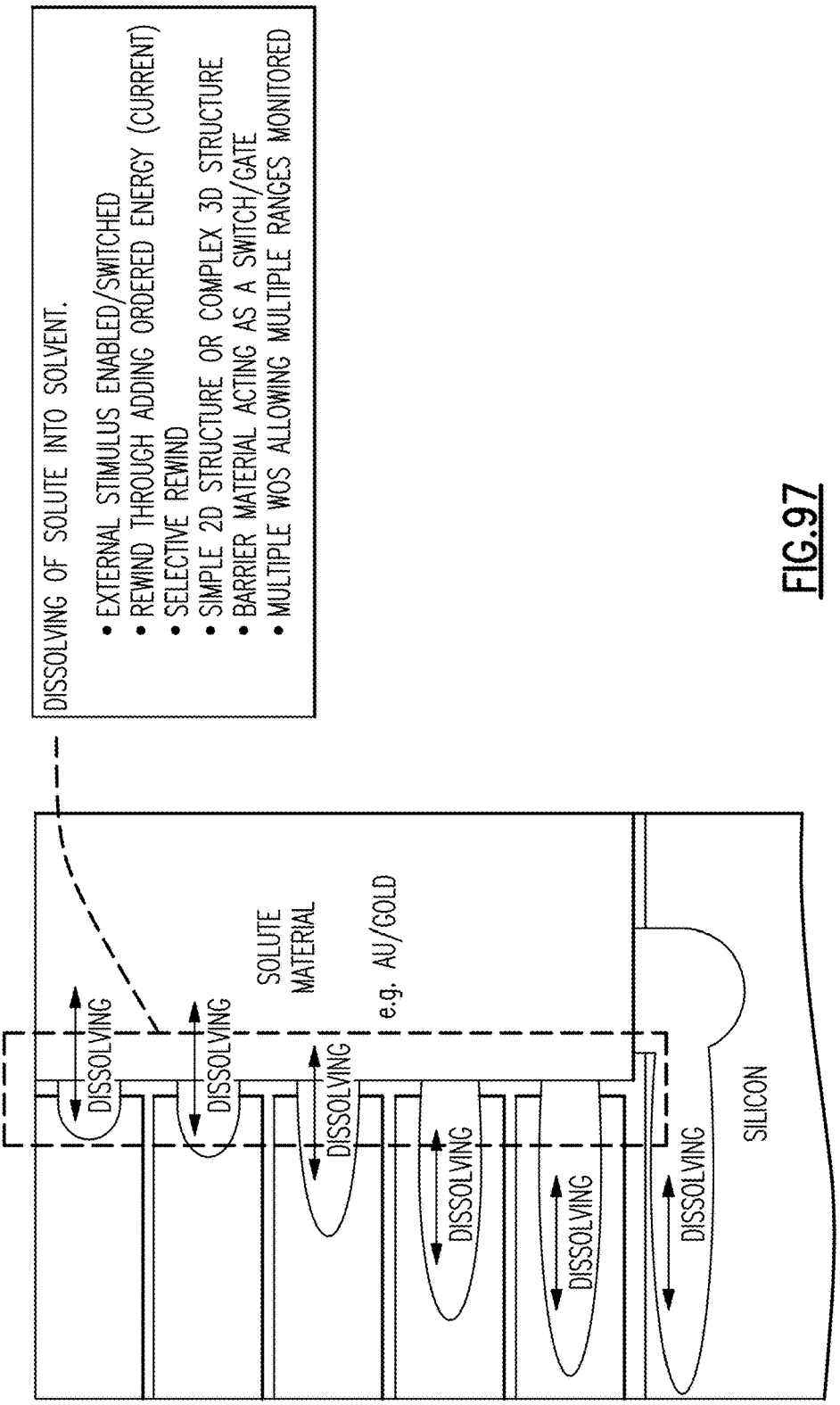

FIG. 97 illustrates a wear-out monitor device having monitor atoms that are adapted to have a charge state when diffused in the monitor region, and configured to apply an electric field to the monitor region such that, when the electric field is applied to the monitor region having the monitor atoms diffused therein, the electric field causes the monitor atoms to diffuse away from the monitor region and back into the reservoir.

Figure 98:
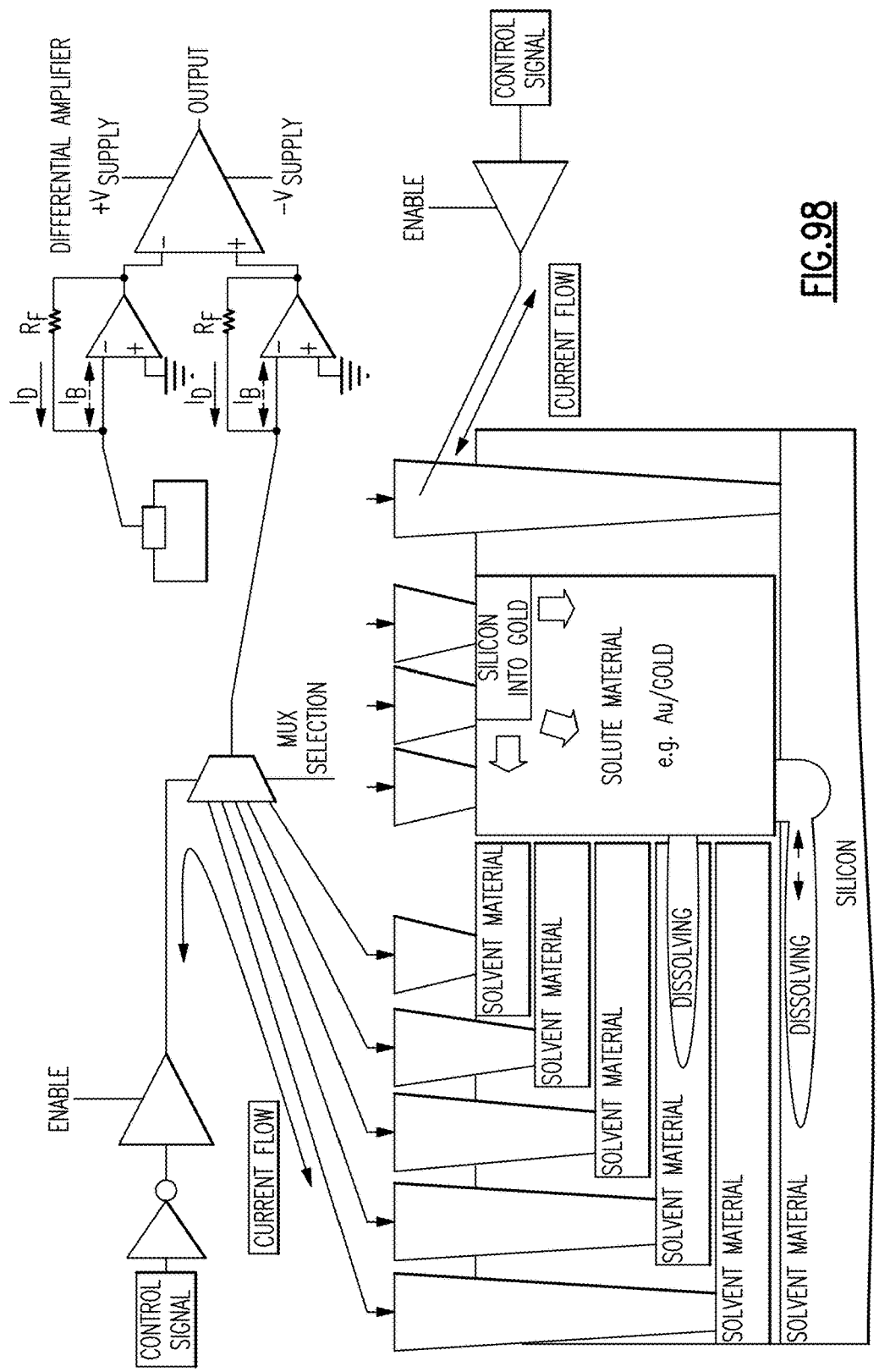

FIG. 98 illustrates a system including sensing and/or control circuitry electrically connected to various regions of the wear-out monitor device illustrated in FIG. 97, according to embodiments.

Figure 99:
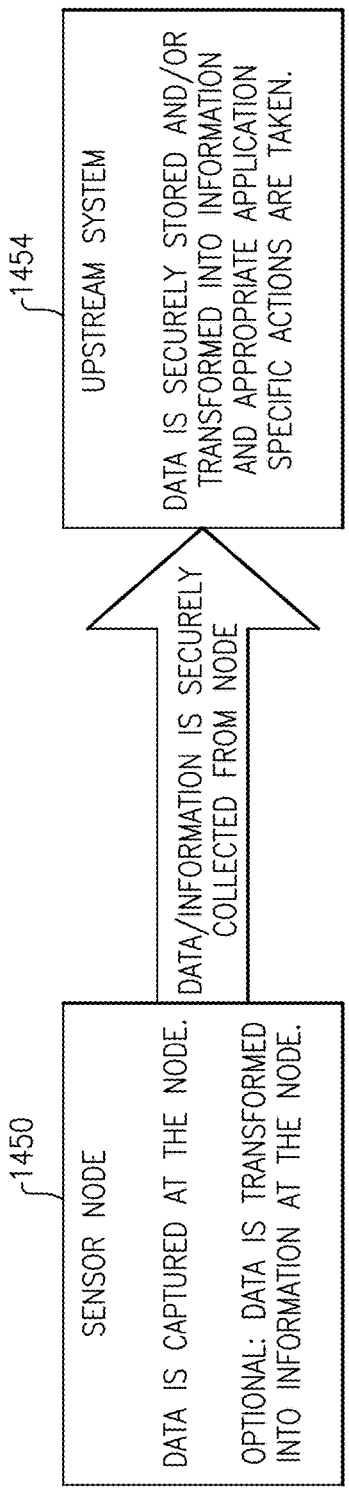

FIG. 99 illustrates a sensor network system configured for monitoring wear-out of a core circuit, according to embodiments.

Figure 100:
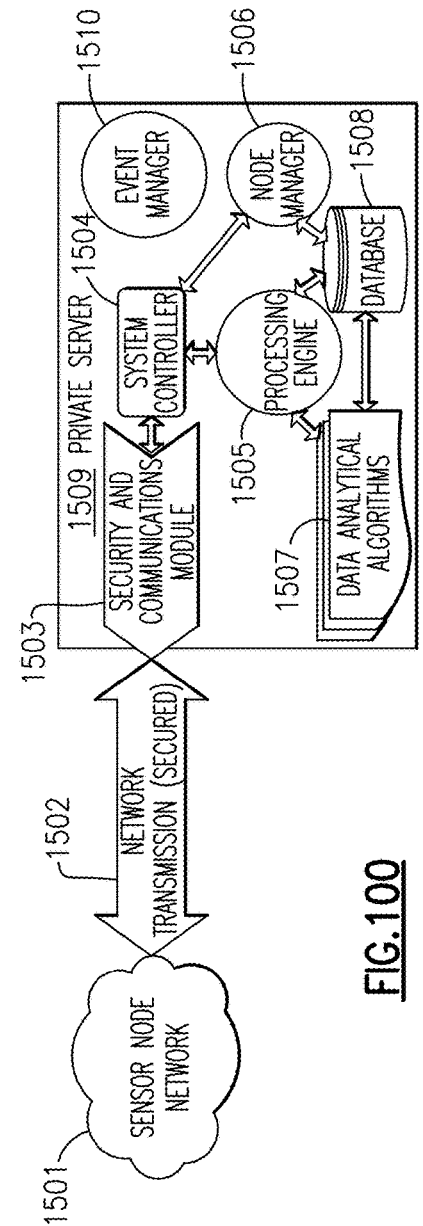

FIG. 100 illustrates a sensor network communicatively coupled to a an upstream system, according to embodiments.

Figure 101:
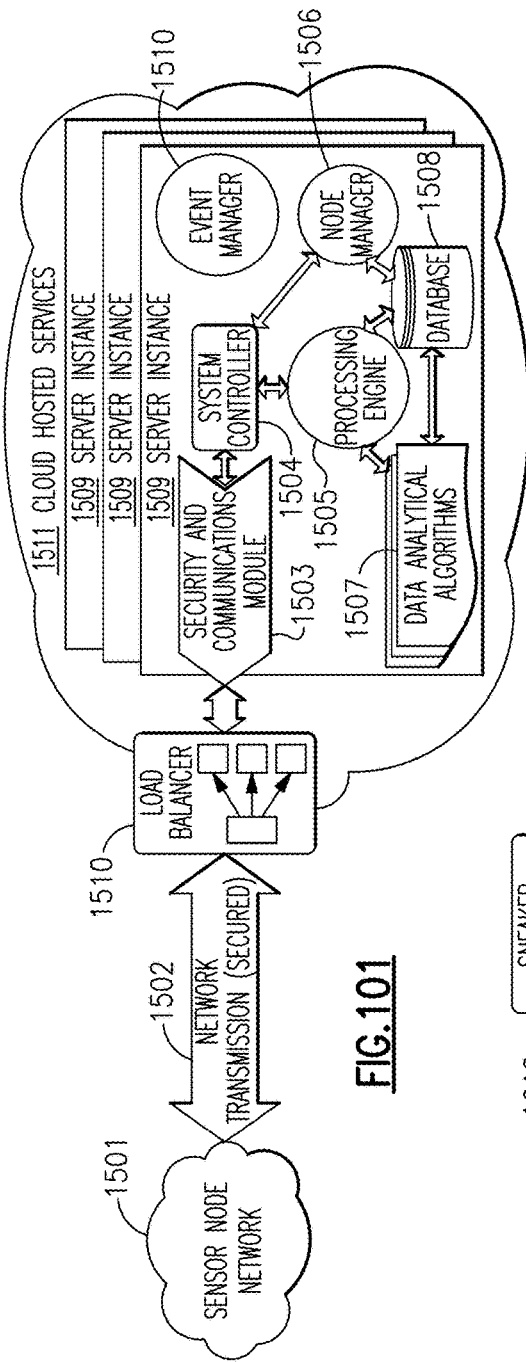

FIG. 101 illustrates a sensor network communicatively coupled to cloud hosted services, according to embodiments.

Figure 102:
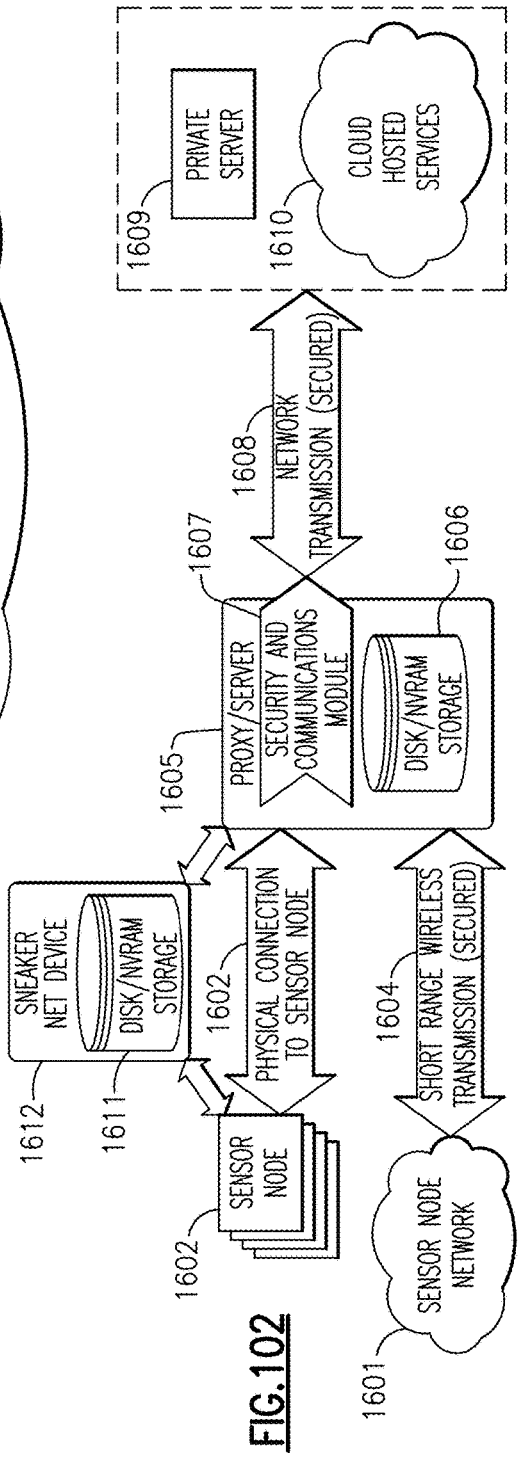

FIG. 102 illustrates a sensor network in which the sensors are configured to collect data by communicating directly with a private server or hosted services, according to embodiments.

Figure 103:
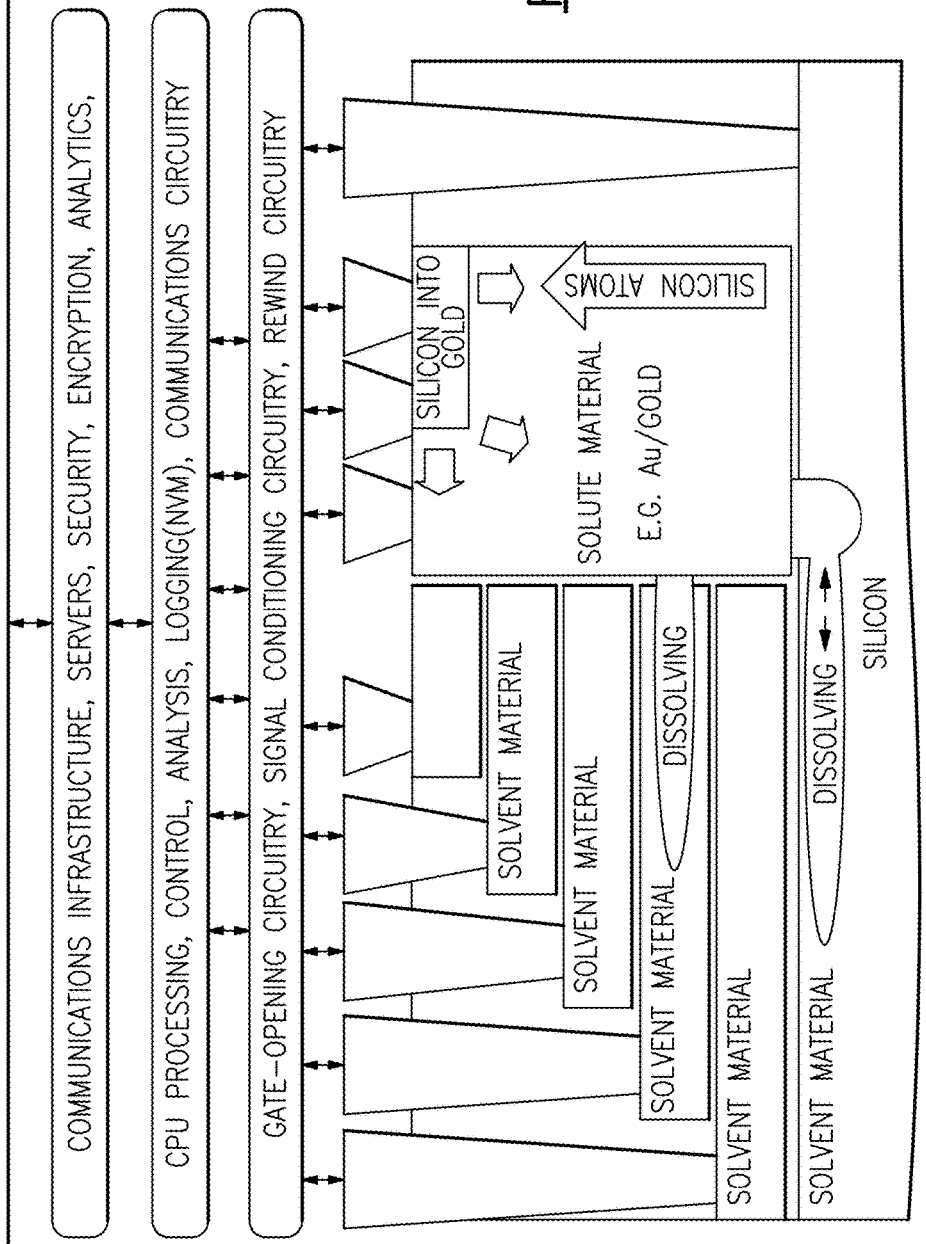

FIG. 103 illustrates various physical and electrical connections that can be made to various wear-out monitor devices, for integration into a sensor network system, according to embodiments.

Figure 104:
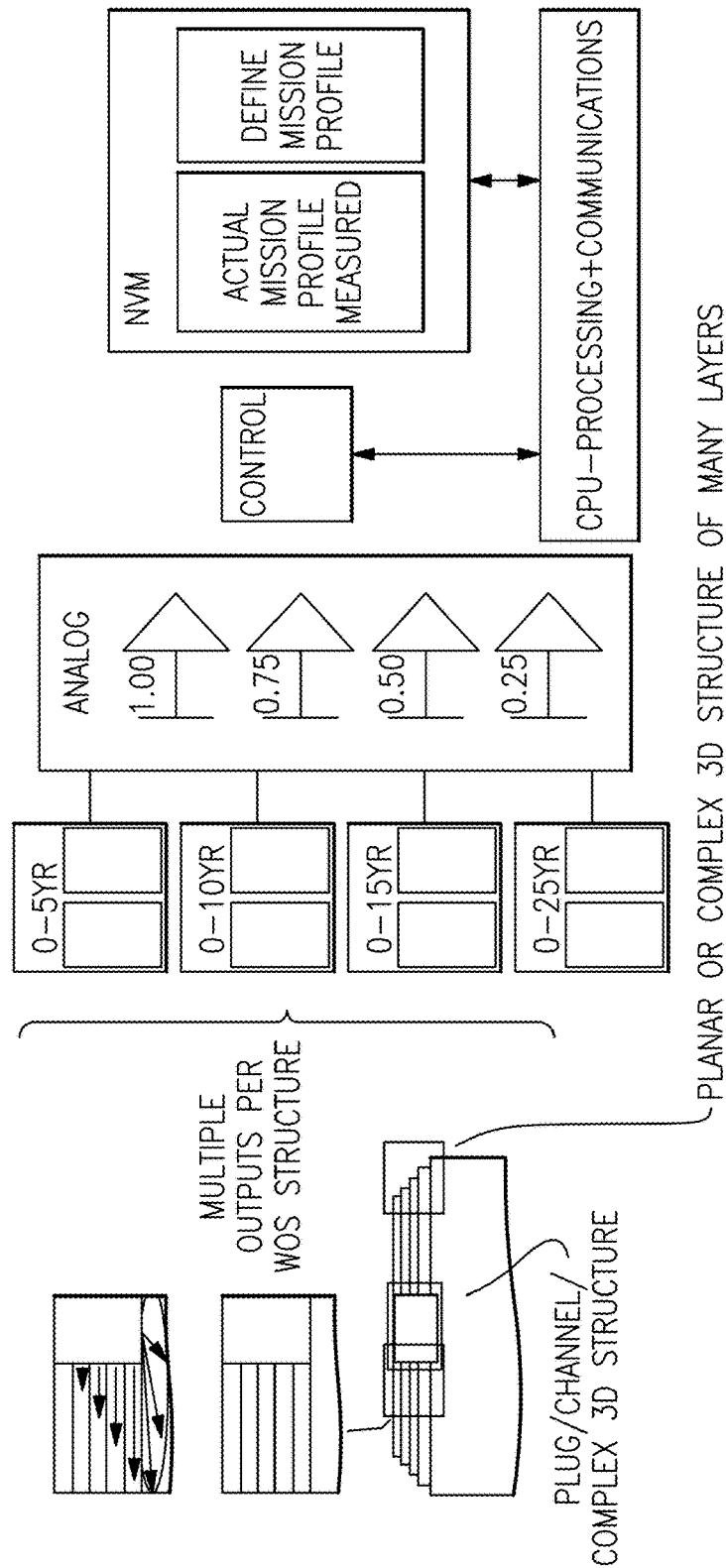

FIG. 104 illustrates an example sensor network system based on wear-out monitor devices according to embodiments.

FIG. 105 illustrates a sensor network communicatively coupled with a hosted service, according to embodiments.

FIG. 106 illustrates a sensor network communicatively coupled with a hosted service, according to embodiments.

DETAILED DESCRIPTION

The following detailed description of certain embodiments presents various descriptions of specific embodiments. However, the innovations described herein can be embodied in a multitude of different ways, for example, as defined and covered by the claims. In this description, reference is made to the drawings where like reference numerals can indicate substantially identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings. The headings provided herein are for convenience only and do not necessarily affect the scope or meaning of the claims.

As described herein, wear-out of an IC device refers to a degradation phenomenon of any component or subcomponent of the IC device caused by usage or environmental factors. As disclosed herein, wear-out monitor devices according to embodiments can monitor wear-out of core circuitry, with or without a power supply, and are capable of monitoring a relatively large range of physical conditions. In addition, wear-out monitors according to embodiments disclosed herein can be integrated, e.g., monolithically integrated, in the same substrate as a core circuit of an IC. The wear-out monitor devices according to embodiments utilize diffusion of a diffusant within or in a diffusion region to record an indication of wear-out of a core device. That is, embodiments utilize atomic diffusion of certain diffusing atoms, also referred to herein as monitor atoms, in a diffusion region, also referred to herein as monitor region, which can be, e.g. a region in a semiconductor substrate, e.g., a silicon substrate, to monitor, record, and store electrical signatures associated with wear-out mechanisms (e.g., temperature, voltage, current, or any combination thereof) over a lifetime of the product. The monitor atoms can be integrated as part of a wear-out monitor device, where the net movement of monitor atoms caused by wear-out stresses, e.g., from a reservoir to a diffusion region in communication with the reservoir, alters the an electrical signature of the wear-out monitor device. The electrical signature can be monitored at any point during the lifetime of the product to quantify the degree of wear-out of core devices in the IC. Since the movement of the monitor atoms can occur without a separate power supply, the wear-out monitor device can be considered to be "passive."

Embodiments of this disclosure can provide many advantages. For example, electrical signatures associated with the wear-out state of an IC device over its lifetime can be recorded without a power supply because the effective "power supply" for the monitor device is provided by the concentration gradient of the dopant concentration, which provides the driving force for the diffusion of monitor atoms. Alternatively or additionally, the movement of the monitor atoms, which can be irreversible, provides a method to "record" cumulative stress(es) the product has been exposed to over a period of time. Alternatively or additionally, because a diffusion mechanism can work over a wide range of conditions beyond the service temperatures of ordinary sensors and their supporting circuitry, the disclosed wear-out monitor devices can provide signatures of cumulative stresses at relatively extreme conditions. Alternatively or additionally, the choice of suitable monitor atoms as the diffusing species can advantageously be made in conjunction with the choice of a suitable device geometry to monitor different wear-out effects at different conditions, e.g., under different temperature and electric field ranges for different periods of time. In certain embodiments, a reference device can be used to provide a reference "initial condition" against which a quantitative monitoring of the time evolution of the monitor atoms can be made, as well as to differentiate drift and noise to enhance the accuracy of the wear-out monitor devices. For example, the wear-out monitor device can have monitor atoms (disclosed infra) that diffuse substantially in the substrate in addition to a "traditional" dopant (e.g., p-type dopants B and n-type dopants P and As in silicon) that does not diffuse substantially in the semiconductor substrate, while the reference device can omit the monitor atoms, such that the reference device provides a semi-permanent "initial condition" that can be provided as the concentration profile of the monitor atoms evolves under wear-out conditions.

Figure 1:
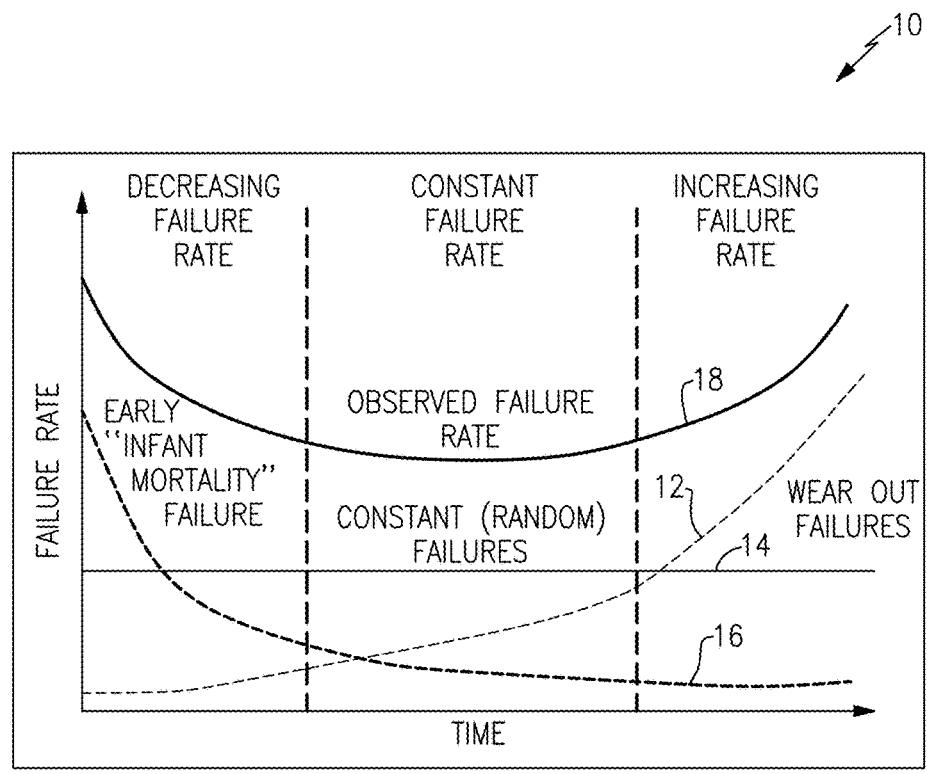
FIG. 1 is a graph illustrating failure rate versus time for a population of integrated circuit devices.

FIG. 1 is a graph 10 schematically illustrating rates (y-axis) of failure of different failure mechanisms versus time (x-axis) for a given population of similarly manufactured IC devices. Wear-out failure mechanisms can generally be categorized into three categories: early "infant mortality" failure, whose failure rate dominates at early stages and decreases over a device service time, represented by the failure rate curve 16; random failure, whose failure rate is relatively independent of the device service time, represented by the failure rate curve 14; and wear-out failure, whose failure rate increases over the device service time, represented by the failure rate curve 12. The observed overall failure rate curve 18, sometimes referred to as a "bathtub curve," can be represented by the sum of the three failure rate curves 12, 14 and 16, and can be described as having three regions: a decreasing failure rate region, followed by a relative constant failure rate region, followed by an increasing failure rate region.

As wafer fab geometries/structures continue to shrink in feature size (e.g., critical lithography dimensions), it has been observed that the relative duration of the constant failure region decreases, and that the increasing failure region dominated by wear out failures is reached at an increasingly service time. Based on this observation, with decreasing feature size, there is an increasing need to be able to identify components, subcomponents or structures within a semiconductor die that are may be in the wear-out failure phase and to flag them sufficiently early such that appropriate action can be taken before catastrophic failure occurs. There is also an increasing need to be able to real-time monitor the actual mission profile/operating conditions of IC devices in the field (as opposed to supposed/theoretical), and where deviations occur, to be able to flag such that appropriate actions can be taken.

IC Apparatuses Comprising Wear-Out Monitor Devices

Figure 2A:
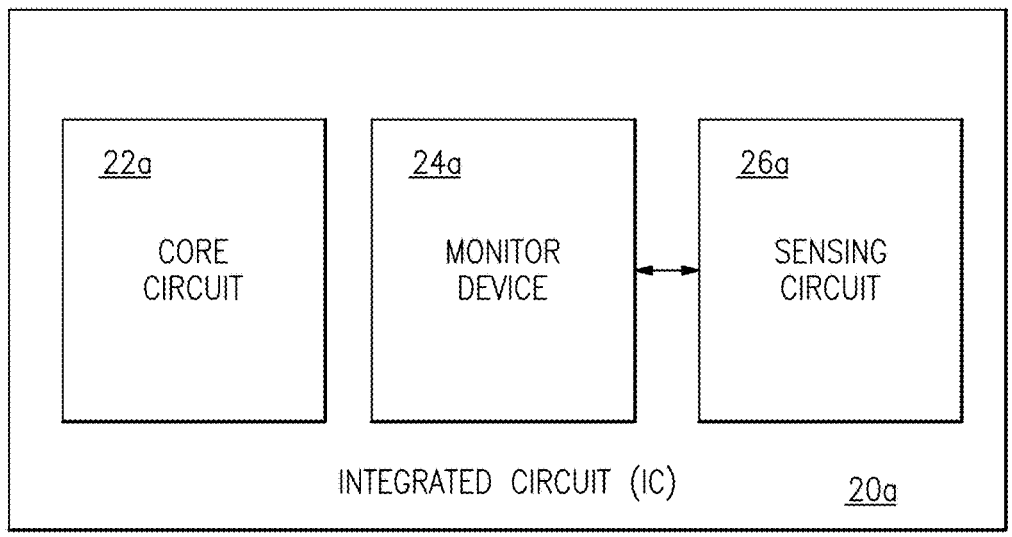
FIG. 2A illustrates an integrated circuit apparatus comprising an on-chip wear-out monitor device, according to embodiments.
Figure 2B:
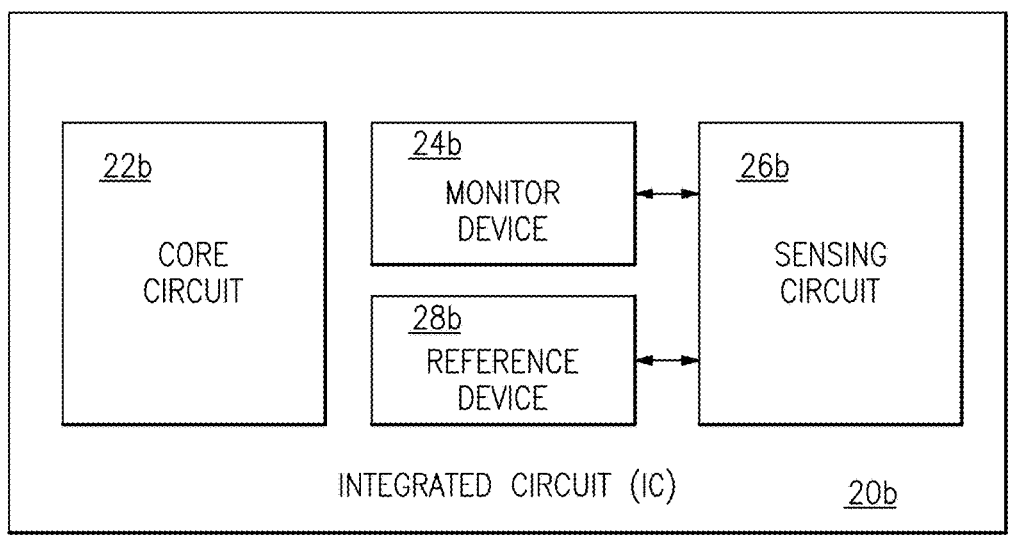
FIG. 2B illustrates an integrated circuit apparatus comprising an on-chip wear-out monitor device and a reference device, according to embodiments.

FIGS. 2A and 2B illustrate integrated circuit (IC) apparatuses 20a and 20b each comprising a wear-out monitor device 24a/24b, e.g., an on-chip wear-out monitor device, according to various embodiments. Each of the IC apparatuses 20a and 20b has a core circuit 22a/22b and a wear-out monitor device 24a/24b for monitoring various types of cumulative stresses (e.g., temperature, voltage, current, etc. or any combination thereof). In various embodiments, the wear-out monitor device 24a/24b is configured to adjust an indication of wear out of the core circuit 22a/22b regardless of whether the core circuit is activated. In some embodiments, the core circuit 22a/22b and the wear-out monitor device 24a/24b are formed in a common semiconductor substrate of the IC apparatuses 20a and 20b, such that they can be subject to common wear-out stresses. In some embodiments, the core circuit 22a/22b and the wear-out monitor device 24a/24b are electrically separated from each other while being formed in a common semiconductor substrate of the IC apparatuses 20a and 20b, such that they can be subject to common wear-out stresses. For example, for monitoring thermal wear-out, the core-circuit 22a/22b and the monitor device 24a/24b formed in a common substrate can be in thermal communication with each other. For monitoring electrical wear-out, the core-circuit 22a/22b and the monitor device 24a/24b formed in a common substrate can be electrically connected with each other in close proximity and fabricated using similar processes. For monitoring mechanical wear-out, the core-circuit 22a/22b and the monitor device 24a/24b formed in a common substrate can be subjected to similar mechanical stress, e.g., elongation, bending, thermal expansion, etc. As a result, cumulative physical stresses experienced by the monitor device 24a/24b are representative of the cumulative physical stresses experienced by the core circuit 22a/22b. Each of the IC apparatuses 20a and 20b includes a sensing circuit 26a/26b coupled to the wear-out monitor device 24a/24b. Unlike the IC apparatus 20a of FIG. 2A, the IC apparatus 20b of FIG. 2B additionally has a reference device 28b electrically connected to the sensing circuit 26b for quantitative determination of the wear-out state of devices in the core circuit 22b.

As described herein and throughout the specification, it will be appreciated that the semiconductor substrates in which IC apparatuses are fabricated can be implemented in a variety of ways, including, but not limited to, a doped semiconductor substrate, which can be formed of an elemental Group IV material (e.g., Si, Ge, C or Sn) or an alloy formed of Group IV materials (e.g., SiGe, SiGeC, SiC, SiSn, SiSnC, GeSn, etc.); Group III-V compound semiconductor materials (e.g., GaAs, GaN, InAs, etc.) or an alloy formed of Group III-V materials; Group II-VI semiconductor materials (CdSe, CdS, ZnSe, etc.) or an alloy formed of Group II-VI materials. The semiconductor substrate can be formed of high temperature materials such as SiC for applications where monitoring temperature is expected to exceed about 500° C.

According to certain embodiments, the substrate can be implemented as a semiconductor on insulator, such as silicon on insulator (SOI) substrate. An SOI substrate typically includes a silicon-insulator-silicon structure in which the various structures described above are isolated from a support substrate using an insulator layer such as a buried $SiO_2$ layer. In addition, it will be appreciated that the various structures described herein can be at least partially formed in an epitaxial layer formed at or near a surface region.

Wear-Out Monitor Device Structures

FIGS. 3A and 3B illustrate a wear-out monitor device 30a/30b having monitor atoms whose rate of diffusion changes in response to a stress condition, according to embodiments. The wear-out monitor device 30a represents an initial monitor device prior to being subjected to a wear-out stress, e.g., a thermal stress, and the wear-out monitor device 30b represents the monitor device after being subjected to the wear-out stress. The wear-out monitor device 30a/30b comprises a semiconductor material 32a/32b, e.g., a semiconductor substrate that is doped with dopant of first type, e.g., a donor-type dopant to a concentration $N_d$, and monitor atoms 34a, e.g., an acceptor-type dopant to a concentration $N_a$. The monitor atoms 34a are configured to diffuse in or into the semiconductor material 32a under a wear-out stress, and the rate at which the monitor atoms 34a diffuse change according to the level of the wear-out stress.

Referring to FIG. 3A, an initial schematic concentration profile 36a through a section AA' of the initial wear-out monitor device structure 30a shows a relatively abrupt concentration profile of the monitor atoms $N_a$ in the vertical direction (x). Referring to FIG. 3B, after the initial wear-out device structure 30a (FIG. 3A) is subjected to a wear-out stress, e.g., a thermal wear-out stress, the monitor atoms 34a diffuse into the semiconductor material 32a, resulting in post-stress wear-out monitor device structure 30b (FIG. 3B), in which the monitor atoms 34b has diffused into the semiconductor material 32b. The resulting schematic concentration profile 36b through a section BB' of the post-stress wear-out monitor device structure 30b shows a relatively diffused concentration profile of $N_a$ in the vertical direction (x). As described infra, the change in concentration profile of monitor atoms $N_a$ can be electrically detected using various methods. Such change, which results from the cumulative wear-out stress on the wear-out monitor device 30a, can induce a corresponding change in electrical properties of the monitor device structure 30a/30b, from which the wear-out level of the core circuit 22a/22b (FIGS. 2A/2B) can be determined.

Of course, in FIGS. 3A and 3B and throughout the specification, it will be appreciated that while monitor atoms 34a may be represented as acceptor-type dopants, the embodiments are not so limited. The monitor atoms can be donor-type dopants, or not be dopants at all, but rather impurities. Furthermore, monitor atoms 34a may be present in addition to dopants, which may be acceptor-type or donor-type dopants.

It will further be appreciated in FIGS. 3A/3B and throughout the specification that monitor atoms 34a may include one or more chemical elements.

FIG. 4A illustrates a wear-out monitor device 40 according to embodiments. The wear-out monitor device 40 comprises a semiconductor substrate 42 doped with a dopant of a first type, e.g., a donor, to a concentration of $N_d$, and monitor atoms 44 having a concentration $N_a$. A schematic initial concentration profile 46a through a section CC' shows a relatively abrupt concentration profile of $N_a$ in a vertical direction (x), while a schematic post-stress concentration profile 46b through the section CC' shows a relatively diffused concentration profile of $N_a$ in the vertical direction (x). In the particular illustrated embodiment, the simulated monitor atoms 44 are phosphorus atoms diffusing in silicon at 125° C.

FIG. 4B is a graph 48 of calculated concentration profiles of monitor atoms 44 of the monitor device 40 of FIG. 4A, according to embodiments. In the illustrated embodiment, the calculated concentrations are those of phosphorus (P) atoms in silicon after diffusing for various times ranging from $10^4$ years to $10^7$ years, in which the x-axis represents the x-axes of schematic concentration profiles 46a and 46b of FIG. 4A, and in which the origin corresponds to the initial interface between the $N_d$ profile and the $N_a$ profile of the concentration profile 46a. As the graph 48 illustrates, because of relatively low diffusion rate of P in Si at 125° C., appreciable diffusion as measured by, e.g., a diffusion length at which the concentration has fallen to about 1% of an initial concentration, is less than 0.1 nm after 10,000 years. That is, based on the calculation, under some circumstances, e.g., ideal conditions, phosphorus may not be monitor atoms for monitoring changes in the rate of diffusion under thermal wear-out stress.

As illustrated by FIGS. 4A/4B, it will be appreciated that selecting appropriate monitor atoms for a given diffusing medium, e.g., semiconductor substrate, can be important for effective wear-out monitor devices. Diffusivity can be expressed as:

$$D(T) = D_0 \exp\left[\frac{E_a}{kT}\right]. \quad \text{Eq. [1]}$$

Inventors have found that selecting a monitor atom/diffusing medium combination to have the diffusion activation energy (Ea) in a certain range, is desirable. For example, the diffusivity of phosphorus in silicon is activated by an activation energy of 3.66 eV, which results in a wear-out monitor device that may impractical for use as a thermal stress monitor under ideal circumstances, as described above. For illustrative purposes and without being bound to any theory or accuracy of the parameters, diffusivities of selected atoms in silicon are as listed in TABLE 1:

TABLE 1

Diffusivity of Selected Atoms and Molecules in Crystalline Si

| Element | Diffusivity, D(T) (cm²/sec) | Diffusion Activation Energy (eV) |
|---------|------------------------------|----------------------------------|
| B  | $0.76 \times 10^{-4} \exp(-3.46/kT)$ | 3.46 |
| P  | $3.85 \times 10^{-4} \exp(-3.66/kT)$ | 3.66 |
| Sb | $0.214 \times 10^{-4} \exp(-3.65/kT)$ | 3.65 |
| Al | $0.5 \times 10^{-4} \exp(-3.0/kT)$ | 3.0 |
| Co | $(9.2 \times 10^{-4}) \exp(-2.8/kT)$ | 2.8 |
| Pt | $(1.5 \times 10^{2}) \exp(-2.22/kT)$ | 2.22 |
| S  | $(0.92) \exp(-2.2/kT)$ | 2.2 |
| Ni | $(0.1) \exp(-1.9/kT)$ | 1.9 |
| Ag | $(2.0 \times 10^{-3}) \exp(-1.6/kT)$ | 1.6 |
| Zn | $(0.1) \exp(-1.4/kT)$ | 1.4 |
| Au | $(1.1 \times 10^{-3}) \exp(-1.12/kT)$ | 1.12 |
| Cr | $(0.01) \exp(-1.0/kT)$ | 1.0 |
| Cu | $(4.0 \times 10^{-3}) \exp(-1.0/kT)$ | 1.0 |
| Fe | $(6.2 \times 10^{-3}) \exp(-0.87/kT)$ | 0.87 |
| Na | $(1.6 \times 10^{-3}) \exp(-0.76/kT)$ | 0.76 |
| K  | $(1.1 \times 10^{-3}) \exp(-0.76/kT)$ | 0.76 |
| $H_2$ | $(9.4 \times 10^{-3}) \exp(-0.48/kT)$ | 0.48 |

The inventors have found that the activation energy Ea of diffusivity can be one criteria for choosing the monitor atoms to be used in the wear-out monitor devices according to embodiments. In some embodiments, the monitor atoms have a diffusion activation energy in the semiconductor substrate that is between about 0.5 eV and about 3.5 eV, between about 0.75 eV and about 2.5 eV, or between about 1.0 eV and about 1.6 eV, depending on the anticipated thermal and/or electrical wear-out stresses. Based on TABLE 1 above, suitable atoms can include Al, Co, Pt, S, Ni, Ag, Zn, Au, Cr, Cu, Fe, Na and K, to name a few. Moreover, suitable monitor atoms can include two or more elements in certain embodiments. For instance, monitor atoms can include two or more of the following elements: Al, Co, Pt, S, Ni, Ag, Zn, Au, Cr, Cu, Fe, Na or K.

Figure 5A:
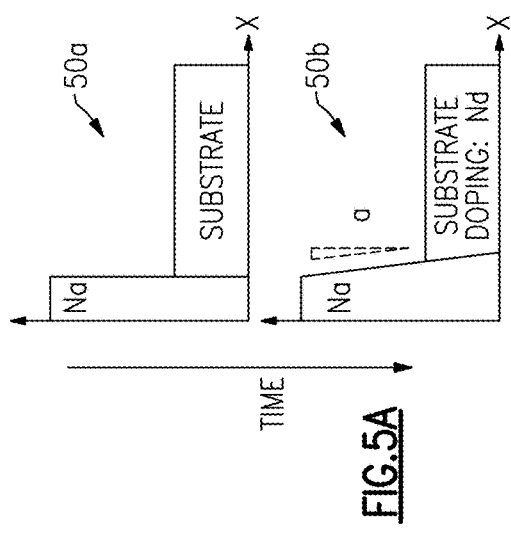
FIG. 5A illustrates a wear-out monitor device having gold as monitor atoms, according to embodiments.
Figure 5B:
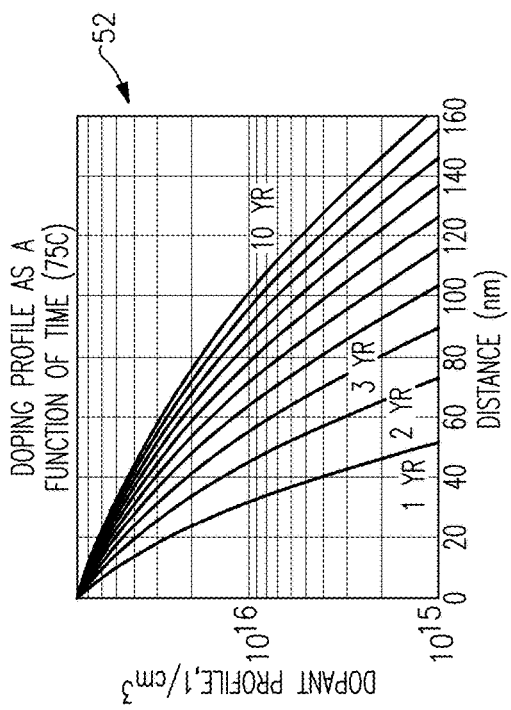
FIGS. 5B-5D are graphs illustrating calculated concentration profiles of gold in silicon substrate of the wear-out monitor device in FIG. 5A, after diffusing at 75° C., 100° C. and 125° C., respectively, for various times.
Figure 5D:
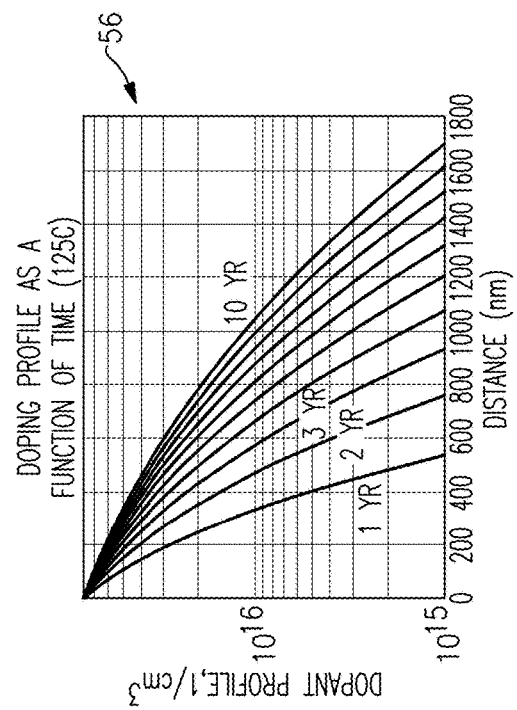
Figure 5C:
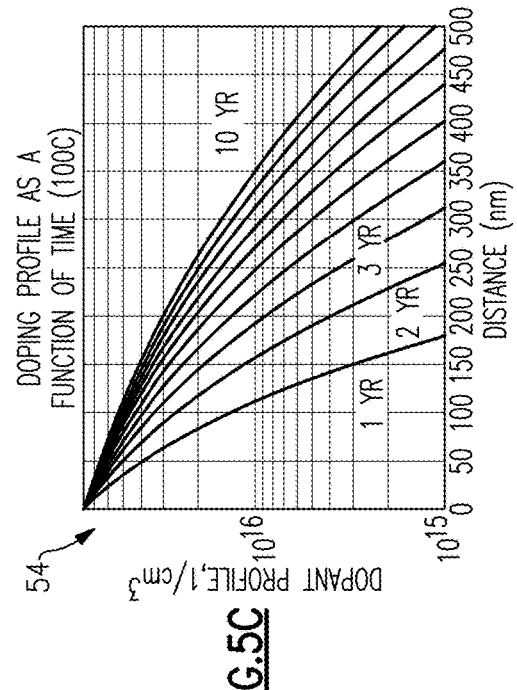

By way of example, FIGS. 5A-5D illustrate time evolution of concentration profiles of gold (Au) in silicon at temperatures of 75° C., 100° C. and 125° C. for durations ranging from 1 year to 10 years. Referring to FIG. 5A, a schematic initial concentration profile 50a and a schematic post-stress concentration profile 50b of a wear-out monitor device structure (not shown) similar to the wear-out monitor device structure 40 of FIG. 4A are illustrated. Unlike the schematic concentration profiles 46a and 46b of FIG. 4A in which the monitor atoms are phosphorus (P) atoms with an activation energy of 3.66 eV, the schematic concentration profiles 50a and 50b represent those in which the monitor atoms are gold (Au) atoms. Referring to FIGS. 5B-5D, graphs 52, 54 and 56 illustrate calculated concentration profiles of gold in silicon at 75° C., 100° C. and 125° C., respectively, after diffusing for various times ranging from 1 year to 10 years, in which the x-axes represents the vertical diffusing direction similar to the x-direction through the section CC' of FIG. 4A, and in which the origin corresponds to the initial interface between the $N_d$ profile and the $N_a$ profile. As the graphs 52, 54 and 56 illustrate, Au has diffusion rate in Si at temperatures of 75° C., 100° C. and 125° C. that are more practical for monitoring changes in rate of diffusion under thermal stress. For example, for Au, a diffusion length at which the concentration has fallen to about 1% of an initial concentration is between about 160 nm and about 1600 nm after about 10 years at 75° C. and 125° C., respectively. That is, based on FIGS. 5B-5D, Au in Si can be a more practical diffusion system for monitoring changes in rate of diffusion under thermal wear-out stress.

Figure 6C:
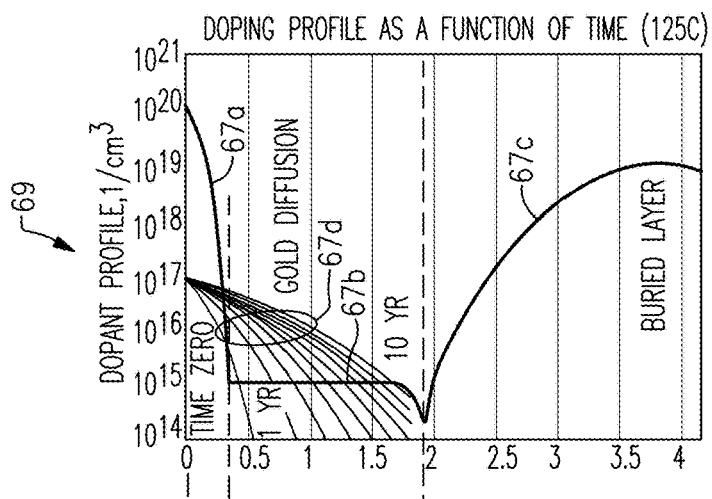
FIG. 6C is a graph illustrating calculated concentration profiles of gold in silicon device substrate of the wear-out monitor device in FIGS. 6A/6B after diffusing at 125° C. for various times.
Figure 6B:
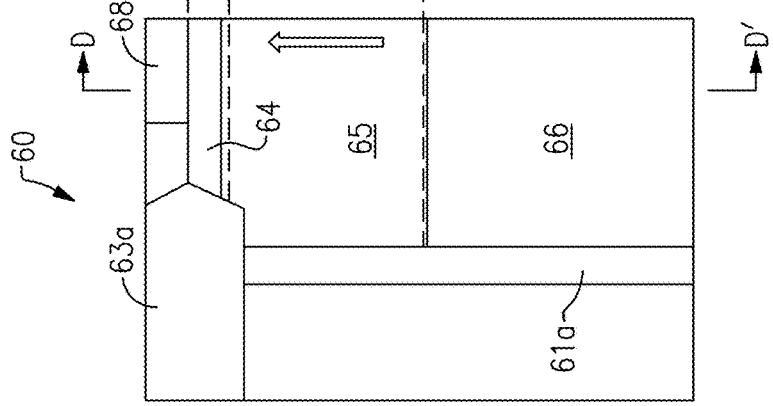
FIG. 6B illustrates a close up view of the boxed region of FIG. 6A.
Figure 6A:
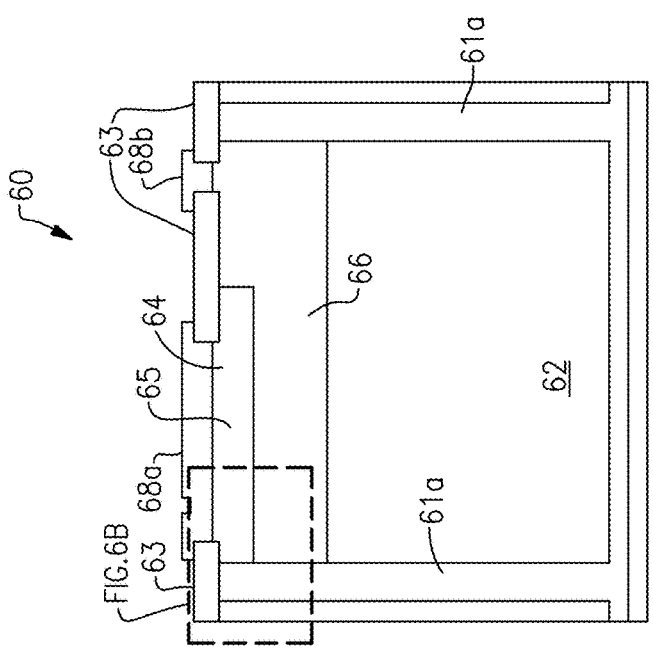
FIG. 6A is an illustration of a wear-out monitor device comprising a semiconductor material and monitor atoms configured to diffuse in the semiconductor material, according to embodiments.

FIG. 6A illustrates a wear-out monitor device 60 having monitor atoms having a diffusion activation energy in the substrate that is between about 0.5 eV and about 3.5 eV, according to embodiments. FIG. 6B is a close up view of the region in the dotted box of FIG. 6A. Similar to IC devices 20A and 20B of FIGS. 2A and 2B, the wear-out monitor device 60 comprises a semiconductor substrate 62 and monitor atoms configured to diffuse therein, wherein the monitor atoms are configured such that a stress condition causes a change in the rate at which the monitor atoms diffuse in the semiconductor substrate 62.

The wear-out monitor device 60 includes a first doped region 64 doped with a first dopant type, which can be n-type or p-type. In the illustrated embodiment of FIGS. 6A/6B, the first doped region 64 is a heavily doped p-doped region, e.g., a heavily doped (p+) region.

The wear-out monitor device 60 additionally includes a second doped region 66 that is doped with a second dopant type opposite to the first dopant type, i.e., p-doped when the first doped region 64 is n-doped, and vice versa. In the illustrated embodiment, the second doped region 66 is an n-doped region, e.g. a heavily doped (n+) region.

In some embodiments, the wear-out monitor device 60 additionally may include an intervening region 65 interposed between the first and second doped regions 64, 66 that is doped either with the first or second dopant types, at a concentration substantially lower than the first or second doped regions 64 or 66. In the illustrated embodiment, the intervening region 65 is a p-doped region. Thus, the wear-out monitor device 60 can include first and second doped regions 64 and 66 and the intervening region 65 configured as a $P^+PN+$ or a structure.

FIG. 6C is a graph showing dopant profiles along the section DD' of FIG. 6B. The profiles 67a and 67c represent p type and n type dopant profiles of the first and second doped regions 64, 66, respectively. In addition, the profile 67b is a p-type dopant profile of the substrate 62.

The doped regions of the wear-out monitor device 60 of FIGS. 6A and 6B are illustrated by way of example only, and other embodiments are possible, where the first and second doped regions 64 and 66 are respectively doped such that the first regions 64 is doped to form any one of $P^+$, P, $P^-$, $N^+$, N or $N^-$ regions, while the second doped region 66 is doped to form any one of $P^+$, P, $P^-$, $N^+$, N or $N^-$ regions that opposite in dopant type to the first doped region 64.

When the intervening region 65 is present between the first and second doped regions 64 and 66, any one of an $N^+NP$ structure, an $N^+N^-P$ or an NIP structure, an $NN^-P$ structure, an NIP structure, a $P^+PN$ structure, $P^+P^-N$ structure, a $P^+IN$ structure, a $PP^-N$ structure, or a PIN structure can be formed.

As described herein and throughout the disclosure, a doped region can generally have a peak dopant concentration between about $1 \times 10^{13}$ cm$^{-3}$ and about $1 \times 10^{22}$ cm$^{-3}$. In addition, heavily doped regions denoted as $N^+$ or $P^+$ regions can have a peak doping concentration exceeding about $1 \times 10^{18}$ cm$^{-3}$ or about $1 \times 10^{19}$ cm$^{-3}$. In addition, lightly doped regions denoted as $N^-$ or $P^-$ regions can have a peak doping concentration lower than about $1 \times 10^{14}$ cm$^{-3}$ or about $1 \times 10^{13}$ cm$^{-3}$.

In the wear-out monitor device 60 of FIG. 6A, the first doped region 64 is formed by implanting dopants, e.g., p-type dopants, through an opening formed in the dielectric layer 63; however, embodiments are not so limited. For example, other masking (e.g., photoresist) and doping (e.g., diffusion) techniques may be used in lieu or in addition to using the dielectric layer 63 as an implantation mask.

Referring back to FIGS. 6A/6B, the wear-out monitor device 60 additionally includes a first electrode 68a and a second electrode 68b contacting the first doped region 64 and the second doped region 66, respectively, through openings in dielectric layer 63. In the illustrated embodiment, the first electrode 68a comprises or is formed of the monitor atoms and serves as a reservoir of the monitor atoms. The first electrode 68a is configured such that, when the wear-out monitor device is subjected to a set of predetermined conditions for a predetermined duration, some of the monitor atoms in the first electrode 68a diffuse into a depletion region formed between the first and second doped regions 64, 66. Depending on the concentration and/or depth of the diffused monitor atoms in the underlying semiconductor material, e.g., in the depletion region, a cumulative wear-out history, e.g., a cumulative thermal wear-out history, of the device 60 can be at least indirectly determined.

By way of example, FIG. 6C is a graph 69 illustrating calculated concentration profiles of gold in a silicon device substrate of the wear-out monitor device in FIGS. 6A/6B, after diffusing at 125° C. for various times. In particular, the concentration profiles 67d illustrate predicted concentration profiles of gold after diffusing for 1-10 years in at 125° C. By obtaining information regarding the depth and/or concentration of dopants in a depletion region, and using the known diffusivity equations such as those in TABLE 1, a cumulative thermal history, or thermal wear-out level, can be obtained.

It will be appreciated that, according to embodiments, the concentrations of dopants and the dimensions/configurations of the first doped region 64, the second doped region 66 and the intervening region 65 are selected such that desired device attributes are obtained. For example, in the illustrated embodiment, because the intervening region 65 is doped to a lower concentration compared to the second doped region 66, a relatively larger depletion region is formed therein. When the monitor atoms diffuse into the depletion region, various electrical properties of the depletion region can be made to determine, qualitatively and/or quantitatively, the relative concentration the monitor atoms in the depletion region, as discussed more in detail infra. Thus, the depletion can serve as a monitor region for quantifying the amount of monitor atoms that may have diffused, from which a cumulative thermal history can be determined.

Thus, as configured, the wear-out monitor device 60 of FIG. 6A/6B has a reservoir of monitor atoms (e.g., first electrode 68a) disposed on a surface of the substrate and a monitor region (e.g., depletion region in the intervening layer 65) formed in the substrate. The monitor atoms have diffusion characteristics in the semiconductor material of the substrate such that when the wear-out monitor device is subjected to a set of predetermined stress conditions for a predetermined duration, some of the monitor atoms diffuse into the monitor region. The reservoir can include, e.g., an electrode containing the monitor atoms or a layer formed of the monitor atoms. The monitor region can include a region in the substrate, e.g., a depletion region formed by a PN junction as described above, for example.

Various embodiments of the wear-out monitor device including the wear-out monitor device 60 of FIGS. 6A/6B, are configured such that a change in a property, e.g., an electrical property, or an electrical signature, associated with the presence of the monitor atoms in the monitor region can be measured. The electrical signature can be, for example, any one or more of: junction leakage, junction capacitance, junction built-in potential, junction reverse recovery time, bipolar base transit time (fT), metal-oxide-semiconductor (MOS) transistor threshold voltage, MOS transistor sub-threshold swing, MOS channel leakage, punch-through breakdown voltage (BV) and impact ionization breakdown voltage (BV), to name a few. Properties other than electrical properties or signatures associated with the presence of the monitor atoms in the monitor region can alternatively or additionally be measured to determine wear out of a device. For example, changes in a magnetic property, an optical property, and/or one or more other physical properties can be detected. Furthermore, the changes in one or more physical properties can be monitored on-chip and/or off-chip, e.g., in a post-mortem failure analysis.

The set of predetermined stress conditions and a predetermined duration, which causes some of the monitor atoms to diffuse into the monitor region can include, e.g., a temperature range between about 20° C. and about 250° C., between about 50° C. and about 200° C. or between about 75° C. and about 125° C.; an electric field, e.g., between 0.01 MV/cm and about 1000 MV/cm, between about 0.1 MV/cm and about 100 MV/cm, or between about 1 MV/cm and about 10 MV/cm; and a time duration, e.g., between about 1 day and about 1000 years, between about 1 month and about 100 years, or between about 1 year and 10 years. In some embodiments, the wear-out monitor device can be configured such that a distance between the surface on which the monitor atoms are disposed and the monitor region can be any distance that is calculated to be a diffusion length, e.g., a distance at which the concentration decreases to about 1/e of the peak surface concentration, based on a combination of the predetermined conditions and the predetermined time duration.

Referring back to FIG. 2B, in some embodiments, some IC devices comprise a monitoring device and a reference device on the same semiconductor substrate. FIGS. 7A and 7B illustrate a wear-out monitor device 60 and a reference device 70 according to such embodiments. The wear-out monitor device 60 of FIG. 7A is similar or substantially identical to the wear-out monitor device 60 of FIGS. 6A/6B, except for relative positions of the first electrode 68a and first doped region 66 relative to the second electrode 68b, whose alterations do not alter the operation of the wear-out monitor device 60, and therefore a detailed description of the wear-out monitor device 60 is omitted herein. The reference device 70 of FIG. 7B is similar or substantially identical to the wear-out monitor device 60 of FIG. 7A, except for the electrodes.

The reference device 70 includes first and second doped regions 64, 66 that form a second PN junction, similar to the PN junction of the wear-out monitor device 60 described above with respect to FIGS. 6A/6B. The first electrode 78a of the reference device 70 may be formed of a material that has different diffusion property than monitor atoms of the first electrode 68a of FIG. 7A. Wear-out levels of a monitored device in an IC can be determined using the difference in diffusion properties between the monitor atoms and the electrode material of the first electrode 78a. Once fabricated, atoms of the first electrode 78a of the reference device 70 do not diffuse substantially into the underlying semiconductor material under the conditions in which monitor atoms diffuse in the monitor device 60 of FIG. 7A. For example, the first electrode 78a of the reference device 70 can be formed of heavily doped poly silicon, tungsten, W, TiN, WN, TaN, TaCN, NiSi, WSi, etc., to name a few. That is, when the IC device including both the wear-out monitor device 60 and the reference device 70 is subjected to a wear-out stress, the monitor atoms of the wear-out monitor device 60 have sufficient diffusion length such that they diffuse into the underlying semiconductor material, e.g., into the depletion region formed in the PN junction. In contrast, the atoms of the first electrode 78a of the reference device 70 have a diffusion length that is negligible (e.g., less than a few angstroms), such that the underlying semiconductor material is essentially free of the atoms of the first electrode 78a after the IC device is subjected to the wear-out stress.

Thus, in the illustrated embodiment of FIGS. 7A and 7B, the IC device has integrated therein the reference device 70 and the wear-out monitor device 60 that are similar, e.g., essentially identical, except for the materials of the respective first electrodes 78a, 68a. For example, each of the wear-out monitor device 60 and the reference device 70 includes a PN junction such as a $P^+PN^+$ junction or an $N^+NP^+$ junction, in which a junction having formed therein a depletion region, from which electrical signals associated with monitor atoms diffused thereto can be detected using various techniques, e.g. reverse bias leakage. However, other embodiments are possible. For example, the materials of the respective second electrodes 78b, 68b may be different instead of or in addition to the respective first electrodes 78a, 68a. For example, the second electrode 78b may contain the monitor atoms instead of or in addition to the first electrode 78a.

As described above with respect to embodiments of FIGS. 2A and 2B, the monitor atoms, while being configured to diffuse into the underlying semiconductor material, may also be integrated in the same substrate of an IC that also has a core circuit and/or a reference device, according to some embodiments. However, without proper precaution, the monitor atoms can undesirably diffuse from the wear-out monitor device to other parts of the IC, such as to the core circuit and/or to the reference device. In addition, some monitor atoms may diffuse faster than their expected velocities based on bulk diffusivities, due to the presence of crystal imperfections such as grain boundaries, dislocations or interfaces. However, many monitor atoms are known to severely degrade semiconductor devices. For example, many metals that may be good candidates for monitor atoms, e.g., gold and copper, are known to form what are known as mid-gap or deep level traps in silicon. Mid-gap centers or deep level traps occupy energy states near the middle of the band gap of the semiconductor material. In operation, when excess minority carriers, e.g., electrons in a p-type semiconductor region or holes in an n-type semiconductor region, are created in a semiconductor device in the core circuit, the mid-gap centers created by the unintended presence of monitor atoms can detrimentally affect the device performance by, among other things, degrading minority carrier lifetimes and increasing leakage. In addition, the presence of monitor atoms in the reference device may defeat its purpose as a reference device. Thus, in various embodiments, it may be desirable to block the diffusion of the monitor atoms such that they do not detrimentally affect semiconductor devices outside of the wear-out monitor device.

Referring to 6A/6B and 7A/7B, to limit undesirable diffusion of monitor atoms from the wear-out monitor devices to other parts of the IC device, each of the wear-out monitor device 60 and the reference device 70 may have, laterally on one or both sides, isolation regions 61a, e.g., shallow trench isolation regions. In addition, each of the wear-out monitor device 60 and the reference device 70 may have a buried isolation region 61b, e.g., a buried oxide (BOX) of a silicon-on-insulator (SOI), laterally extending between adjacent isolation regions 61a such that an isolation tub formed of the isolation regions 61a and 61b encloses the first and second doped regions 64 and 66 and the intervening region 65. The isolation tub is configured to prevent unintended lateral and vertical diffusion of monitor atoms from the wear-out monitor device 60 into other parts of the IC device, including, e.g., the reference device 70 and/or devices in the core circuitry (not shown for clarity, see FIGS. 2A/2B) formed in the same substrate.

As described above with respect to FIGS. 2A and 2B, the IC devices according to embodiments include a sensing circuit for sensing an electrical signature associated with atoms of the monitor atoms and determine therefrom a cumulative history of wear-out stresses, e.g., thermal or electrical wear-out stresses, that the IC device may have been subjected to. For example, for each of the wear-out monitor device 60 and the reference device described with respect to FIGS. 6A/6B and 7A/7B, a reverse bias may be applied between the first electrodes 68a, 78a and the second electrode 68b, 78b, such that a reverse bias leakage can be measured across the PN junction. By comparing the reverse bias currents between the wear-out monitor device 60 and the reference device 70, which may be proportional to the concentration of impurity atoms in the respective depletion regions, a determination of the degree of wear-out of monitored devices in the core circuitry can be determined.

Figure 8:
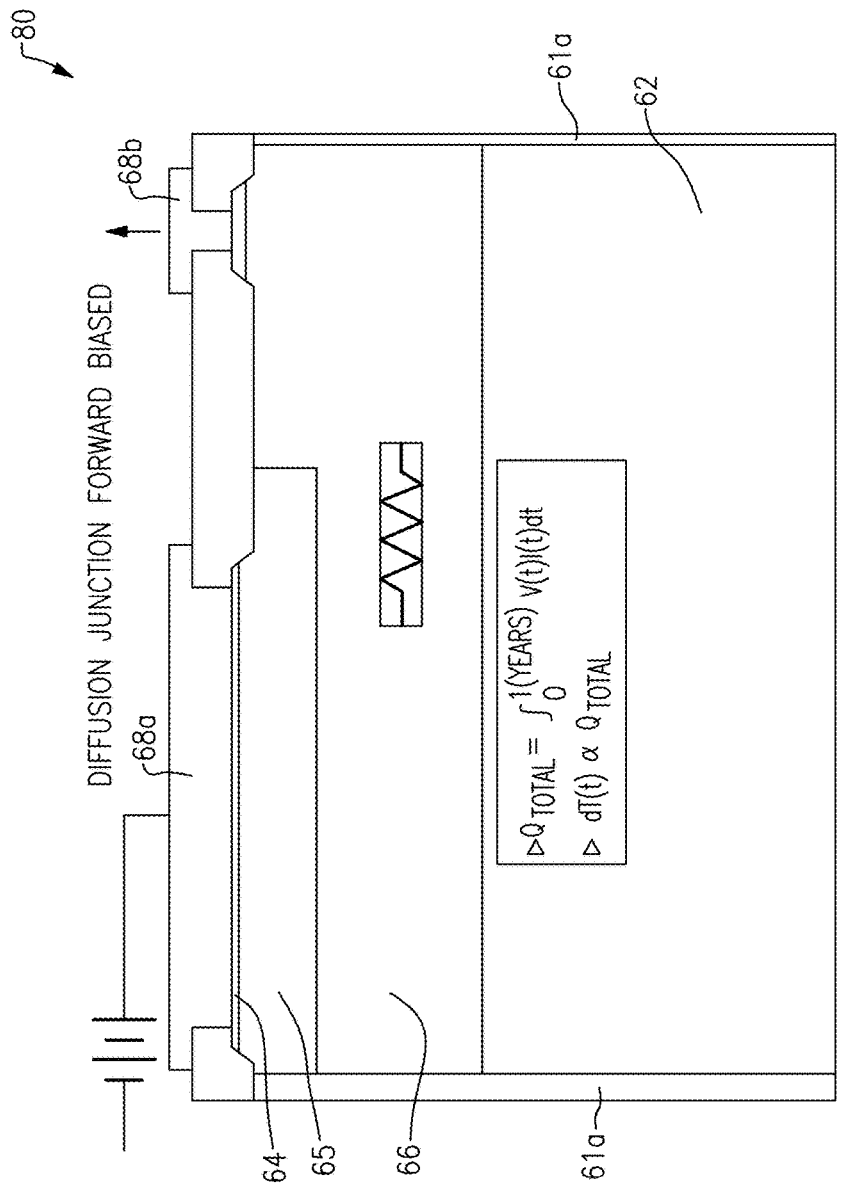
FIG. 8 is an illustration of a wear-out monitor device configured as a current-induced wear-out monitor device, according to embodiments.

Referring to FIG. 8, a wear-out monitor device 80 according to some other embodiments is illustrated. Structural features of the wear-out monitor device 80 are similar to corresponding features of the wear-out monitor device 60 of FIG. 6A/6B, and therefore a detailed description is omitted herein. The wear-out monitor device 80 is configured as a current monitor for monitoring, e.g., the degree of wear-out related to cumulative current passed through a monitored structure in the core circuitry (not shown for clarity, see FIGS. 2A/2B), which may be a similar device in the core circuitry. By placing the monitor structure in electrical series with the monitored structure, for example, the cumulative current passed through the monitored structure can be monitored. In the illustrated embodiment, the current is monitored indirectly by measuring the effect of diffusion rate of the monitor atoms caused by Joule-heating of the wear-out monitor device. In operation, the PN junction of the wear-out monitor device 80 is forward-biased in series with the monitored structure for repeated generation of current-based wear-out stress. In FIG. 8, the region in which Joule-heating occurs is represented as a resistor formed in series with the forward-biased PN junction between a first electrode 68a containing the diffusing material (e.g., Au) and a second electrode 68b. In response to the forward bias, the series resistor of the monitor structure generates the heat which causes the monitor atoms in the first electrode 68a to diffuse into the underlying substrate, e.g., a depletion region formed in the PN junction. While not shown, the IC may include a reference device (not shown for clarity, see FIG. 2B) similar to the reference device 70 of FIG. 7B, which is does not have monitoring atoms. Alternatively, a reference device may be similar or substantially identical to the wear-out monitor device 80 except that it not configured to receive the forward current-based wear-out stress. Subsequently, by comparing reverse bias currents between the wear-out monitor device 80 and the reference device, the wear-out state of the monitored structure can be determined therefrom, in a similar manner as described above.

Figure 9:
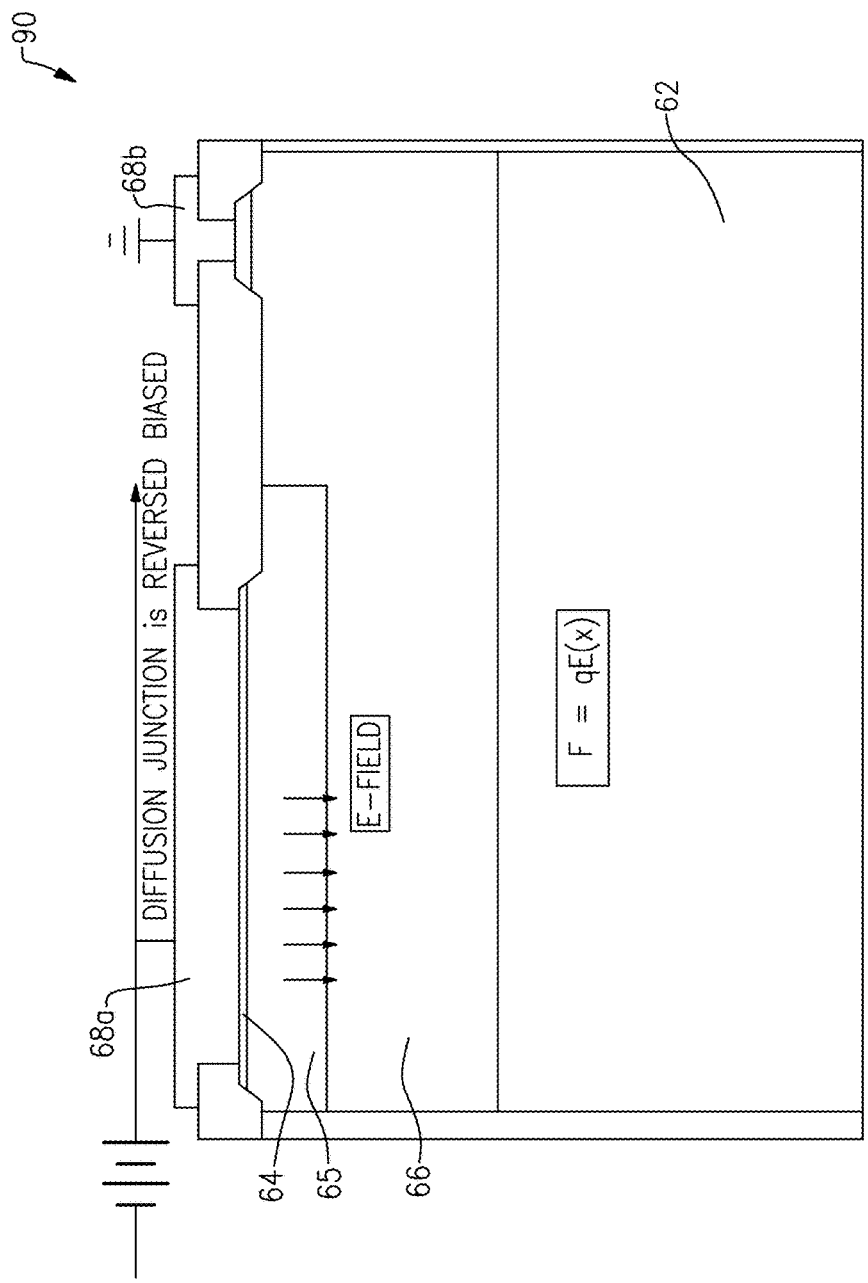
FIG. 9 is an illustration of a wear-out monitor device configured as a voltage-induced wear-out monitor device, according to embodiments.

Referring to FIG. 9, a wear-out monitor device 90 according to some other embodiments is illustrated. The wear-out monitor device 90 is configured as a voltage monitor or electric field monitor for monitoring, e.g., cumulative electric field-based wear-out stress applied to a monitored device in the core circuitry (not shown for clarity, see FIGS.

2A/2B). Structural features of the wear-out monitor device 90 are similar to corresponding features of the wear-out monitor device 60 of FIG. 6A/6B, and therefore a detailed description is omitted herein. The wear-out monitor device 90 is configured to be reverse-biased and electrically connected, e.g., electrically in parallel, with the monitored device to receive repeated electric field-based wear-out stress from electric field generated by the reverse-biased PN junction. In response to the electric field-based wear-out stress, the monitored impurity atoms, e.g., charged impurity atoms, may be caused to diffuse into a monitored region, e.g., the depletion region of the reverse biased PN junction. The IC device may include a reference device (not shown for clarity, see FIGS. 2A/2B) similar to the reference device 70 of FIG. 7B, which does not have monitoring atoms that diffuse. Alternatively, a reference device may be substantially identical to the wear-out monitor device 90 except that it not configured to receive the electric field wear-out stress caused by the reverse biased PN junction. Subsequently, by comparing reverse bias currents between the wear-out monitor device 90 and the reference device, the wear-out state of the monitored structure can be determined therefrom.

Figures 10A, 10B:
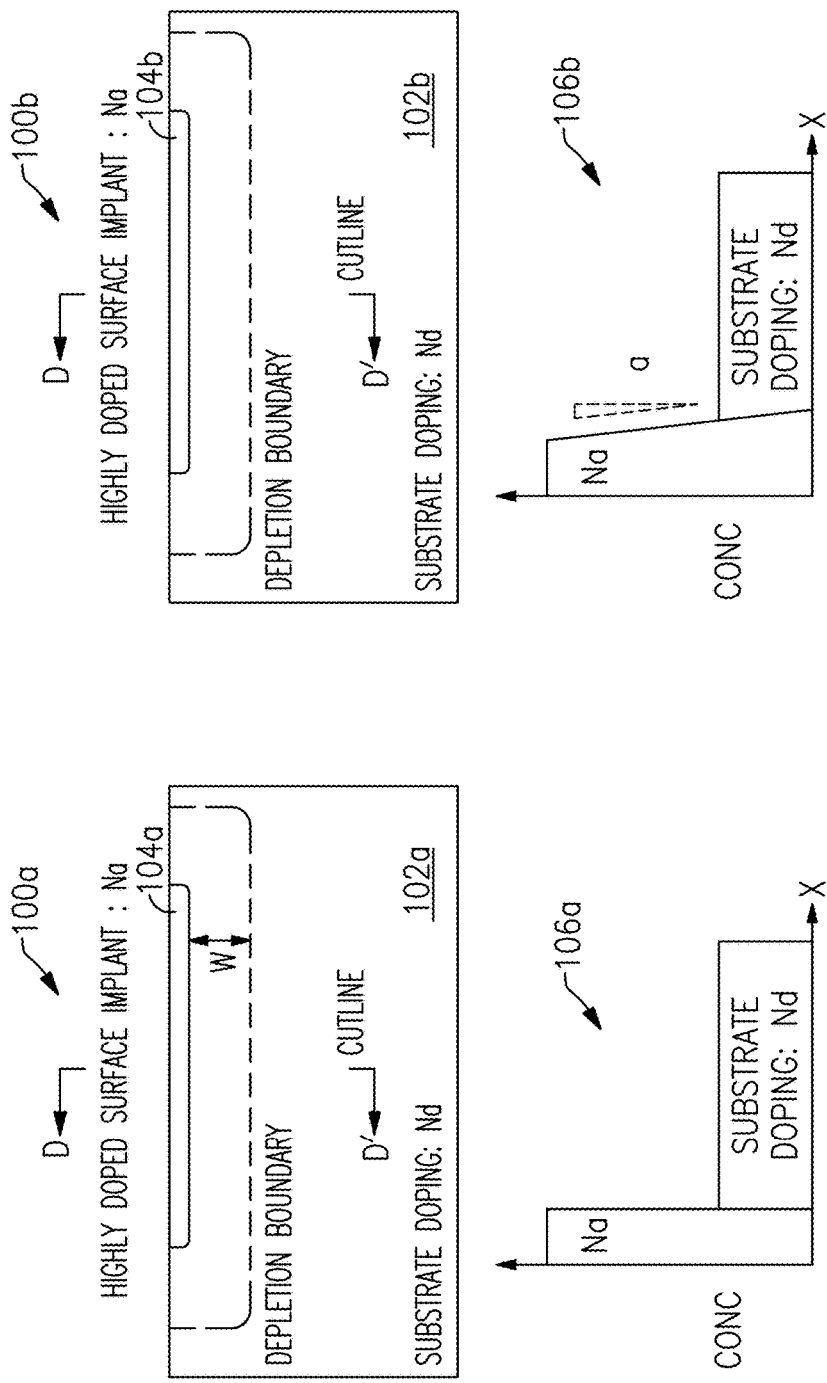
FIGS. 10A and 10B are illustrations of a wear-out monitor device configured as a PN junction wear-out monitor device, according to embodiments.

Referring to FIGS. 10A and 10B, a wear-out monitor device 100a/100b configured for monitoring the wear out level of a PN junction is illustrated. FIGS. 10A and 10B represent the wear-out monitor device prior to (100a) and subsequent to (100b) being subjected to usage-related wear-out stress, e.g., repeated wear-out stress. The wear-out monitor device 100a/100b comprises a first doped region 102a/102b doped with a first dopant type, e.g., a donor, to a concentration $N_d$, and a second doped region 104a/104b doped with a second dopant type, e.g., an acceptor, to a concentration $N_a$. The second doped region 104a/104b comprises monitor atoms, where the monitor atoms are configured to diffuse into the underlying semiconductor material, e.g., into the depletion region of the PN junction. In some embodiments, the monitor atoms may be present in addition to the acceptor atoms having the concentration $N_a$. In other embodiments, the monitor atoms may serve as acceptor atoms such that the acceptor atoms having the concentration $N_a$ may at least in part be the monitor atoms. In other embodiments, the monitor atoms may be present as part of an electrode layer, as described above with respect to FIGS. 6A/6B. As described above, a wear-out stress causes a change in a rate at which the monitor atoms diffuse into the underlying semiconductor material. An initial schematic concentration profile 106a through a section DD' of the initial wear-out monitor device 100a shows a relatively abrupt concentration profile of $N_a$ in a vertical direction (x). The wear-out monitor device 100a may be subjected to a wear-out stress, e.g., thermal wear-out stress as described in FIG. 6A-6C, in forward bias as described in FIG. 8, and/or reverse bias as described in FIG. 9. After being subjected to the wear-out stresses, the schematic concentration profile 106b through a section DD' of the cycled wear-out monitor device 100b shows a relatively diffuse concentration profile of $N_a$ in a vertical direction (x). By comparing the electrical signatures (e.g., reverse bias leakage) associated with the concentration profiles 106a and 106b, the wear-out state of the monitored structure 106b may be determined.

FIGS. 11A and 11B illustrate a wear-out monitor device 110a/110b configured for monitoring punch-through characteristics between adjacent heavily doped regions. As described herein, a punch-through effect refers to a phenomenon in which depletion regions of two separated but adjacent heavily doped regions merge. For example, in a metal-oxide-semiconductor (MOS) transistor, a punch-through effect between a source and a drain causes a rapid increase in channel current with increasing drain-source voltage, which can be undesirable because the voltage at which the punch-through occurs may limit the operating voltage of the IC device. FIGS. 11A and 11B represent the wear-out monitor device prior to (110a) and subsequent to (110b) being subjected to a usage-related wear-out stress. The wear-out monitor device 110a/110b comprises a first heavily doped region 116a/116b, which may be a buried doped region, that is doped with a first dopant type, e.g., a donor, to a concentration $N_d$, and a second heavily doped region 114a/114b doped with a second dopant type, e.g., an acceptor, to a concentration $N_a$. In some embodiments, the monitor atoms may be present in addition to the acceptor atoms having the concentration $N_a$. In other embodiments, the monitor atoms may serve as acceptor atoms, such that the acceptor atoms having the concentration $N_a$ may at least in part be the monitor atoms. In other embodiments, the monitor atoms may be present as part an electrode layer, as described above with respect to FIGS. 6A/6B. After repeated cycling of the monitor structure, e.g., by repeatedly reverse-biasing the first heavily doped region 116a/116b and the second heavily doped region 114a/114b, the effective width between the first heavily doped region 116a/116b and the second heavily doped region 114a/114b reduces from W to W' as illustrated, and the associated electrical signatures (e.g., punch-through voltage) may be used to determine therefrom a wear-out state of a monitored device in the core circuitry.

Figure 12:
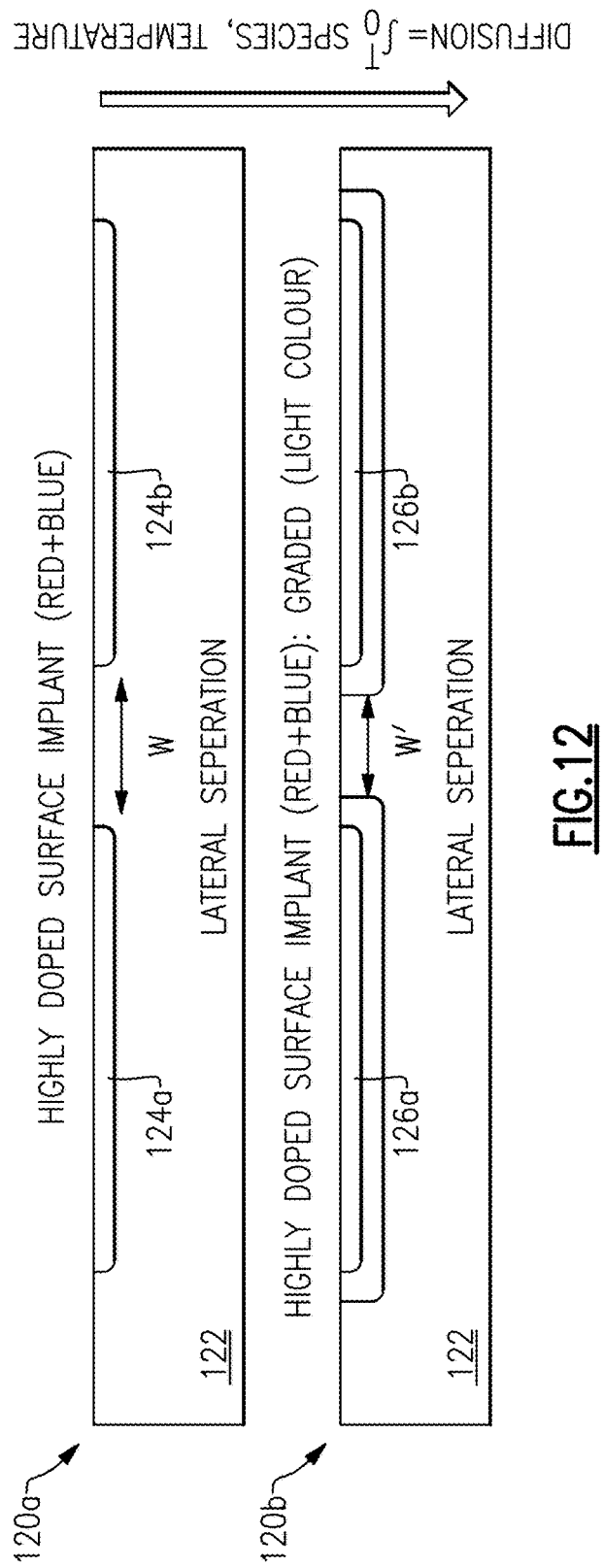
FIG. 12 is an illustration of a wear-out monitor device configured as a lateral punch-through wear-out monitor device, according to embodiments.

Referring to FIG. 12, a wear-out monitor device 120a/120b similar to the wear-out monitor device 110a/110b of FIGS. 11A and 11B and configured for monitoring punch-through characteristics between adjacent heavily doped regions is illustrated. However, in contrast to the wear-out monitor device 110a/110b of FIGS. 11A/11B, a first heavily doped region 124a/126a and a second heavily doped region 124b/126b are laterally separated instead of being vertically separated. Monitor atoms may be present in one or both of the first and second heavily doped regions 124a, 124b in a similar manner as described above with respect to the second heavily doped region 114a/114b of FIGS. 11A and 11B. FIG. 12 represents the wear-out monitor device prior to (120a) and subsequent to (120b) being subjected to the usage-related wear-out stress in an analogous manner as described above with respect to FIGS. 11A and 11B. In an analogous manner as described above with respect to FIGS. 11A and 11B, the effective width between the first heavily doped region 124a/126a and the second heavily doped region 124b/126b reduces from W to W' as illustrated, and the associated electrical signatures (e.g., punch-through voltage) may be used to determine therefrom a wear-out state of a monitored structure.

Figure 13A:
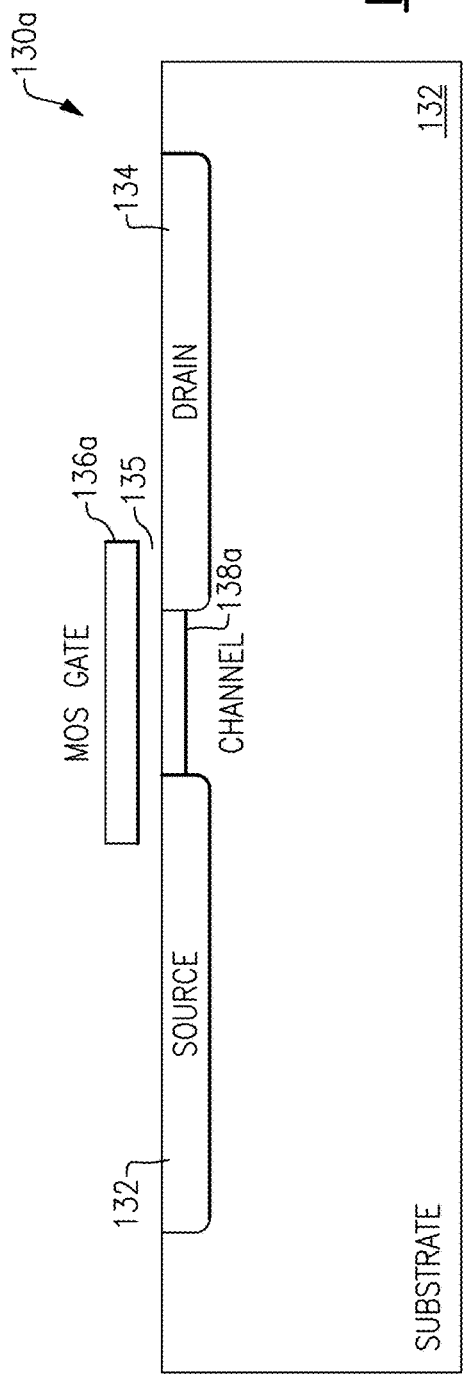
FIGS. 13A and 13B are illustrations of a wear-out monitor device configured as a metal-oxide-silicon (MOS) wear-out monitor device, according to embodiments.
Figure 13B:
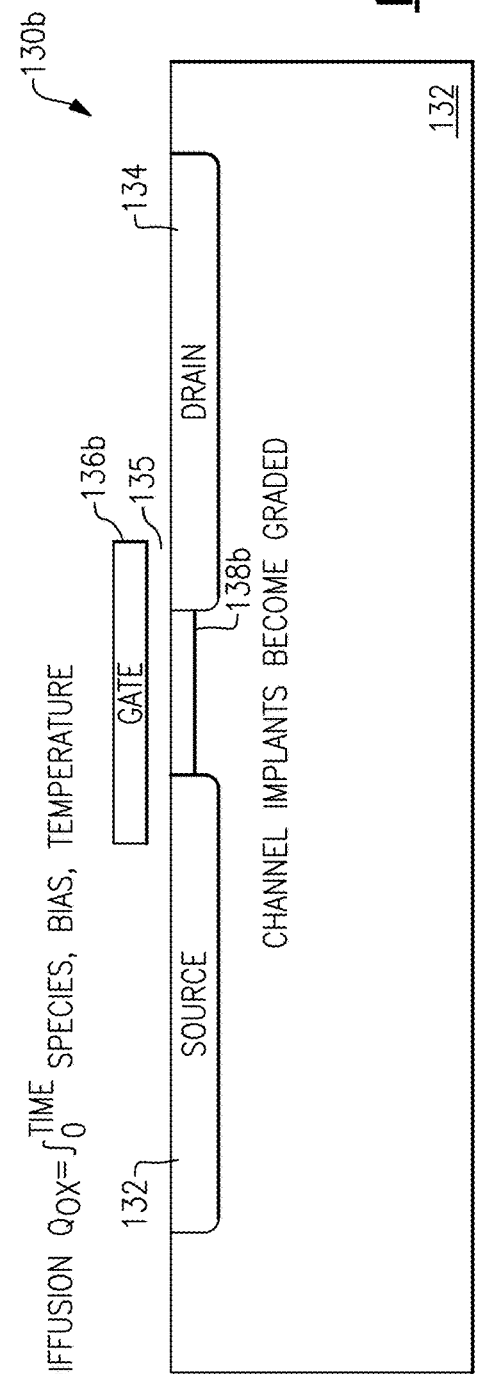

Referring to FIGS. 13A and 13B, a wear-out monitor device 130a/130b configured for monitoring channel degradation of metal-oxide-semiconductor (MOS) transistors is illustrated, according to embodiments. The wear-out monitor device 130a/130b comprises a source 132 and a drain 134 formed in a semiconductor substrate 132. The wear-out monitor device 130a/130b additionally comprises a gate dielectric 135 and a gate 136a/136b. FIGS. 13A and 13B represent the wear-out monitor device prior to (130a) and subsequent to (130b) being subjected to a usage-related wear-out stress. The wear-out monitor device 130a/130b can be used to monitor, e.g., usage-related wear of a monitored device (not shown for clarity, see FIG. 2B), which may be a similarly configured MOS transistor in the core circuit. In the wear-out monitor device 130a/130b, the monitor atoms may be disposed on any one of the source 132, the drain 134 or the gate 136a/136b of the wear-out monitor device 130a/130b configured as a MOS transistor. After subjecting to a wear-stress, e.g., a thermal stress or repeated cycling of the wear-out monitor device 130a/130b in a similar manner as the monitored structure, the level of wear-out of the monitored device may be determined. For example, by comparing the wear-out monitor device 130b that has been subjected to the wear-out stress to a reference device (not shown for clarity, see FIG. 2B), which may be another monitor structure that has not gone through the wear-out stress, the associated electrical signatures may be used to determine therefrom a wear-out state of a monitored structure 130a/130b. For example, the monitor atoms may diffuse into an initial channel region 138a of FIG. 13A to form a diffused channel region 138b of FIG. 13B. Such degradation can be detected, e.g., by measuring transistor parameters such as a current-voltage measurements.

Figure 14A:
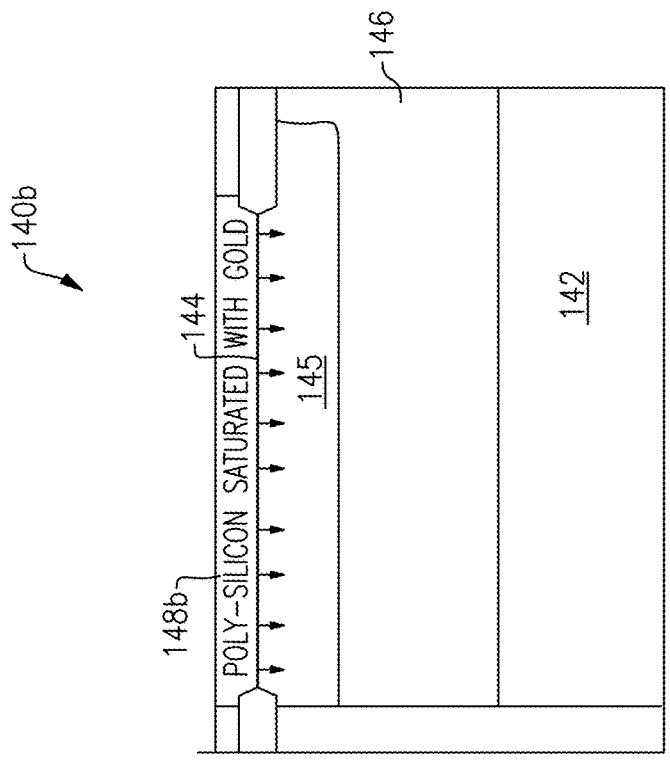
FIGS. 14A and 14B illustrate a method of forming an electrode incorporating monitor atoms for a wear-out monitor device, according to embodiments.
Figure 14B:
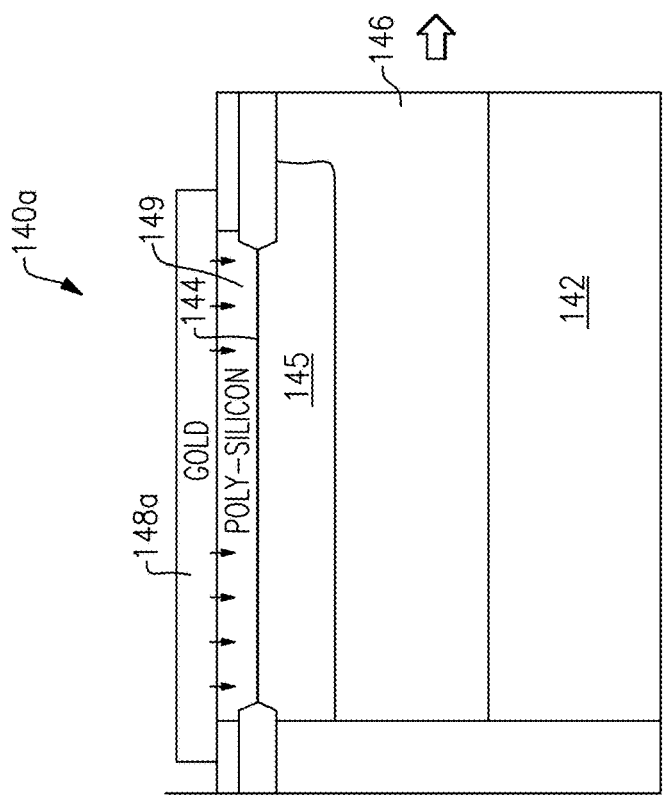

Referring to FIGS. 14A-14B, a method of manufacturing a wear-out monitor device is illustrated, according to some embodiments. In particular, the method relates to forming the reservoir of monitor atoms. It will be appreciated that directly contacting a layer of monitor atoms such as a layer of gold can result in defects, such as poor contact and/or delamination due to poor adhesion. Without being bound to any theory, such defects may be caused by a relatively high interfacial energy between some diffusing material and the semiconductor substrate. In order to create a reservoir of such impurity atoms without such defects, a mixture layer having the diffusing material may be formed, instead of a pure layer of the diffusing material. The mixture may be an alloy layer, a compound, a doped layer or a mechanical mixture, among other forms of mixture.

By way of example, an intermediate monitor structure 140a is shown in FIG. 14A, which includes a substrate 142 in which a first doped region 144 and a second doped region 146 interposed by an intervening region 145 are formed, similar to the monitor structures described above with respect to FIGS. 6A/6B. Unlike FIGS. 6A/6B, instead of forming a layer of monitor atoms, e.g., gold atoms, directly on the surface of the first doped region, an adhesion layer 149, such as a polysilicon layer, may be formed between a layer 148a of monitor atoms and the underlying semiconductor material of the first doped region 144. Subsequently, the intermediate monitor structure 140a may be subjected to a thermal anneal, resulting in a wear-out monitor device 140b having an adhesion layer, e.g., a polysilicon layer, that is impregnated or at least partially saturated with the monitor atoms, e.g., gold. An electrode 148b serving as a reservoir of monitor atoms is thus formed, with improved adhesion properties with the underlying silicon, compared to a pure layer of the monitor atoms. Other embodiments are possible, e.g., a mixture layer of gold and polysilicon can be formed directly on the silicon surface, or another material such as a dielectric material or a chalcogenide material that can hold a relatively high concentration of gold with good adhesion properties can be used as the intervening layer 149. It will be appreciated that the specific combination of the intervening layer and the method of forming can depend on the type and concentration of the specific wear-out diffusing material that is to be used.

Referring to FIGS. 15A-15D, various configurations 150a-150d of a wear-out monitor device including a PN junction are illustrated, according to embodiments. In each of the configurations 150a-150d, a PN junction may be formed in a substrate 152. A first doped region 154a-154d doped with a first dopant type contacts the first electrode 158a-158d serving as reservoirs of monitor atoms, while a second doped region doped with a second dopant type is formed in various configurations. In the configurations 150a-150d, the second doped region is configured as the substrate 152 (FIG. 15A), a well 155b (FIG. 15B) formed in a substrate 152, a buried collector region 156c formed in the substrate 152 (FIG. 15C) and a buried collector region 156d formed in a well 155 formed in the substrate 152 (FIG. 15D). It will be appreciated that dopant concentrations of the first and second doped regions can be varied to tailor the characteristics of the monitor region, e.g., to tailor the dimensions of the depletion region formed therein and/or to tailor the built-in voltage, among other characteristics, as described supra. For example, where a relatively large depletion region is desired, the doped region contacting the reservoir may be doped heavily, while the doped region not contacting the reservoir may be doped relatively lightly.

Referring FIGS. 16A-16D, various configurations of a wear-out monitor device are illustrated, in which the flux or the diffusion rate of monitor atoms diffusing into the underlying substrate are controlled by physically limiting access to the substrate, according to embodiments. Referring to FIG. 16A, the area (represented by the width) of contact between the first electrode 168a serving as the reservoir of monitor atoms and the first doped region 164a may be restricted by restricting the size of the opening through the dielectric mask 163 formed over the substrate, thereby limiting the diffusion of the monitor atoms into the substrate. Referring to FIG. 16B, in addition to restricting the size of the openings through the dielectric mask 163, the number of openings can be further increased or decreased as needed. Referring to FIG. 16C, the area of contact between the first electrode can be further reduced by forming additional diffusion-blocking layers 165, e.g., nitride layers, in the openings formed between or though field oxide regions. Referring to FIGS. 16D-16E, the flux of monitor atoms available for diffusion into the underlying substrate can be further restricted using an adhesion layer 169d-169g under the first electrodes 168a-168d that serve as the reservoir of monitor atoms. The wear-out monitor devices 160d, 160e and 160f of FIGS. 16D, 16E and 16F are substantially identical to the wear-out monitor devices 160a, 160b and 160c of FIGS. 16A, 16B and 16C, respectively, except for the presence of the adhesion layers 169d-169f, which can be formed of, e.g., a polysilicon, and interposed between the respective first electrodes 168a, 168b, and 168c and the respective first doped regions 164a, 164b and 164c. Referring to FIG. 16G, the area of contact between the first electrode 168c and the first doped region 164c can be further reduced by forming spacers 167, e.g., nitride spacers layers, in the openings formed though the additional diffusion-blocking layers 165.

Referring to FIGS. 17A and 17B, wear-out monitor devices 170a and 170b configured as bipolar junction transistors (BJTs) are illustrated, according to embodiments. A first doped region 174 doped with a first dopant type, which is contacted by a first electrode 178a serving as a reservoir of impurity atoms, may be formed at a surface region and configured as an emitter of a BJT. A second doped region 175 doped with a second dopant type opposite the first dopant type, which is contacted by a second electrode 178b, may serve as a base of the BJT. Third doped regions 176a and 176b doped with the first dopant type, which are contacted by the third electrodes 178c, may serve as a collector of the BJT. In FIG. 17A, the collector region is formed of a deep well, while in FIG. 17B, the collector region is formed of a buried collector region. In addition, in FIG. 17B, the buried region doped with the first dopant type can be formed below the well doped with the second dopant type, thereby forming a base/collector junction of the BJT. Thus formed BJT can be configured for monitoring wear-out resulting from various stresses including thermal, current and/or voltage stresses.

Referring to FIGS. 18A-18D, wear-out monitor devices 180a-180d configured as MOS transistors are illustrated, according to embodiments for monitoring wear-out of a monitored structure in a core circuitry (not shown for clarity, see FIGS. 2A/2B), which may be a similarly configured MOS transistor elsewhere on the same substrate, e.g., in the core circuitry. Each of the wear-out monitor devices 180a-180d comprises a source 182 and a drain 184 formed in a semiconductor substrate 182. Each of the wear-out monitor devices 180a-180d additionally comprises a gate dielectric 185 and a gate 186a-186d. Each of the wear-out monitor devices 180a-180d has a different configuration for disposing the reservoir of monitor atoms. For example, the monitor atoms may be disposed as a separate layer 189a, e.g., a polysilicon layer, over a gate 186a (FIG. 18A), as a separate layer 189b (FIG. 18B), e.g., a buried oxide doped with the diffusing material, over a gate 186b, or on one or both of the source 182 and the drain 184, either as a layer 187c of monitor atoms directly on the source/drain 182/184 (FIG. 18C), or as reservoir layers 187d doped with the monitor atoms formed on the source/drain 182/184 (FIG. 18D). When disposed on or as part of the gate 186a/186b, the wear-out monitor devices 180a/180b may be used to monitor various wear-out mechanisms related to degradation in threshold voltage, subthreshold slope, interfacial charge, gate dielectric (e.g., time-dependent dielectric breakdown), off state leakage, on/off ratio, hot channel injection, etc. When disposed on or as part of one or both of the source 182 and the drain 184, the wear-out monitor devices 180c/180d may be used to monitor punch-through, short-channel effect, junction capacitance, etc.

Referring FIG. 19A, a wear-out monitor device 190a configured for sensing impedance as an indicator of the state of wear-out is illustrated, according to embodiments. The wear-out monitor device 190a includes a substrate 198 having formed therein a monitor structure 194a and a reference structure 192 that are commonly connected to a first terminal T1. The reference structure 192 is further connected to a second terminal T2 and has an impurity region 193 doped with monitor atoms. The monitor structure 194a is further connected to a third terminal T3 and has an impurity region 196a doped with the same monitor atoms as the impurity region 193 of the reference structure 192. While the impurity region 193 of the reference structure 192 is enclosed by a diffusion barrier structure 195, no such enclosure exists for the monitor structure 194. In some embodiments, the impurity region 193 and the impurity region 193 have the same or similar concentration profile of monitor atoms. Upon receiving a wear-out stress, e.g., a thermal wear-out stress, the impurity region 196a of the monitor structure 194a would have a lower concentration of the monitor atoms compared to an initial concentration and compared to the impurity region 196a of the monitor structure 194a, due to free diffusion of the monitor atoms in the impurity region 196a compared to limited diffusion of the monitor atoms in the impurity region 193. In contrast, the impurity region 192 of the reference structure 192 would have a relatively unchanged concentration of the impurity atoms. The degree of wear-out of a monitored device in a core circuitry (not shown for clarity, see FIGS. 2A/2B) can be measured based on the resulting changes in impedance measurements, which can resolve relatively small changes in concentration of the monitor impurity atoms at small time scales and/or lower temperatures, thereby making the wear-out monitor device 190a particularly suitable for shelf-life applications. FIG. 19B illustrates a graph 191 schematically illustrating time evolutions of the impedance $Z_a$ of the reference structure 192 measured between T1 and T2 and the varying impedance $Z_b(t)$ of the monitor structure 196a measured between T1 and T3. As illustrated, the Za changes by a relatively small degree after receiving the wear stress, while the $Z_b(t)$ changes by a relatively large degree as illustrated. Based on the time evolution of the $Z_b(t)$, the wear-out state of the monitored device in the core circuitry can be determined.

Referring FIG. 19C, a wear-out monitor device 190c configured for sensing impedance as an indicator of the state of wear-out is illustrated, according to embodiments. The wear-out monitor device 190c is substantially identical to the wear-out monitor device 190a of FIG. 19A except, in the wear-out monitor device 190c, an impurity region 196b of a monitor structure 194a is partially enclosed by a partial diffusion barrier structure 197. The partial diffusion barrier structure 197 has an opening such that diffusion of the monitor atoms out of the impurity region 196b is partially restricted. Such configuration can be beneficial when the expected diffusion of the monitor atoms is relatively rapid, to prevent too rapid of a change in concentration of the monitor atoms, or in the $Z_b(t)$.

Referring FIG. 19D, a wear-out monitor device 190d configured for sensing impedance as an indicator of the state of wear-out is illustrated, according to embodiments. Unlike the wear-out monitor devices 190a of FIG. 19A and 190c of FIG. 19C, the wear-out monitor device 190d does not have a monitor structure and a reference structure that are discrete. Instead, the wear-out monitor device 190d has a monitor region 194d and reference region 192d that are enclosed by a barrier structure 195d, such the monitor atoms in the reference region 192d are configured to laterally diffuse into the monitor region 194d.

It will be appreciated that the wear-out monitor devices 190a, 190b and 190d can be advantageous, among other reasons, because a semiconductor junction is not needed for impedance measurement-based determination of the wear-out level. As a result, the material of the substrate 198 can be any suitable diffusing medium, including an insulator (e.g., SiO2, sapphire) or any semiconductor substrate disclosed herein. Thus, an additional degree of freedom, i.e., the diffusing medium, is available for designing the monitor device. In addition, because the monitor atoms are prevented from freely diffusing away at least from the reference region, relatively small amount of monitor atoms may be needed.

Sensing Circuitry for Wear-Out Monitors

In the following, various circuitry that can be included in the sensing circuitry for sensing the various electrical signatures associated with the wear-out monitor devices and the reference devices according to embodiments are described. It will be appreciated that each of the various circuitry disclosed herein can be part of the sensing circuit 25a/25b described above with respect to FIGS. 2A/2B.

FIGS. 20A-21B illustrate various conversion circuits configured for converting measured input signals from wear-out and/or reference monitor devices described herein into output signals, according to various embodiments.

Figure 20A:
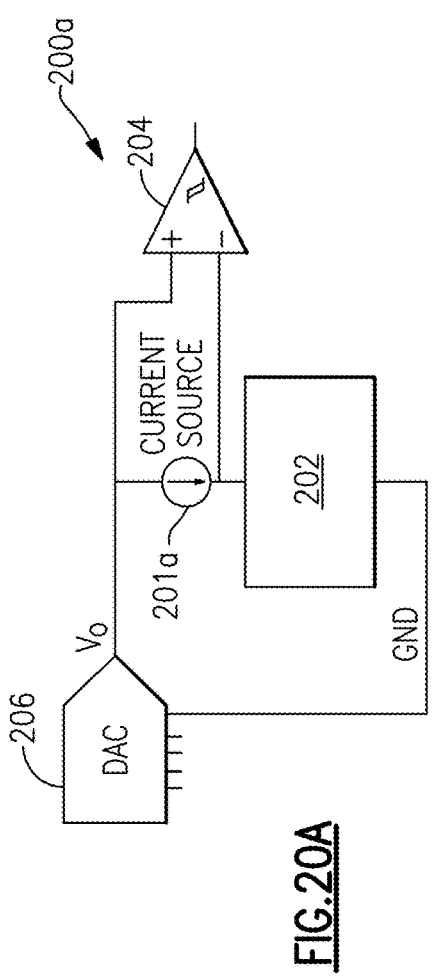
FIGS. 20A-20C illustrate conversion circuits configured to be used with wear-out monitor devices, according to some embodiments.

FIG. 20A illustrates a punch-through wear-out monitor conversion circuit 200a configured for conversion of monitor signals from various monitor devices and reference devices described above, according to embodiments. In particular, the conversion circuit 200a may be configured for monitoring punch-through characteristics of semiconductor devices. For example, the conversion circuit 200a may be electrically connected to wear-out monitor devices configured for monitoring punch-through characteristics described above, e.g., with respect to FIGS. 11A-11B and 12A-12B. The conversion circuit 200a is configured such that, below a predetermined punch-through voltage, no current flows through a punch-through monitor device 202. When no current flows through the punch-through the device 202, potentials of the + and − terminals of a comparator 204 are equal. Once a punch-through occurs, the comparator 204 is activated, and a current flows through the punch-through device 202. The punch-through voltage is output through a DAC 206, which may be recorded.

Figure 20C:
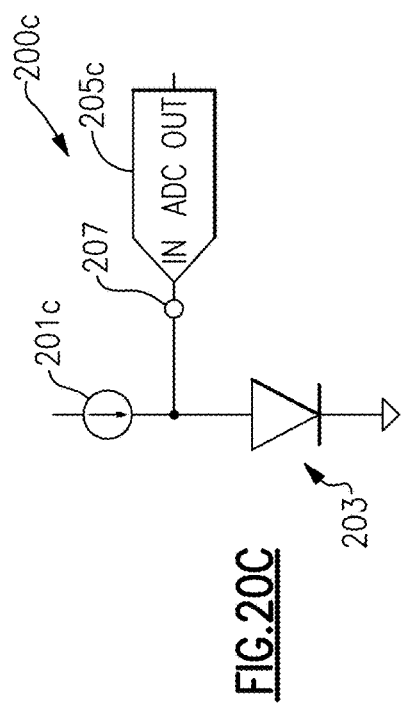
Figure 20B:
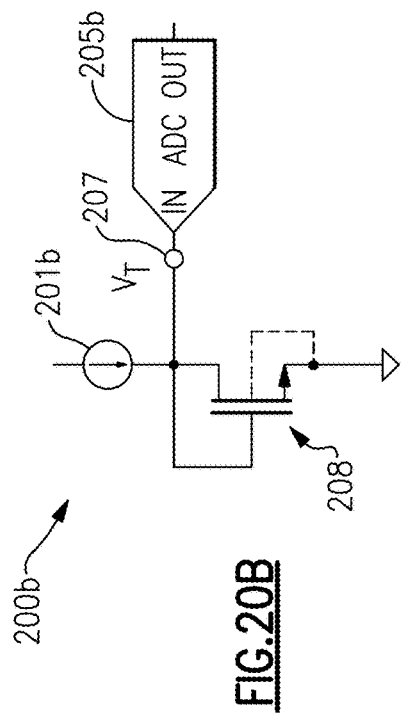

FIG. 20B illustrates a threshold voltage (Vth) wear-out monitor conversion circuit 200b configured for conversion of monitor signals from various monitor devices and reference devices described above, according to embodiments. In particular, the conversion circuit 200b may be configured for monitoring Vth variation characteristics of MOS devices. In operation, the current source 201b raises the voltage on a VT node 207 (ADC input) until the voltage saturates. If a constant current is output from the current source 201b, the saturation in voltage at the VT node 207 varies according to the variation of Vth of the transistor 208. The Vth voltage is output to ADC 205b and recorded over time.

FIG. 20C illustrates a diode forward voltage wear-out monitor conversion circuit 200c configured for conversion of monitor signals from various monitor devices and reference devices described above, according to embodiments. In particular, the conversion circuit 200c may be configured for monitoring forward voltages of diodes. In operation, the current from current source 201c raises the voltage on a node 207 (ADC input) until the voltage saturates. If a constant current is output from the current source 201c, the saturation voltage at the node 207 will vary with of forward voltage of the diode 203, which can be output to ADC 205c and recorded over time.

Figure 21A:
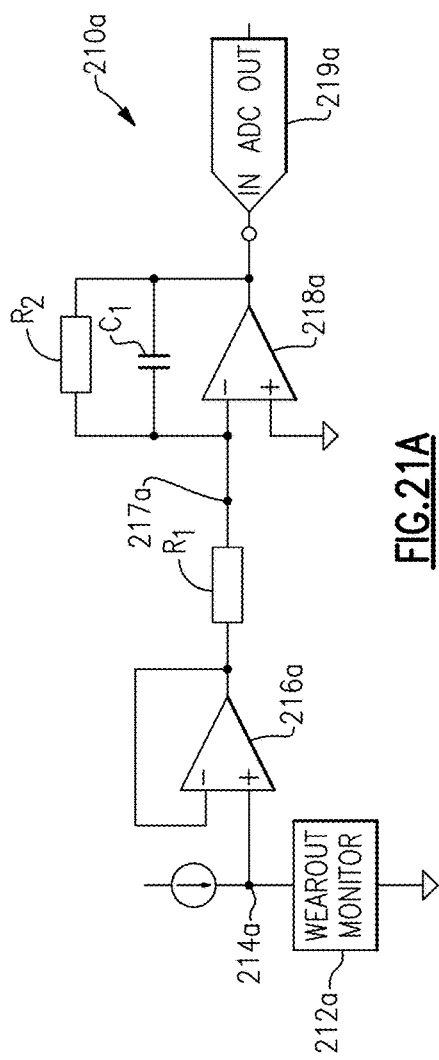
FIGS. 21A-21B illustrate conversion circuits configured to be used with wear-out monitor devices, according to some other embodiments.

FIG. 21A illustrates a conversion circuit 210a configured for conversion of monitor signals from various monitor devices and reference devices described above, according to some embodiments. In operation, in a first stage, the conversion circuit 210a is configured to monitor a voltage on a wear-out monitor 212a at a node 214a. This is achieved by, in a first stage, buffering the voltage of a wear-out monitor device 212a at the node 214a using a first amplifier 216 and a first resistor R1. In a second stage, the buffered voltage at a node 217 is subsequently gained up by a second amplifier 218a, and subsequently converted for output at an ADC 219a.

Figure 21B:
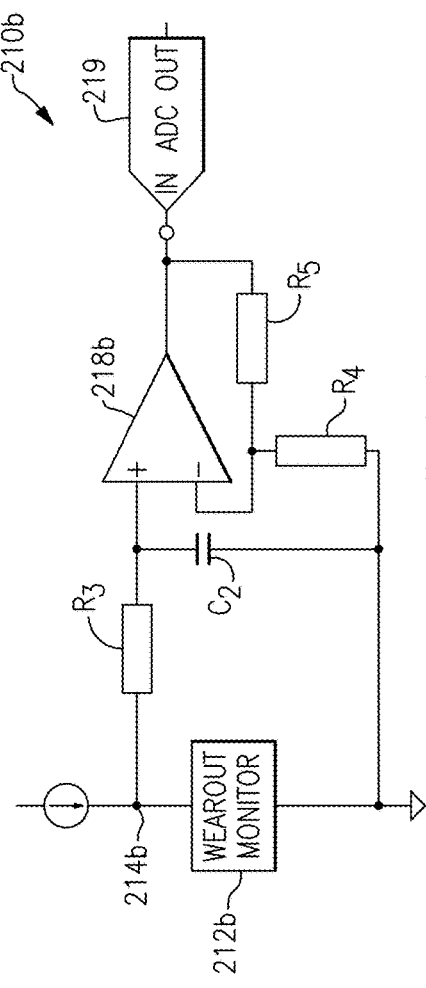

FIG. 21B illustrates a conversion circuit 210b configured for conversion of monitor signals from various monitor devices and reference devices described above, according to some embodiments. In operation, in a first stage, the conversion circuit 210b is configured to monitor a voltage on a wear-out monitor 212b at a node 214b by first low pass-filtering the input signal, followed by gaining using a first amplifier 218a, and subsequently converting for output at ADC 219.

Figure 22A:
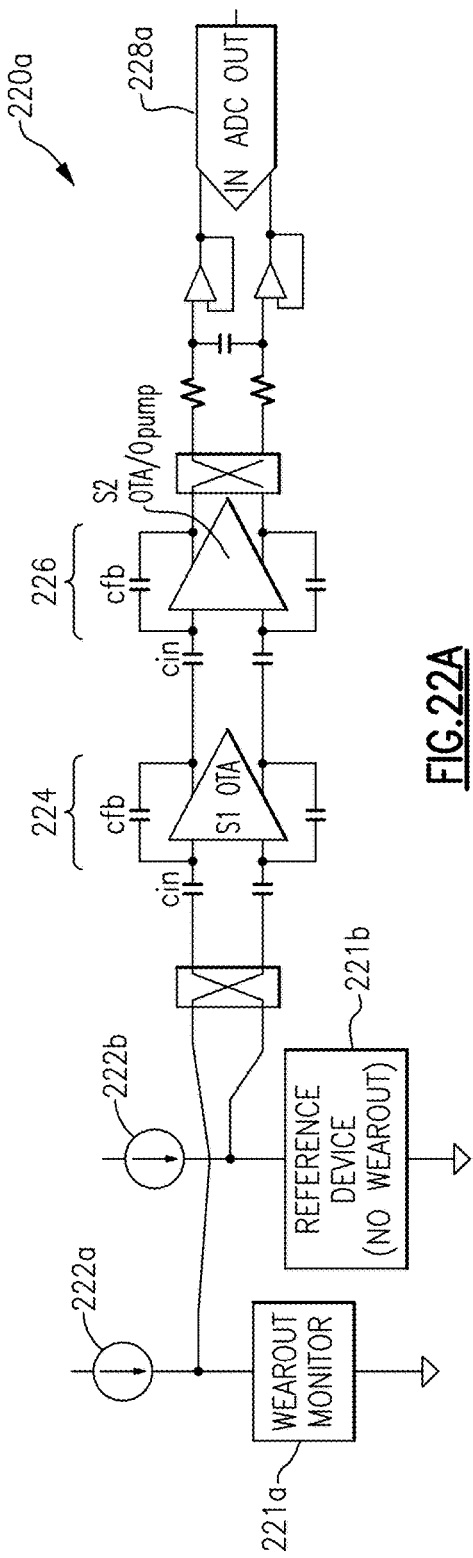
FIGS. 22A-22C illustrate a capacitive programmable gain amplifier (PGA) circuits configured to compare output signals between a wear-out monitor device and a reference device, according to embodiments.

FIG. 22A illustrates a capacitive programmable gain amplifier (PGA) circuit 220a configured to compare output signals between a wear-out monitor device 221a and a reference device 221b, according to embodiments. The PGA circuit 220a includes two current sources 222a and 222b configured to supply currents to a wear-out monitor 221a and a reference device 221b, respectively. The PGA circuit 220a further includes two fully differential voltage-mode capacitive amplifiers 224 and 226 connected to each of the wear-out monitor device 221a and the reference device 221b. As illustrated, the PGA circuit 220a is configured as a chopped capacitive PGA with an output filter and a buffer, and is particularly adapted for amplifying small signal differences (~tens to hundreds of nV) between outputs of the wear-out monitor device 221a and the reference device 221b.

Figure 22B:
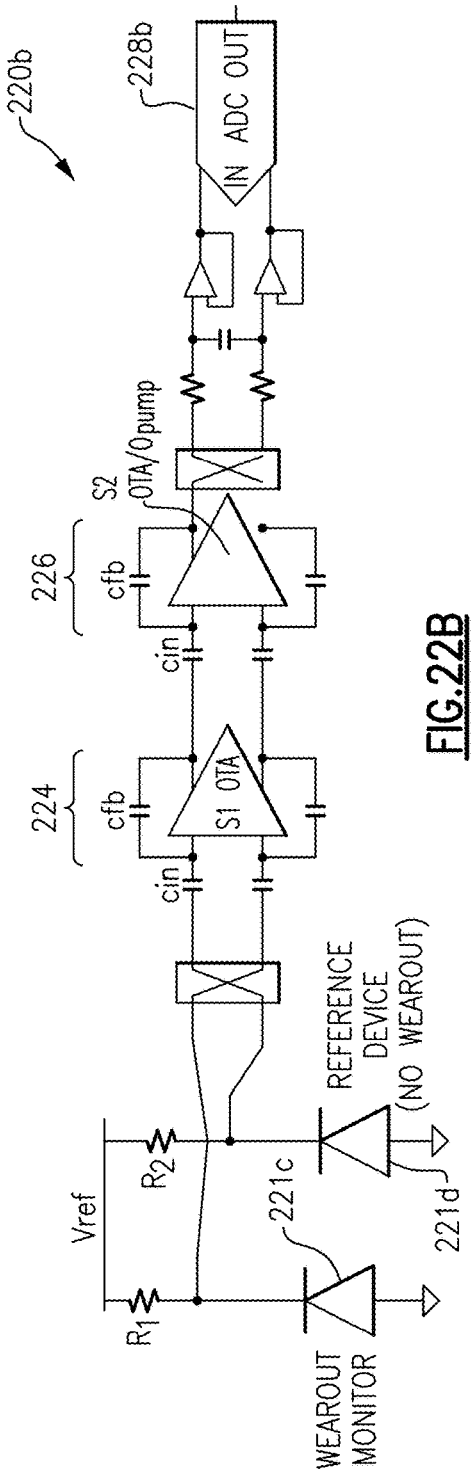

FIG. 22B illustrates a capacitive programmable gain amplifier (PGA) circuit 220b configured to compare output signals between a wear-out monitor device 221c comprising a diode, and a reference device 221d comprising a diode, according to embodiments. Unlike the PGA circuit 220a of FIG. 22A, in the PGA circuit 220b, the wear-out monitor device 221c and reference device 221d are each connected to a common reference voltage, Vref. Similar to the PGA circuit 220a of FIG. 22A, the PGA circuit 220b is configured as a chopped capacitive PGA with an output filter and a buffer, and is particularly adapted for amplifying small signal differences (~nV~100 nV) between outputs of a wear-out monitor device 221c and a reference device 221d.

Figure 22C:
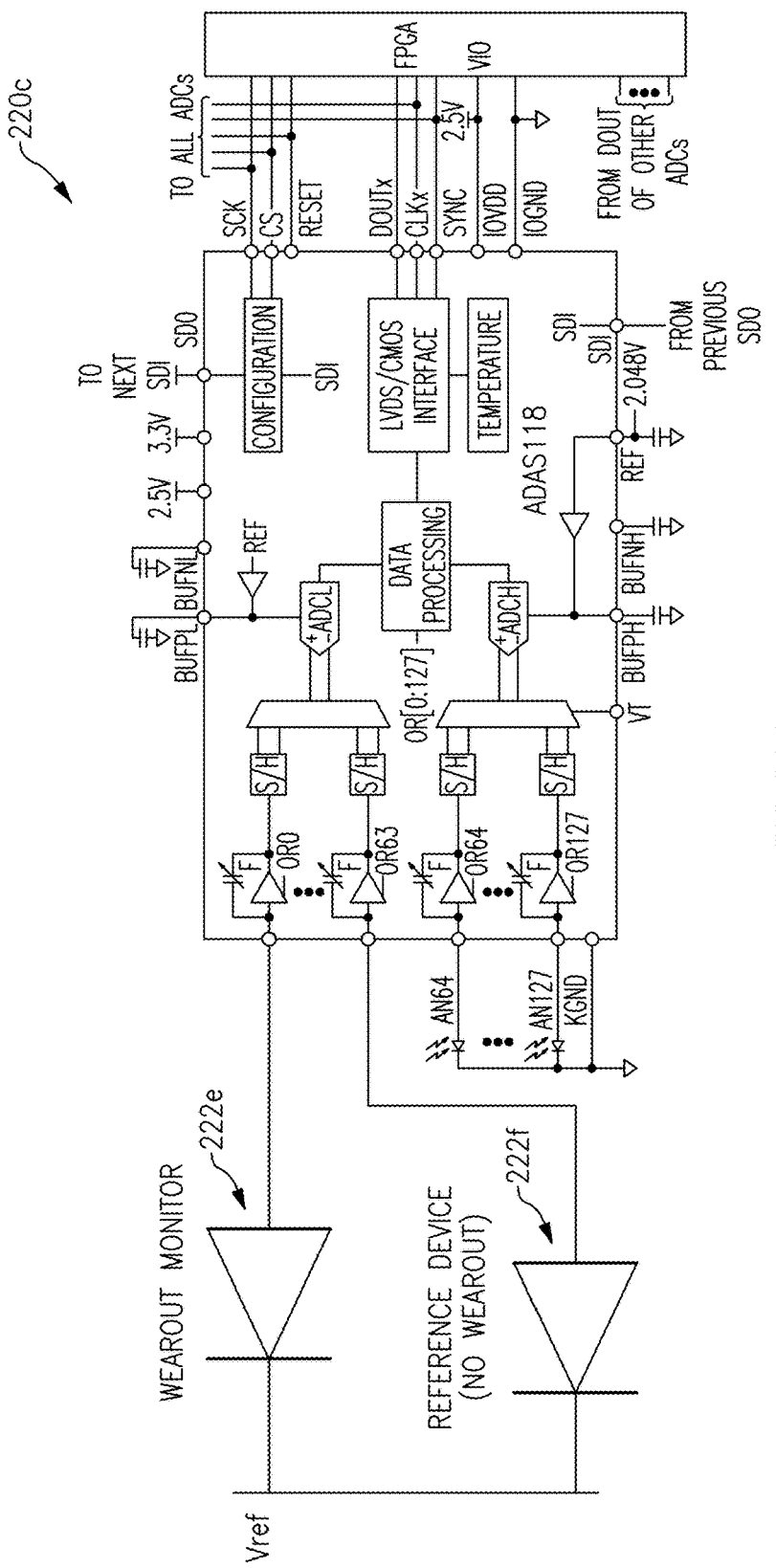

FIG. 22C illustrates a current-to-digital ADC conversion circuit 220c configured to compare output signals between a wear-out monitor device 221e comprising a diode and a reference device comprising a diode, according to embodiments. For illustrative purposes, in the illustrated embodiment, the ADC conversion circuit 220c is a 128-channel, current-to-digital, analog-to-digital converter (ADC). The ADC conversion circuit 220c includes 128 low power, low noise, low input current integrators, simultaneous sample-and-holds, and two high-speed, high-resolution ADCs with configurable sampling rate and resolutions up to 24 bits. The converted channel results are output on a single LVDS self-clocked serial interface, which reduces external hardware. An SPI-compatible serial interface allows configuration of the ADC using the SDI input. The SDO output allows the user to daisy-chain several ADCs on a single, 3-wire bus. The ADC circuit 220c can use the separate supply IOVDD to reduce digital noise effect on the conversions.

Figure 23A:
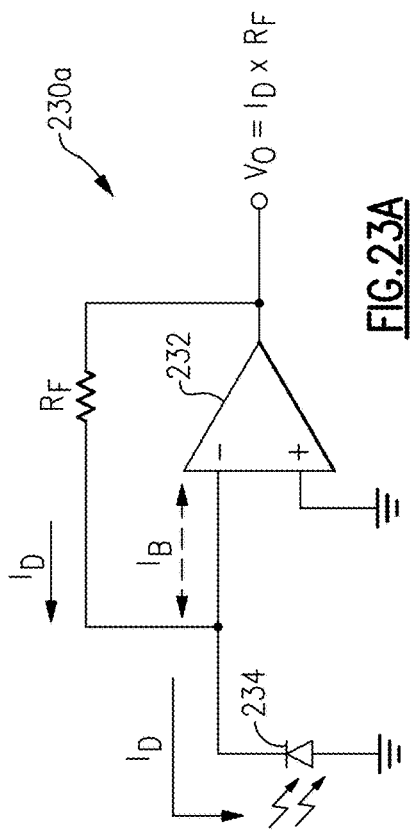
FIGS. 23A-23C illustrate trans-impedance amplifiers (TIAs) configured to amplify and to convert current output of wear-out monitor devices to a voltage signal, according embodiments.
Figure 23C:
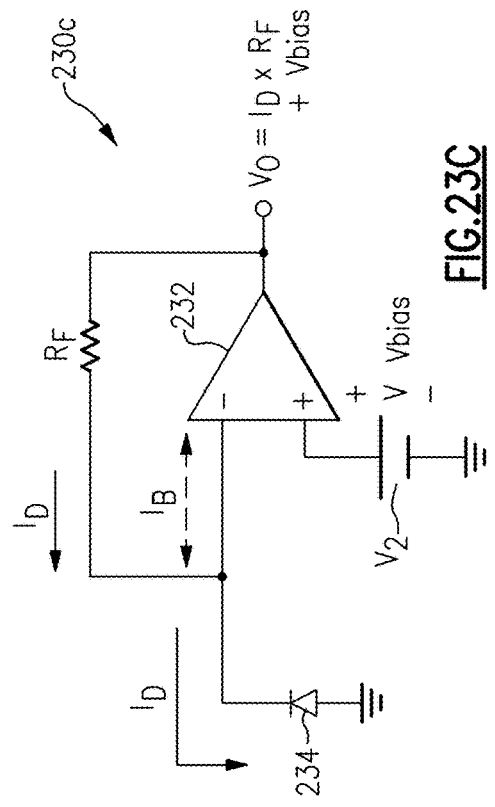
Figure 23B:
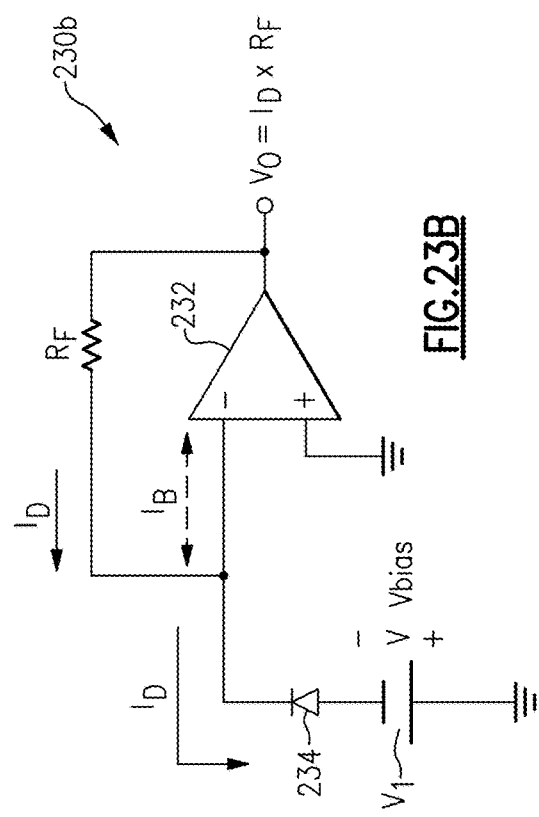

FIGS. 23A-23C illustrate trans-impedance amplifiers (TIAs) 230a-230c, respectively, each configured to amplify and to convert current output of monitor signals from various wear-out monitor devices or reference devices described herein to a voltage signal, according to embodiments. In some embodiments, the TIAs can be used where a wear-out monitor has a current response that is more linear than the voltage response. For example, the illustrated TIAs 230a-230c can be used with a wear-out monitor 234 which include a diode, e.g., a photodiode, where the current response may have better than, e.g., 1% linearity over a wide range of light input. The TIAs 230a-230c present low impedance to the wear-out monitor 234 and isolate it from the output voltage of the operational amplifier. Each of the TIAs 230a-230c has an amplifier 232 in an inverting configuration and a feedback resistor, $R_F$, which sets the gain of the amplifier 232, whose value is $-R_F$. The output each of TIAs 230a-230c can be converted by an ADC. Each of the TIAs 230a-230c is particularly suitable for converting low-level current of a wear-out monitor to a voltage, as described infra.

Referring to FIG. 23A, in operation, the wear-out monitor device 234 is connected between ground and the inverting input of the amplifier 232. The non-inverting input of the amplifier 232 is also connected to ground. This provides a low impedance load for the wear-out monitor device 234, which keeps the bias low. The high gain of the amplifier 232 keeps the current through the wear-out monitor device 234 equal to the feedback current through $R_F$.

Referring to FIG. 23B, the TIA 230b is similar to the TIA 230a of FIG. 23A, except, the TIA 230b includes a DC supply $V_1$, e.g., a battery, between the wear-out monitor device 234 and ground, such that a wear-out monitor can be measured with a positive output voltage. For example, if a reverse bias leakage current ($I_D$) through a wear-out monitor device 234 having a diode is 5 nA, and $R_F$ is 1 MΩ, and $V_{bias}$ is =–0.1V, $V_{out}$=5 nA*1MΩ=5 mV.

Referring to FIG. 23C, the TIA 230c is similar to the TIA 230a of FIG. 23A, except, the TIA 230c includes a DC supply $V_2$, e.g., a battery, having a $V_{bias}$ between the non-inverting input of the amplifier 232 and ground, such that a wear-out monitor can be measured with a positive output voltage. For example, if a reverse bias leakage current through a wear-out monitor device 234 having a diode is 5 nA, and $R_F$ is 1 MΩ, and $V_{bias}$ is =+0.1V, $V_{out}$=(5 nA*1MΩ)+0.1V=105 mV.

Thus, the trans-impedance amplifiers (TIAs) 230a-230c have input offset voltage due to the monitor device 234 that is very low while the gain is very high, such that they allow for very low input bias current (~+/–20 fA) to be measured and amplified.

Figure 24:
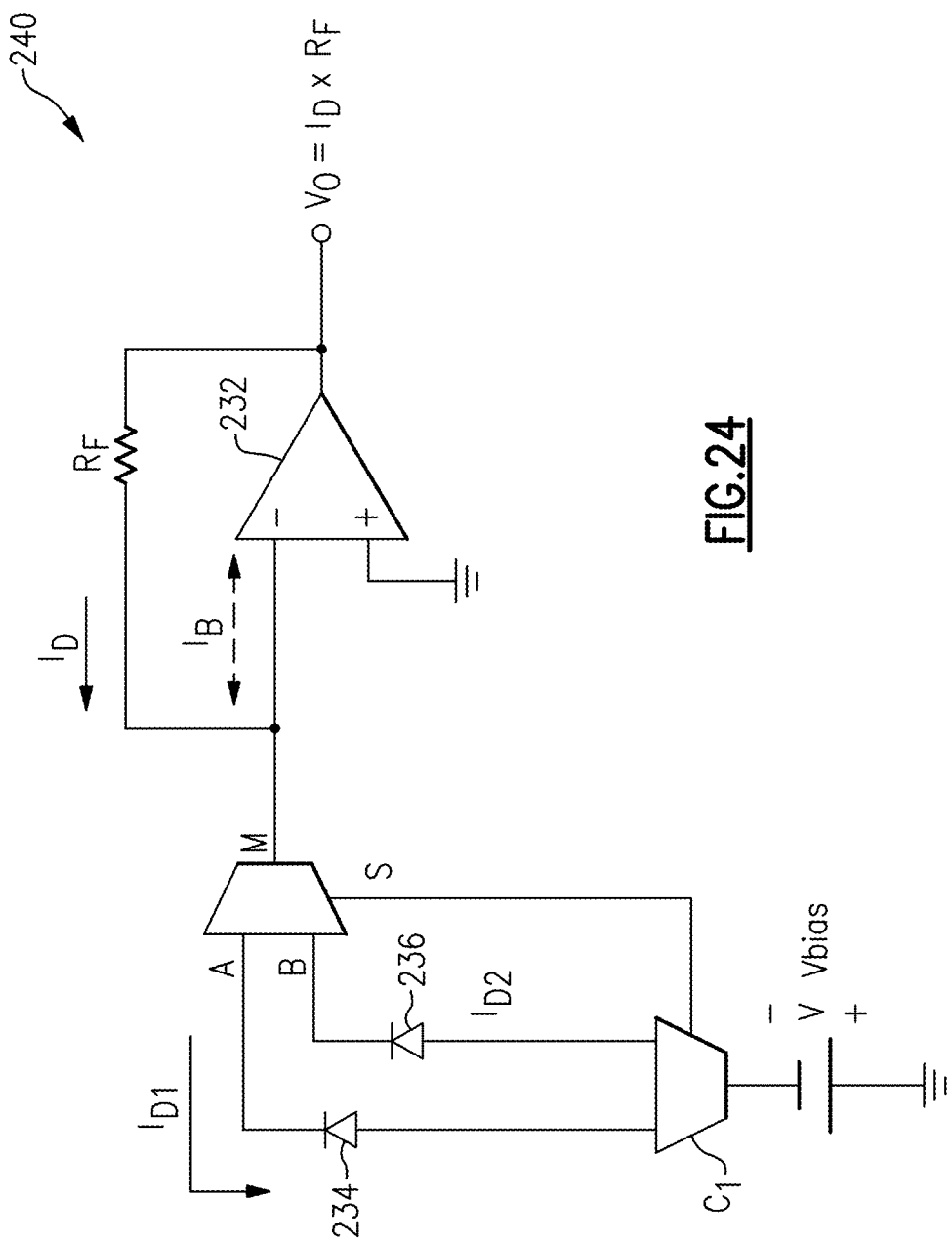
FIG. 24 illustrates a trans-impedance amplifier (TIA) with anode bias multiplexed to amplify and to convert current outputs of a monitor device and a reference device to a voltage signal, according to some embodiments.

FIG. 24 illustrates a trans-impedance amplifier (TIA) 240 with anode bias multiplexed such that the TIA amplifier 240 is configured to amplify and to convert current outputs ($I_{D1}$, $I_{D2}$) of monitor signals from both a monitor device 234 and a reference device 236 into voltage outputs, according to some embodiments. Advantageously, since the monitor device 234 and the reference device 235 use the same $V_{bias}$ and the same amplifier 232, errors in conversion of the current outputs ($I_{D1}$, $I_{D2}$) are cancelled. In operation, the TIA 240 can be part of the front end of a sensing circuit. The output from each device can be converted by an ADC whose result can be stored, and subsequently subtracted to calculate a difference in leakage current, for example. Storing the difference in leakage current over time would track, e.g., the temperature the wear-out monitor device was exposed to over time.

Lifetime Indicator Systems

Figure 25:
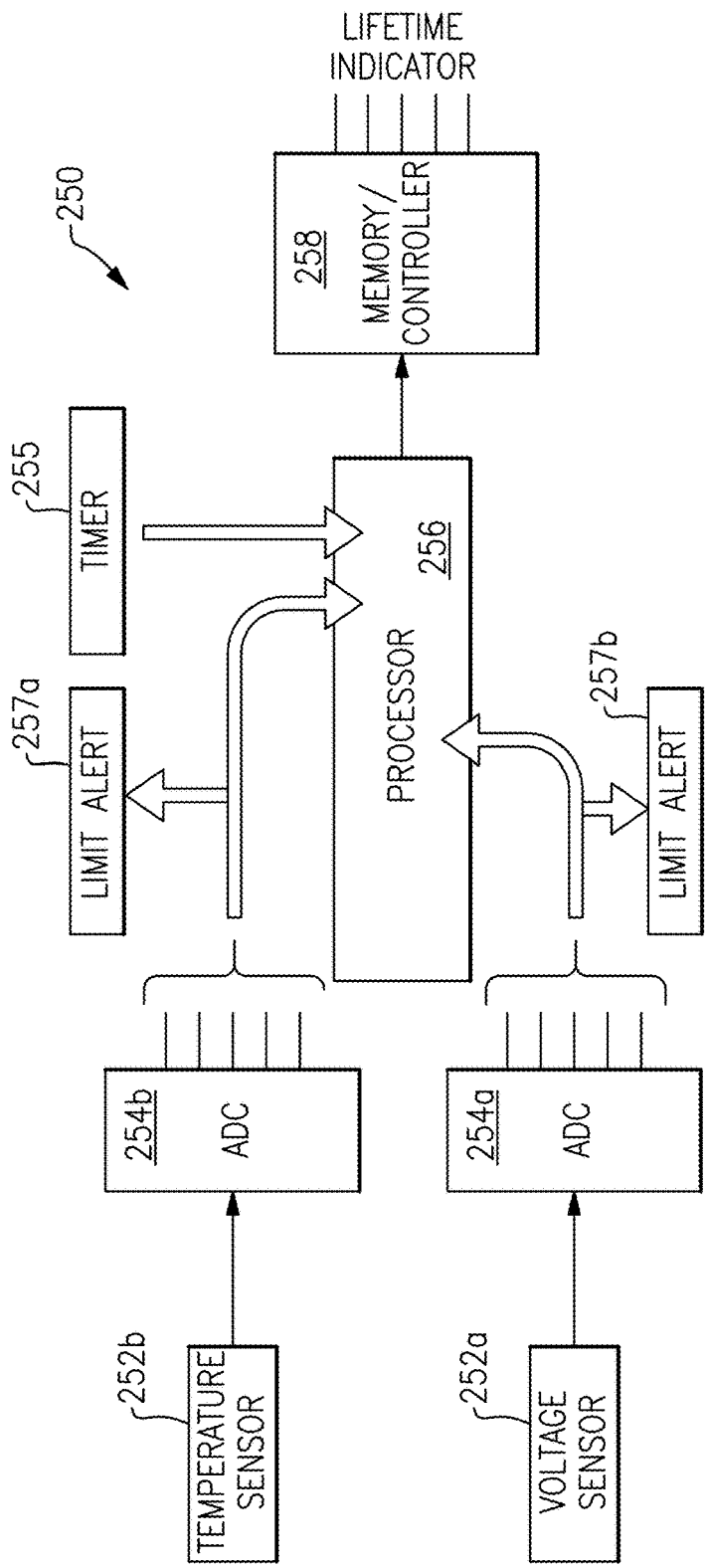
FIG. 25 illustrates a lifetime indicator system having one or more wear-out monitor devices, according to embodiments

FIG. 25 illustrates a lifetime indicator system 250 having one or more wear-out monitor devices, according to embodiments. It will be appreciated that the lifetime indicator system 250 disclosed herein can be part of the sensing circuit 25a/25b described above with respect to FIGS. 2A/2B.

The plurality of different monitor devices 252a, 252b, can be different types wear out monitor devices formed in a common platform (e.g., a single chip or a single substrate), according to embodiments. The one or more different monitor devices 252a, 252b can provide, e.g., parallel and/or simultaneous monitoring data of different types of wear-out stresses. In the illustrated embodiment, the one or more wear-out monitor devices include a temperature wear-out monitor 252b and a voltage or current wear-out monitor 252a. In operation, the one or more wear-out devices 252a, 252b can provide parallel and/or simultaneous monitoring data to a respective ADC 254a, 254b, whose output can be fed into a common processor 256. Simultaneously, respective limit alerts 257a, 257b can be generated based on the monitoring data from each of the one or more wear-out devices 252a, 252b. Each limit alert 257a, 257b can be pre-established based on individual minimum and maximum values limits placed by the user for respective monitors. The lifetime indicator system 250 can also include a timer 255. The processor 256 is configured to receive the monitoring data from each of the wear-out monitor devices 250a, 250b and to determine, either based on information from an individual wear-out monitor device 252a or 252b, or by combining information from the more than one monitor devices 252a, 252b, a wear level of a relevant core circuit device (not shown for clarity, see FIGS. 2A/2B) in a core circuitry. Thus, calculated wear-out level may be stored in a memory device 258, e.g., a nonvolatile memory device. In some implementations, the calculated wear-out level data stored in the memory device can be transmitted in an encrypted form for protection.

In some embodiments, the lifetime indicator system 250 can be configured as a supply current wear-out monitoring system. Many IC failures are caused by wear-out of supply current modules, such as supply current modules configured for providing standby or power-save currents. Failures can occur when the supply current degrades due to wear-out caused by EOS, ESD, corrosion and latent defects to name a few. When configured as a supply current wear-out monitoring system, the wear-out monitor 252a can be configured as a supply current wear-out monitor. When a failure does occur, by monitoring time-stamped supply current values and recording them in the memory 258, and "playing back" such current values leading up to failure, information related to the cause of the failure can be obtained.

In other embodiments, the lifetime indicator system 250 can be configured as a device failure monitoring system, e.g., a transistor device wear-out monitoring system for monitoring device failures that depend on voltage, current, temperature, and/or time. Examples of such wear out mechanisms include wear-out due to hot carrier injection (HCI) and negative bias temperature instability (NBTI), which are known to negatively affect transistor performance (speed and voltage). Accuracy of wear-out models for failures resulting from such mechanisms can be improved by simultaneously monitoring a cumulative voltage stress on the transistor, while also monitoring the temperature at which the voltage stress is applied.

Mission Profile Monitoring Systems

A mission profile generally describes loads and stresses acting on an item, e.g., a component, a device or a system in actual use. As used herein, a mission profile refers to a time-phased description of events and environments the item experiences from initiation to completion of a specified mission for a specified time. The events and environments, e.g., loads and stresses, include, for example, changes in temperature, temperature profile, humidity, vibration, electric/magnetic fields, or a combination of these factors, among other environmental factors. It can be important to specify the relevant stresses in their nature, intensity and duration of exposure, as well as the mix as closely as possible. With these details it is possible, within specified accuracy, projections regarding reliability of application and its components in field applications.

Generally two different types of mission profiles exist. A pre-determined mission profile refers to a mission profile that is predetermined before the item is put in use and may be pre-programmed to a storage device, such as a nonvolatile memory device. In contrast, a "smart" mission profile is an evolving mission profile that self-adjusts over time based on the output from on-board sensors, e.g., wear-out sensors, that sense the mission profile parameters under actual operating conditions. Thus, a "smart" mission profile more closely reflects the actual conditions that the component, the device or the system sees over its lifetime. The "smart" mission profile can be particularly important in applications where specific mission profiles are not well known, because the "smart" mission profile can be updated and improved periodically based on the changing output from the on-board sensors. In the following, a mission profile monitoring system comprising on-chip wear-out sensors is described, according to embodiments.

Figure 26:
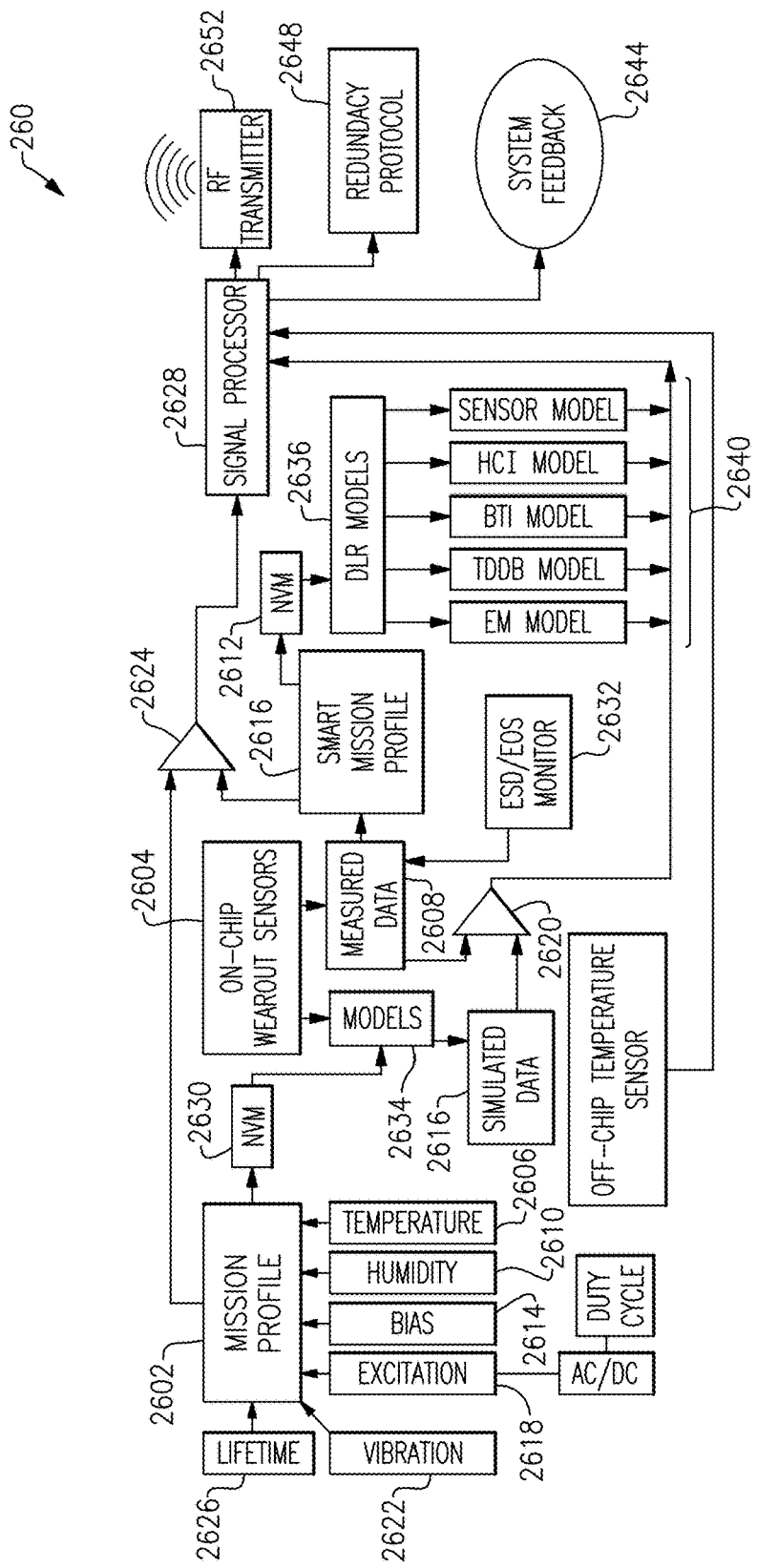
FIG. 26 illustrates a mission profile monitoring system comprising one or more wear-out sensors, according to embodiments.

Referring to FIG. 26, a block diagram of a mission profile monitoring system 260 comprising one or more wear-out sensors is illustrated for monitoring a mission profile of a component, a device or a system, according to embodiments. The component, a device or a system can be included or electrically connected to the core circuitry (not shown for clarity, see FIGS. 2A/2B). The one of more wear out sensors 2604 can include one or more of any of the wear-out sensors described herein, including sensors configured to measure wear-out from temperature, voltage, current, humidity, motion (e.g. vibration), etc. The system 260 is configured to periodically generate measured output data 2608 from the wear-out sensors 2604 over the lifetime of the component, the device or the system. The output data can be stored in a first storage/memory component 2612, which can be, e.g., a non-volatile memory device or a volatile memory device. The stored data can include instantaneous data as well as statistical data, e.g., average data and variability data. The output data cumulated over time that is stored in the first storage/memory component 2612 make up a "smart" mission profile 2616.

The system 260 additionally includes a predetermined mission profile 2602, which includes a set of pre-determined mission profiles that can be used as reference profiles. The predetermined mission profiles include temperature profile 2606, humidity profile 2610, bias (voltage) or current profile 2614, excitation profile 2618, vibration profile 2622 and lifetime profile 2626, among other profiles. The predetermined mission profile 2602 can be stored in a second storage/memory component 2630, e.g., a non-volatile memory device or a volatile memory device. The system 260 additionally includes a modelling module 2634 that is configured to retrieve the predetermined mission profiles from the second storage component/memory component 2630 and to generate simulated data 2616 of the wear-out state of the component, the device or the system using a predetermined set of physical models 2634.

The system 260 additionally includes a first comparator 2620 configured to compare the simulated data from the modelling module 2634 and the measurement output data from the on-chip wear-out sensors 2604. The output from the first comparator 2620 can be sent to a signal processor 2628 configured to determine the health of the component, the device or the system being monitored based at least in part on the output from the first comparator 2620.

The system 260 may additionally include a second comparator 2624 configured to compare the pre-determined mission profile 2602 and the "smart" mission profile 2616. The output from the second comparator can also be sent to the signal processor 2628. The processor 2628 is further configured to, based on a deviation or a difference between the pre-determined mission profile and the "smart" mission profile, determine whether a system fault exists.

The monitoring system 260 can be used to monitor the mission profile of the component, the device or the system throughout its lifetime using the one or more wear-out sensors 2604. In some other embodiments, the monitoring system 260 can additionally employ an electrostatic discharge (ESD)/electrical overstress (EOS) monitor 2632. An output from the ESD/EOS monitor 2632, which can signify a triggered event, can be utilized in conjunction with the output data from the one or more wear-out sensors 2604. When an ESD/EOS event occurs, the output from the wear-out sensors 2604 before and after the ESD/EOS event can be compared. Any significant change in output characteristics may indicate damage internal to the IC that is induced by the ESD/EOS event. Such information can also be stored in the first storage/memory component 2612, e.g., non-volatile memory or a volatile memory, and cumulated over time to make up the "smart" mission profile 2616.

In some embodiments, the system 260 additionally includes a device-level reliability (DLR) modelling module, according to embodiments. The DLR modelling module 2636 includes therein various modeling modules 2640 associated with various wear-out mechanisms, including, e.g., hot carrier injection (HCI) modelling module, time-dependent-dielectric-breakdown (TDDB) modelling module, electromigration (EM) modelling module, bias temperature instability (BTI) modelling module and magnetoresistance (MR) modelling module. The modeling modules 2640 can also include one or more internet-of-things (IOT) sensor modelling modules including one or more of energy harvesting modelling module, gas-sensing modelling module, humidity sensing modelling module, resonator modelling module and biometric sensing modelling module, to name a few. Using these models and data from the "smart" mission profile, potential wear-out issues can be detected and used to alert the user of latent system failure. The data can also be used as part of a feedback loop 2644 to adjust the performance of the component, the device or the system and/or to initiate a redundancy protocol 2648. The system 260 additionally can include a communication module 2652, which include wired or wireless means for alerting the user of potential or latent component, device or system failure. In some implementations, the data generated and transmitted by the communication module 2652 can be encrypted for protection.

Applications of mission profile monitoring include, e.g.:
Functional Safety Standard (FuSa ISO26262) applications;
Internet-of-Things (IOT) wear-out sensors;
Warranty Returns/Mis-use: The mission profile monitoring system can be utilized to highlight component, device, or system mis-use. For example, while the on-chip wear-out sensor can monitor junction temperature it may be desirable to also monitor the ambient temperature, which can help distinguish between an IC fault, a product specific fault and a system fault. The information stored on chip can be useful for failure analysis and in particular warranty failures. The system can be utilized in conjunction with an EOS/ESD monitor to aid fault analysis.
IC/System Redundancy Protocol: For safety critical applications, redundancy is often desirable. The mission profile monitoring system can be used to trigger the redundancy protocol prior to IC/product failure hence preventing potential system damage via thermal runaway and other effects.
Temperature Mapping: Some wear-out sensors capable of monitoring temperature can be used in conjunction with the mission profile monitoring system to map temperature gradients of systems. On screen temperature maps can be displayed along with system alerts to highlight wear-out and latent system failure.
Humidity Mapping: Some wear-out sensors capable of monitoring humidity can be used in conjunction with the mission profile monitoring system to map humidity gradients of systems. On screen humidity maps can be displayed along with system alerts to highlight wear-out and latent system failure.

Vibration Mapping: Some wear-out sensors capable of monitoring vibration can be used in conjunction with the mission profile monitoring system to map vibration gradients of systems. On screen vibration maps can be displayed along with system alerts to highlight wear-out and latent system failure.

Operating Voltage Guard Banding

Figure 27:
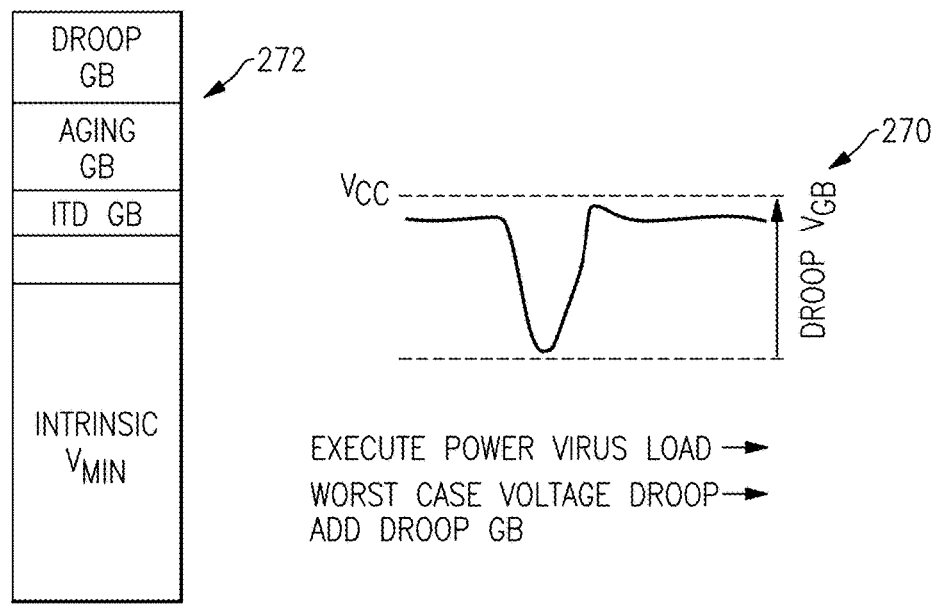
FIGS. 27-28 illustrate supply voltage guard-banding in IC devices for application of wear-out monitor devices, according to embodiments.
Figure 28:
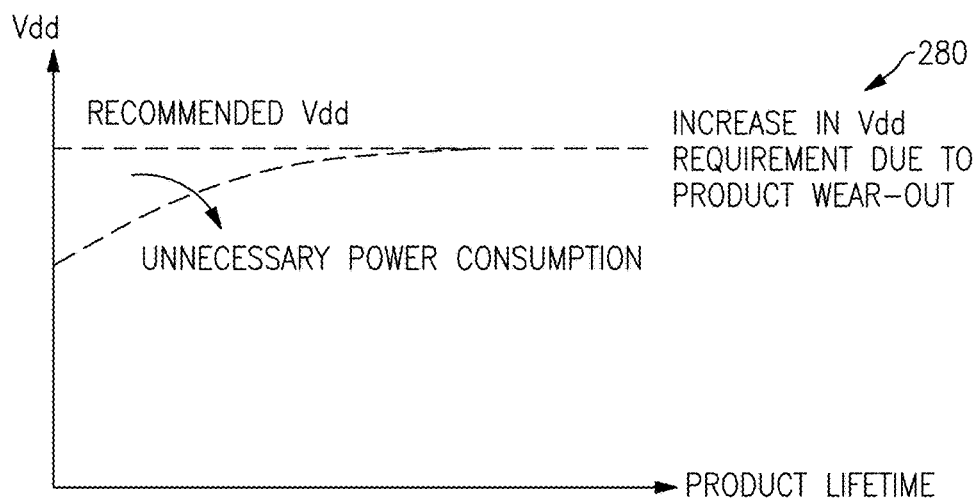

FIGS. 27-28 illustrate a method of supply voltage guard-banding in IC devices using wear-out monitor devices, according to embodiments. While not shown, the sensing circuit 25a/25b described above with respect to FIGS. 2A/2B can be configured to implement the method described with respect to FIGS. 27-28.

Generally, the operating voltage of an IC device can be determined during manufacturing test and characterization processes based on the IC's intended operating environment. Referring to FIG. 27, at the test and characterization steps, various extra margins can be added to the intrinsic minimum voltage, to arrive at an overall voltage guard banding budget 272. For example, a voltage droop guard band can be added to the guard banding budget 272 in an attempt to guarantee proper operation even during worst-case voltage droop events, as illustrated in the schematic time evolution curve 270 of the guard-banded operating voltage of the IC device. Additional guard bands can be added, e.g., aging guard band.

Referring to FIG. 28, under typical conditions, the voltage droop experienced by an IC device can be much smaller than under worst-case conditions depicted in the time evolution curve 270, and the IC can operate correctly with a much smaller guard band. However, because the actual wear-out state of the IC device that may be causing the voltage droop is unknown, the IC devices are often operated under such worst-case conditions. For example, referring to graph 280 of FIG. 28, the IC device may be operated under a "recommended Vdd" which may represent the Vdd level which takes into account of the worst-case conditions. However, using an unnecessarily large voltage guard band can waste energy. By using various wear-out monitor devices, e.g., in conjunction with the lifetime indicator system 250 (FIG. 25) or mission profile monitoring system 260 (FIG. 26), the amount of guard banding can be minimized, thereby saving energy consumed by the IC device. That is, by tracking the actual wear-out state of the IC, the difference between the recommended Vdd and the actual Vdd can be minimized, thereby saving valuable energy.

Thus, in various embodiments, a method of voltage guard banding includes periodically determining the wear-out state of the IC using a wear-out monitor according to various embodiments described herein, and determining therefrom an instantaneous expected voltage droop that corresponds to the wear-out state. Once the expected instantaneous voltage droop that corresponds to the wear-out state is determined, the recommended Vdd curve can be updated. By increasing the periodicity of such determination, the amount of wasted energy can be minimized.

Self-Powering Wear-Out Monitors

Figure 29:
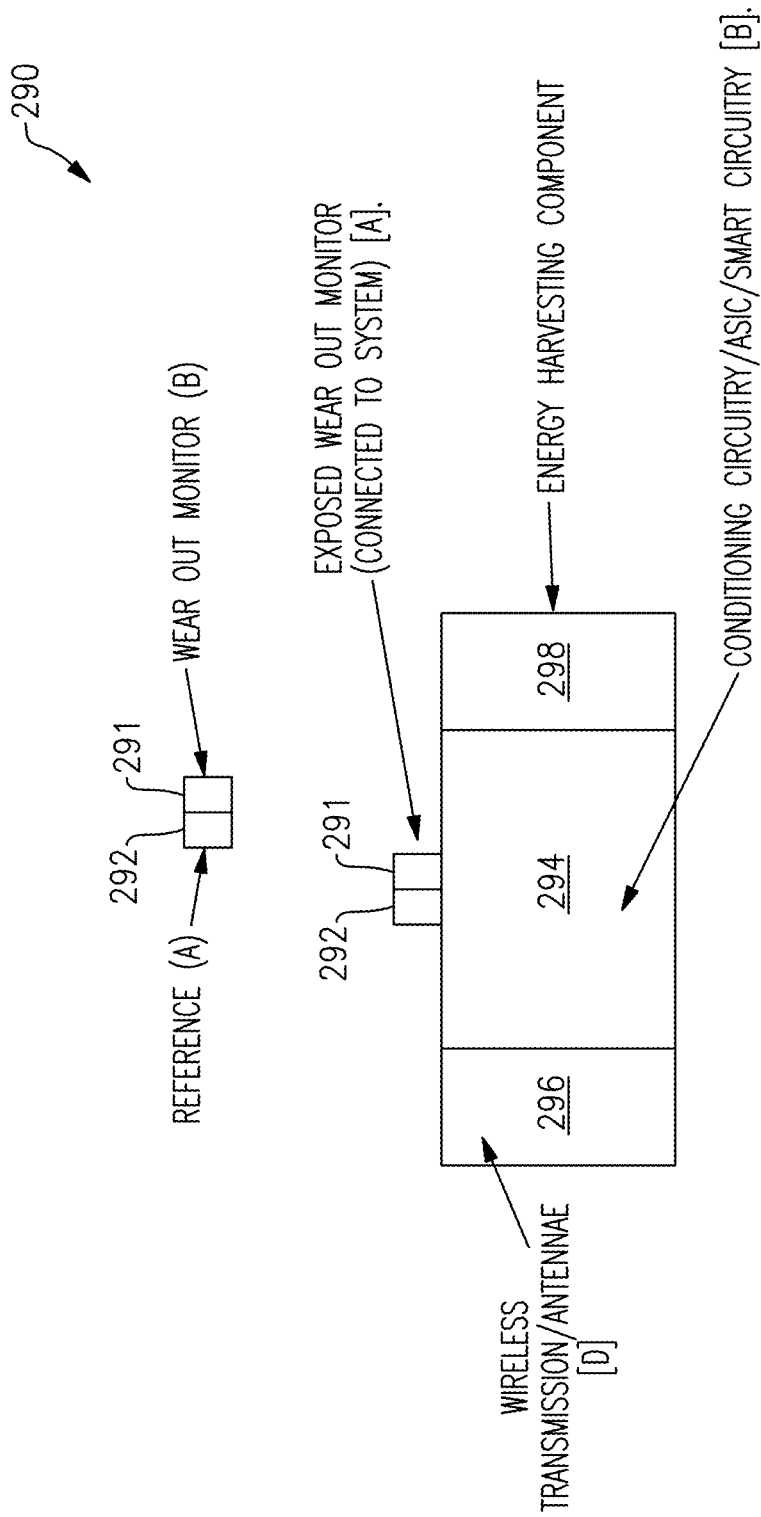
FIG. 29 illustrates an IC apparatus comprising a wear-out monitor device and configured to wirelessly transmit the monitored data while using minimum or no energy, according to embodiments.

FIG. 29 illustrates an IC apparatus 290 comprising a wear-out monitor 291 and configured to wirelessly transmit the monitored data while using minimum or no energy supplied by a power source, or using energy scavenged from the environment in the form of, e.g., solar energy, according to embodiments.

The IC apparatus 290 comprises a wear-out monitor 291, which can be one of wear-out monitor devices described supra, a sensing circuit 294 for sensing the wear-out signal from the wear-out monitor device 291, a wireless communications module 296 for wirelessly communicating the wear-out signal and an energy harvesting component 298 for powering the sensing circuit 295 and the wireless communications module 296. The IC apparatus 290 may also include a reference device 292, which can be configured as one of reference devices described supra. As described supra, the wear-out monitor device 291 and the reference device 292 rely on atomic diffusion and do not include a separate power supply to monitor wear-out stresses that cause the atomic diffusion. However, the sensing circuitry 294 and the wireless communication module 296 can still include a separate power supply. However, for usage in remote, harsh or otherwise difficult-to-access locations, e.g., top of a skyscraper, a bridge or remote base stations, extended monitoring using battery power may not be desirable or practical. Advantageously, the IC apparatus 290 includes the energy harvesting component 298. Energy harvesting can involve converting a non-electrical form of energy into charge. The energy harvesting component 298 can be any suitable device configured to harvest energy from the environment, e.g., a photovoltaic device, a thermoelectric device or a piezoelectric device. The energy harvesting component 298 is configured to partially or fully supply the power to the sensing circuit 294 and the wireless communication module 296 of the IC apparatus 290, such that the IC apparatus 290 can be used for an extended period of time in remote, harsh or otherwise difficult-to-access locations, while receiving the monitor information at the cost of little or no separate power supply. Furthermore, it will be appreciated that the IC apparatus 290, by being remotely located from processing circuitry (not shown for clarity) while being communicatively coupled thereto using the wireless communication module 296, the monitor device can be operated in an environment that is much more harsher than the environment in which the processing circuitry is operated, such as, e.g., a processing environment of a remote server.

Oxidation/Corrosion Wear-Out Monitors

In addition to detecting changes in the rate of atomic diffusion, chemical reactions, e.g., oxidation and/or corrosion reactions, can be used to gauge the wear-out level of some IC devices. Various reactions between the environmental atoms and the monitor impurity atoms, which can include corrosion and/or oxidation, can provide a history of the wear-out stresses associated with the environmental atoms. According to various embodiments, substances/materials that chemically react, e.g., corrode and/or oxidize, can additionally be included in monitor devices that include monitor impurity atoms, e.g., Au or other materials that diffuses at a defined/predictable rate. In some implementations, the rate of reaction of oxidizing/corroding materials can be directly correlated to a measurable electrical quantity. In some other implementations, the oxidizing/corroding materials can produce a discernible effect on the rate of diffusion of monitor impurity atoms, e.g., Au atoms, and thereby be indirectly correlated to a measurable electrical quantity. A system can thus be constructed that could provide an indication of a level of corrosion or oxidation, which could be used independently or in combination with other wear-out mechanisms and conditions described in other embodiments disclosed herein. Similar to diffusion, the wear-out stresses associated with oxidation and/or corrosion can also be thermally activated, such that the concepts described above with respect to diffusion can be applicable in monitor devices described herein with respect to FIGS. 30A-30D.

FIGS. 30A-30D illustrate various embodiments of monitor devices 300a-300d having structures that oxidize/corrode under various usage environments, where changes in the rate of oxidation/corrosion can be used to determine the state of wear-out of the core circuitry. The structures that oxidize/corrode can be used by themselves, i.e., without structures that have monitor atoms configured to diffuse, or in conjunction with structures having monitor atoms configured to diffuse. When structures that oxidize/corrode are used in conjunction with structures having monitor atoms that diffuse, the presence of structures that oxidize/corrode can affect the rate of diffusion of the monitor atoms, and the presence of structures having monitor atoms can affect the rate of oxidation/corrosion. Such monitor devices can be configured to detect wear-out stresses associated with certain environmental atoms, including various gases or liquids, e.g., oxygen, moisture, water, $CO_2$, etc.

Referring to FIGS. 30A-30D, each of the wear-out monitor devices 300a-300d includes a substrate 302, which can include measurement structures described supra, e.g., PN junctions or impedance measurement structures, a diffusion barrier 304 formed thereon to limit or inhibit the diffusion, oxidation, or corrosion of the underlying substrate 302.

Referring to FIG. 30A, the wear-out device 300a includes a plurality of layers 306a of monitor atoms configured to diffuse into the underlying layers and a plurality of oxidizing layers 308a that are adapted to oxidize at a predetermined rate for known oxidizing environments. The oxidizing layers 308a can include a metal or a semiconductor material that have known oxidation rates. The layers 306a of monitor atoms and the oxidizing layers 308a laterally alternate in the illustrated embodiment.

Referring to FIG. 30B, the wear-out device 300b is similarly arranged as the wear-out device 300a of FIG. 30A, except, instead oxidizing layers of the monitor device 300a, the wear-out device 300b includes a plurality of layers 308b that are adapted to corrode at a predetermined rate for known corroding environments. The corroding layers 308b of can include a metal or a semiconductor material that have known corrosion rates. The layers 306b of monitor atoms and the corroding layers 308a laterally alternate in the illustrated embodiment.

Referring to FIG. 30C, the wear-out device 300c is similarly arranged as the wear-out monitor devices 300a/300b of FIG. 3A/FIG. 30B, except, the wear-out device 300c of FIG. 30C has a stacked configuration in which the oxidizing layer/corroding layer 308 is formed on top of the layer 306c of monitor atoms.

Referring to FIG. 30D, the wear-out device 30d is similarly arranged as the wear-out devices 300c of FIG. 30C, except, instead of a stacked configuration in which the oxidizing layer 308c is formed on top of the layer 306c of monitor atoms, the wear-out device 300d of FIG. 30D the oxidizing layer/corroding layer 308d formed below the layer 306d of monitor atoms.

Wear-Out Monitor Arrays

Figure 31:
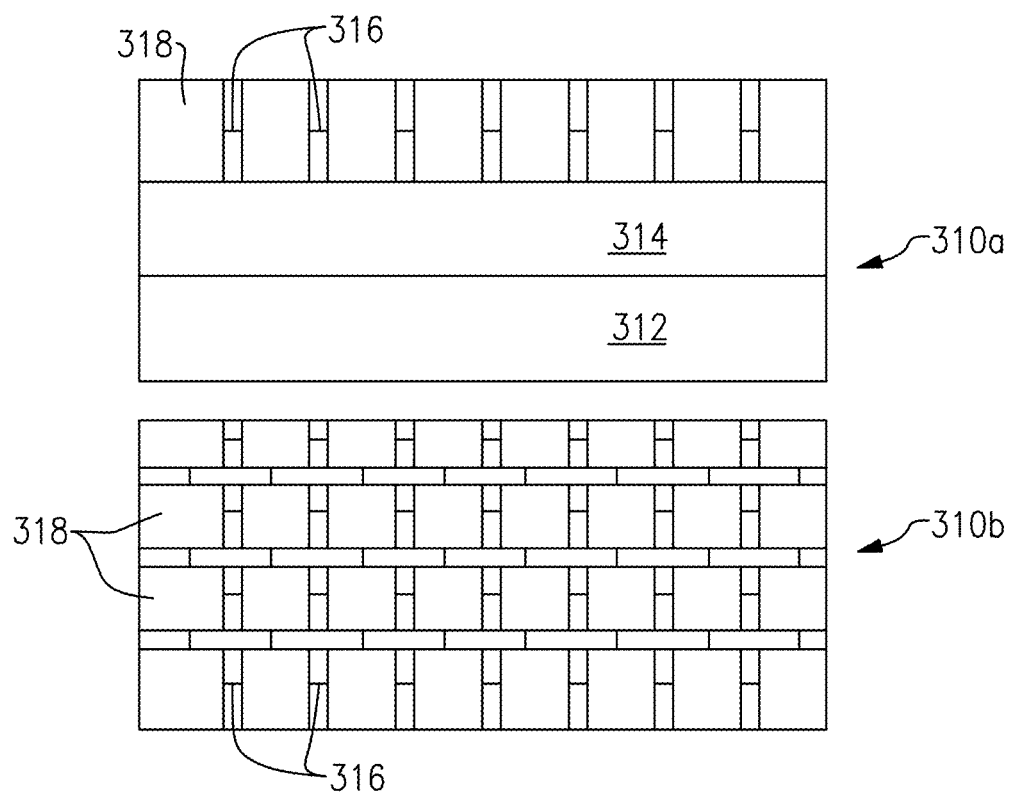
FIG. 31 illustrates a plurality of wear-out monitor devices that are laterally arranged as an array of wear-out monitor devices, according to embodiments.

FIG. 31 illustrates a plurality of wear-out monitor devices that are laterally arranged as an array 310a (cross-sectional view)/310b (plan view) of wear-out monitor devices 318, according to embodiments. The array 310a/310b can be implemented as part of a system, such a system in a chip (SoC) or a system in a package (SIP). The array 310a/310b comprises the plurality of monitor devices 318 formed over a substrate 312 and can include a diffusion barrier 314. The monitor devices 318 may be the same type or different types, depending on the application. For example, for some applications, some of the monitor devices 318 may be configured to monitor thermal stresses, while other monitor devices 318 may be configured to monitor voltage or current stress. When the monitor devices 318 are of the same type, they may be configured to monitor stresses over the same or different stress ranges. For example, some of the monitor devices 318 may be configured to monitor wear-out under a first temperature range, while others of the monitor devices 318 may be configured to monitor wear-out under a second temperature range. In some implementations, the monitor devices 318 may interconnected and communicatively coupled by electrical links or connections 316 that may allow for sensing a plurality of monitor devices 318 in series or in parallel. In some implementations, the electrical links 316 may be fuse link or antifuse links that can be modified after fabrication to form a particular pattern of active monitor devices 318 to target specific regions of the core IC device and/or particular ranges of stresses (e.g., temperature range).

Figure 32A:
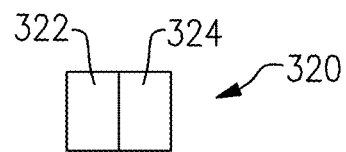
FIGS. 32A and 32B illustrate a plurality monitor devices paired with reference devices and laterally arranged as an array, according to embodiments.
Figure 32B:
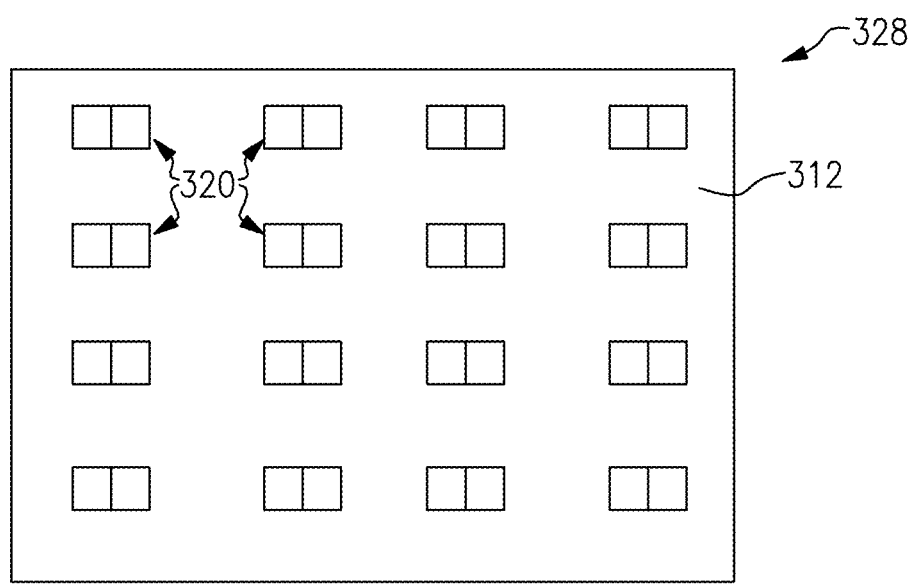

FIGS. 32A and 32B illustrate a plurality monitor device/reference device pairs 320 (FIG. 32A) that are laterally arranged as an array 328 (FIG. 32B), according to embodiments. The array 328 may be configured similarly to the array 310a/310b of FIG. 31, and the description of similar aspects will be omitted. However, unlike the array 310a/310b of FIG. 31, each monitor device 322 of the array 328 is paired with a reference device 324, whose arrangements and advantages for reasons described supra.

Figure 33A:
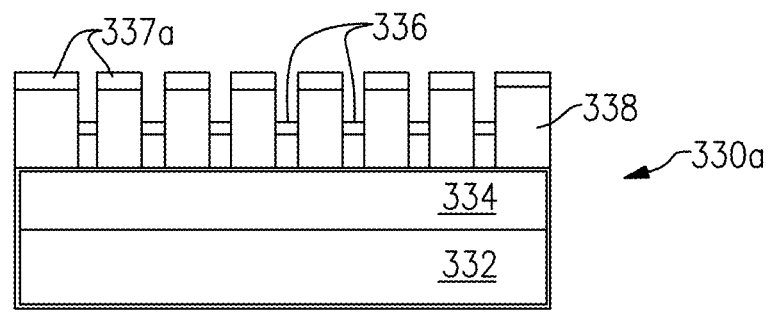
FIGS. 33A-33C illustrate a plurality of monitor devices that are laterally arranged as an array, according to embodiments.
Figure 33B:
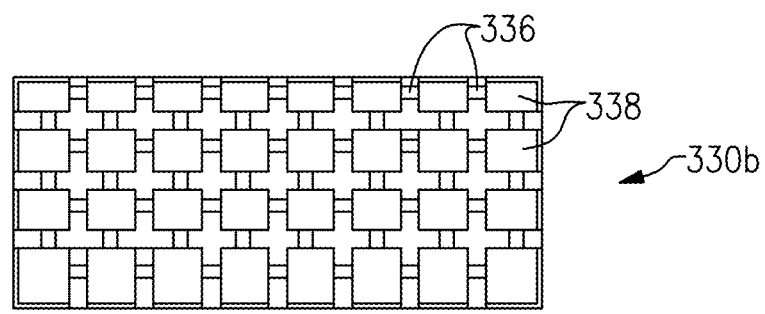

FIGS. 33A-33B illustrate a plurality of monitor devices that are laterally arranged as an array 330a (cross-sectional view)/330b (plan view) of monitor devices 338 formed over a substrate 332 and a diffusion barrier 334, according to embodiments. Similar to the array of wear-out monitor device described above with respect to FIG. 31, the array 330a/330b includes monitor devices 338 that are interconnected and communicatively coupled by electrical links or connections 336. The electrical links or connections 336 are configured to be intentionally exposed to conditions that may result in their corrosion and/or oxidation, and are formed of materials that can corrode/oxidize under such conditions. As a result, a system is created in which a discernible electrical change develops over time based on the corrosion/oxidation (and potentially the consumption of the links or connections 336 themselves). The array 330a/330b of FIGS. 33A-33B may be configured similarly to the array 310a/310b of FIG. 31, and the description of similar aspects will be omitted. Unlike the array 310a/310b of FIG. 31, however, at least some of the monitor devices 338 have formed thereon a passivation layer 337a, which can be a polymeric passivation layer or a dielectric passivation layer.

Figure 33C:
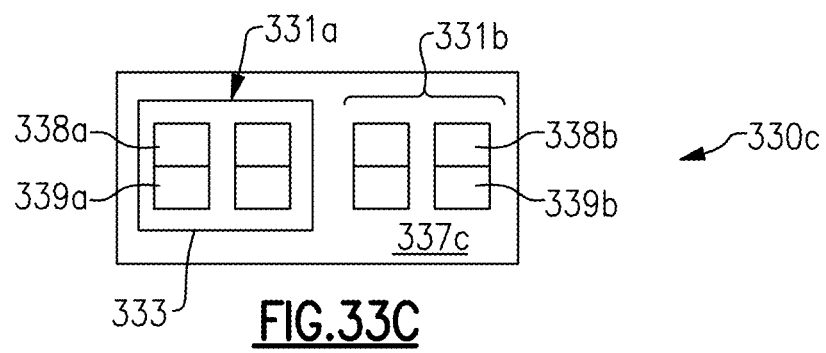

FIG. 33C illustrates another embodiment of an array 330c of monitor devices 338a in which, unlike the passivation layer 337a of FIG. 33A, the passivation layer 337c forms a blanket layer over a plurality of monitor devices 338a, except where openings 333 are formed through the blanket passivation layer 337c. In the illustrated embodiment, an array of monitor device/reference device pairs 331a/331b, which includes monitor devices 338a/338b and reference devices 339a/339b, similar to the monitor device/reference device pairs 320 of FIG. 32A, is illustrated. In the plan view of a portion of an array 330c, exposed pairs 331a are directly exposed to the environment, while unexposed pairs 331b remain covered by the passivation layer 337c. The illustrated array 330c may be particularly beneficial in monitoring environments where at least some of the monitor devices 338a and reference devices 339a are exposed to oxidizing or corroding environments as described supra, while others of the monitor devices 338b and reference devices 339b and of electrical links 336 are prevented from being exposed to oxidizing and/or corroding environments to preserve the integrity of the electrical interconnections between the monitor devices 338a/338b and the reference devices 339a/339b.

System in a Package Wear-Out Monitor

Figure 34:
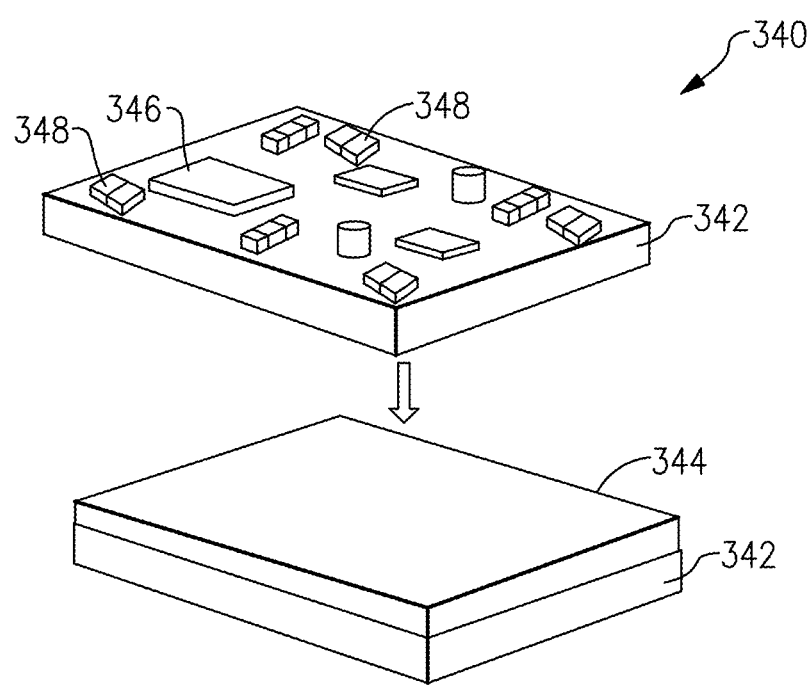
FIG. 34 is a diagram of a system in a package (SIP) or a system having embedded components that includes one or more wear-out monitor devices, according to embodiments

FIG. 34 is a diagram of a system in a package (SIP), or a system with embedded components embedded, e.g., systems with components embedded within a substrate(s). 340 that includes one or more wear-out monitor devices 348, according to embodiments. In the illustrated embodiment, the substrate 342 has formed thereon the wear-out monitor devices 348 in close proximity to core circuit devices 346 to be monitored, thereby providing a relatively accurate indications of the level of wear of the core circuit devices 346. For example, the wear-out monitor devices 348 can be disposed immediately adjacent to the core circuit devices 346. The die 342 and the other components can be encased within a single package to form the system 340. The monitor devices 348 can be disposed at a suitably specific location that may be a particular area of concern, e.g., suitably adjacent a high power device or a sensitive/critical processing device. The SIP 340 can include an over mold compound 344 that encapsulates the die 342 and other components. The SIP 340 can be configured such that signals can be communicated externally to and from the SIP 340 by the die 342 and/or the other components, for example, wirelessly or by being provided to an output contact of the SIP 340.

Electrical Overstress (EOS) and Electrostatic Discharge (ESD) Wear-Out Monitors Transient electrical events such as electrostatic discharge (ESD), electrical overstress (EOS) or electromagnetic compatibility (EMC) transients can cause wear-out of IC devices. As described herein transient electrical events are electrical events having a time duration less than DC regime. Without being bound to any theory, it has been predicted that there are three regimes of device failure due to transient electrical events. In the adiabatic regime, the duration of transient electrical events is of the order of <100 ns. Due to such short duration, there is little heat transfer and the time-to-fail roughly shows a 1/t correlation. In the thermal diffusion regime, the duration of transient electrical events is of the order of about 100 ns to about 10 ms. In this regime, heat transfer duration is of the order of heat transfer time and the time-to-fail roughly shows a $1/t^{1/2}$ correlation. In the DC/steady state regime, the duration of electrical events is greater than about 0.1/10 ms. In this regime, the device is in thermal equilibrium and the time-to-fail roughly shows no correlation with time. These regimes have been described in what is known as Wunch-Bell curve.

Various protection devices for protection against various transient electrical events can be incorporated into apparatuses as off-chip modules or be integrated on-chip, e.g., as part of a multi-die package with built-in protection. Various protection devices include a combination of PN diodes, BJTs and field-effect transistors. Using various configurations of wear-out monitor devices described above with respect to these and other devices, some protection devices can be used to monitor wear-out caused by transient electrical events. According to various embodiments herein, a wear-out monitor device can detect non catastrophic electrical overstress (EOS) events. Such functionality can monitor an IC with slightly lower breakdown than other circuits and provide wear-out information about the IC device.

FIGS. 35A and 35B illustrate schematic diagrams of ESD detection circuits 350a and 350b, respectively, according to embodiments. Each of the ESD detection circuits 350a and 350b includes a first ESD protection device 352 and a second ESD protection device 354.

The first ESD protection device 352 can include, e.g., a diode having a relatively low breakdown voltage and a relatively small physical area and the second ESD protection device 352 include, e.g., a diode having a relatively high breakdown voltage and a relatively large physical area. These ESD protection devices can include diodes, bipolar junction transistors and semiconductor-controlled rectifiers (SCRs). The first ESD protection device 352 can trigger at a lower voltage than the second ESD protection device 354. In an illustrative example, the first protection device 352 can trigger at, e.g., about 6.5 Volts and the second ESD protection device 354 can trigger at, e.g., about 7 Volts. The second ESD protection device 354 can handle more current than the first ESD protection device 352. In the illustrated embodiment of FIG. 35A, a resistor 355 (FIG. 35A) or a fuse 367 (FIG. 35B) is in series with the first ESD protection device 352, for example, to prevent thermal runaway and/or to provide a voltage for the detection circuit 356.

With the first ESD protection device 352, ESD events below the threshold for triggering the second ESD protection device 354 can be detected and associated data can be used to determine the wear-out of a component, device or a system. The ESD protection offered by the first ESD protection device 354 may not be sufficient to protect an internal circuit, but the ESD protection offered by the first ESD protection device 352 can provide a way to monitor what is happening in the second ESD protection device 354 without including a resistance, which should diminish the effectiveness of the second ESD protection device 3544, in series with the second ESD protection device 354.

The ESD detection circuits 350a and 350b can detect an ESD event using the voltage across the resistor 355 (FIG. 35A). Alternatively, the detection circuit 350b can blow the fuse 357 when an ESD event is detected. After a certain number of ESD events (e.g., 10 events) are detected, an alarm signal can be provided. For instance, the alarm signal can be toggled when all fuses can be blown and/or memory cells can overflow. The alarm signal can provide an alert to warn that a device has been aged by ESD events.

EOS detection circuitry can provide functional safety information at the die level and/or at a system level. At the die level, recording and monitoring EOS events can provide an indication of the functional safety of the die. Such information can be reported external to the die. An alarm signal can be provided external to the die to provide a warning about the functional safety of the die and/or to suggest that action be taken, such as replacement of the die. At the system level, detecting EOS events can provide information about functional safety at a system level. Such information can be used for predictive maintenance, for example.

Certain physical layouts of ESD protection devices can be implemented for high performance. The physical layouts discussed below can be implemented in connection with any of the EOS protection devices discussed herein. Example physical layouts are illustrated in FIGS. 36A to 36C.

Figure 37A:
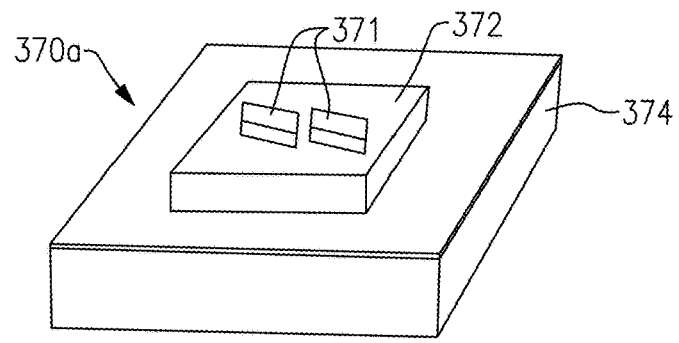
FIG. 37A-37C schematically illustrate vertically integrated systems that include one or more wear-out or corrosion monitor devices integrated with ESD protection and/or energy harvesting circuitry on a single chip, according to embodiments.

FIG. 36A provides an example of a physical layout of an ESD protection device 360. In FIG. 37A, the ESD protection device is an annular structure in plan view. This can enable relatively high current handling capability. Anode 362 and cathode 364 of the ESD protection device 360 can be provided around a bond pad 366. The weakest point of an ESD protection device can be at the end of a finger, even with increased spacings, resistances and/or curvature, as this is the location of that typically has the highest electric field. An annular ESD silicon controlled rectifier (SCR) can be used for system level ESD protection to mimic a circular device enclosing a bond pad. Such a SCR can include any combination of features described in U.S. Pat. No. 6,236,087, the entire technical disclosure of which is hereby incorporated by reference herein.

An annularly shaped ESD protection device in plan view can have a relatively large perimeter area and hence a relatively large cross sectional area through which the current can flow. As one example, the perimeter can be about 400 µm and the diode junction can be about 3 µm deep, thus the cross section area can be about 1200 µm². Additionally, with the annular structure, metal can come out from a bond pad on four sides. This can combine to substantially minimize the resistance to an ESD zap and hence the voltage experienced by sensitive circuitry internal in the chip can be substantially minimized. Another approach that may provide an even lower resistance path to an ESD zap is a pure vertical diode where the conduction is vertically down through the silicon. In such a diode, for a 100 µm by 100 µm pad, the cross section area is 10,000 µm² and the metal resistance can also be relatively small as there can be a thick low resistance metal paddle on one side and a low resistance bond wire in close proximity on the other side.

In some instances, an ideal ESD device can be circular, as substantially the same electric field can be present along the entire a junction in such a structure. Circular ESD device layouts may not be area efficient and/or an inner anode can be smaller in junction area than an outer cathode. Circular ESD device layouts can conduct larger currents than some other common ESD layouts that consume approximately the same area. Circular ESD device layouts can conduct relatively large currents, such as currents associated with EOS events. Accordingly, such ESD device layouts can be desirable in certain applications in which an ESD device is used to harvest energy associated with an EOS event.

FIG. 36B provides an example of a physical layout of an ESD device 361. The physical layout of the ESD device 361 is a relatively large circular shape in plan view. This can reduce the difference between junction area between the anode 362 and the cathode 364.

FIG. 36C provides an example of a physical layout of an ESD device 368. The ESD device 368 is implemented by a relatively dense array of smaller circular ESD devices 369. The smaller circular ESD devices 369 can be butted against each other laterally and/or vertically. An array of smaller circular ESD devices 369 can be implemented in wearable computing devices such as smart watches, for example.

FIG. 37A is a schematic diagram of a vertically integrated system 370a that includes one or more wear-out or corrosion monitor devices 371 integrated with an ESD protection and/or energy harvesting circuitry on a single chip, according to embodiments. A combined ESD protection and storage chip 372 with the one or more wear-out monitor device includes, in addition to circuitry capable of harnessing energy from ESD events and storage elements configured to store charge associated with the ESD events, circuitry for sensing the wear out level of the system or components of the system. The combined chip 372 can be stacked with an ASIC 374. Combining the ESD protection devices and storage elements in a single die can reduce height of the vertically integrated system relative to two separate die stacked in a pyramid configuration. Combining the ESD protection devices and storage elements in a single die can reduce the length and/or resistance of a path from a surge conduction point and storage elements relative to two separately stacked die. The ASIC 374 can receive charge from storage elements of the combined chip 372. Having the energy harvesting circuitry on a different chip than the ASIC can allow EOS protection devices, such as ESD protection devices, to be scaled up to store charge from larger EOS events, such as larger ESD events. It will be appreciated that the one or more wear-out or corrosion monitor devices 371 can be integrated within any SIP (System in package) or system independently to monitor or measure different stress conditions, e.g., temperature, voltage, etc., as discussed elsewhere herein.

Figure 37B:
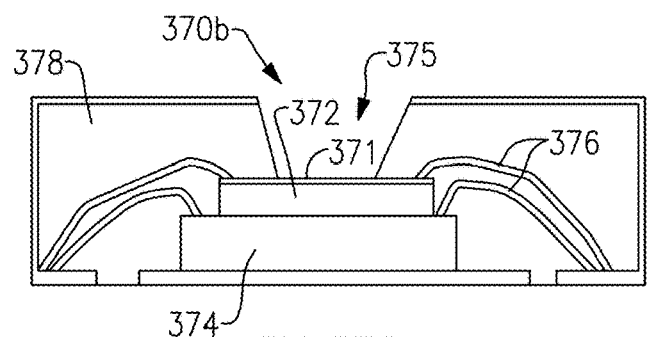

FIG. 37B is a cross-sectional view 370b of a fully packaged vertically integrated system 370a illustrated in FIG. 37A. The cross-sectional view 370a shows an opening (or an aperture, a conduit or a path) 375 formed through a packaging material (or a barrier or an encapsulant) 378 such that air or moisture can directly contact the wear-out or corrosion monitor device 371. The combined chip 371 and the ASIC main die are electrically connected to each other and externally through wire bonding 376, or some other suitable electrical connection or a conductive path.

Figure 37C:
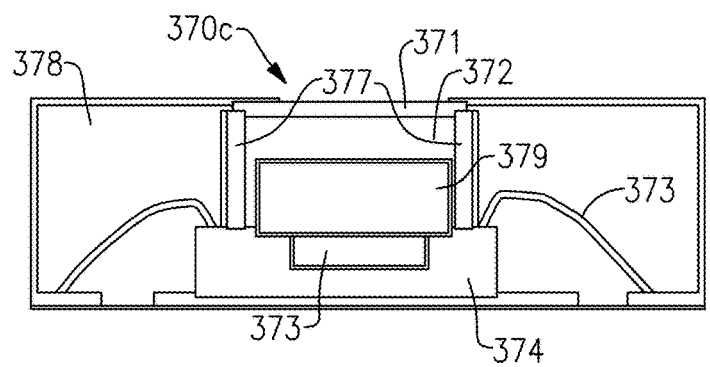

FIG. 37C is a cross-sectional view a fully packaged vertically integrated system 370c similar to that of the system 370a/b of FIGS. 37A/37B, except the system 370c additionally includes micro electro mechanical sensor (MEMS) 373 electrically connected to the sensor die. In addition, unlike the system 370a/b of FIGS. 37A/37B, the system 370c additionally includes a plurality of through-silicon vias (TSVs) 377 electrically connecting a wear-out or corrosion monitor device 371 to an ASIC 374 (or a processing die within a system) that is physically separated from the MEMS 373 and/or the ASIC 374 by a cavity 379. By separating the monitor device 371 from the MEMS 373 and/or the ASIC 374, the circuitry of the monitor device 371 could be selectively exposed, e.g., through openings formed at the package/module/system level. Advantageously, by doing so, the monitor device 371 can be kept separated from the ASIC 374, and can be configured to be exposed to higher temperatures and/or harsher environments. In the illustrated embodiment, the cavity 379 is formed by etching a portion of the substrate of the monitor device 371 such that the cavity overlaps with the MEMS 373. However, embodiments are not so limited and other suitable processes can be used to dispose the cavity 379 between the monitor device 371.

The combined chip 372 and the ASIC main die are electrically connected to each other and externally through wiring 376. The combined chip 372 can be electrically connected by one or more through-silicon vias (TSV's) 377 as illustrated, or using wire bonding 376 as illustrated in FIG. 37B.

Diffusion-Enhancing Monitor Device Structures

For some applications, it may be desirable to monitor effects of mechanical wear-out stress on core devices. In some applications, the core device to be monitored may be a static device under stress, e.g., a transistor device under a stress from adjacent shallow trench isolation or a semiconductor device under a stress from a flexible substrate on which it is formed. In other applications, the core device to be monitored may be may be a dynamic device, e.g., a micro electro mechanical system (MEMS) device. For these applications, it can be desirable to monitor wear-out stress arising from such mechanical wear-out stress.

Under some circumstances, mechanical stress can cause changes in diffusion rate of dopant atoms. FIGS. 38A-38E illustrate various embodiments of wear-out monitor devices that are formed in or on a flexible substrate such that wear-out stresses associated with mechanical deformation can be monitored, e.g., by utilizing mechanical stress-enhanced diffusion of monitor atoms. Each of monitor devices 380*a*-380*e* has a plurality of doped regions formed in a flexible substrate 383. The plurality of doped regions may form an array. The flexible substrate 382 can be formed of a flexible material, e.g., flexible polymeric materials, or a semiconductor/dielectric substrate that has been substantially thinned, e.g. to less than about 500 μm such that the semiconductor/dielectric substrate is flexible. The substrate 382 may be doped, e.g., lightly doped, with a first dopant type, or be undoped. The monitor device is configured such that a mechanical deformation caused by, e.g., bending or deflection, results in an electrical signatures associated with the wear-out stress such as fatigue. In some embodiments, the substrate 382 may include or at least be partially formed of materials such as piezoelectric materials to convert the mechanical deformations into electrical signals.

Figure 38A:
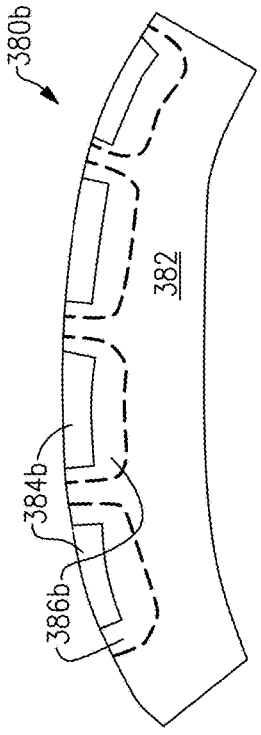
FIGS. 38A-38E illustrate various embodiments of wear-out monitor devices formed in or on a flexible substrate for monitoring wear-out stresses associated with mechanical deformation, according to embodiments.
Figure 38B:
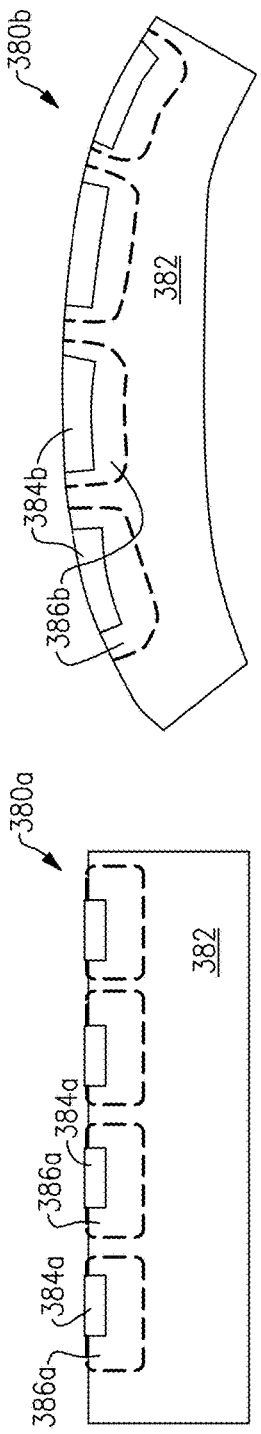

FIGS. 38A and 38B illustrate a wear-monitor device 380*a*/380*b* before (FIG. 38A) and after (FIG. 38B) the substrate 382 has undergone bending, according to embodiments. The monitor devices 380*a* and 380*b* each has a plurality of doped regions 384*a* and 384*b*, which can be doped with a second dopant type. When the substrate 382 is doped with a first dopant type, a PN junction is formed, such that depletion regions 386*a* and 386*b* are formed, which can be used for detecting diffused monitor atoms, as described with respect to various embodiments described supra. As described above, the doped regions 384*a* and 384*b* may include monitor atoms that are adapted to diffuse into the underlying substrate, e.g., into the depletion region. In some embodiments, the monitor atoms may be formed on the doped regions 384*a* and 384*b*, while in other embodiments the monitor atoms may be formed in addition to, or to at least partially replace the dopants of the doped region that is doped with the second dopant type. In operation, bending of the monitor device 380*a* into a bent monitor device 380*b* as shown in FIG. 38B results in the doped regions 384*b* being placed under either a tensile strain as shown, or under a compressive strain when bent in an opposite direction (not shown). The tensile or compressive strain may change the rate of the diffusion of monitor atoms into the underlying substrate material, whose change can be detected using the sensing circuit, as described supra.

Figure 38C:
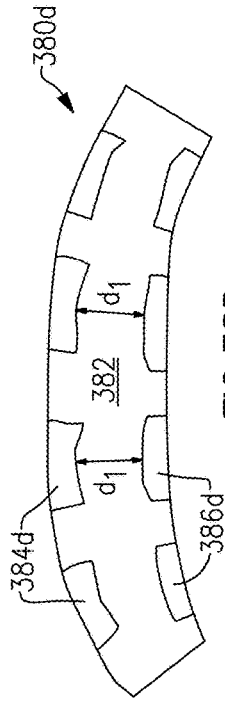

FIG. 38C illustrates another wear-monitor device 380*c* that is configured for monitoring stresses associated with mechanical deformation, according to embodiments. Similar to the wear-out device 380*a*/380*b* of FIGS. 38A/38B, the wear-out monitor device 380*c* has a plurality of doped regions 384*c* in a flexible substrate 382. However, unlike the wear-out monitor device 380*a*/380*b*, the doped regions 384*c* are merged to form a plurality of connected doped regions 384*c* and a corresponding depletion region 386*c*.

Figure 38D:
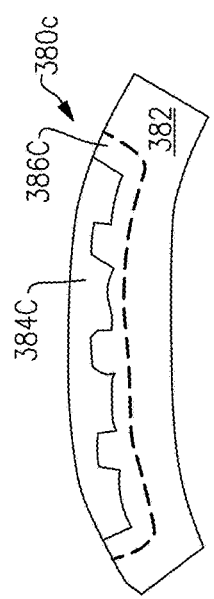
Figure 38E:
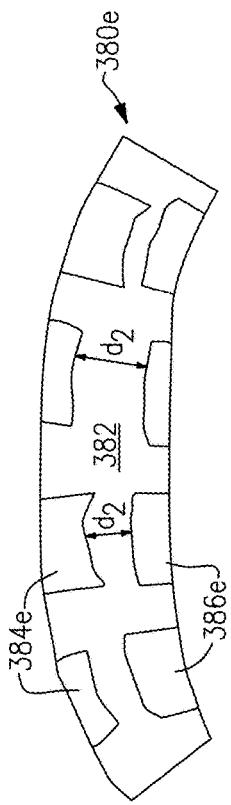

FIGS. 38D and 38E illustrates additional embodiments of wear-out monitor device 380*d* and 380*e* that are configured for monitoring stresses associated with mechanical deformations, according to embodiments. Similar to the wear-out device 380*a*/380*b* of FIGS. 38A/38B, the wear-out monitor devices 380*c* and 380*d* have a plurality of first doped regions 384*d* and 384*e*, respectively, in a flexible substrate 382. However, unlike the wear-out monitor device 380*a*/380*b*, the wear-out monitor devices 380*d* and 380*e* have a plurality of second doped regions 386*d* and 386*e* in a flexible substrate 382. The second doped regions 386*d* and 386*e* may be oppositely doped compared to the first doped regions 384*e* and 384*e* and configured as a punch-through monitor, as described supra with respect to FIGS. 11A and 11B. In some embodiments, as illustrated in FIG. 38D, laterally adjacent first doped regions 384*d* and laterally adjacent second doped regions 386*d* may have similar or varying dopant concentrations while having similar depths such that the vertical separation distances $d_1$ between corresponding first and second doped regions 384*d* and 386*e* is relatively constant. In some other embodiments, laterally adjacent first doped regions 384*e* and laterally adjacent second doped regions 386*e* may have similar or varying dopant concentrations and different depths such that the vertical separation distances $d_2$ between corresponding first and second doped regions 384*e* and 386*e* are varying, as illustrated and in the wear-out monitor device 380*e* of FIG. 380E.

For some applications, it may be desirable to monitor wear-out effects resulting from electric field enhancement of certain device structures. In some applications, the core device to be monitored may have structural features that having relatively sharp features, such that electric field is enhanced compared to adjacent regions. Furthermore, such enhancement of electric field can lead to EOS/ESD events, which can in turn produce lattice defects in semiconductor materials, through which the rate of atomic diffusion can be substantially enhanced. Thus, for various applications, it is be desirable to monitor wear-out stress arising from such field-enhancement effects.

Figure 39A:
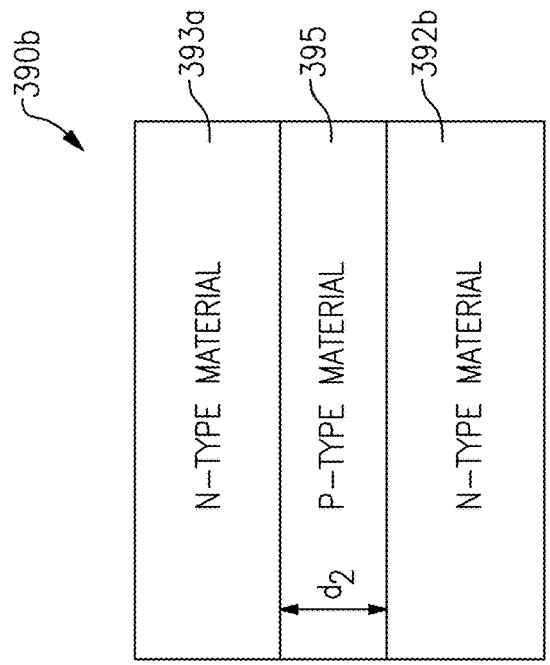
FIG. 39A illustrates a wear-out monitor device having one or more serrated structures for monitoring wear-out stresses associated with electric field enhancement, according to embodiments.

FIG. 39A illustrates a wear-out monitor device 390*a* having one or more serrated structures 392*a* that can serve as electrodes under an electric field. In some embodiments, upper and lower serrated structures 392*a* and 392*b*, respectively, are formed of a first material, which can be a semiconductor material or a conductive material. The serrated structures 392*a*/392*b* are interposed by an interposed structure 394 formed of a second material, which can be a semiconductor material or a dielectric material. In the illustrated embodiment, the first material comprises a semiconductor material doped with a first dopant type, e.g., n-type, and the second material comprises a semiconductor material dope with a second dopant type, e.g., p-type. The wear-out monitor device 390*a* of FIG. 39A includes monitor atoms, which can be present in either of the serrated structure 392*a* or the interposed structure 394, where the monitor atoms are configured to diffuse in the wear-out monitor device 390*a*. The serrated structures 392*a*/392*b* comprise a plurality of field-enhancement regions 396 that are configured to enhance electric field when an electric field is applied between the upper and lower serrated structures 392*a*/392*b*. In the illustrated embodiment, a gap $d_1$ and/or radii of curvature between different pairs of opposing field-enhancement regions 396 can vary, such that different pairs can be subject to a discharge event, e.g., EOS/ESD events, under different electric field values. When one or more EOS/ESD events occur between pairs of opposing field-enhancement regions 396, certain lattice defects 398, e.g., stacking faults or dislocations, can form, thereby providing an enhanced diffusion paths for monitor atoms. In operation, by applying an electric field between the upper and lower serrated structures 392*a*, an EOS/ESD event can be induced therebetween, leading to enhanced atomic diffusion of monitor atoms, e.g., through lattice defects 398 in the serrated structures 392*a*/392*b*. A level of wear-out of a monitored structure, e.g., in the core circuit, can be determined therefrom, as described above.

Figure 39B:
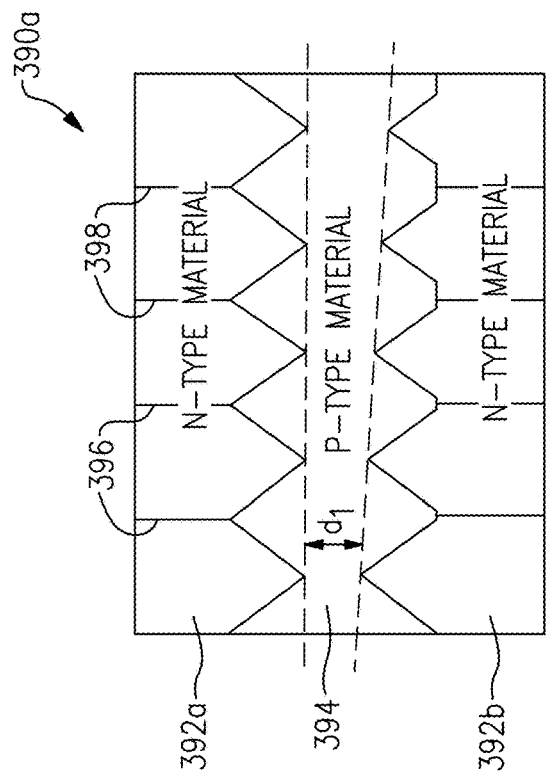
FIG. 39B illustrates a reference device for the wear-out monitor device of FIG. 39A, according to embodiments.

In some embodiments, a reference device 390*b* illustrated in FIG. 39B can be provided with the wear-out monitor device 390*a* of FIG. 39A. Unlike the monitor device 390*a*, the reference device 390*b* comprises upper and lower regions 393*a* and 393*b*, respectively, formed of the same material as the serrated structures 392*a*/392*b* of the monitor device 390*a* (FIG. 39A), and an interposed structure 395 formed of the same material as the interposed structure 394 of the monitor device 390a (FIG. 39A). In operation, by applying a similar electric field between the upper and lower structures 393a and 393b as the electric field applied between upper and lower serrated structures 392a and 392b, an EOS/ESD event can be induced between upper and lower serrated structures 392a and 392b, while a similar EOS/ESD event is not induced between upper and lower structures 393a and 393b. Therefore, the level of wear-out of a monitored structure, e.g., in the core circuit, can be determined, as described above.

FIG. 40 is an illustration of a wear-out monitor device 400 comprising monitor atoms that are configured to diffuse in a semiconductor material and configured such that a stress condition causes a change in the rate at which the monitor atoms diffuse in the semiconductor substrate 450, according to embodiments. The wear-out monitor device includes, laterally on one or both sides, isolation regions 401a, e.g., shallow trench isolation regions. The wear-out monitor device additionally includes a buried layer 401b, which may be a buried oxide layer 401b, such as a buried oxide (BOX) of a silicon-on-insulator (SOI). Thus, the device 400 may be electrically isolated from surrounding regions by the isolation regions 401a and the buried layer 401b. In some embodiments, the semiconductor substrate 450 may at least an upper portion in which various doped regions are formed, which may be an epitaxial region. The illustrated wear-out monitor device 400 additionally comprises a buried layer region 462 vertically above the buried oxide layer 401b and laterally extending between the isolation regions 401a. The wear-out monitor device 400 additionally includes a first doped region 458 formed within the semiconductor substrate 450 and may or may not be in contact with the buried layer region 462. The substrate 450, the buried layer region 462 and the first doped region may be doped with the same dopant type, according to some embodiments. For example, the substrate 450 may doped with a first dopant type, which may be an n-type dopant or a p-type dopant, at a first concentration. The first doped region 458 may be doped with the first dopant type at a higher concentration relative to the substrate 450. Similarly, the buried layer region 458 may be doped with the first dopant type at a higher concentration relative to the substrate 450. In the illustrated embodiment, each of the substrate 450, the first doped region 458 and the buried layer region 462 are doped with an n-type dopant.

The wear-out monitor device 400 includes a first heavily doped region 454a doped with the first dopant type. In the illustrated embodiment of FIG. 40, the first doped region 454a is a heavily doped n-doped (n+) region. The wear-out monitor device 400 additionally includes a second doped region 454b that is doped with a second dopant type opposite to the first dopant type. In the illustrated embodiment, the second doped region 454b is an p-doped region, e.g. a heavily doped (p+) region.

In the illustrated embodiment, a portion of the substrate 450 forms an intervening region which laterally separates the first and second doped regions 454a and 454b such that is doped either with the first or second dopant types, at a concentration substantially lower than the first or second heavily doped regions 454a or 454b. In the illustrated embodiment, the intervening region is an n-doped region. Thus, the wear-out monitor device 400 can include first and second heavily doped regions 454a and 454b and the first doped region 458 and the substrate 450 intervening the first and second doped regions 454a and 454b such that a PN junction comprising, e.g., p+ second heavily doped region 454b/the substrate 450/the first doped region 458/n+ first heavily doped region 454a formed of P+/N−/N/N+ regions, in one example embodiment. However, it will be appreciated that various doped regions of the wear-out monitor device 400 are illustrated by way of example only, and other embodiments are possible, where each of the p+ second heavily doped region 454b, the substrate 450, the first doped region 458 and n+ first heavily doped region 454a is doped to form any one of P$^+$, P, P$^-$, N$^+$, N or N$^-$ regions, such that a PN junction is formed.

In the wear-out monitor device 400 of FIG. 40, the first and second doped regions 454a and 454b are formed by implanting respective dopants through openings formed in the dielectric layer 463; however, embodiments are not so limited. For example, other masking (e.g., photoresist) and doping (e.g., diffusion) techniques may be used in lieu or in addition to using the dielectric layer 463 as an implantation mask.

Still referring to FIG. 40, the wear-out monitor device 400 additionally includes a first electrode 408a and a second electrode 408b formed over the first heavily doped region 454a and over the second heavily doped region 454b, respectively, through openings in dielectric layer 463. One or both of the first and second electrodes 408a and 408b comprise or is formed of the monitor atoms, and serves as a reservoir of the monitor atoms, as described supra. In the illustrated embodiment, the first electrode 408a and a second electrode 408b are formed on first adhesion layer 412a and a second adhesion layer 412b, respectively. As described supra with respect to FIGS. 6A/6B, the adhesion layers 412a, 412b can enhance adhesion of the first and second electrodes 408a, 408b. One or both of the first and second electrodes 408a and 408b are configured such that, when the wear-out monitor device is subjected to a set of predetermined conditions for a predetermined duration, some of the monitor atoms in the respective electrodes diffuse thorough the respective first and second heavily doped regions 454a and 454b into a depletion formed thereunder. Depending on the concentration and/or depth of the diffused monitor atoms in the underlying semiconductor material, e.g., in the depletion region, a cumulative wear-out history, e.g., a cumulative thermal wear-out history, of the monitor device 400 can be at least indirectly determined.

Thus, as configured, the wear-out monitor device 400 has one or more reservoirs of monitor atoms (i.e., first and/or second electrodes 408a, 408b) disposed on a surface of the substrate and a monitor region (e.g., depletion region formed underneath the second heavily doped region 454b) formed in the substrate 450. The monitor atoms have diffusion characteristics in the semiconductor material of the substrate such that when the wear-out monitor device is subjected to a set of predetermined stress conditions for a predetermined duration, some of the monitor atoms diffuse into the monitor region. The reservoir can include, e.g., an electrode containing the monitor atoms or a layer formed of the monitor atoms. The monitor region can include a region in the substrate, e.g., a depletion region formed by a PN junction as described above, for example.

Various embodiments of the wear-out monitor device including the wear-out monitor device 400 of FIG. 40 are configured such that an electrical property, or an electrical signature, associated with the presence of the monitor atoms in the monitor region can be measured. The electrical signature can be, for example, any one or more of: junction leakage, junction capacitance, junction built-in potential, junction reverse recovery time, bipolar base transit time (fT), metal-oxide-semiconductor (MOS) transistor threshold voltage, MOS transistor subthreshold swing, MOS channel leakage, punch-through breakdown voltage (BV) and impact ionization breakdown voltage (BV), to name a few.

Figure 41A:
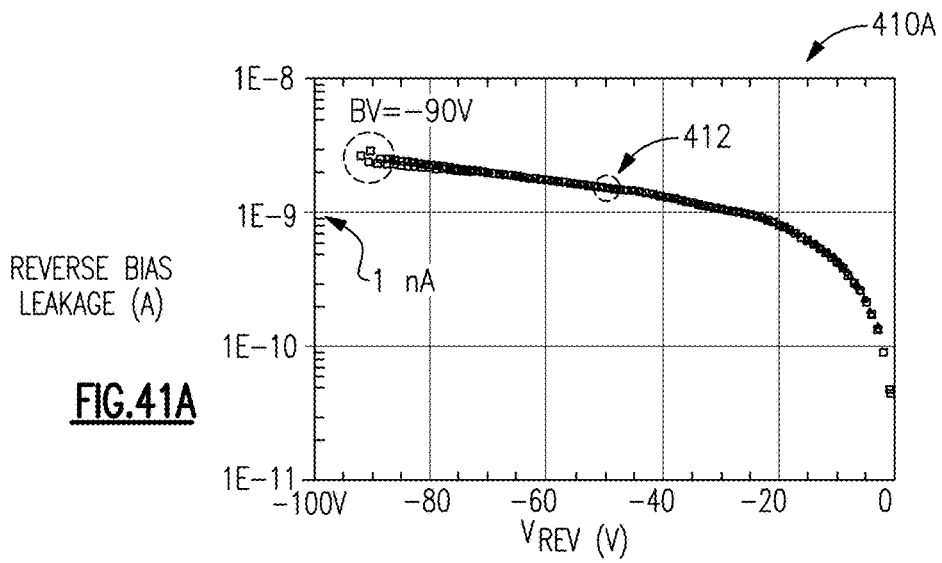
FIG. 41A is a graph showing experimental current-voltage curves under reverse bias and breakdown under reverse bias of fabricated wear-out monitor devices similar to the device schematically illustrated in FIG. 40.

FIG. 41A illustrates a graph 410A showing experimental current-voltage (IV) curves 412 under reverse bias and breakdown under reverse bias of fabricated wear-out monitor devices similar to the device schematically illustrated in FIG. 40. The IV curves 412 are those of 50 different as-fabricated devices, indicating a high degree of device-to-device uniformity in electrical performance, as indicated by similar breakdown voltages (BV) and leakage currents between different devices.

Figure 41B:
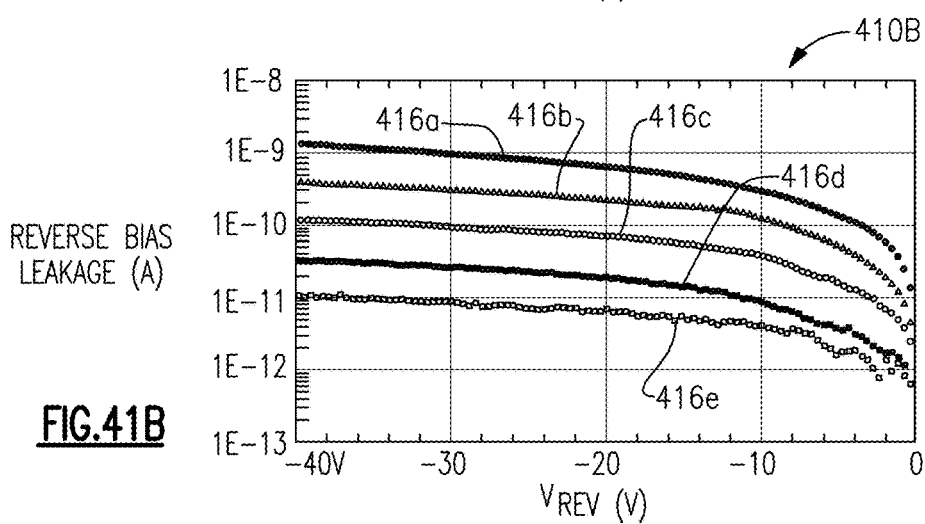
FIG. 41B is a graph showing experimental current-voltage curves under reverse bias of a fabricated wear-out monitor device similar to the device schematically illustrated in FIG. 40, after being subject to different durations of thermal stress at 200° C.

FIG. 41B illustrates a graph 410B showing experimental current-voltage (IV) curves under reverse bias of a fabricated wear-out monitor device similar to the device schematically illustrated in FIG. 40, after being subject to different durations of thermal stress at 200° C. In particular, the IV curves 416a-416e represent measurements taken after various bake times, including as fabricated (416e), after baking for approximately 1 day (416d), after baking for approximately 2 days (416c), after baking for approximately 3 days (416b) and after baking for approximately 4 days (416a), As illustrated, the leakage current increases with increasing bake time.

Figure 41C:
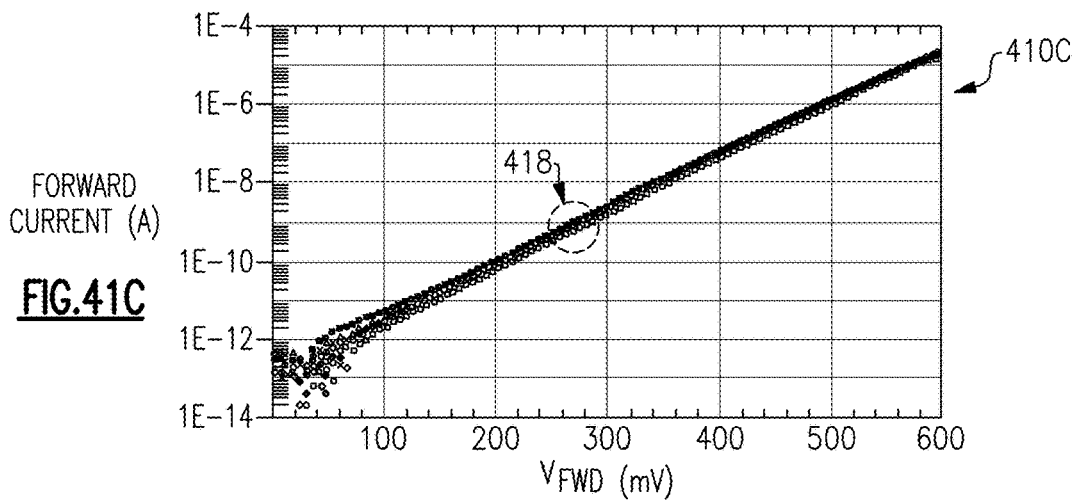
FIG. 41C is a graph showing experimental current-voltage curves under forward bias of a fabricated wear-out monitor device similar to the device schematically illustrated in FIG. 40.

FIG. 41C illustrates a graph 410C showing experimental current-voltage curves under forward bias of a fabricated wear-out monitor device similar to the device schematically illustrated in FIG. 40. In particular, the IV curves 418 represent overlapping measurements under a forward bias, taken after various bake times, including as-fabricated and after baking for approximately 1 day to 4 days, corresponding to IV curves (416e-416a) of FIG. 41B under reverse bias.

Figure 42A:
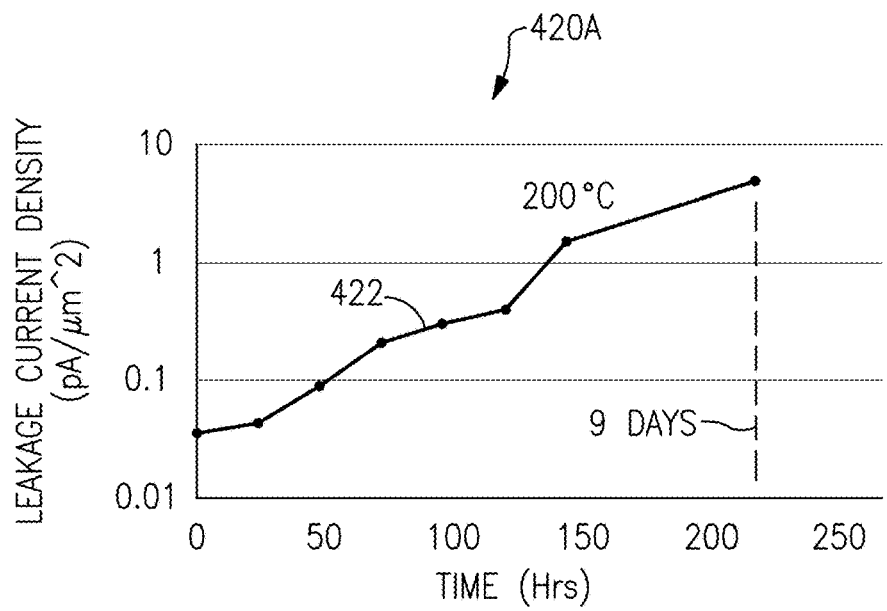
FIG. 42A is a chart plotting experimental leakage currents under reverse bias of a fabricated wear-out monitor device similar to the device schematically illustrated in FIG. 40, after being subject to different durations of thermal stress at 200° C.

FIG. 42A illustrates a chart 420A plotting experimentally measured leakage currents under reverse bias of a fabricated wear-out monitor device similar to the device schematically illustrated in FIG. 40, after being subjected to different durations of thermal stress at 200° C. The chart 420A shows a plot 422 of experimental leakage current measured at 5 V after being subject to different durations of thermal stress at 200° C. In particular, the plot 422 plots measurements taken after various bake times, including as fabricated and after baking for approximately 1-9 days. As illustrated, the leakage current increases with increasing bake time.

Figure 42B:
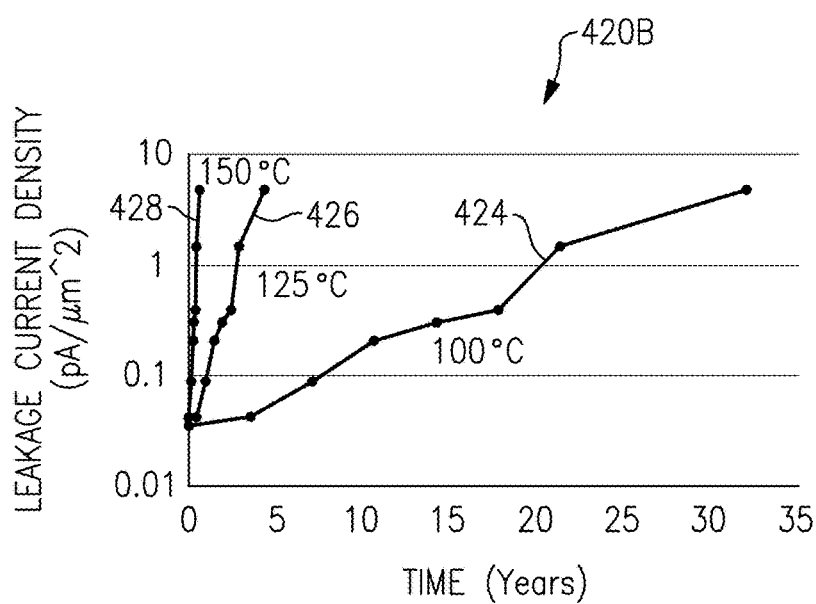
FIG. 42B is a chart plotting calculated leakage currents under reverse bias of a fabricated wear-out monitor device similar to the device schematically illustrated in FIG. 40, after being subject to different durations of thermal stress at different temperatures.

FIG. 42B is a chart 420B plotting calculated leakage currents under a reverse bias after being subjected to different durations of thermal stress at different temperatures, based on the chart 420A of FIG. 42A which plots experimentally measured leakage currents of a fabricated wear-out monitor device similar to the device schematically illustrated in FIG. 40. In particular, the chart 420B shows calculated plots 424, 426 and 428, whose calculations are based on the experimental leakage currents illustrated above with respect to the plot 422 of FIG. 42A, which represents measurements taken after various bake times, including as fabricated and after baking for approximately 1-9 days. For example, without being bound to any theory, the leakage current density as a function of bake time can be calculated based on an expression that can be derived analogously to a time-dependent diffusion equation based on Fick's Second Law, for example. Based on such expression, experimentally determined time dependence of leakage current at one bake temperature can be used to predict the time dependence of leakage current at other bake temperatures. As illustrated, the leakage current increases at a faster rate with increasing bake temperature.

Figure 42C:
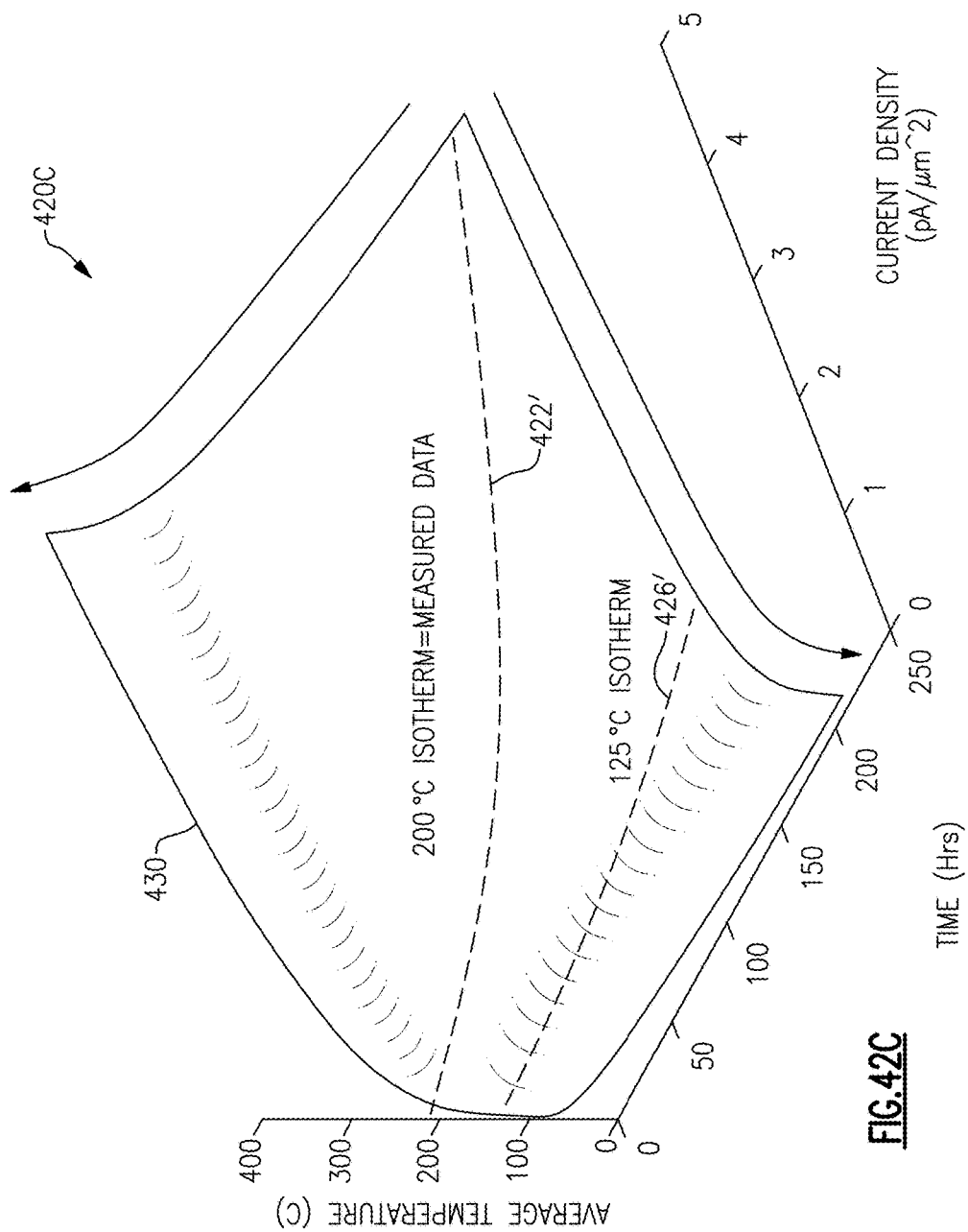
FIG. 42C is a contour chart plotting leakage currents under reverse bias of a fabricated wear-out monitor device similar to the device schematically illustrated in FIG. 40, as a function of different durations and temperatures of thermal stress.

FIG. 42C is a contour chart 420C plotting leakage currents under a reverse bias after being subjected to different durations of thermal stress at different temperatures, based on the chart 420A of FIG. 42A, which plots experimentally measured leakage currents, and based on the chart 420B of FIG. 42B, which plots calculated leakage currents, of a fabricated wear-out monitor device similar to the device schematically illustrated in FIG. 40. Based on such a contour plot, a predictive time and temperature dependence of leakage current can be determined for any temperature range and any time range in which the diffusion of monitor atoms is expected to follow a predictive behavior, as discussed supra.

Wear-Out Monitor Devices Configured with Controlled Activation

As described above, the wear-out monitor devices according to various embodiments have monitor atoms whose rate of diffusion changes in response to stress conditions. As described above, wear-out monitor devices based on atomic diffusion have many advantages, including the ability to monitor wear out of a core circuit regardless of whether the core circuit and/or the wear-out monitor device is activated, because atomic diffusion can occur independent of whether the core circuit and/or the wear-out monitor device is activated. However, for some applications, it may be desirable to control the timing of a starting point of monitoring. In the following, embodiments of wear-out monitor devices are described, in which the starting point or the time of initiation of the diffusion the wear-out monitor device can be controlled by, e.g., preventing or limiting the atomic diffusion until the wear-out device is initialized or activated by using, e.g., a voltage pulse or a current pulse to a diffusion region having the diffusant. Various embodiments disclosed below address these and other needs.

Figure 43A:
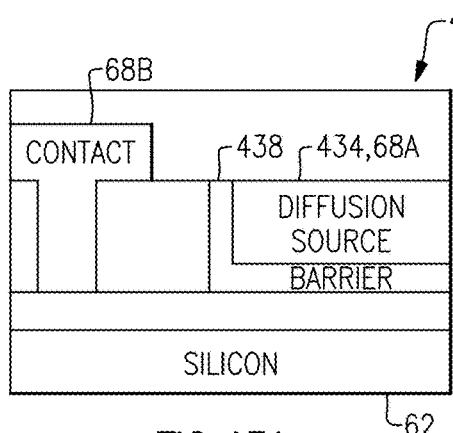
FIG. 43A illustrates a wear-out monitor device configured to record an indication of wear out of a core circuit based on localized atomic diffusion of monitor atoms, where the device has a reservoir of monitor atoms that is separated from the substrate by a barrier, according to embodiments.
Figure 43B:
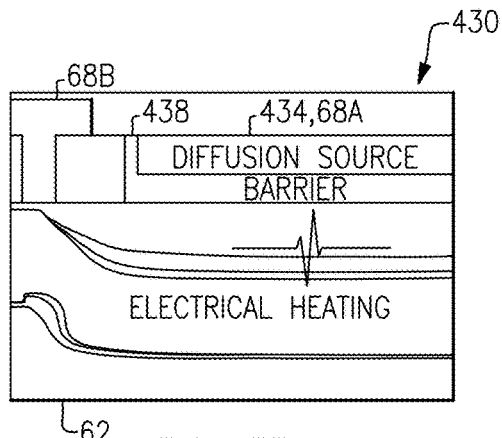
FIG. 43B illustrates a simulation of Joule-heating caused by an electrical stimulus applied to the wear-out monitor device illustrated in FIG. 43A, according to embodiments.

FIG. 43A illustrates a wear-out monitor device 430 configured to record an indication of wear out of a core circuit based on atomic diffusion of monitor atoms that is localized within the wear-out monitor device, according to embodiments. FIG. 43B illustrates a close-up view of the monitor device 430 of FIG. 43A. In particular, the wear-out monitor device 430A/430B comprises a first region, e.g., a reservoir 434 comprising the monitor atoms that is separated from a second region, e.g., a substrate 62, by a barrier 438. The wear-out monitor device is configured such that the monitor atoms diffuse through the barrier and into to the second region in response to an electrical stimulus. The monitor device has monitor atoms having a diffusion activation energy in the substrate that is between about 0.5 eV and about 3.5 eV, according to embodiments. Similar to the monitor device 60 described above with respect to FIGS. 6A and 6B, the wear-out monitor device 430 comprises a semiconductor substrate 62 and monitor atoms configured to diffuse therein, wherein the monitor atoms are configured such that a stress condition causes a change in the rate at which the monitor atoms diffuse in the semiconductor substrate 62. Various regions of the monitor device The wear-out monitor device 430 includes a first doped region 64 doped with a first dopant type, which can be n-type or p-type. In the illustrated embodiment, the first doped region 64 is a heavily doped p-doped region, e.g., a heavily doped (p$^+$) region.

The wear-out monitor device 430 additionally includes a second doped region 66 that is doped with a second dopant type opposite to the first dopant type, i.e., p-doped when the first doped region 64 is n-doped, and vice versa. In the illustrated embodiment, the second doped region 66 is an n-doped region, e.g. a heavily doped (n+) region.

The wear-out monitor device 430 additionally includes the reservoir 434 of the monitor atoms. In some embodiments, the reservoir 434 serves as a first electrode 68a contacting the first doped region 64, in a similar manner as described above with respect to FIGS. 6A/6B. In these embodiments, the wear-out monitor device 430 additionally includes a second electrode 68b (not shown) contacting and the second doped region 66. In some other embodiments, the reservoir 434 does not serve as an electrode. In these embodiments, the monitor device 430 further includes a first electrode 68a contacting the first doped region 64 and a second electrode 68b contacting the second doped region 66, where the reservoir 434 containing the monitor atoms may be disposed between the first and second electrodes 68a and 68b. A detailed description of various other structural features of the wear-out monitor device 430 that are similar to corresponding features of the wear-out monitor device 60 of FIG. 6A/6B, is omitted herein.

The reservoir 434 can be formed of various materials that incorporate the monitor atoms. For example, when configured as the first electrode 68a, the reservoir 434 can be similar to the first electrode 68a described above with respect to FIGS. 6A/6B, e.g., with respect to an electrically conducting composition that comprises or is formed of the monitor atoms and serves as a reservoir of the monitor atoms. However, in embodiments where the reservoir 434 does not or need not serve as an electrode, the composition of the reservoir 434 need not be electrically conducting. For example, the monitor atoms can be formed of or include an electrically insulating material which contains, is impregnated with, is doped or otherwise is saturated with the monitor atoms such that while serving as a reservoir, the reservoir 434 itself need not be electrically conducting. For example, the reservoir 434 can be formed of or include a dielectric material (e.g., oxides, nitrides, polymers, etc.) or be formed of or include a semiconductor doped with a relatively low concentration of electrically active dopants.

As a further difference from wear-our monitor devices illustrated above, the reservoir 434 may be separated from the semiconductor substrate 62 by the barrier 438. In the illustrated embodiment, the barrier 438 is interposed between the reservoir 434 and the substrate 62 and encloses the reservoir 434. As formed, the barrier 438 is a physical barrier formed of a material that blocks diffusion of the monitor atoms from the reservoir 434 to the substrate 62 without being altered.

Figure 44A:
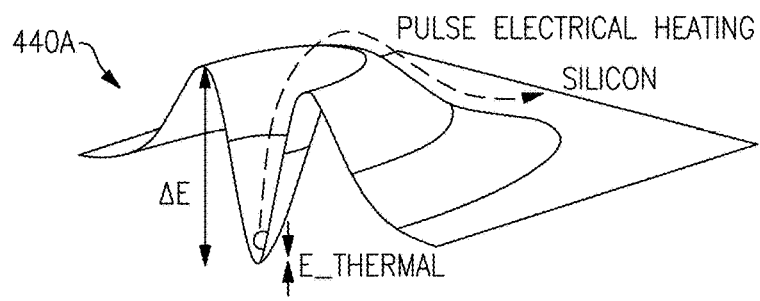
FIG. 44A illustrates a schematic three-dimensional energy-space diagram illustrating activation energy levels for a monitor atom, according to embodiments.
Figure 44B:
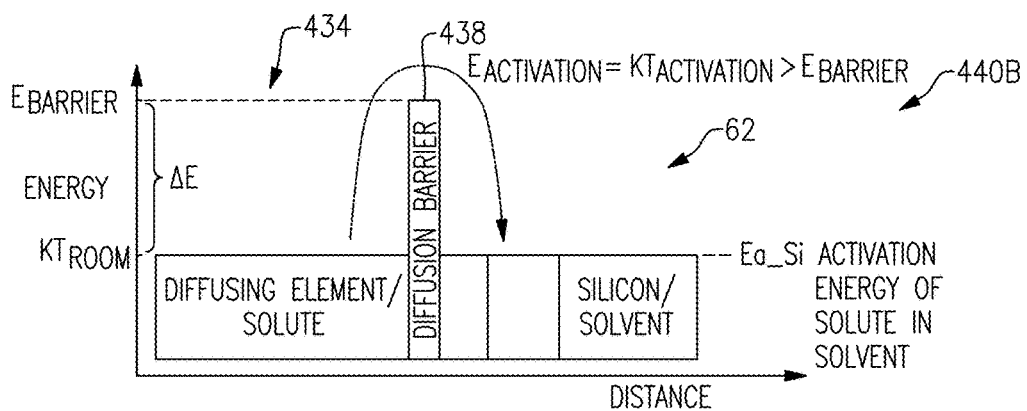
FIG. 44B illustrates a schematic two-dimensional energy-space diagram illustrating activation energy levels for a monitor atom in a wear-out monitor device having a reservoir of monitor atoms that is separated from the substrate by a physical barrier, according to embodiments.

FIGS. 44A and 44B illustrate three- and two-dimensional energy-space diagrams 440A and 440B depicting potential barriers as "seen" by a monitor atom in a wear-out monitor device such as that illustrated above with respect to FIGS. 43A/43B, according to embodiments. The well region of the diagram 440A and the left region of the diagram 440B represent, in energy space, the energy level as "seen" by the monitor atom in the reservoir 434, and the outside-the-well region of the diagram 440A and the right region of the diagram 440B represent, in energy space, the energy level as "seen" by the monitor atom in the substrate 62. As illustrated, the reservoir 434 and the substrate 62 are separated by a physical barrier having an energy level as "seen" by the monitor atoms that is higher than the energy levels of the reservoir 434 and the substrate 62. The height of the energy barrier is such that, under ordinary operating conditions of the core circuit, e.g., within thermal energy corresponding to temperatures less than or equal to about 85° C., 125° C. or 250° C., for example, the probability of atoms overcoming the energy barrier is negligible. That is, the difference in average energy levels, $\Delta E$, between the barrier 438 and the reservoir 434 may be, e.g., substantially higher than (kT~0.023 eV), e.g., 0.058 eV (400° C.) or higher, 0.75 eV (600° C.) or higher, 0.092 eV (800° C.) or higher, 0.11 eV (1000° C.) or higher, according to embodiments. Thus, at temperatures lower than the $\Delta E$ between the barrier 438 and the reservoir 434, the rate of diffusion of the monitor atoms through the barrier 438 that is associated with thermal energy of the monitor atoms (e.g., kT) may be negligible. Thus, without altering the barrier 438, the monitor atoms are substantially prevented from diffusing into the substrate 62.

In the embodiment illustrated with respect to the energy-space diagram 440B, the energy levels of the reservoir 434 and the substrate 62 are substantially similar. Such may be the case, e.g., when the reservoir 434 may be formed of the same material as the substrate, e.g., silicon, and impregnated with the monitor atoms, e.g., gold. However, embodiments are not to limited, and the energy levels of the reservoir 434 and the substrate 62 may be substantially different. Such may be the case, e.g., when the reservoir 434 may be formed of a different material than the substrate, e.g., an electrode metal impregnated with the monitor atoms, e.g., gold.

In some embodiments, the $\Delta E$ between the barrier 438 and the reservoir 434 may correspond to, e.g., the difference in activation energies of the monitor atoms in the barrier 438 and the reservoir 434. In these embodiments, the activation energy of the monitor atoms in the barrier 438 may be greater than the activation energy of the monitor atoms in the reservoir 434 by, e.g., 0.058 eV (400° C.) or higher, 0.75 eV (600° C.) or higher, 0.092 eV (800° C.) or higher, 0.11 eV (1000° C.) or higher, according to embodiments.

Examples of insulating or dielectric materials used for the barrier 438 include various inorganic dielectric materials compatible with semiconductor processing, e.g., $SiO_x$, $SiO_xN_y$, and $SiN_x$, to name a few. Examples of insulating or dielectric materials used for the barrier 438 also include various inorganic or organic polymeric materials compatible with semiconductor processing, including electroactive polymers and conjugated conducting polymers. For example, the barrier 438 can be formed of polypyrrole (PPy), poly 3,4-ethylenedioxythiophene (PEDOT), poly[2-methoxy-5-(2'-ethylhexyloxy)-p-phenylene vinylene] (MEH-PPV), polyfluorene, fluorocarbon films, polytetrafluoroethylene (PTFE), among various other suitable polymeric materials, where the monitor atoms "see" the higher barrier as described above, according to embodiments. Advantageously, these materials can be formed using various deposition processes that are compatible with semiconductor processing, e.g., chemical vapor deposition, atomic vapor deposition, or physical vapor deposition, among other processes.

Examples conductive materials used for the barrier 438 include various metals or doped semiconductors compatible with semiconductor processing, in which the monitor atoms "see" the higher barrier as described above, according to embodiments.

According to embodiments, the barrier 438 is formed of an insulating or a conductive material configured such that, in response to an electrical stimulus, e.g., a voltage or a current stimulus, the barrier 438 is substantially altered, or lowered. Alternatively or additionally, in response to an electrical stimulus, e.g., a voltage or a current stimulus, the diffusant or the monitor atoms gain sufficient energy to diffuse into a substrate. In various embodiments, the alteration of the barrier 438 or the gaining of sufficient energy by the diffusant initiates or activates the wear-out monitor device 430, such that the monitor atoms begin to diffuse into the substrate under various stresses subjecting the core circuit, as described supra.

In some embodiments, the voltage or the current stimulus may in turn induce Joule heating of a monitor region below the reservoir 434. In the illustrated embodiment, the Joule heating may occur in a manner similar to Joule heating of a current monitor described above with respect to FIG. 8. Except for the reservoir 434 being disposed between the first electrode 68a and the second electrode 68b, the configuration of the wear-out monitor device 430 may be structurally similar to the wear-out monitor device 80 described above with respect to FIG. 8. In addition to or in lieu using the current between the first and second electrodes 68a, 68b to measure the effect of diffusion rate of the monitor atoms caused by Joule-heating, the current flowing between the first and second electrodes 68a, 68b is used to alter the barrier 438 thermally and/or electrically. To alter the barrier 438 by Joule heating of without substantially diffusing the monitor atoms into the substrate, the monitor region below the reservoir 434, represented as a resistor formed in series with the forward-biased PN junction between the first electrode 68a and the second electrode 68b in FIGS. 43A/43B, may be subjected to a transient voltage or a current pulse. The voltage or current pulse may be applied under a bias condition in which the PN junction of the wear-out monitor device 430 is forward-biased, such that sufficient current density may be supplied for efficient Joule heating. In response to the forward bias, the series resistor of the monitor structure generates sufficient heat, which causes the barrier 438 to be altered, e.g., permanently altered, such that the $\Delta E$ is substantially lowered or eliminated. For example, under the Joule heating, the barrier 438 may develop structural modifications, e.g., bond breakages or pinholes. Once the $\Delta E$ is substantially lowered or eliminated, the atomic diffusion of monitor atoms occur as in various embodiments described above. For example, once the barrier 438 is altered by a voltage or a current pulse, when the wear-out monitor device 430 is subsequently subjected to a set of predetermined conditions for a predetermined duration, some of the monitor atoms in reservoir 434 diffuse into a depletion region formed between the first and second doped regions 64, 66. Depending on the concentration and/or depth of the diffused monitor atoms in the underlying semiconductor material, e.g., in the depletion region, a cumulative wear-out history, e.g., a cumulative thermal wear-out history, of the device 60 can be at least indirectly determined. Further details of the device structure and the operation of the monitor device 430 that have been described above will be omitted. Thus, as described above, the wear-out monitor device 430 depicted by the energy-space diagrams 440B can be configured as, e.g., a use-activated wear-out monitor.

Figure 45:
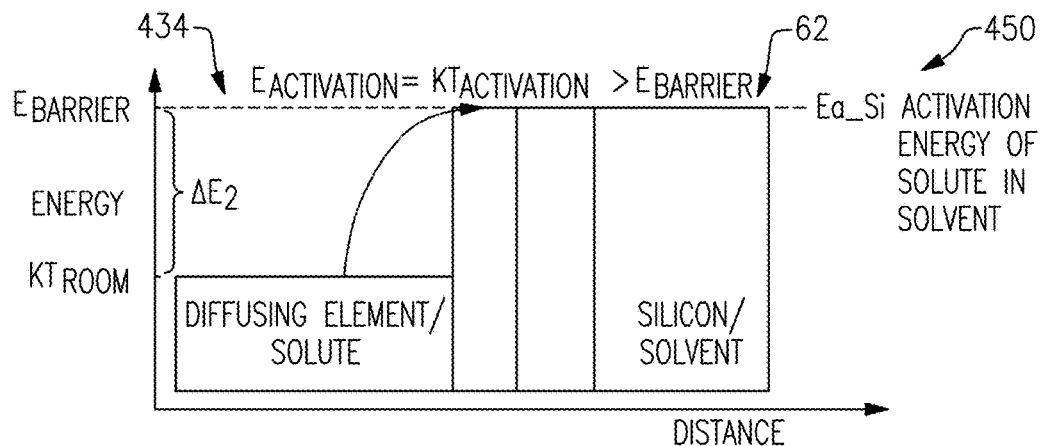
FIG. 45 illustrates a schematic two-dimensional energy-space diagram illustrating activation energy levels for a monitor atom in a wear-out monitor device having an energy barrier between a reservoir of monitor atoms and a monitor region, according to embodiments.

FIG. 45 illustrates a two-dimensional energy-space diagram 450 depicting potential barriers as "seen" by a monitor atom in a wear-out monitor device, according to embodiments. In particular, the energy-space diagram 450 corresponds to a wear-out monitor device similar to the wear-out monitor device 430 except, the barrier 438 is omitted. In addition, unlike the wear-out monitor described with respect to the energy-space diagram 440B (FIG. 44B), in which the energy levels of the reservoir 434 and the substrate 62 are substantially similar, the wear-out monitor device corresponding to the energy-space diagram 450 the energy levels of the reservoir 434 (left side) is substantially lower than the energy level of the substrate 62 (right side). Such may be the case, e.g., when the reservoir 434 is be formed of a different material than the substrate, e.g., an electrode metal impregnated with the monitor atoms or an electrode formed of the monitor atoms, e.g., gold. In these embodiments, while the barrier 438 is omitted, the monitor atoms still "see" a barrier represented by the difference $\Delta E_2$ in the energy levels between the reservoir 434 and the substrate 62. The $\Delta E_2$ may be similar, greater or smaller in magnitude compared to the $\Delta E$ described above with respect to FIG. 44. Thus, while, unlike the monitor device 430 described above with respect to FIG. 43, the barrier 438 is omitted, the monitor atoms nevertheless overcomes a barrier prior to diffusing into the substrate 62. The barrier $\Delta E_2$ can be overcome by the monitor atoms upon receiving an electrical energy, e.g., a current or a voltage pulse, which results in the Joule heating of the monitor region below the reservoir 434, in a similar manner as described above with respect to FIG. 43. The monitor atoms that have overcome the energy barrier $\Delta E_2$ can now diffuse further into the substrate 62, in a manner substantially similar to various embodiments described above.

Figure 46:
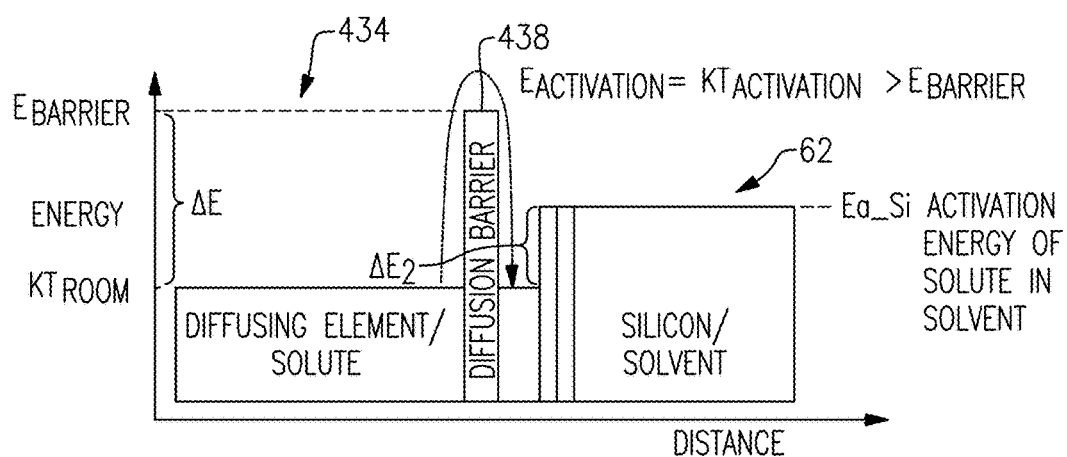
FIG. 46 illustrates a wear-out monitor device configured to record an indication of wear out of a core circuit based on localized atomic diffusion of monitor atoms, where the device has a reservoir of monitor atoms that is separated from the substrate by a physical barrier, and having an energy barrier between a reservoir of monitor atoms and a monitor region, according to embodiments.

FIG. 46 illustrates a two-dimensional energy-space diagram 460 depicting potential barriers as "seen" by a monitor atom in a wear-out monitor device, according to embodiments. In particular, the wear-out monitor device depicted by the energy-space diagram 460 is similar to the wear-out monitor device described above with respect to the energy-space diagram 450 (FIG. 45), except, the depicted wear-out monitor device additionally includes, similar to the wear-out monitor device depicted above with respect FIG. 43, a barrier 438. Similar to the energy-space diagram 450, the energy levels of the reservoir 434 (left side) is lower than the energy level of the substrate 62 (right side), and the barrier 438 is formed within the reservoir 434. Such may be the case, e.g., when the reservoir 434 is be formed of a different material than the substrate, e.g., an electrode metal impregnated with the monitor atoms or an electrode formed of the monitor atoms, e.g., gold, and the barrier 438 is formed within the reservoir 434. As a result, the reservoir 434 is divided by the barrier 438 into a first (left) region and a second (right) region. In these embodiments, when the barrier 438 is lowered or eliminated by, e.g., Joule heating via an electrical pulse, the wear-out monitor device is initialized, in a similar manner as described above with respect to FIGS. 43 and 44A/44B. However, the monitor atoms still "see" a barrier represented by the difference $\Delta E_2$ in the energy levels between the reservoir 434 and the substrate 62. Thus, in addition to and subsequent to being initialized by lowering or removing the barrier 438 in a similar manner as described above with respect to FIGS. 43 and 44A/44B, the monitor atoms additionally overcomes the second barrier $\Delta E_2$ prior to diffusing further into the substrate 62 in a similar manner as described above with respect to FIG. 45.

Figure 47:
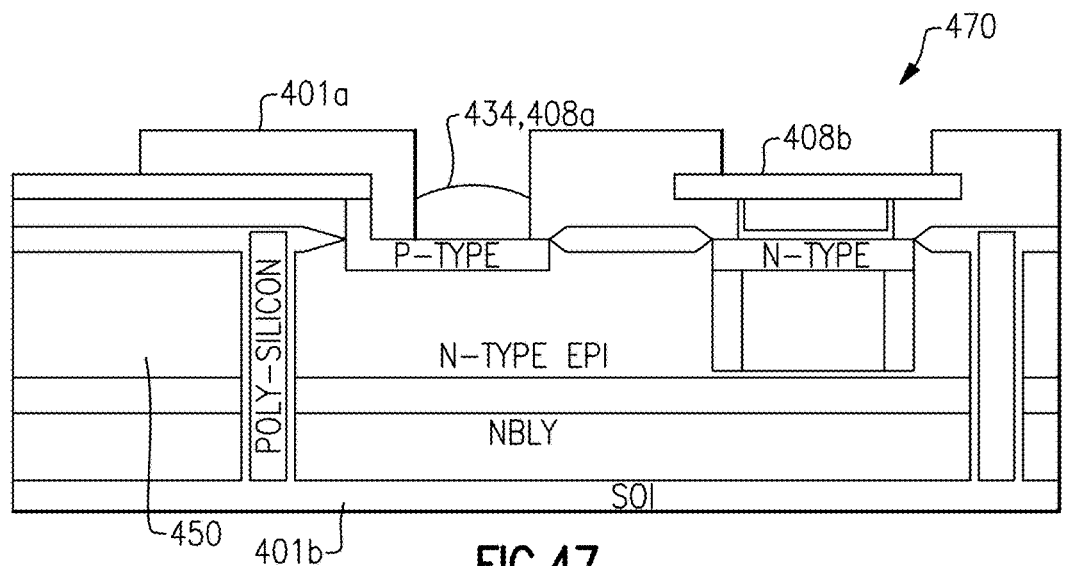
FIG. 47 illustrates a wear-out monitor device configured to record an indication of wear out of a core circuit based on localized atomic diffusion of monitor atoms, where the device has an energy barrier between a reservoir of monitor atoms and a monitor region, according to embodiments.

FIG. 47 is an illustration of a wear-out monitor device 470 configured to record an indication of wear out of a core circuit based on atomic diffusion of monitor atoms that is localized within the wear-out monitor device, according to embodiments. In particular, the monitor device 470 includes monitor atoms arranged in accordance with the energy-space diagram depicted in FIG. 45, where the energy level of the monitor atoms in the reservoir is substantially lower than the energy level of the monitor atoms in the substrate. Various structures of the monitor device 470 are arranged similarly to those of the monitor device described above with respect to FIG. 40. For instance, the monitor device 470 is laterally isolated by isolation regions 401a, e.g., shallow trench isolation regions, formed on one or both sides, and a buried layer 401b, which may be a buried oxide (BOX) layer 401b extending laterally below the active regions of the wear-out monitor device 470. The wear-out monitor device 470 additionally comprises a buried layer (NBLY) region 462 vertically above the buried oxide layer 401b and laterally extending between the isolation regions 401a. The wear-out monitor device 400 additionally includes a first doped region 458 formed within the semiconductor substrate 450. The substrate 450, the buried layer region 462 and the first doped region may be doped with the same dopant type, according to some embodiments. For example, the substrate 450 may doped with a first dopant type, which may be an n-type dopant or a p-type dopant, at a first concentration. The first doped region 458 may be doped with the first dopant type at a higher concentration relative to the substrate 450. Similarly, the buried layer region 458 may be doped with the first dopant type at a higher concentration relative to the substrate 450. In the illustrated embodiment, each of the substrate 450, the first doped region 458 and the buried layer region 462 are doped with an n-type dopant. The wear-out monitor device 400 includes a first heavily doped region 454*a*, e.g., a heavily doped n-doped (n+) region and a second heavily doped region 454*b*, e.g., a heavily doped p-doped (p+) region. Detailed relative doping concentrations and processing methods of various doped regions may be similar to as described above with respect to FIG. 40, and their detailed descriptions will be omitted.

Still referring to FIG. 47, the wear-out monitor device 470 additionally includes a first electrode 408*a* and a second electrode 408*b* formed over the first heavily doped region 454*a* and over the second heavily doped region 454*b*, respectively, through openings in dielectric layer 463. One or both of the first and second electrodes 408*a* and 408*b* serve as a reservoir of monitor atoms similar to the reservoir 434 illustrated above with respect to FIG. 43, which comprise or is formed of the monitor atoms that are arranged in accordance with the energy-space diagram depicted in FIG. 45. That is, one or both of the first and second electrodes 408*a* and 408*b* have monitor atoms are arranged such that the energy level of the monitor atoms in the reservoir is substantially lower than the energy level of the monitor atoms in the substrate.

Thus, as configured, the wear-out monitor device 470 has one or more reservoirs of monitor atoms (i.e., first and/or second electrodes 408*a*, 408*b*) disposed on a surface of the substrate and a monitor region (e.g., depletion region formed underneath the second heavily doped region 454*b*) formed in the substrate 450. The relative energy levels of the monitor atoms in the reservoir and the substrate are such that, upon overcoming the energy barrier $\Delta E_2$ as described above with respect to FIG. 45, the monitor atoms in the semiconductor material of the substrate further diffuse into the monitor region of the substrate as described above with respect to FIG. 40. That is, when the wear-out monitor device is subjected to a set of predetermined stress conditions for a predetermined duration, some of the monitor atoms diffuse into the monitor region, where the monitor region can include a region in the substrate, e.g., a depletion region formed by a PN junction as described above, for example. Various electrical properties of the monitor region that can be measured has been described above with respect to FIG. 40, and is omitted herein.

Figure 48:
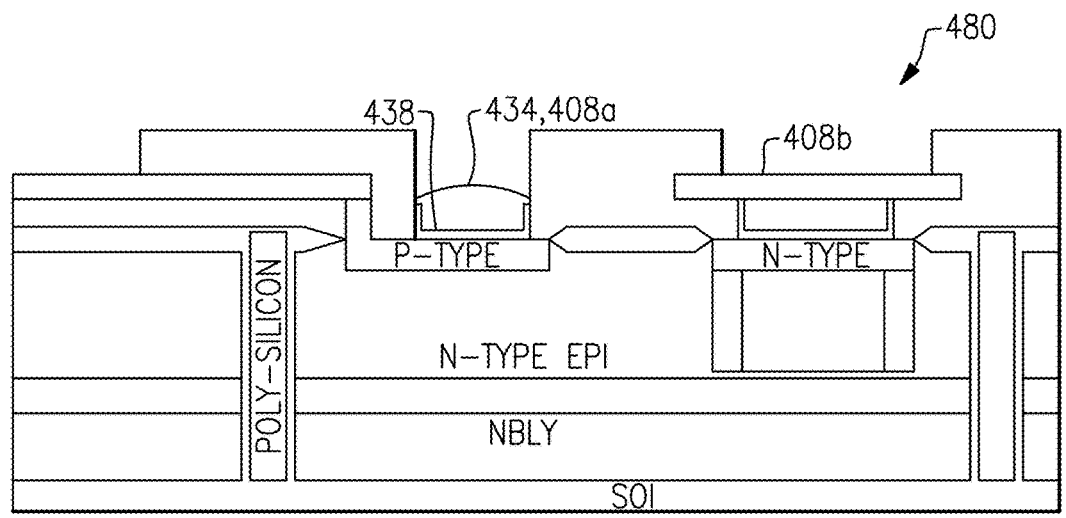
FIG. 48 illustrates a wear-out monitor device configured to record an indication of wear out of a core circuit based on localized atomic diffusion of monitor atoms, where a reservoir of monitor atoms is separated from the substrate by a physical barrier, according to embodiments.

FIG. 48 is an illustration of a wear-out monitor device 480 configured to record an indication of wear out of a core circuit based on atomic diffusion of monitor atoms that is localized within the wear-out monitor device, according to some other embodiments. In particular, the monitor device 480 includes monitor atoms arranged in accordance with the energy-space diagram depicted in FIG. 44A/44B or 46, where a barrier 438 is present between the reservoir and the substrate that has an energy barrier that is higher than the energy levels of the reservoir and the substrate. The energy level of the monitor atoms in the reservoir may be substantially similar (FIG. 44A. 44B) or substantially lower (FIG. 46) compared to the energy level of the monitor atoms in the substrate. Various structures of the monitor device 480 are arranged similarly to those of the wear-out monitor device 470 described above with respect to FIG. 47, except for the presence of the barrier 438, whose descriptions are omitted herein. In addition, various physical properties as well as physical and energy configurations of the barrier 438 have been described above with respect to FIGS. 43, 44A/44B and 46, and are omitted herein.

Figure 49A:
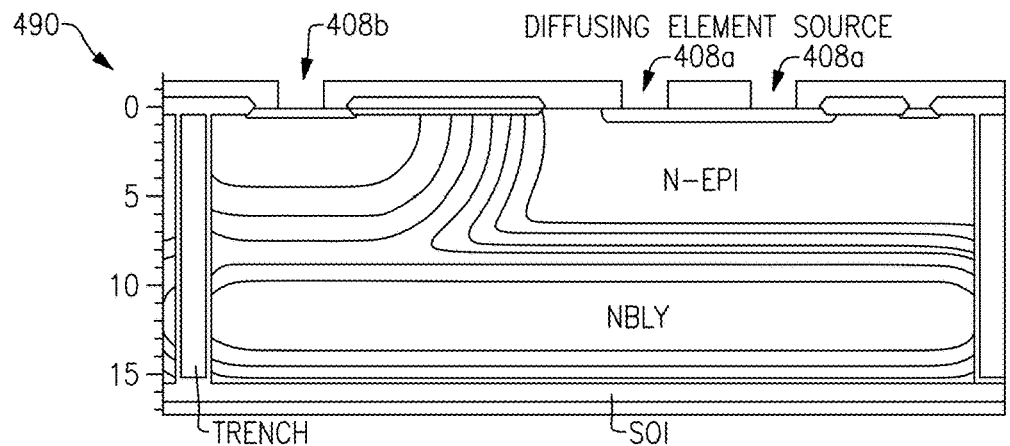
FIG. 49A illustrates a wear-out monitor device configured to record an indication of wear out of a core circuit based on localized atomic diffusion of monitor atoms, where the device has an energy barrier between a reservoir of monitor atoms and a monitor region, according to embodiments.
Figure 49B:
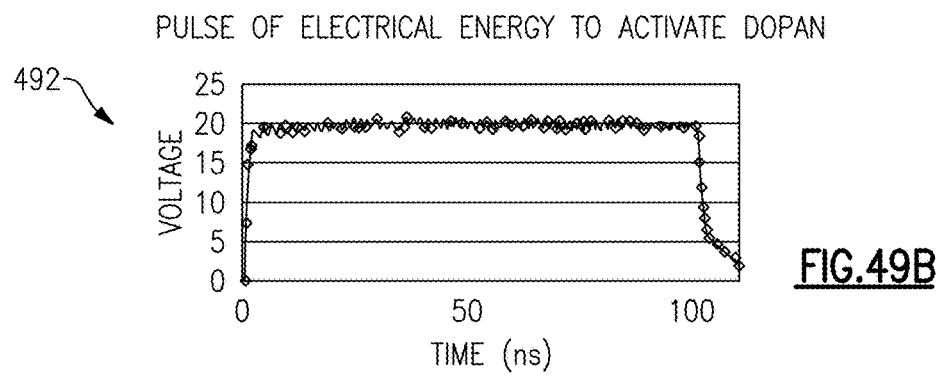
FIG. 49B illustrates a cross-sectional view of an example electrical stimulus applied to the reservoir of the wear-out monitor device illustrated in FIG. 49A, according to embodiments.
Figure 49C:
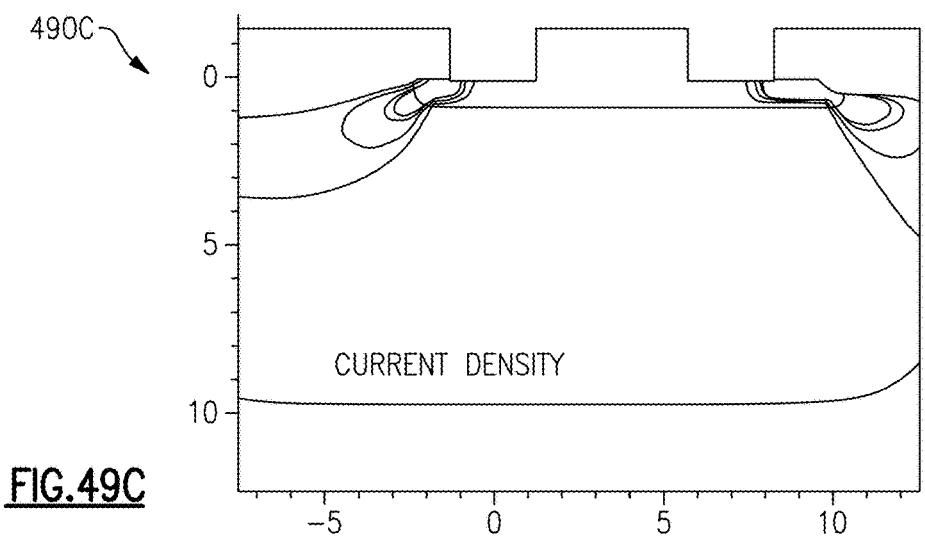
FIG. 49C illustrates a cross-sectional view of the simulated current density distribution resulting from the electrical pulse illustrated in FIG. 49B.
Figure 49D:
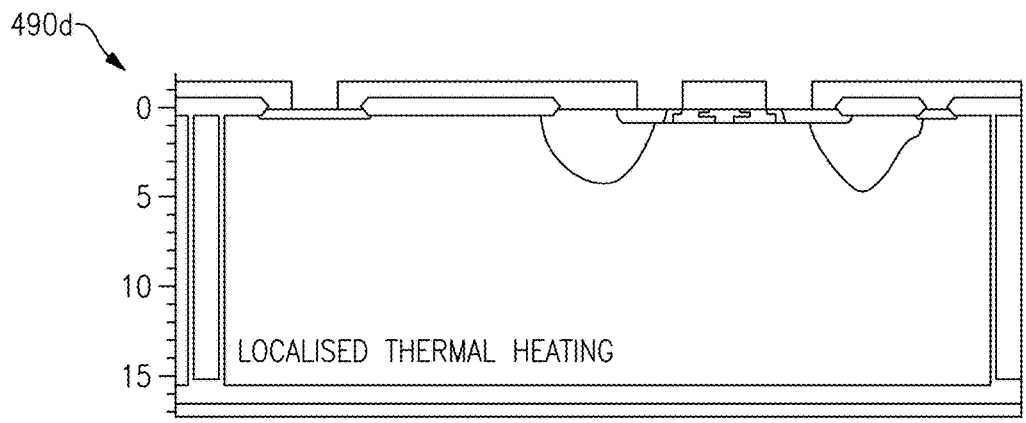
FIG. 49D illustrates a cross-sectional view of the simulated heat distribution resulting from the Joule heating.
Figure 49E:
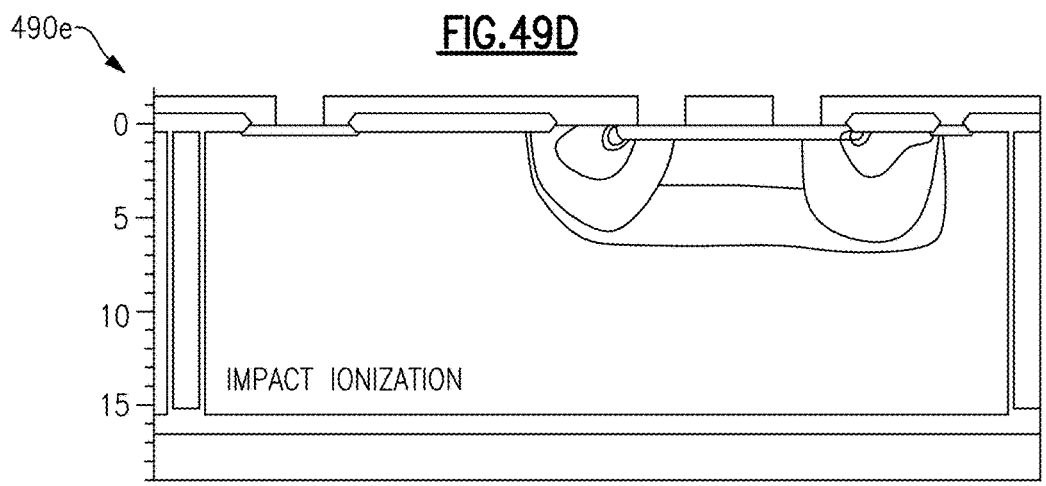
FIG. 49E illustrates a cross-sectional view of the simulated impact ionization resulting from the electrical pulse illustrated in FIG. 49B.
Figure 49F:
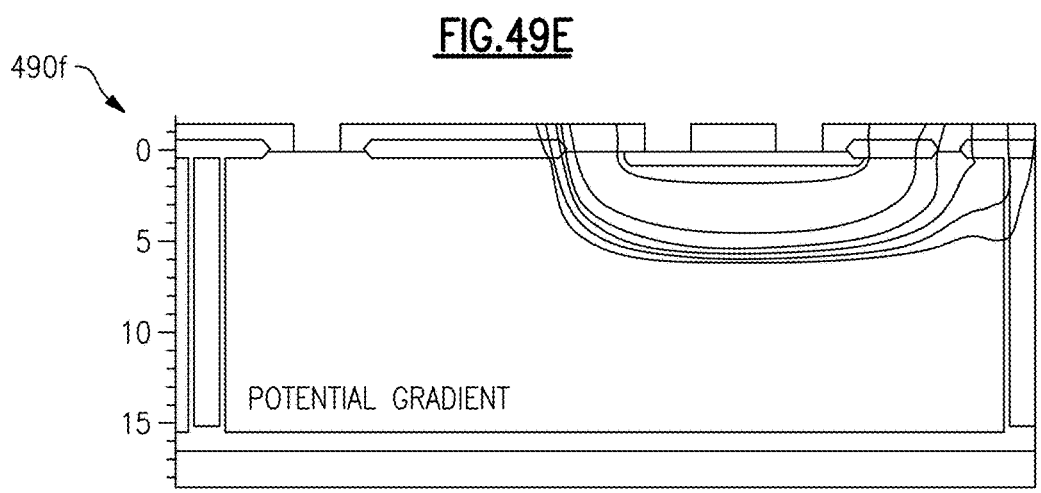
FIG. 49F illustrates a cross-sectional view of the simulated potential gradient resulting from the electrical pulse illustrated in FIG. 49B.

FIGS. 49A-49F illustrate electrical responses of a wear-out monitor device 490 configured to record an indication of wear out of a core circuit based on atomic diffusion of monitor atoms that is localized within the wear-out monitor device, according to some other embodiments. FIG. 49A illustrates a cross-sectional view of the structures of the monitor device 490, which includes monitor atoms arranged in a similar manner as in the wear-out monitor device 470 illustrated above with respect to FIG. 47, where the energy level of the monitor atoms in a plurality of reservoirs 438 is substantially lower than the energy level of the monitor atoms in the substrate, such that the wear-out monitor 490 is activated upon application of an electrical pulse to the a plurality of reservoirs 438. The arrangements of various structures of the monitor device 490 are substantially similar to the wear-out monitor device 470 illustrated above with respect to FIG. 47 except that the wear-out monitor device 490 includes a plurality of reservoirs configured as first electrodes 408*a*. FIG. 49B illustrates an example electrical pulse 492 that can be applied to the reservoirs 438. In the illustrated embodiment, the reservoirs 438 configured as the first electrodes 408*a* are in contact with a p-doped region, e.g., a heavily doped p+ region formed within an n-doped region, e.g., an n-doped epitaxial region, and the electrical pulse applied is a positive voltage applied between the first electrodes 408*a* and the second electrodes 408*b*, such that the PN junction formed by the p-doped region and the n-doped region is forward-biased. FIG. 49C illustrates a cross-sectional view of the simulated current density distribution 490*c* resulting from the electrical pulse illustrated in FIG. 49B; FIG. 49D illustrates a cross-sectional view of the simulated heat distribution 490*d* resulting from the Joule heating; FIG. 49E illustrates a cross-sectional view of the simulated impact ionization distribution 490*e* resulting from the electrical pulse illustrated in FIG. 49B; and FIG. 49F illustrates a cross-sectional view of the simulated potential gradient distribution 490*f* resulting from the electrical pulse illustrated in FIG. 49B. For the various simulations illustrated with respect to FIGS. 49C-49F, the PN junction formed by the heavily doped p+ region formed within the n-doped region in the wear-out monitor device 490 of FIG. 49A is configured such that, under a voltage pulse illustrated with respect to FIG. 49B having a nominal pulse width of about 100 ns at a nominal voltage of about 20V between the first electrodes 408*a* and the second electrodes 408*b*, the PN junction is forward biased and the peak current density exceeding about $1 \times 10^3$ A/cm$^2$ is achieved, as illustrated in FIG. 49B, which in turn induces a peak temperature exceeding about 420K (or about 147° C.), as illustrated in FIG. 49D.

In the above with respect to FIGS. 43-49, various embodiments of wear-out monitor devices having a monitor structure are described, where the monitor structure is configured to be initialized prior to serving as a wear-out monitor based on atomic diffusion. For various applications, it may be desirable for a wear-out monitor device to include a plurality of monitor structures, where each monitor devices includes a reservoir and can also include a barrier, as described below.

FIG. 50A illustrates a cross-sectional view of a wear-out monitor device 500 configured to record an indication of wear out of a core circuit based on atomic diffusion of monitor atoms that is localized within the wear-out monitor device, where the wear-out monitor device 500 includes a plurality of monitor structures D1, D2, . . . Dn. Each one of the monitor structures D1, D2, . . . Dn includes a reservoir 434 according to any of the embodiments described above with respect to FIGS. 43-49, and can also include a barrier 438 according to any of the embodiments described above with respect to FIGS. 43, 44A/44B, 46 and 48. In the illustrated embodiment, each of the monitor structures D1, D2, . . . Dn has nominally the same structures and are separated by nominally the same spacing. Such configuration may be advantageous, e.g., for obtaining a spatial profile of wear-out stresses, obtaining a time-evolution of wear-out stresses and/or for initializing different regions of the wear-out monitor device at different times and/or conditions, as described further infra, among other advantages. However, embodiments are not so limited, as illustrated in FIG. 51.

FIG. 50B illustrates an example implementation of a control circuit having a current supply transistor 504 electrically connected to the wear-out monitor device and configured to supply the electrical stimulus. In particular, the current supply transistor is a sufficiently large transistor such that, as illustrated above with respect to FIGS. 49C and 49D, a peak current density exceeding about $1\times10^3$ A/cm$^2$, about $1\times10^4$ A/cm$^2$ or about $1\times10^5$ A/cm$^2$ can achieved, according to embodiments as illustrated in FIG. 49B, which in turn can induces a peak temperature of about 420K (or about 147° C.), 470K (or about 197° C.) or about 520K (or about 247° C.).

FIG. 51A illustrates a cross-sectional view (upper drawing) and a top-down plan-view (lower drawing) of a wear-out monitor device 510A configured to record an indication of wear out of a core circuit based on atomic diffusion of monitor atoms that is localized within the wear-out monitor device. In the illustrated embodiment, the wear-out monitor device 510A includes a plurality of different monitor structures G, F, D, and E. Similar to the wear-out monitor device 500 illustrated above with respect to FIG. 50, each one of the monitor structures G, F, D, E includes a reservoir 434 according to any of the embodiments described above with respect to FIGS. 43-49, and can also include a barrier 438 according to any of the embodiments described above with respect to FIGS. 43, 44A/44B, 46 and 48. However, unlike the wear-out monitor device 500, in the illustrated embodiment, each one of the monitor structures G, F, D, E is configured differently compared to an adjacent one of the monitor structures, with respect to one or more of the structures including the reservoir and/or the barrier, including their material compositions, dimensions and or lateral configurations. In addition to obtaining a spatial profile of wear-out stresses, for obtaining a time-evolution of wear-out stresses, and/or for initializing different regions of the wear-out monitor device at different times and/or conditions, the configuration of the wear-out monitor device 510A may further be advantageous for obtaining different rates of diffusion in different regions, among other advantages.

Figure 51B:
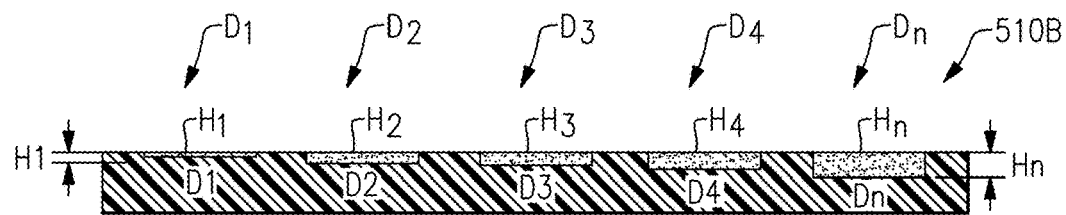
FIG. 51B illustrates a cross-sectional view of a wear-out monitor device configured to record an indication of wear out of a core circuit, according to some other embodiments.

FIG. 51B illustrates a cross-sectional view of a wear-out monitor device 510B configured to record an indication of wear out of a core circuit based on atomic diffusion of monitor atoms that is localized within the wear-out monitor device, according to some other embodiments. The wear-out monitor device 510B includes a plurality of different monitor structures D1, D2 . . . Dn each having a differently arranged barrier. In particular, the different monitor structures D1, D2 . . . Dn can have the barriers having thicknesses H1, H2, . . . Hn, respectively, such that the different monitor structures are initialized under different electrical stimuli, e.g., different voltage pulses. In addition, the different monitor structures D1, D2 . . . Dn can include different monitor atoms and/or different matrix material including the monitor atoms when the reservoir is formed of a matrix containing the monitor atoms.

Figure 52:
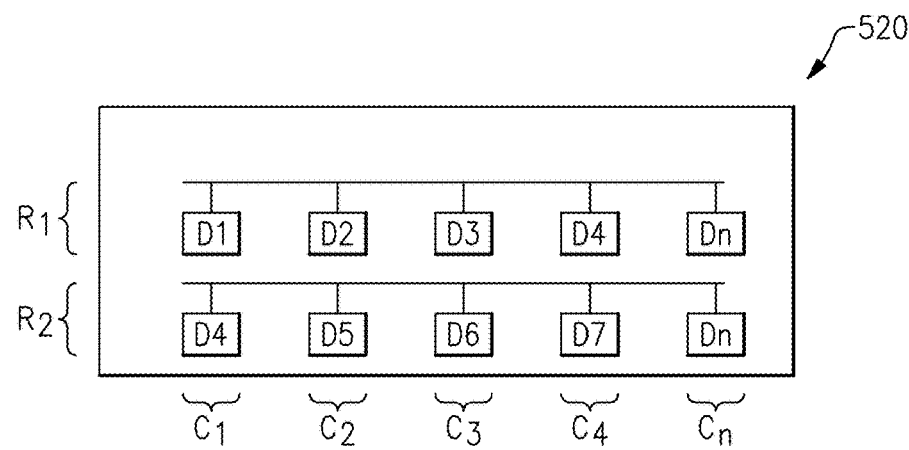
FIG. 52 illustrates a top-down plan-view of a wear-out monitor device configured to record an indication of wear out of a core circuit based on localized atomic diffusion of monitor atoms, where the wear-out monitor device includes an array having a plurality of rows, according to embodiments.

FIG. 52 illustrates a top-down plan-view of a wear-out monitor device 520 configured to record an indication of wear out of a core circuit based on atomic diffusion of monitor atoms that is localized within the wear-out monitor device, where the wear-out monitor device 520 includes an array having a plurality of rows, e.g., a first row R1 including monitor structures D1, D2, . . . Dn and a second row R2 including monitor structures D4, D5, . . . Dm. The array can further have a plurality of columns, e.g., a first column C1 including monitor structures D1, D4, . . . Di and a second column C2 including monitor structures D2, D5, . . . Dj. The monitor structures D1, D2, . . . Dn and D4, D5, . . . Dm can be nominally the same, as described above with respect to FIG. 51, or be nominally different, as described above with respect to FIG. 52. In the illustrated embodiment, the monitor structures are configured to be electrically connected in a regular array having a plurality of rows R1, R2, . . . and/or columns C1, C2, . . . . In some embodiments, the electrical connections can be such that each of the rows including the monitor structures D1, D2, . . . Dn can be electrically accessed, e.g., for initialization, in parallel and/or simultaneously. In some other embodiments, the electrical connections can be such that each of the discrete monitor structures can be electrically accessed individually, e.g., for initialization, in a "bit-addressable" manner by applying appropriate electrical signals to a particular rows and a column. The array configuration of may be advantageous, e.g., for obtaining a spatial profile of wear-out stresses, for obtaining a temporal and/or spatial evolution of wear-out stresses and/or for initializing different regions of the wear-out monitor device at different times and/or conditions, as described further infra, among other advantages.

Figure 53:
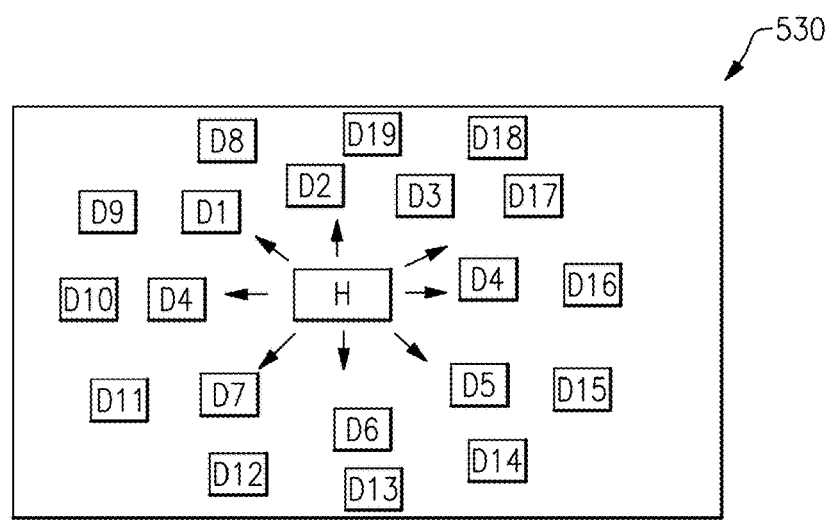
FIG. 53 illustrates a top-down plan-view of a wear-out monitor device configured to record an indication of wear out of a core circuit based on localized atomic diffusion of monitor atoms that is localized within the wear-out monitor device, where the wear-out monitor device includes an array having a plurality of monitor structures arranged at different radial distances from a reference point or a central position, according to embodiments.

FIG. 53 illustrates a top-down plan-view of a wear-out monitor device 530 configured to record an indication of wear out of a core circuit based on atomic diffusion of monitor atoms that is localized within the wear-out monitor device, where the wear-out monitor device 530 includes an array having a plurality of monitor structures D1, D2, . . . Dn arranged at different radial distances from a reference point or a central position, according to embodiments. Similar to the wear-out monitor device 520 illustrated above with respect to FIG. 52, the monitor structures D1, D2, . . . Dn can be nominally the same, as described above with respect to FIG. 51, or be nominally different, as described above with respect to FIG. 52. Unlike FIG. 52, however, instead of being arranged to have rows and/or columns, the monitor structures D1, D2, . . . Dn of the wear-out monitor device 530 are arranged such that the monitor structures have different radial distances r1, r2, . . . rn, respectively, relative to a central position or a central structure H, which may be a heat source. The array configuration of may be advantageous, e.g., for obtaining a spatial profile of wear-out stresses, e.g., a radial profile, for obtaining a temporal and/or spatial evolution of wear-out stresses and/or for initializing different regions of the wear-out monitor device at different times and/or conditions, as described further infra, among other advantages.

In the above with respect to FIGS. 43-53, various embodiments of wear-out monitor devices having a monitor structure are described, where the monitor structure is configured to be initialized prior to serving as a wear-out monitor based on atomic diffusion in a vertical direction, e.g., in a direction normal to the substrate surface, and into the substrate. For various applications, it may be desirable for a wear-out monitor to include a monitor structure that is configured to be initialized prior to serving as a wear-out monitor based on atomic diffusion in a lateral direction, e.g., in a direction parallel to the substrate surface.

Figure 54A:
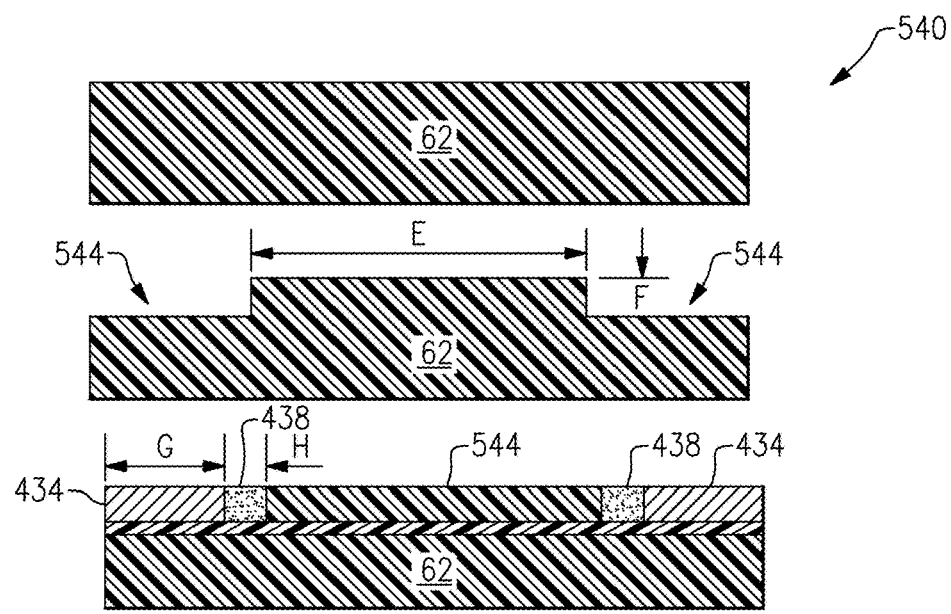
FIGS. 54A and 54B illustrate a cross-sectional view and a top down plan-view of a wear-out monitor device configured to record an indication of wear out of a core circuit based on localized atomic diffusion of monitor atoms in a radially outward direction, according to embodiments.
Figure 54B:
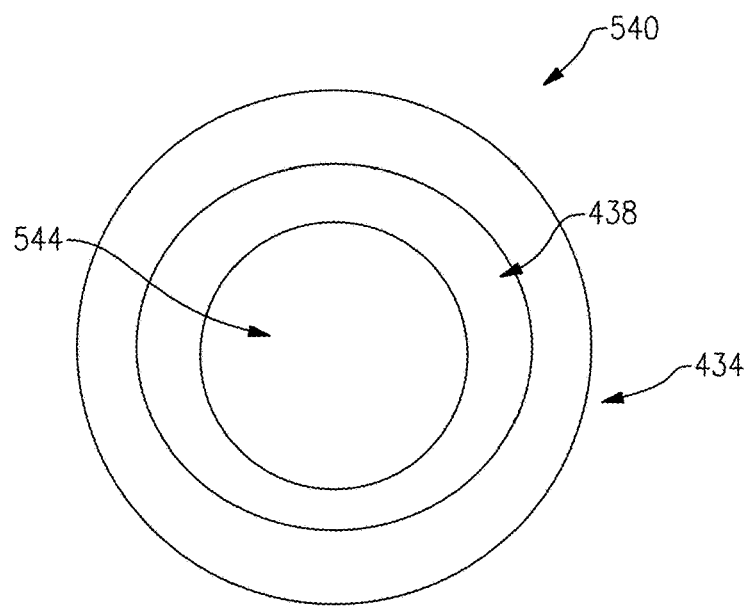

FIGS. 54A and 54B illustrate a cross-sectional view and a top down plan-view of a wear-out monitor device 540 configured to record an indication of wear out of a core circuit based on atomic diffusion of monitor atoms that is localized within the wear-out monitor device, according to embodiments. The wear-out monitor 540 is configured to be initialized prior to serving as a wear-out monitor based on atomic diffusion in a lateral direction, according to embodiments. Unlike the monitor device illustrated above with respect to, e.g., FIG. 43, in the monitor device 540, the monitor atoms have a net direction of diffusion that is a lateral direction along a substrate surface. Referring to FIGS. 54A and 54B, the illustrated wear-out monitor device 540 includes a substrate 62 having formed thereon a monitor region 544, e.g., a circular monitor region, surrounded by a recessed region 546, e.g., a circular recessed region. The wear-out monitor device 540 additionally includes, formed in the recessed region 546, a reservoir 434 surrounding, e.g., circularly surrounding, the monitor region 544, and a barrier 438 surrounding, e.g., circularly surrounding, the reservoir 434. The monitor region 544 can have a lateral dimension, e.g., a diameter, E adapted such that the monitor atoms diffusing laterally can give an indication of a wear-out of the core circuit during its life time. The recessed regions 546 have a depth F adapted for accommodating the reservoir 434 and the barrier 438. Except for the lateral arrangement, various other configurations including materials, energetic relationships between the monitor region 544, the barrier 438 and the reservoir 434, the possibility of omission of the barrier 438, and various semiconductor doped regions that the monitor region 544 can include, are substantially similar to various embodiments described above, and as such, their detailed descriptions are omitted herein.

In some embodiments, the monitor region 544, the reservoir 433 and the barrier 438 can be separated from the bulk substrate by a permanent diffusion barrier 548. While the illustrated embodiment includes the monitor region 544, the barrier 438 and the reservoir 434 configured as circularly concentric regions. However, other embodiments are possible, where the monitor region 544, the barrier 438 and the reservoir 434 are configured as any suitable shape adapted for recording an indication of wear out of a core circuit based on atomic diffusion of monitor atoms in a lateral direction, according to embodiments.

Figure 55A:
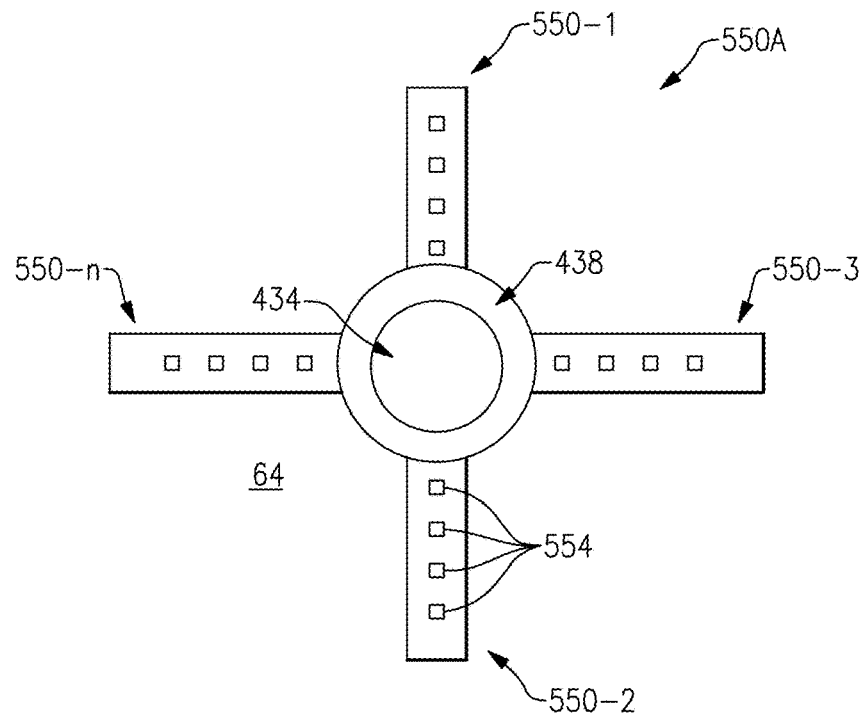
FIG. 55A illustrates a plan-view of a wear-out monitor device that is configured to record an indication of wear out of a core circuit based on localized atomic diffusion in a radially inward direction, where the wear-out monitor device includes a plurality of monitor structures including a barrier, according to embodiments.
Figure 55B:
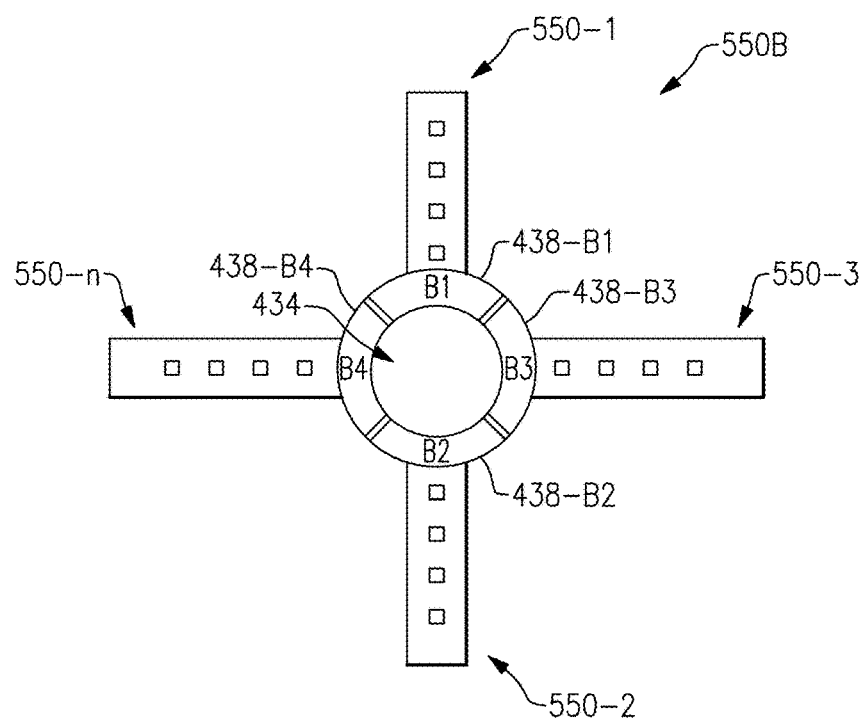
FIG. 55B illustrates a plan-view of a wear-out monitor device that is configured to record an indication of wear out of a core circuit based on localized atomic diffusion in a radially inward direction, where the wear-out monitor device includes a plurality of monitor structures each including a different barrier, according to embodiments.
Figure 55C:
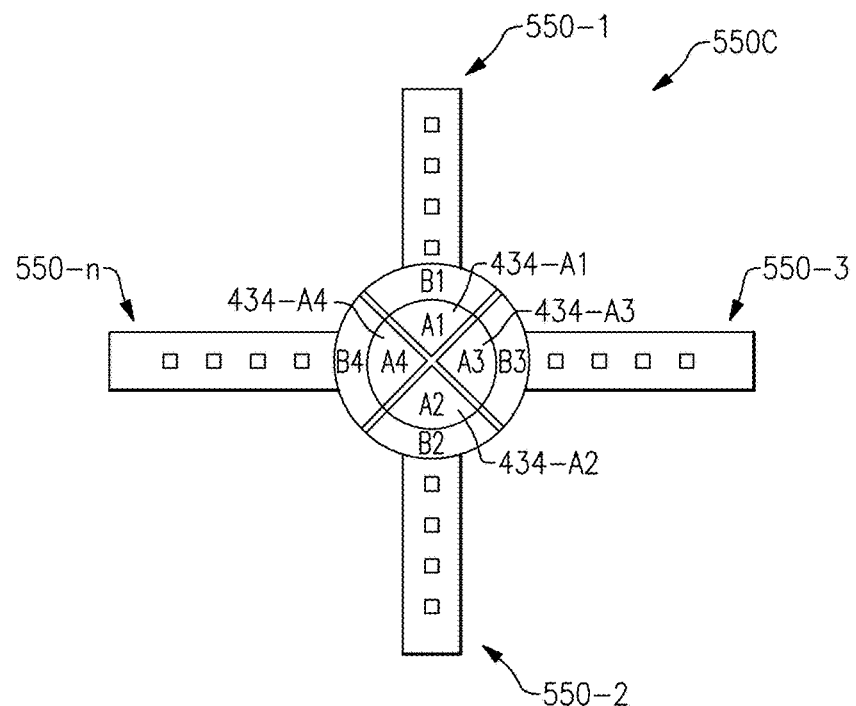
FIG. 55C illustrates a plan-view of a wear-out monitor device that is configured to record an indication of wear out of a core circuit based on localized atomic diffusion in a radially inward direction, where the wear-out monitor device includes a plurality of monitor structures each including a different barrier and a different reservoir, according to embodiments.

FIGS. 55A-55C illustrate top down plan-views of wear-out monitor devices 550A, 550B and 550C, respectively, that are configured to record an indication of wear out of a core circuit based on atomic diffusion of monitor atoms that is localized within the wear-out monitor device, according to embodiments. Similar to the wear-out monitor device 540 illustrated with respect to FIGS. 54A/54B, the wear-out monitor devices 550A, 550B and 550C are configured to be initialized prior to serving as a wear-out monitor based on atomic diffusion in a lateral direction, according to embodiments. However, unlike the monitor device illustrated above with respect to FIGS. 54A/54B, in which the monitor atoms diffuse in a radially inward direction, e.g., inward from the reservoir towards the monitor region formed at a central location, in the wear-out monitor devices 550A, 550B and 550C, the monitor atoms diffuse in a radially outward direction, e.g., outward from the reservoir formed at a central location towards the monitor region formed at an outer location. Each of the wear-out monitor devices 550A, 550B and 550C includes a substrate 62 having formed thereon one or more monitor structures 550-1, 550-2, 550-3, . . . 550-n. While four monitor structures are illustrated, there can be one or any suitable number of monitor structures that can be included in a manner similar to the illustrated four monitor structures.

Each of the one or more monitor structures 550-1, 550-2, 550-3, . . . 550-n include a dedicated or shared reservoir having, e.g., a circular shape, a dedicated or shared barrier having, e.g., a circular or a ring shape, surrounding the dedicated or shared reservoir, and a respective one of monitor regions 552-1, 552-2, 552-3, . . . 552-n extending in a radial direction. Each of the one or more monitor regions 552-1, 552-2, 552-3, . . . 552-n has one end contacting the barrier 438 such that monitor atoms crossing the barrier 438 can diffuse in a radial direction along one of the monitor regions 552-1, 552-2, 552-3, . . . 552-n. In the illustrated embodiment, each one or more monitor regions 552-1, 552-2, 552-3, . . . 552-n is formed as a strip, a track or a channel structure extending in a lateral direction parallel to the substrate surface such that monitor atoms diffuse laterally outward in each of the one or more monitor regions 552-1, 552-2, 552-3, . . . 552-n.

According to embodiments, the one or more monitor regions 552-1, 552-2, 552-3, . . . 552-n can be formed of the same or different materials, can have the same or different dimensions (e.g., lengths) or can otherwise have the same or different configurations, such that different ones of the one or more monitor regions 552-1, 552-2, 552-3, . . . 552-n can diffuse the monitor atoms at different rates and/or different concentration profiles.

Still referring to FIGS. 55A-55C, each of the monitor regions 552-1, 552-2, 552-3, . . . 552-n has a length and one or more measurement structures 554 formed along the length for measuring an electrical property associated with each of the monitor regions. For the example, the one or more measurement structures 554 can include, e.g., contacts or probes, for measuring the electrical property associated with each of the monitor regions. In some embodiments, neighboring ones of the more measurement structures 554 may be separated by a constant distance.

In some embodiments, the reservoir 434, the barrier 438 and the one or more monitor regions 552-1, 552-2, 552-3, . . . 552-4 may be formed on the substrate 62, e.g., a common planar substrate.

In some other embodiments, at least the reservoir 434 and the barrier 438 may be formed in a recessed region formed in the substrate 62. The recessed region may, e.g., be an inverse of the recessed region described above with respect to FIGS. 54A/54B. For example, the barrier 438 may be formed by depositing the barrier material on sidewalls of a recessed region formed at a central location, e.g., on sidewalls of a circular recessed region, and depositing the reservoir material in the recessed region, e.g., in the circular recessed region, In addition, the one or more monitor regions 552-1, 552-2, 552-3, . . . 552-n may be formed in the substrate 62, e.g., when the one or more monitor regions 552-1, 552-2, 552-3, . . . 552-*n* are formed of a material different from the substrate. For example, the one or more monitor regions 552-1, 552-2, 552-3, . . . 552-*n* formed by first forming recessed regions having the shape of the one or more monitor regions 552-1, 552-2, 552-3, . . . 552-*n* and filling the recessed regions with the material of the one or more monitor regions 552-1, 552-2, 552-3, . . . 552-4.

Each of the one or more monitor regions 552-1, 552-2, 552-3, . . . 552-*n* has a lateral dimension, e.g., a length adapted such that the monitor atoms diffusing radially outward can give an indication of a wear-out of the core circuit during its life time. The reservoir 434 and the barrier 438 can have thicknesses corresponding to the depth F adapted for accommodating the reservoir 434 and/or the barrier 438 in a recessed region, as described above with respect to FIGS. 54A/54B. Except for the lateral arrangement, various other configurations including materials, relative energy levels between the monitor region 544, the barrier 438 and the reservoir 434, the possibility of omission of the barrier 438, and various semiconductor doped regions that the monitor region 544 can include, are substantially similar to various embodiments described above, and as such, their detailed descriptions are omitted herein.

In operation, upon lowering or eliminating the energy barrier associated with the barrier 438 by an electrical stimulus the wear-out monitor device is initialized, as described supra. After being initialized, in response to a wear-out stress, the monitor atoms start to diffuse from the reservoir 434 into the one or more monitor regions 552-1, 552-2, 552-3, . . . 552-*n* that are elongated in a lateral direction. The plurality of measurement structures 554 located at intervals along the length direction of each of the one or more monitor regions 552-1, 552-2, 552-3, . . . 552-*n* can provide a spatially-dependent electrical indication, e.g., leakage current. The spatially-dependent electrical indication can in turn provide a temporal history of the wear-stress experienced by the core circuit, based on the time-dependence of the diffusion of monitor atoms described supra.

Referring to the monitor device 550A of FIG. 55A, in some embodiments, the one or more monitor regions 552-1, 552-2, 552-3, . . . 552-*n* contact a common barrier 438 and are configured to be supplied with monitor atoms from a common reservoir 434. As configured, the plurality of measurement structures 554 located at intervals along the length direction of each of the one or more monitor regions 552-1, 552-2, 552-3, . . . 552-*n* can provide spatially-dependent electrical indication in different directions, which can in turn provide a corresponding temporal history of the wear-stress experienced by the core circuit.

Referring to the monitor device 550B of FIG. 55B, in some embodiments, a separate barrier 438-B1, 438-B2, 438-B3 and 438-B4 is dedicated for each of the one or more one or more monitor regions 552-1, 552-2, 552-3, . . . 552-*n* are the same. The barriers 438-B1, 438-B2, 438-B3, . . . 438-B*n* can be physically separated by a thermally robust division that does not become substantially altered in response to an electrical stimulus that alters the barriers 438-B1, 438-B2, 438-B3, . . . 438-B*n*. Each of the separate barriers 438-B1, 438-B2, 438-B3, . . . 438-B*n* is configured to be independently modified by an electrical stimulus, such that the each of the one or more monitor regions 552-1, 552-2, 552-3, . . . 552-*n* is configured to initialized independently from each other. Thus, a plurality of wear-out indications can be initialized at different times based on a user's preference.

In some embodiments, the separate barriers 438-B1, 438-B2, 438-B3 . . . 438-B*n* can be formed of same or different materials, have the same or different dimensions (e.g., thicknesses) or otherwise have the same or different configurations such that they are configured to be altered correspondingly in response to the same or different electrical stimuli.

Referring FIG. 55C, in some embodiments, in addition to separate barriers 438-B1, 438-B2, 438-B3, . . . 438-B4 for the one or more monitor regions 552-1, 552-2, 552-3, . . . 552-*n* as described above with respect to FIG. 55B, the monitor device 550C can additionally include separate reservoirs 434-A1, 434-A2, 434-A3, . . . 434-A*n* dedicated for each of the one or more monitor regions 552-1, 552-2, 552-3, . . . 552-*n*. The barriers 438-B1, 438-B2, 438-B3, . . . 438-B*n* can be configured as described above with respect to FIG. 55B. In addition, each of the separate reservoirs 434-A1, 434-A2, 434-A3, . . . 434-A4 can be configured to independently supply the monitor atoms to be diffused in the one or more monitor regions 552-1, 552-2, 552-3, . . . 552-*n*, after a corresponding one of the barriers 438-B1, 438-B2, 438-B3, . . . 438-B*n* is modified by an electrical stimulus, such that the each of the one or more monitor regions 552-1, 552-2, 552-3, . . . 552-*n* is configured to initialized independently from each other and to be independently supplied with the monitor atoms. Thus, in addition to being initialized at different times based on user's preference. a plurality of wear-out indications can be independently supplied with the monitor atoms.

In some embodiments, the separate reservoirs 434-A1, 434-A2 434-A3, . . . 434-A*n* can contain the same or different monitor atoms, can contain the same or different matrix material incorporating the monitor atoms, have the same or different dimensions (e.g., volumes) or otherwise have the same or different configurations, such that they are configured to supply the same or different monitor atoms to the respective ones of the one or more monitor regions 552-1, 552-2, 552-3, . . . 552-*n*.

Thus, in the illustrated embodiment in FIG. 55C, different ones of the one or more monitor structures 550-1, 550-2, 550-3, . . . 550-*n* having different combinations of the reservoir, the barrier and the monitor region can be configured to be particularly sensitive to different types, different magnitudes and/or different durations of wear-out stresses. For example, each of the one or more monitor structures 550-1, 550-2, 550-3, . . . 550-*n* can be adapted for different temperature ranges and/or different durations of wear-out stresses.

In the embodiments described above with respect to FIGS. 55A-55C, various embodiments of a wear-out monitor device including a plurality of monitor structures configured to be initialized prior to serving as a wear-out monitor based on atomic diffusion in a lateral direction are described. In particular, in the embodiments described above with respect to FIGS. 55A-55C, the plurality of monitor structures are arranged laterally on a substrate. In the following, embodiments of a wear-out monitor device including a plurality of monitor structures that are arranged vertically, e.g., in a vertically stacked configuration, are described. The monitor structures according to these embodiments can occupy a more compact lateral footprint and provide indications of wear-out stress at different depths within the monitor device. Similar to the embodiments described above with respect to FIGS. 55A-55C, these embodiments can have the same or different barriers, the same or different reservoirs of monitor atoms, and/or the same or different monitor regions.

Figure 56A:
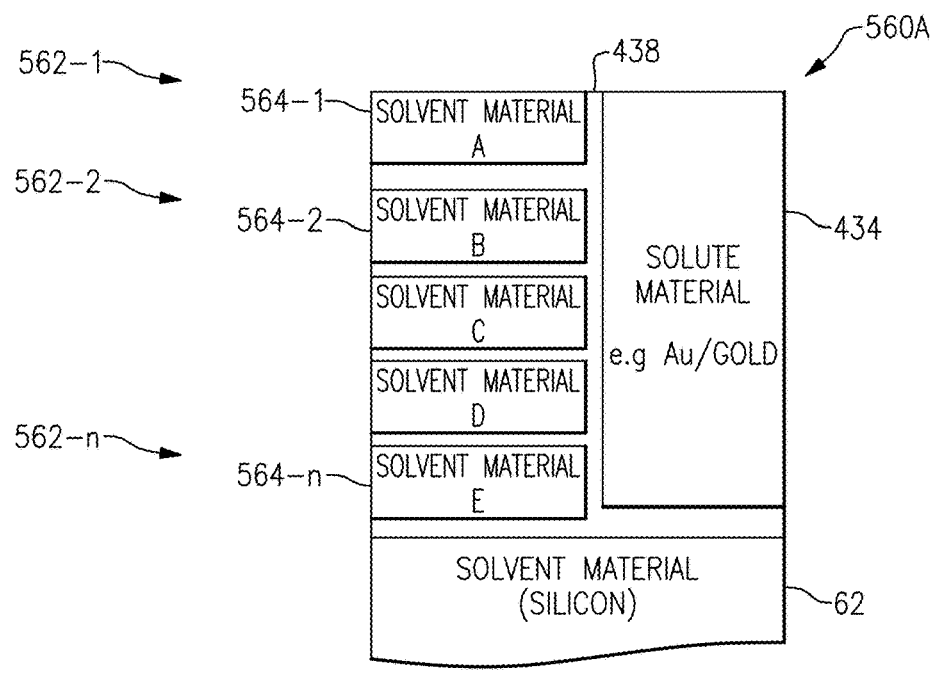
FIG. 56A illustrates a cross-sectional view of a wear-out monitor device that is configured to record an indication of wear out of a core circuit based on localized atomic diffusion in a lateral direction, where the wear-out monitor device includes a plurality of monitor structures including a barrier and differently configured monitor regions, according to embodiments.

FIG. 56A illustrates a cross-sectional view of a wear-out monitor device 560A that is configured to record an indication of wear out of a core circuit based on atomic diffusion of monitor atoms that is localized within the wear-out monitor device, according to embodiments. Similar to the wear-out monitor devices 550A, 550B and 550C described above with respect to FIGS. 55A-55C, the wear-out monitor 560A is configured to be initialized prior to serving as a wear-out monitor based on atomic diffusion in a lateral direction, according to embodiments. However, unlike the monitor devices illustrated above with respect to FIGS. 55A-55C, in which the monitor structures are arranged laterally on a substrate, the monitor structures of the monitor device 560A includes a plurality of monitor structures 562-1, 562-2, . . . 562-n formed on a substrate 62 including corresponding ones of monitor regions 564-1, 564-2, . . . 564-n. The monitor regions 564-1, 564-2, . . . 564-n are separated from a reservoir 464 by a barrier 468. Each of the plurality of monitor regions 562-1, 562-2, . . . 562n are elongated and extend in a radial direction and has one end contacting the barrier 438 such that monitor atoms crossing the barrier 438 can diffuse away from the reservoir 434 in a radial direction along a length direction. Furthermore, the substrate 64 is separated from the reservoir 434 such that it can also serve as a monitor region. In the illustrated embodiment, each one or more monitor regions 564-1, 564-2, . . . 564-n is formed as a strip, a track or a channel structure extending in a lateral direction parallel to the substrate surface such that monitor atoms diffuse laterally outward in each of the one or more monitor regions 562-1, 562-2, . . . 562-n.

Still referring to FIG. 56A, similar to embodiments illustrated with respect to FIGS. 55A-55C, in some embodiments, the monitor device 560A has the monitor regions 562-1, 562-2, . . . 562-n that are formed of the same or different materials, have the same or different dimensions (e.g., lengths) or otherwise have the same or different configurations, such that different ones of the monitor regions 562-1, 562-2, . . . 562-n are configured to diffuse the monitor atoms at different rates and/or different concentration profiles. However, embodiments are not so limited and in other embodiments, the monitor regions 562-1, 562-2, . . . 562-n are configured to be substantially the same.

Figure 56B:
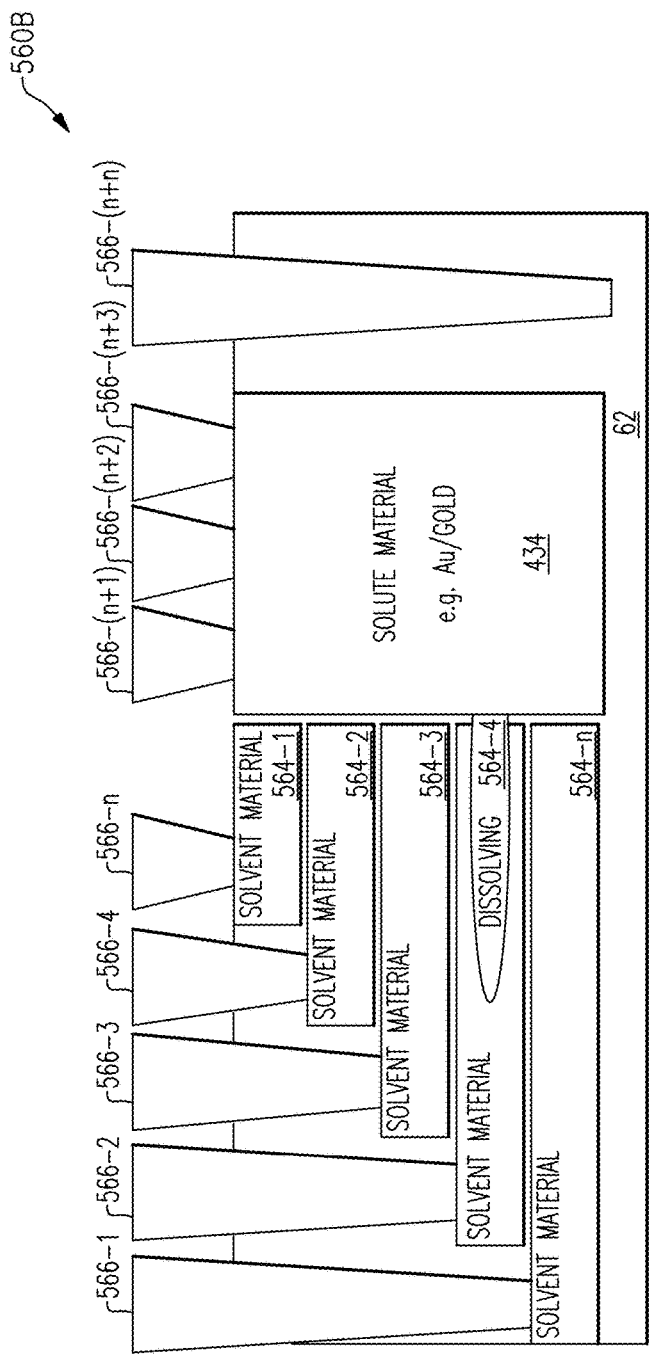
FIG. 56B illustrates the wear-out monitor device illustrated in FIG. 56A, further illustrating electrical connections to different regions of the wear-out monitor device, according to embodiments.

FIG. 56B illustrates a cross-sectional view of a wear-out monitor device 560B similar to the wear-out monitor device 560A of FIG. 56A, including electrical connections to the reservoir 434 and to the monitor regions 562-1, 562-2, . . . 562-n. As illustrated, the wear-out monitor device 560A includes a plurality of electrical contacts 566-1, 566-2, . . . 566-n, e.g., via contacts, electrically connecting the monitor regions 562-1, 562-2, . . . 562-n to various circuitry, including, e.g., control circuitry and/or sensing circuitry, as described more in detail, infra. In addition, a plurality of electrical contacts 566-(n+1), 566-(n+2), . . . 566-(n+m), e.g., via contacts, electrically connecting the reservoir 434 and the substrate 64 to various circuitry, including, e.g., control circuitry and/or sensing circuitry, as described more in detail, infra.

Figure 56C:
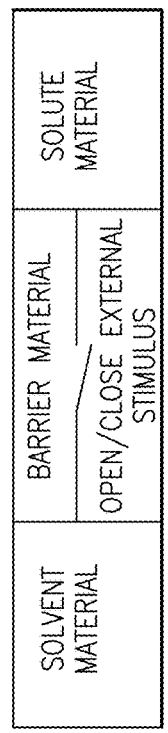
FIG. 56C illustrates an equivalent circuit diagram of the wear-out monitor device illustrated in FIG. 56A that is configured to be initialized by individually applying an electrical stimulus to a respective region of the barrier between the reservoir and the each of the monitor regions, according to embodiments.

Referring to an equivalent circuit diagram 560C of FIG. 56C, each of the regions of the monitor regions 562-1, 562-2, . . . 562-n of the wear-out monitor device 560 is initialized by individually applying an electrical stimulus to a respective region of the barrier 438 between the reservoir 434 and the each of the monitor regions 562-1, 562-2, . . . 562-n via respective ones of the electrical connections, thereby locally altering the respective region of the barrier 438. Once initialized, the monitor atoms start to diffuse from the reservoir 434 into the respective one of the monitor regions 562-1, 562-2, . . . 562-n in response to a wear-out stress. Thus, as configured, by altering respective regions of the barrier 438 at different times, different ones of the monitor regions 562-1, 562-2, . . . 562-n can advantageously be initialized at different times according to the user's preference. In embodiments where the monitor regions 562-1, 562-2, . . . 562-n are formed of the same material and/or otherwise configured to have the substantially the same rate of diffusion of the monitor atoms therein, a plurality of monitoring runs can be performed using the plurality of the monitor regions 562-1, 562-2, . . . 562-n. Furthermore, by configuring the monitor regions 562-1, 562-2, . . . 562-n to have different lengths as illustrated in FIG. 56A, different monitoring runs can be performed for different durations of time. In addition, where the monitor regions 562-1, 562-2, . . . 562-n are formed of different materials and/or otherwise configured to have the substantially different rates of diffusion of the monitor atoms therein, different ones of the monitor regions 562-1, 562-2, . . . 562-n optimized for different wear-out stresses or levels of the wear-out stress can be initialized at different times according to a user's preference. For example, where a core circuit is experiences substantially different levels of thermal wear-out stresses at different times, a barrier region adjacent to one of the monitor regions 562-1, 562-2, . . . 562-n configured to diffuse the monitor atoms relatively slowly and/or having a longer monitor region length may be altered when the core circuit is exposed to a relatively high level of thermal stress (e.g., relatively higher temperature and/or relatively long duration). On the other hand, a barrier region adjacent to one of the monitor regions 562-1, 562-2, . . . 562-n configured to diffuse the monitor atoms relatively rapidly and/or having a shorter length may be altered when the core circuit is exposed to a relatively lower level of thermal stress (e.g., relatively lower temperature and/or relatively shorter duration). By way of example, different ones of the monitor regions 562-1, 562-2, . . . 562-n may be formed of or include a material AxBy having different compositions, where A and B are elements that can be proportionally mixed to alter the diffusion rate of monitor atoms therein. For example, A may be a substrate material such as Si, and B may be Ge, C, Sn, O, and N, to name a few.

Figures 56D, 56E:
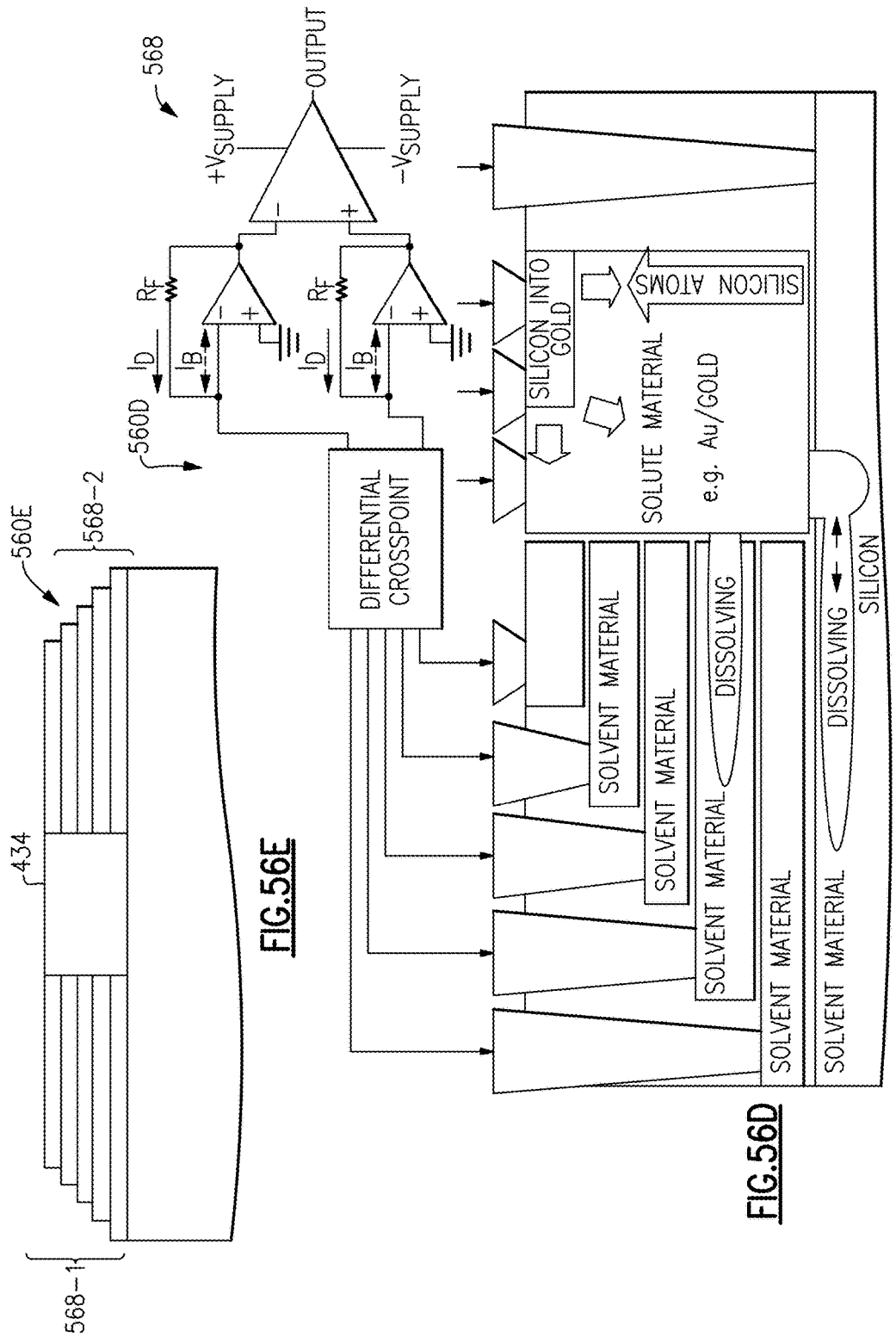
FIG. 56D illustrates one example embodiment of a sensing circuit electrically connected to the wear-out monitor device illustrated in FIG. 56A that is configured to measure changes in electrical properties of the monitor regions, according to embodiments.
FIG. 56E illustrates a cross-sectional view of a wear-out monitor device that is configured to record an indication of wear out of a core circuit based on localized atomic diffusion in a lateral direction, where the wear-out monitor device includes two sets of monitor regions commonly connected to a reservoir, according to embodiments.

After being initialized and being subjected to wear-out stresses, changes in the electrical properties of monitor regions 562-1, 562-2, . . . 562-n resulting from diffusion of monitor atoms from the reservoir 434 into the monitor regions 562-1, 562-2, . . . 562-n can be measured through the plurality of electrical contacts 566-1, 566-2, . . . 566-n, e.g., using a suitable sensing circuitry. FIG. 56D illustrates one example embodiment of a wear-out monitor device 560D having a sensing circuit 568 electrically connected to the wear-out monitor device 560B of FIG. 56B and configured to measure the changes in electrical properties of the monitor regions 562-1, 562-2, . . . 562-n. In the illustrated example, the monitor regions 562-1, 562-2, . . . 562-n are electrically connected to a differential measurement circuit 568 including a differential amplifier and configured to, based on a difference in the measured electrical properties of from different ones of the monitor regions 562-1, 562-2, . . . 562-n, a determination of relative wear-out stress received by the different monitor regions 562-1, 562-2, . . . 562-n can be determined. The differential measurement circuit 568 can measure difference(s) in the electrical properties between any two or more of the monitor regions 562-1, 562-2, . . . 562-n, which can arise from varying any one of the monitor atoms, the reservoir composition, the composition of the monitor regions 562-1, 562-2, . . . 562-n, the shapes and dimensions of the monitor regions 562-1, 562-2, . . . 562-n, barrier material and initialization times, among other parameters arising from various configurations of the wear-out device 560 described above. The resulting electrical measurement can include any one of electrical properties described above, e.g., resistivity, leakage current, capacitance, etc.

Referring to FIG. 56E, a cross-sectional view of a wear-out monitor device 560E is illustrated, according to some other embodiments. The wear-out monitor device 560D is similar to the wear-out monitor device 560A/560B described above with respect to FIGS. 56A/56B, except, the wear-out monitor device 560D has two sets 568-1, 568-2 of monitor regions commonly connected to a reservoir. The monitor regions on the two sides can be configured to be the same or different, including the barrier and the monitor regions.

While in the illustrated embodiment of FIGS. 56A/56B, the one of the monitor regions 562-1, 562-2, . . . 562-n are connected to a common reservoir 434 through a common barrier 438, embodiments are not so limited. For example, while not shown, in other embodiments, separate and/or dedicated barriers 438-B1, 438-B2, . . . 438-Bn and/or separate and/or dedicated reservoirs 434-A1, 434-A2, . . . 434-An may be connected to respective ones of the monitor regions 562-1, 562-2, . . . 562-n. Thus, in a similar manner as described above with respect to the embodiment of FIG. 55C, in addition to being configurable to have the same or different monitor regions 562-1, 562-2, . . . 562-n, the monitor device 560 can additionally be configured to have barriers 438-B1, 438-B2, . . . 438-Bn that are altered in response to different levels of electrical stimuli and/or reservoirs 434-A1, 434-A2, . . . 434-An that have different types and/or concentrations of monitor atoms and/or different matrices or media in which monitor atoms are contained.

Thus, in the illustrated embodiment of FIGS. 56A/56B, in a similar manner to the embodiments described above, different combinations of the reservoir, the barrier and the monitor region can be configured to be particularly sensitive to different types, different magnitudes and/or different durations of wear-out stresses.

Controlled initialization or activation of wear-out monitor devices described above with respect to FIGS. 43-56B can be implanted in context of semiconductor packaging. The wire bonding technology is widely used for interconnecting integrated circuits to the outside word. In the following, implementation of the controlled initialization of wear-out monitor devices in the context of wire bonding is described.

Figure 57:
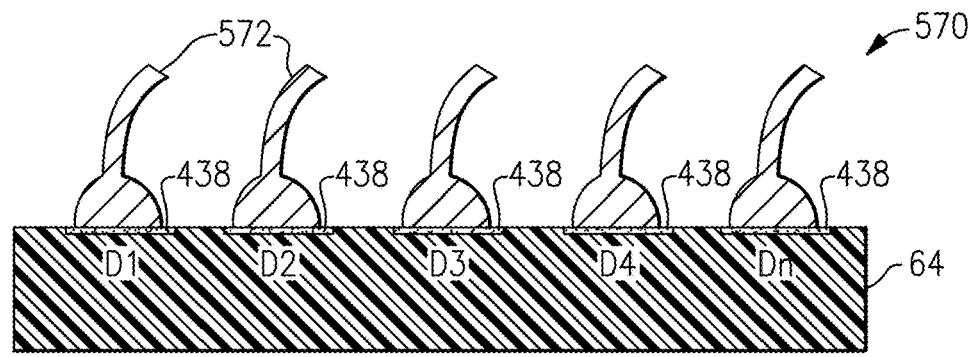
FIG. 57 illustrates a cross-sectional view of a wear-out monitor device that is configured to record an indication of wear out of a core circuit based on localized atomic diffusion, where a plurality of reservoirs of monitor atoms are configured as wire bonds, according to embodiments.

FIG. 57 is an illustration of a wear-out monitor device 570 configured to record an indication of wear out of a core circuit based on atomic diffusion of monitor atoms that is localized within the wear-out monitor device, according to embodiments. In particular, the wear-out monitor device 570 includes a substrate 64, which can be an integrated circuit (IC) including metallization levels integrated therein. The wear-out monitor device 570 includes one or more monitor regions D1, D2, . . . Dn formed in the substrate 64. The one or more monitor regions D1, D2, . . . Dn can be formed in or on, e.g., directly in or on the semiconductor material of the IC in some embodiments, or be formed over metallization levels of the IC in other embodiments. The wear-out monitor device 570 additionally includes one or more barriers 438 formed on the one or more monitor regions D1, D2, . . . Dn, and one or more wire bonds 572 formed on the one or more barriers 438 to serve as reservoirs 434. The one or more barriers 438 can be formed of and configured in a manner similar to various embodiments described supra. In addition, the one or more wire bonds can be formed of and configured in a manner similar to various embodiments described above and compatible with the wire bonding technology. In the monitor device 570, advantageously, the wire bond itself includes the monitor atoms and therefore serves as the reservoir 434. Elements such as gold, silver, copper and platinum, for example, can serve as the monitor atoms as well as providing the electrical connection to the IC.

In operation, a barrier 438 may be altered in any manner described above to initialize the diffusion of monitor atoms, in response to a wear-out stress, into a respective one of the monitor regions D1, D2, . . . Dn. Subsequently, when the monitor atoms diffuse into the a respective on the monitor regions D1, D2, . . . Dn, and/or when atoms of the respective monitor region diffuse into the respective wire bond, the resistance across the wirebond-barrier-monitor region. Without being bound to any theory, one mechanism that can cause a change in resistance can arise from a phenomenon known as Kirkendall effect, which is associated with inter-diffusion of atoms giving rise to formation of atomic vacancies and voiding over time.

Figure 58:
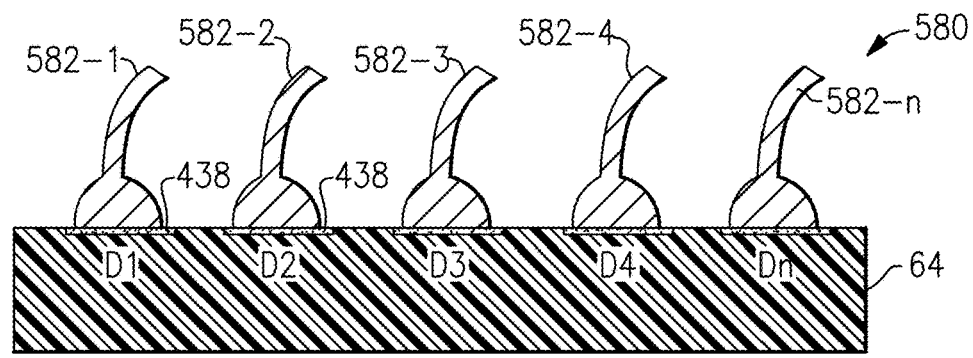
FIG. 58 illustrates a cross-sectional view of a wear-out monitor device that is configured to record an indication of wear out of a core circuit based on localized atomic diffusion, where a plurality of reservoirs of monitor atoms are configured as different wire bonds, according to embodiments.

FIG. 58 is an illustration of a wear-out monitor device 580 configured to record an indication of wear out of a core circuit based on atomic diffusion of monitor atoms that is localized within the wear-out monitor device, according to embodiments. The monitor device 580 is similar to the wear-out monitor device 570 described above with respect to FIG. 57 except, different ones of the one or more wire bonds 582-1, 582-2, . . . 582-n serving as the reservoirs 438 are formed of or incorporate different monitor atoms, such as gold, silver, copper and platinum, to name a few. The description of other features of the wear-out monitor device 580 that are similar to those of the wear-out monitor device 570 illustrated above with respect to FIG. 57 is omitted herein. Thus, in the illustrated embodiment of FIG. 58, in a similar manner to various embodiments described above, different combinations of the reservoir, the barrier and the monitor region can be configured to be particularly sensitive to different types, different magnitudes and/or different durations of wear-out stresses.

Figure 59:
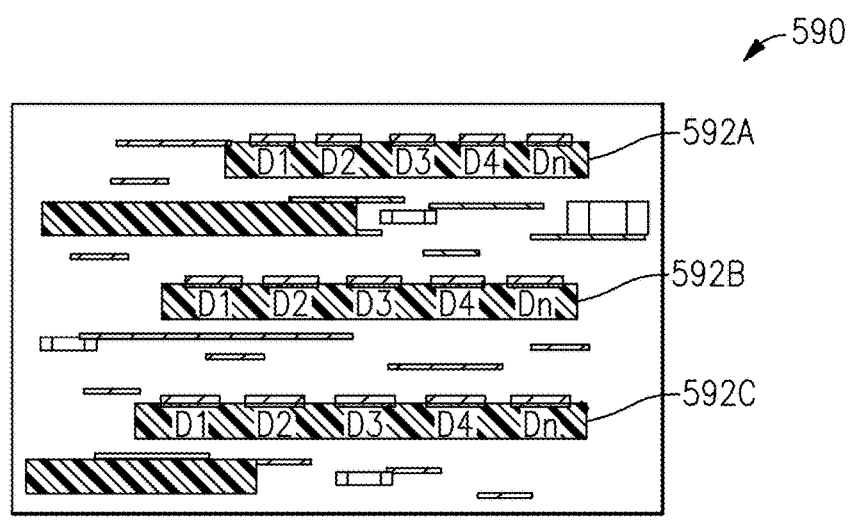
FIG. 59 illustrates a plan-view of a plurality of wear-out monitor devices that are embedded or incorporated as part of a package-level integrated system along with other passive/discrete components and/or microprocessors that include core circuits to be protected, according to embodiments.

FIG. 59 illustrates a cross-sectional view of a system 590, e.g., a package-level or a board-level integrated system, including a plurality of wear-out monitor devices 592A, 592B, 592C, where each wear-out monitor device is configured to record an indication of wear out of a core circuit based on atomic diffusion of monitor atoms that is localized within the wear-out monitor device, according to embodiments. In some implementations, the system 590 is an embedded system, where various components are embedded within layers of a substrate (e.g., a PCB substrate) during the fabrication process. In particular, the cross sectional view shows a plurality of wear-out monitor devices 592A, 592B, 592C that are embedded within respective layers of a substrate, where each monitor devices can be configured to monitor, among other things, temperature fluctuations and/or mission profiles of different layers (or next/near to specific components) within the system 590.

Still referring to FIG. 59, the wear-out monitor devices 592A, 592B, 592C can have various features configured differently for monitoring different wear-out stresses and/or monitoring wear-out stresses at different times. As illustrated, the wear-out monitor devices can be embedded or incorporated as part of a package-level integrated system along with other passive/discrete components and/or microprocessors that include core circuits to be protected, according to embodiments. In addition, the wear-out monitor devices can be connected or linked to a co-ordinating ASIC and also links that could be modifiable (e.g., fuses that could be blown or electrically modified), according to embodiments.

Figure 60A:
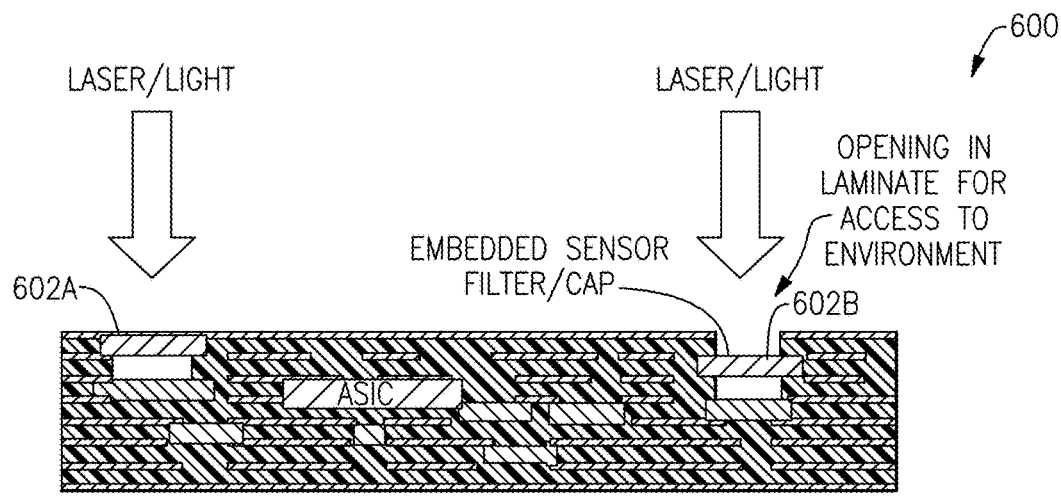
FIG. 60A illustrates a cross-sectional view of a package-level integrated system including a plurality of wear-out monitor devices that are embedded or incorporated with other passive/discrete components and/or microprocessors that include core circuits to be protected, where the barrier is formed of a material that is configured to be altered by photons of light, according to embodiments.

In various embodiments described above, wear-out monitor devices configured to record an indication of wear out of a core circuit have been described in which a barrier can be altered by an electrical stimulus to initialize wear-out monitoring. However, embodiments are not so limited and in other embodiments, the barrier can be altered using optical energy. FIG. 60A illustrates a cross-sectional view of a system 600, e.g., a package-level or a board-level integrated system including a plurality of wear-out monitor devices 602A, 602B, where each wear-out monitor device is configured to record an indication of wear out of a core circuit based on atomic diffusion of monitor atoms that is localized within the wear-out monitor device, according to embodiments. Unlike the wear-out monitors described above with respect to FIGS. 43-59, in which the barrier, when present, is configured to be altered to initialize the wear-out monitor devices 600A, 600B in response to an electrical stimulus, e.g., voltage or current pulses, which in turn may generate heat by Joule heating which causes the barrier to be altered, in the wear-out monitor devices 600A, 600B, the barrier is configured to be modified in response to optical energy. The system 600 may include various other components, e.g., passive/active components, ASIC, etc., as described above.

The illustrated package of the package-level system 590 is an organic laminate-based package. However, embodiments are not so limited and the package can also be based on a ceramic material to protect the packaged components. As illustrated, the various components may be embedded or covered by the packaging material, e.g., an organic laminate material to protect various components against moisture, etc. To allow optical access of the barriers in the wear-out monitors, in some embodiments, optically transparent openings or apertures may be formed through the passivating layer, and/or the insulating package of the wear-out devices 600A, 600B when present. The openings or apertures may be sealed in some embodiments with a cap. In some other embodiments, the openings may include an optically active cap, which can be configured as a lens, a filter or other optical components. When present, a filter can selectively pass desired wavelengths, and when present, a lens can focus the light to provide an increased intensity of the light for causing a local increase in temperature. In some other embodiments, the cap can also be configured to protect the wear-out sensor.

Still referring to FIG. 60A, in some embodiments, the barrier is formed of a material that is directly altered by photons of light. For example, the barrier may be formed of an organic material, e.g., a polymeric material, which can be altered by photons. In other embodiments, the barrier is formed of a material that is indirectly altered by light, e.g., by the heat generated by the light. The optical energy source that can alter the barrier can light sources, e.g., visible, infrared, ultraviolet and X-ray sources, including lasers, light emitting diodes, lamps, etc.

Figure 60B:
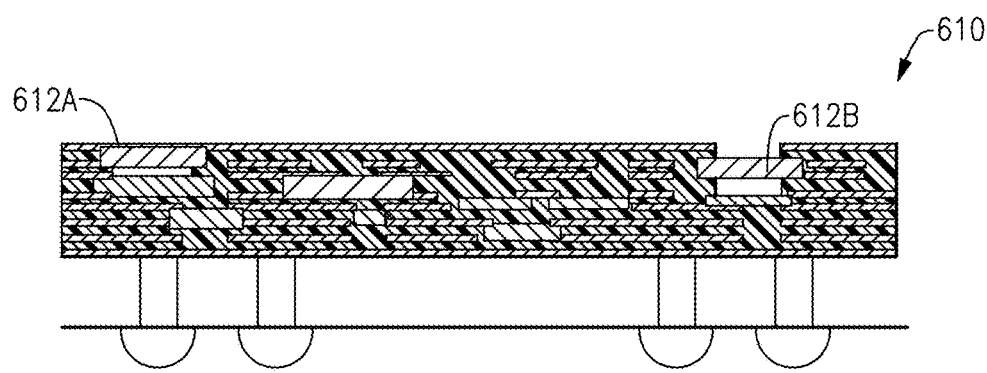
FIG. 60B illustrates the system illustrated in FIG. 60A mounted on another system that includes control and/or sensing circuitry, according to embodiments.

FIG. 60B illustrates a cross-sectional view of a system, e.g., a package-level or a board-level integrated system 610 including a plurality wear-out monitor devices 612A, 612B integrated therein, where each wear-out monitor device is configured to record an indication of wear out of a core circuit based on atomic diffusion of monitor atoms that is localized within the wear-out monitor device, according to embodiments. The system 610 may be a pre-fabricated system similar to the system 600 illustrated above with respect to FIG. 60, which includes wear-out monitors 602A, 602B. The system 610 may be configured to be mounted on another system 614. In embodiments, the system 614 can include various control and sensing circuitry to control and sense the wear-out monitor devices 612A, 612B, which can be implemented in an ASIC. Advantageously, the illustrated configuration allows for a customized/prefabricated system 610 including various embedded wear-out monitor devices 612A, 612B to be coupled to the system 614 that co-ordinate the various activities of the system 610.

Wear-Out Monitor Devices with Wear-Out Indication Based on Interdiffusion

In various embodiments of wear-out monitor devices described above, indications of wear-out of a core circuit are based on measuring an electrical property associated with the effect of atomic diffusion of monitoring atoms into a monitoring region from a reservoir. For example, the reservoir may be a layer containing the monitor atoms that is formed on the surface of a substrate. The monitoring region may be, e.g., a volume of substrate material that serves as a diffusing medium for the monitoring atoms.

For some combinations of materials, when a first material is in contact with a second material, atoms of the first material diffuse into the second material while atoms of the second material diffuse into the first material. This phenomenon is referred to as interdiffusion. According to various embodiments described herein, the monitoring region and the reservoir of monitor atoms are configured such that the monitor atoms and the atoms of the monitoring region interdiffuse in response to wear-out stresses. In these embodiments, the resulting compositional change in the reservoir can give rise to measurable electrical signatures of the wear-out stresses. Thus, in the embodiments described below, unlike the embodiments described above, the reservoir can be considered as the monitor region, and the substrate can be considered as the source of the diffusant, or monitor atoms.

Figure 61:
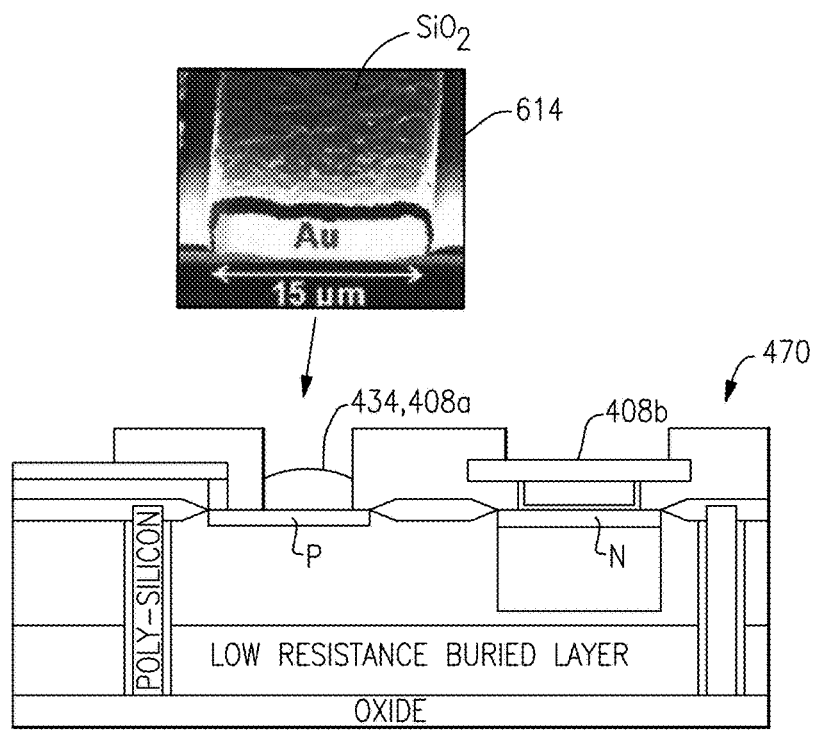
FIG. 61 illustrates a wear-out monitor device configured to record an indication of wear out of a core circuit based on localized atomic diffusion of monitor atoms, where the indication is based on interdiffusion between the monitor region and the reservoir of monitor atoms, according to embodiments.

FIG. 61 illustrates how wear-out monitor devices can be configured such that an indication of wear-out of a core circuit based on interdiffusion of atoms can be utilized, according to embodiments. FIG. 61 illustrates the wear-out monitor device 470 described above with respect to FIG. 47, which is configured to record an indication of wear out of a core circuit based on atomic diffusion of monitor atoms that is localized within the wear-out monitor device, according to embodiments. As described above, the wear-out monitor device 470 has one or more reservoirs of monitor atoms (i.e., first and/or second electrodes 408a, 408b) disposed on a surface of the substrate and a monitor region (e.g., depletion region formed underneath the second heavily doped region 454b) formed in the substrate 450. As described above, e.g., with respect to FIG. 42A, one approach to quantifying wear-out of a core circuit is to measure leakage current, e.g., reverse bias leakage current across a PN junction, after exposure to wear-out stress at different times. Thus, as illustrated in FIG. 42A, the increasing leakage current with increasing wear-out stress, e.g., thermal stress, can be used to quantify the wear-out of the core circuit.

A scanning electron microscope (SEM) image 614 illustrates another approach of quantifying the wear-out. The SEM image 614 is a representative image of the first electrode 408a serving as the reservoir formed of gold, after being subjected to a wear-out stress used to generate the experimental data illustrated with respect to FIG. 42A. As illustrated in the SEM image 614, after being subjected to thermal wear out stress at 200° C. for 1-9 days, formation of silicon dioxide on the first electrode 408a serving as the reservoir of gold indicates that interdiffusion has occurred. That is, while diffusion of gold from the gold electrode into the PN junction in the silicon substrate causes an increase in the reverse bias current, diffusion of silicon from the substrate into the gold electrode leads to formation of silicon oxide resulting from oxidation of silicon atoms that has reached the surface of the gold electrode.

Figure 62A:
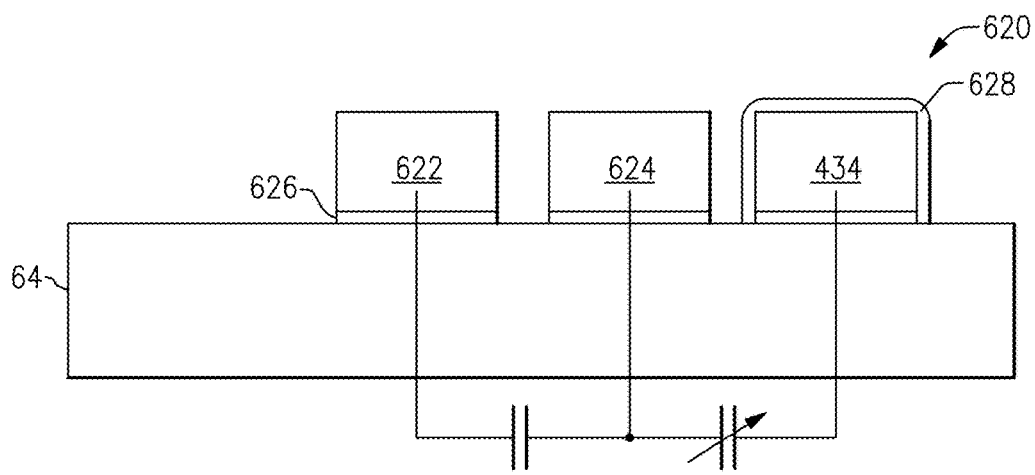
FIG. 62A illustrates a wear-out monitor device configured to record an indication of wear out of a core circuit based on localized atomic diffusion of monitor atoms, where the indication is based on interdiffusion between the monitor region and the reservoir of monitor atoms, according to embodiments.

FIG. 62A illustrates a cross-sectional view of a wear-out monitor device 620 configured such that electrical signatures based on interdiffusion of atoms can be utilized, according to embodiments. The wear-out monitor device 620 has formed on a substrate 64 one or more electrodes, e.g., first reference electrode 622 and a second reference electrode 624, and a reservoir 434. Each of the first and second reference electrodes 622, 624 are separated from the substrate 64 by a permanent diffusion barrier 626. In some embodiments, the first and second reference electrodes 622, 624 and the reservoir 434 initially have the same composition and/or dimensions comprising the monitor atoms. Furthermore, in some embodiments, the spacing between the first and second reference electrodes 622, 624 and the spacing between the second reference electrode 624 and the reservoir 434 initially have the same dimensions.

In operation, as described above with respect to FIG. 61, the reservoir 434 and the substrate 64 have compositions such that, under a wear-out stress, e.g., a thermal stress, the monitor atoms in the reservoir 434 and the atoms of the substrate 64 interdiffuse such that the monitor atoms diffuse into the substrate and the atoms of the substrate 64 diffuse into the reservoir 434. In contrast, the presence of the permanent diffusion barrier 626 prevents diffusion into and out of the first and second reference electrodes 622, 624 from and into the substrate 64. The interdiffusion between the substrate 64 and the reservoir 434 results in a change in the chemical composition of the reservoir 434, which in turn leads to changes in electrical characteristics of the reservoir 434, while the chemical composition and the electrical characteristics of the first and second reference electrodes 622, 624 remain relatively unchanged. The electrical characteristics of the reservoir 434 that can change include the resistivity of the reservoir 434 and capacitances between the reservoir 434 and other conductive structures, e.g., the second reference electrode 624.

As one illustrative example, when the reservoir 434 is formed of gold and the substrate 64 is formed of silicon, gold diffuses into the substrate 64 while silicon diffuses into the reservoir 434. As described above with respect to FIG. 61, inventors have found that the interdiffusion results in a structural change in the reservoir 434, reservoir 434 and/or due to the formation of silicon oxide 628 on the reservoir 434. The structural change in turn leads to changes in electrical property of the reservoir 434 that can be electrically measured using a sensing circuit.

FIG. 62B illustrates a close-up view of the wear-out monitor device 620 illustrated in FIG. 62A electrically connected to a sensing circuit 629 configured to detect electrical signatures associated with the structural modifications to the reservoir 424 resulting from interdiffusion of atoms, according to embodiments. One example electrical signature of wear-out of a core circuit that can be measured on the wear-out monitor device 620 using the sensing circuit 629 is the electrical resistivity of the reservoir 424. The electrical resistivity of the reservoir 424 may increase, due to the presence of silicon atoms in the reservoir 424 and/or the formation of silicon oxide on the reservoir 424 as described above. Another example electrical signature of wear-out of a core circuit that can be measured on the wear-out monitor device 620 is the capacitance between the reservoir 434 serving as a first plate and another conductive structure serving as a second plate of a capacitor. For example, the second reference electrode 624 can serve as the second plate of the capacitor, whose capacitance value may change with exposure to wear-out stresses, e.g., thermal wear-out stresses. As the thickness of silicon oxide 628 in the gap between the second reference electrode 624 and the reservoir 434 increases, the capacitance changes, e.g., increases, whose change can be quantitatively correlated to the aggregate wear-out stress that core circuit has been exposed to. Furthermore, in embodiments where the first reference electrode 622 is included, the capacitance between the first and second reference electrodes 622 and 624 can serve as a reference capacitance that does not change or changes significantly less relative to the change in capacitance between the second reference electrode 624 an the reservoir 434. Advantageously, because the changes in electrical properties resulting from the diffusion of substrate atoms into the reservoir 434, the wear-out monitor device 624 does not rely on semiconductor device structures such as PN junctions formed in the substrate 64.

FIGS. 63A-63D illustrate cross-sectional views of a wear-out monitor device 630 configured such that electrical signatures based on interdiffusion of atoms can be utilized to measure wear-out of a core circuit, according to embodiments. The wear-out monitor device 630 is configured similarly to the wear-out monitor device 560 described above with respect to FIGS. 56A-56D, where the monitor regions 562-1, 562-2, . . . 562-n may be electrically connected to the sensing circuit 568 described above with respect to FIG. 56D configured such that the electrical properties of the monitor regions 562-1, 562-2, . . . 562-n, e.g., electrical resistance and/or capacitance associated with the reservoir 434, resulting from substrate atoms of the bulk substrate 64 diffusing into the reservoir 434, can be individually measured.

Figure 63A:
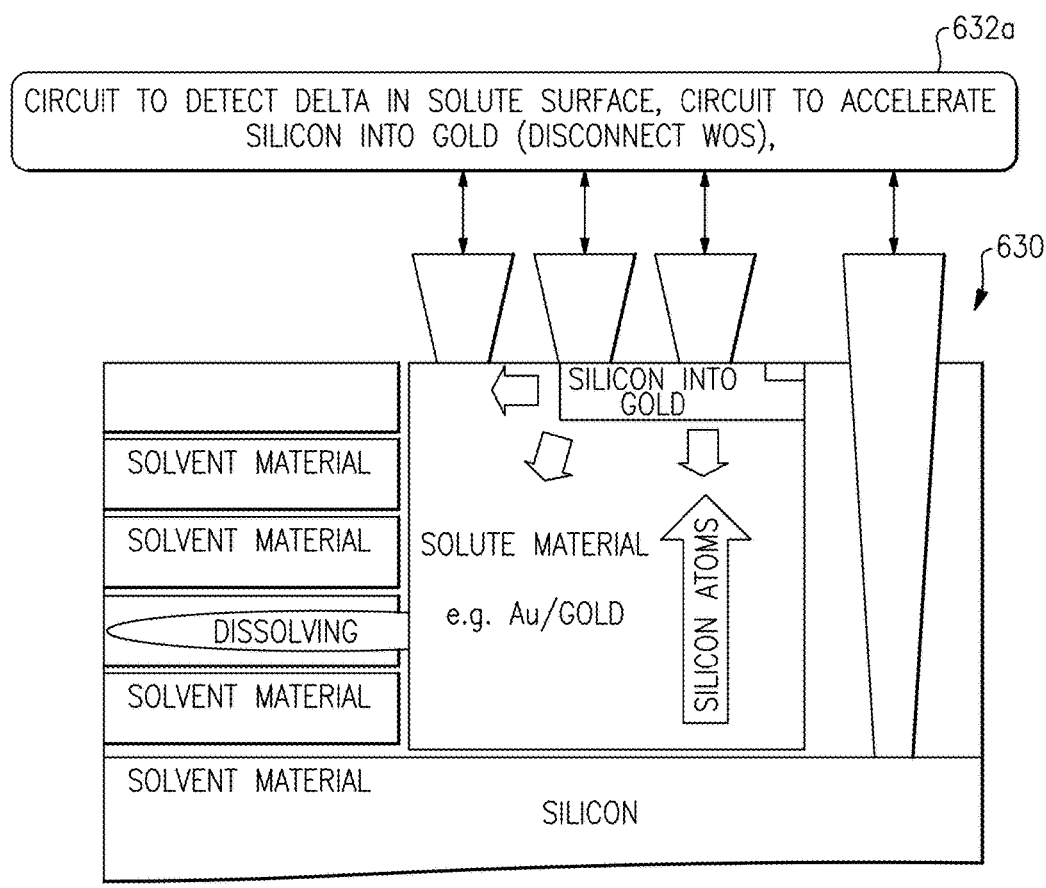
FIGS. 63A-63D illustrate cross-sectional views of a wear-out monitor device configured such that electrical signatures based on interdiffusion of atoms can be utilized to measure wear-out of a core circuit, according to embodiments.
Figure 63B:
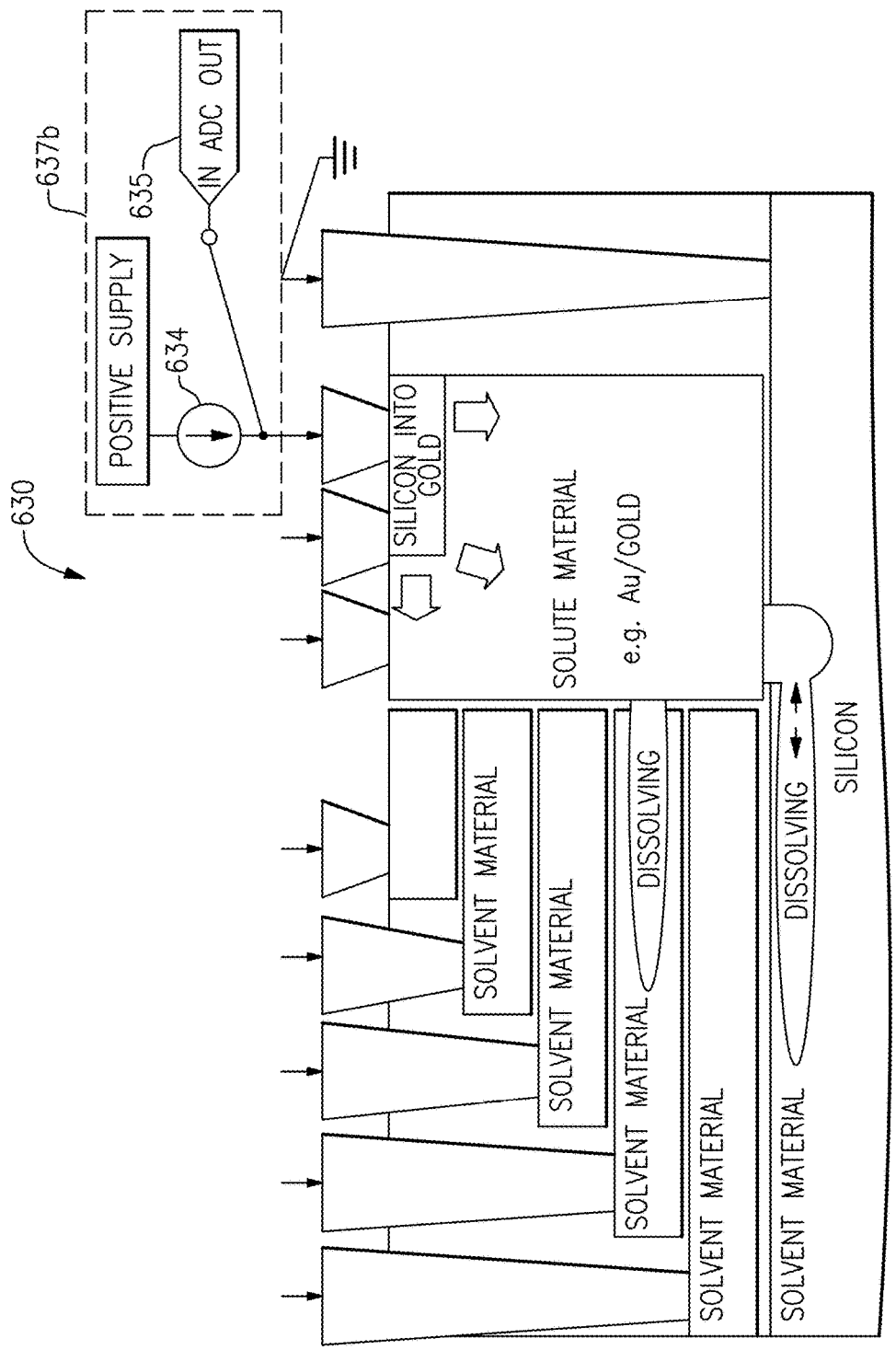
Figure 63C:
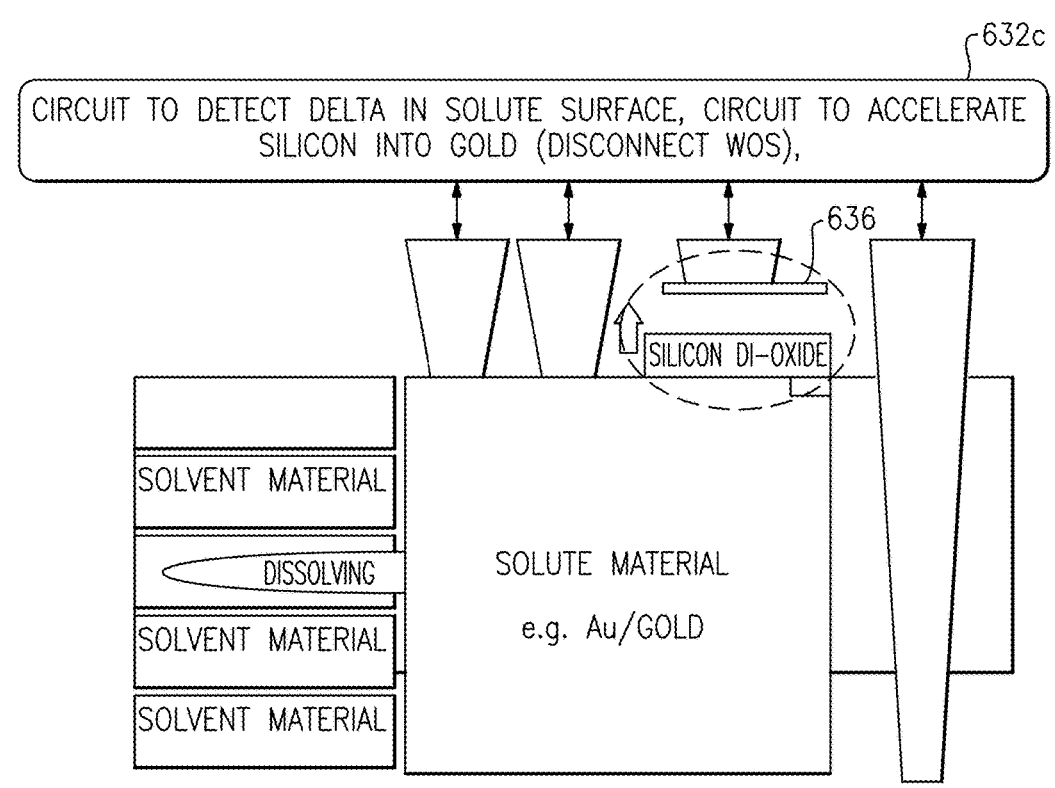

In the wear-out monitor device 630, in addition to or in lieu of being connected to the monitor regions 562-1, 562-2, . . . 562-n, as described above with respect to FIGS. 56A-56D, the monitor device 630 is connected to the reservoir 434 and configured to measure changes in electrical properties of the reservoir 434 caused by diffusion of atoms of the substrate 64 into the reservoir 434, including resistance (FIG. 63B) and capacitance (FIG. 63C/63D). Thus, unlike the sensing circuit 568 described above with respect to FIGS. 56A-56D, the sensing circuits 632a-632c illustrated with respect to FIGS. 63A-63D can measure the changes in electrical properties of the reservoir 434 with or without electrical connections to the monitor regions 562-1, 562-2, . . . 562-n, thereby providing an independent indication of wear-out of a core circuit.

In addition, as illustrated in FIGS. 63A-63C, changes in electrical properties of the reservoir 434, e.g., electrical resistance and/or capacitance associated with the reservoir 434, can result from substrate atoms of the bulk substrate 64 diffusing into the reservoir 434. Additionally or alternatively, changes in electrical properties of the reservoir 434 can be caused by diffusing atoms from a seed material formed on the surface of the reservoir 434.

FIG. 63B illustrates the wear-out monitor device 630 electrically connected to a sensing circuit 632b configured to measure changes in the electrical resistance associated with diffusion of atoms of the substrate 64 into the reservoir 434. The sensing circuit illustrated with respect to FIG. 63B includes, for example, a voltage change detection circuit, including an analog-to-digital converter (ADC) 635 and a current supply 634, for detecting resistance changes associated with diffusion of the atoms of the substrate, e.g., silicon, into the reservoir 434, e.g., formed of gold, or with growth of silicon oxide on the reservoir 434, as described above with respect to FIGS. 56A-56D.

Figure 63D:
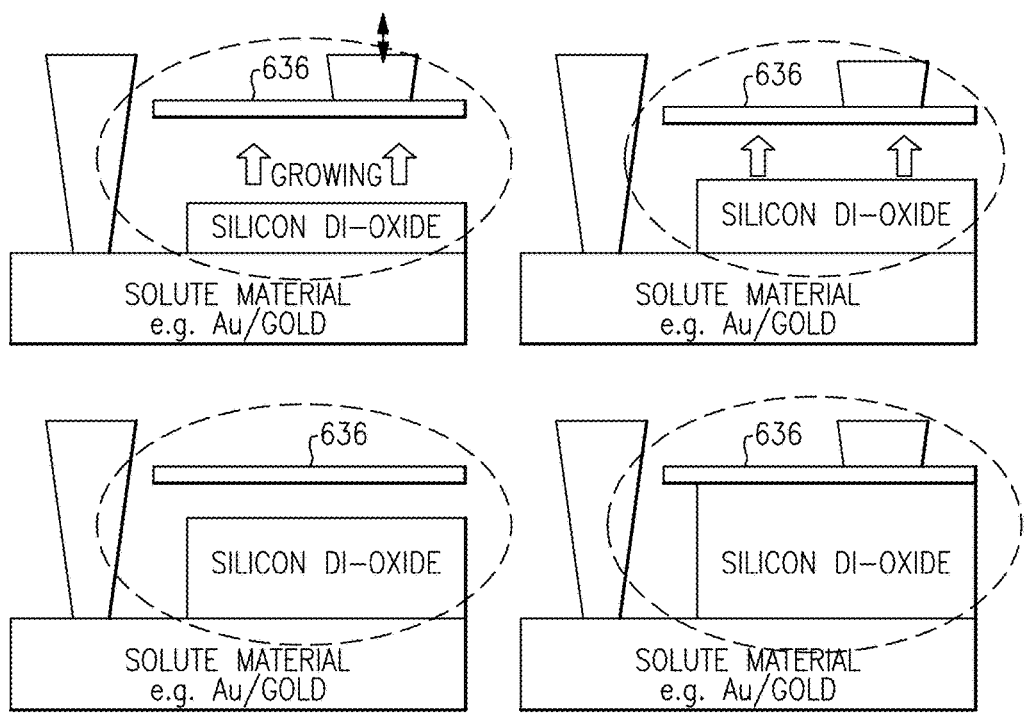

FIG. 63C illustrates the wear-out monitor device 630 electrically connected to a sensing circuit 634 configured to measure changes in capacitance associated with formation of an oxide on the surface of the reservoir 434. The sensing circuit 634 illustrated with respect to FIG. 63C includes, for example, instead of direct connection to the reservoir 434, a gap electrode 636 having an initially predefined gap spacing between the gap electrode 636 and the surface of the reservoir 434. Referring to FIG. 63D, as the oxide on the surface of the reservoir increases in thickness with increasing exposure to wear-out stresses as described above with respect to FIGS. 56A-56D, the gap spacing continues to reduce in proportion to the increasing oxide thickness. The resulting changes in the capacitance between the gap electrode 636 and the reservoir 434 can be correlated to the wear-out stress.

Wear-Out Monitor Devices Configured for Time-Resolved Monitoring

Figures 64A, 64B:
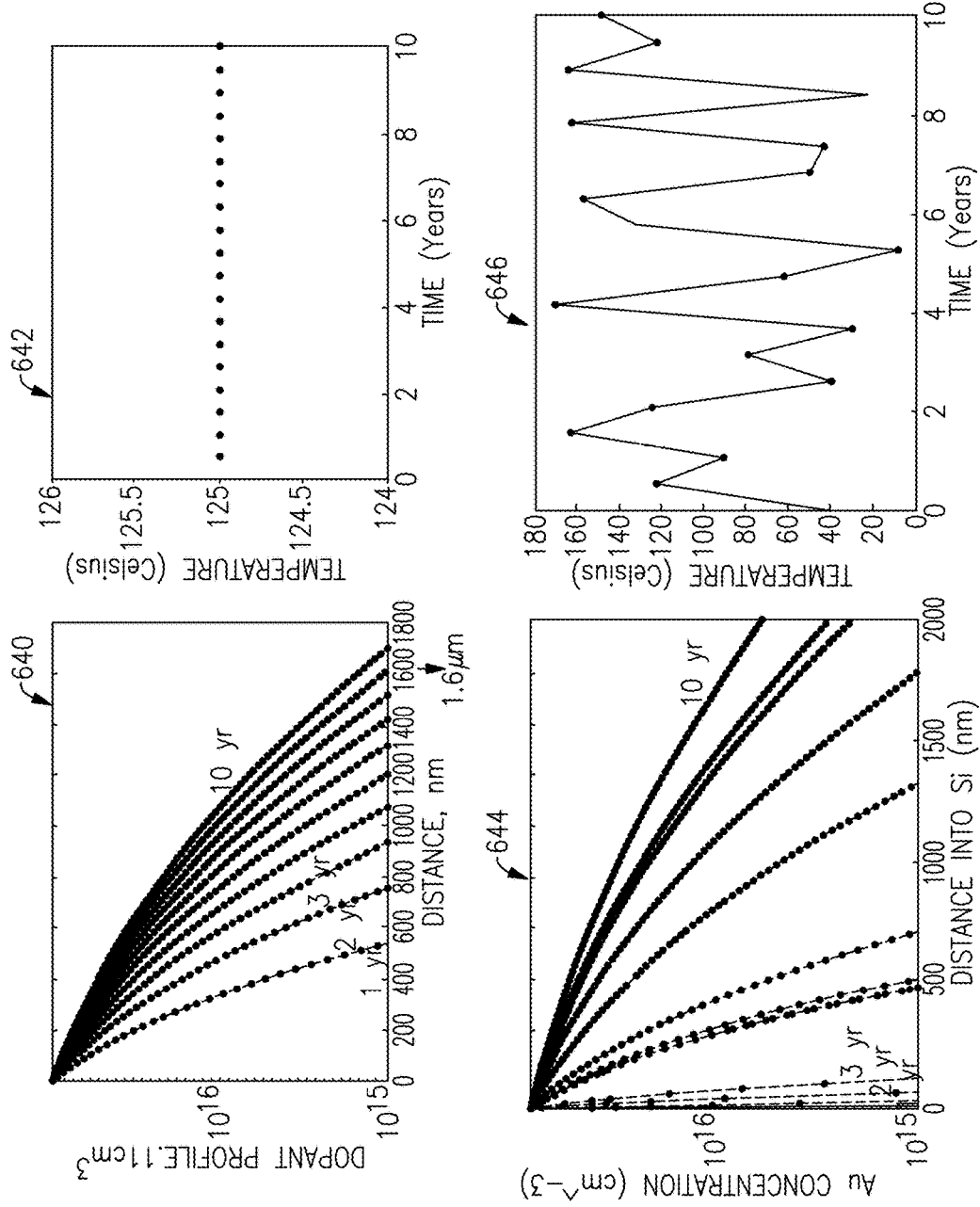
FIG. 64A illustrates concentration profiles of monitor atoms resulting from a cumulative equivalent constant thermal wear-out stress.
FIG. 64B illustrates concentration profiles of monitor atoms resulting from a cumulative time-varying thermal wear-out stress.

As described with respect to various embodiments above, electrical properties such as the leakage current, the resistance or the capacitance of a monitor region can be used to obtain the concentration of monitor atoms at certain locations of the monitor region. The concentration of the monitor atoms in turn can be indicative of a diffusion profile, which can be used to construct an integrated history of the wear-out stress. In addition, as illustrated in FIG. 64A, based on initial and final concentration profiles 640 of the monitor atoms before and after being subjected to a wear-out stress, information related to a cumulative history of the wear-out stress, e.g., a constant thermal wear-out stress, as illustrated by a temperature time plot 642 can be obtained. However, in various applications, as illustrated with respect to FIG. 64B, the core circuit may be subjected to wear-out stresses whose magnitude varies over time, such as, e.g., a temperature stress on the core circuit that varies over time, as illustrated by a temperature-time plot 646 and the resulting concentration profiles 644. In these applications, it may be desirable to configure a wear-out monitor device such that the indication of time-variable wear-out stresses can be recorded.

To address this and other needs, according to various embodiments, a wear-out monitor device is configured such that, after recording a diffusion profile in a monitor region in response to a wear-out stress, e.g., a thermal wear-out stress, the wear-out monitor device is configured to apply an electric field to the monitor region in a lateral direction The monitor atoms diffused in the monitor region have a charge state such that, when the electric field is applied to the monitor region having the monitor atoms diffused therein, the electric field causes the monitor atoms to further diffuse in monitor region the lateral direction. That is, a diffusion profile resulting from a wear-out stress is laterally translated, in a manner analogous to a conveyor belt.

Measuring the average temperature is useful for estimating the working lifetime of a device, but the averaging process by its very nature means that the peaks and troughs in the temperature profile are not recorded. It would be beneficial to be able to discern the temperature history of a device with greater granularity as the periods of higher temperature do most damage. FIG. 65 is a schematic graph 650 illustrating varying temperature profiles as a function of time. As can be seen from the graph, the temperature in this example varies between peaks of 180° C. to around 30° C., and over the time period averages about 110° C., resulting in snapshots of concentration profiles 652 of the monitor atoms in the monitor region at different times $t_1$, $t_2$ and $t_3$.

However, if we could form a moving average as represented by the line 12, then it would be possible to more accurately record the damage caused by temperature extremes experienced by the device. This would allow the impact of the damaging high temperature to be evaluated more accurately.

Recording temperature as a function of time by an active circuit into memory would of course be feasible for a powered device although the memory or processing capacities may be onerous for a device over a long period of time. However, if the device were unpowered or in an extremely low power state then such a recording process would not work.

The inventor realized that the diffusion process could be coupled with a suitable monitor structure, sometimes referred to herein as a recording structure, such that the variation of temperature as a function of time could be recorded in a device. Furthermore, such recordation could be achieved even if the device was unpowered or in a non-power consuming state.

As described herein, recording a physical state of a component represented by diffusion profiles of monitor atoms can occur regardless of whether the wear-out monitor device, also referred to herein as the wear-out monitor sensor, and/or the monitor structure is powered. Electrically measuring the state can be performed, however, with power supplied to the wear-out monitor device and/or the monitor structure. In this context, recording the physical state associated with diffusion profiles is to be distinguished with recording digital information, e.g., in a memory device.

Figure 66B:
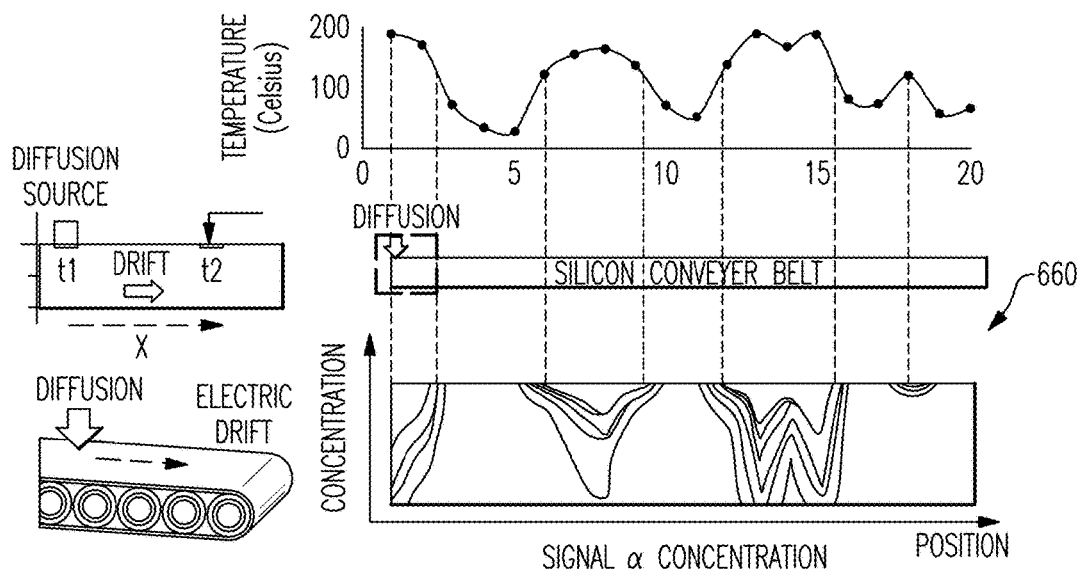
Figure 66C:
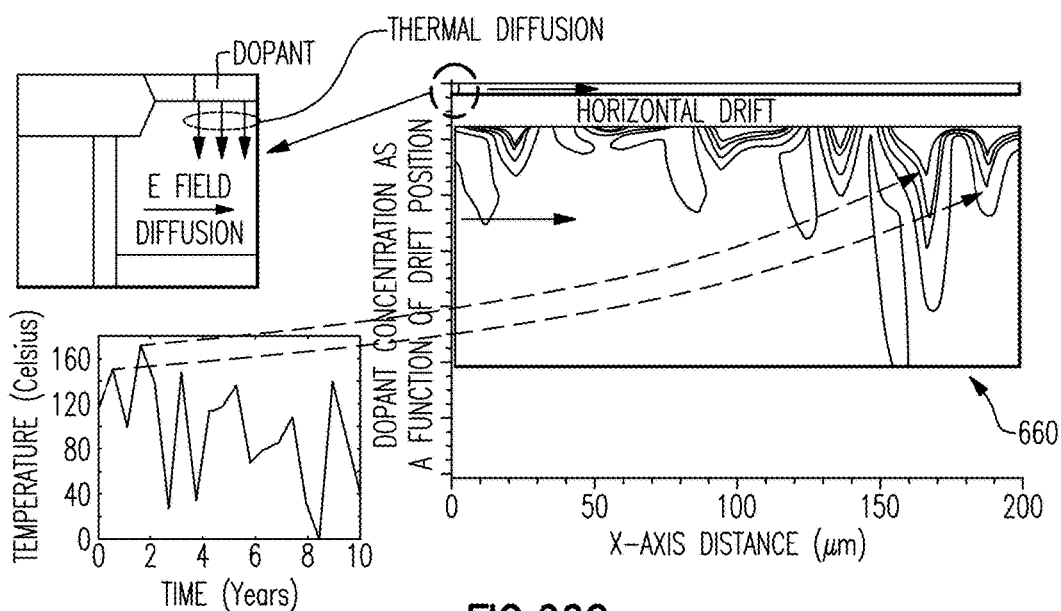

FIGS. 66A-66C are a cross sectional views of a temperature wear-out monitor device 660 in accordance with a first embodiment of this disclosure. The temperature wear-out monitor device comprises a first region 1020 which is exposed to a suitable material, in this example a small volume of gold 1022 which is in contact with an upper surface 1024 of the first region 1020. The first region 1020 is in contact with a second region 1030 which acts as a diffusion history memory capturing the diffusion rate as a function of time. In use, the second region 1030 is subjected to an electric field which may be an externally applied electric field or an intrinsic electric field resulting from graded impurity concentrations within the semiconductor material, much like the internal potential difference created across a p-n junction. The conceptual arrangement shown in FIGS. 66A/66B may be embodied in many different ways. The regions 1020 and 1030 may be regions within a semiconductor. In use, the monitor atoms, sometimes referred to herein as solute, will interact with the semiconductor to become either a donor or acceptor impurity. In the case of gold as monitor atoms/impurity, the gold becomes effectively charged by accepting an electron (lower energy state), and this electron cloud around the gold atom(s) is pulled by the electric field. The electron cloud then pulls the gold atoms. This is known as ambipolar motion.

Figure 67:
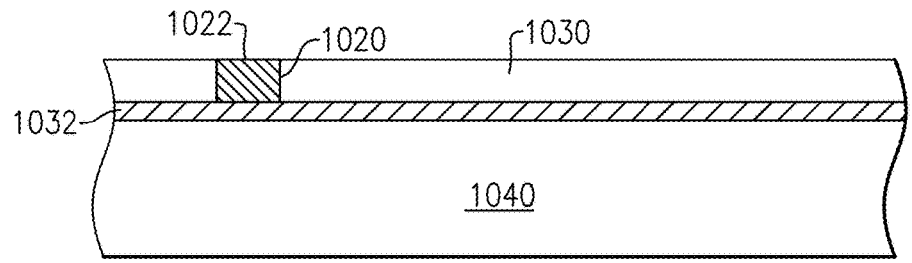
FIG. 67 a schematic diagram of a temperature sensor, according to some other embodiments.

FIG. 67 shows a variation on the structure of FIG. 66A where the metallic block of gold 1022 has been deposited over an insulating layer of silicon dioxide 1032 and the first region 1020 is formed by a vertical interface between the block 1022 and a layer of semiconductor material 1030 also deposited also over the insulating layer 1032 and acting as the second region. The layer 1032 can be formed over a substrate 1040. Further variations on this theme are possible.

Figure 68:
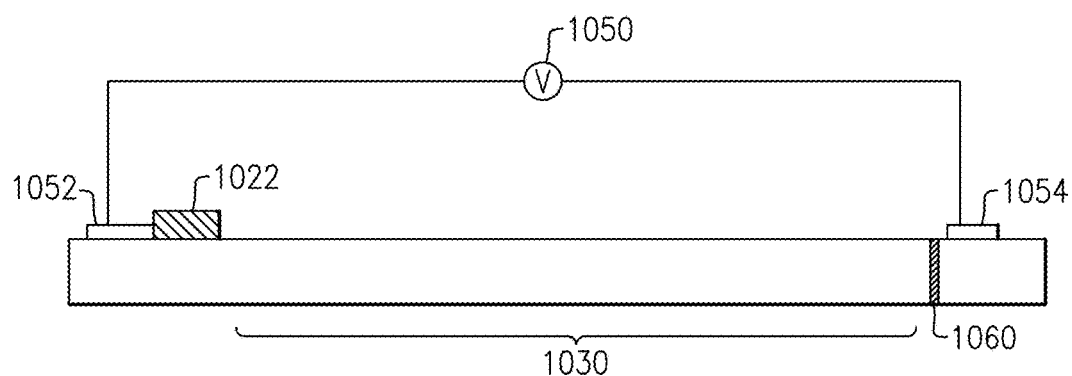
FIG. 68 is a schematic diagram of a temperature sensor including an external voltage source for migrating diffused material along the body of the sensor, according to embodiments.

In order to record the variation of temperature with respect to time, the material which has entered the silicon at region 1020 moves away from that region and is stored in a memory structure. While region 30 provides the memory for storing the material, moving the material, e.g., diffused gold (in this example) from the region 1020 is provided by another mechanism. This can be done by applying a potential across the device such that the gold drifts along the second region 1030 at a known and controllable rate. The potential could be provided by an external source as shown in FIG. 68. Here a voltage source 1050 is connected to electrodes 1052 and 1054. Electrode 1052 may, as shown, be proximate or in contact with the gold 1022. The electrode 1054 is placed remotely from the first electrode 1052 such that the second region 1030 is interposed between the electrodes 1052 and 1054. An insulating barrier, for example in the form of a silicon dioxide filled trench 1060 may serve to inhibit current flow between the electrodes 1052 and 1054 such that substantially no energy is drawn from the voltage source 1050 during the operation of the memory. Thus, the voltage source 1050 might be implemented by a capacitor which is given an initial charge during the manufacture and/or packaging of the temperature wear-out monitor device with the expectation that the capacitor can hold a suitable voltage over the working life of the circuit associated with the temperature wear-out monitor device. The separation between the electrodes 1052 and 1054 and/or the voltage provided by the voltage source 1050 effects the E-field strength acting along the second portion of semiconductor 1030, and consequently changes the drift velocity of the gold therein and hence the time period over which the element 1030 acts as a memory as well as the granularity or resolution within which the temperature may be resolved.

The drift velocity of the impurity (e.g. gold) is proportional to the E-field, and hence is proportional to V.

As a result, an arbitrary distance L along the region 1030 relates to a time period $t_L$ from implantation at L=0, with $$t_L = K_D \frac{L}{V} \quad \text{Eq. [2]}$$

where $K_D$ is a drift velocity coefficient.

Figure 69:
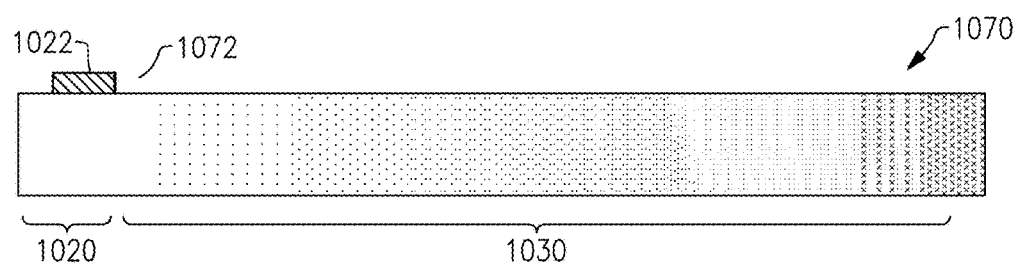
FIG. 69 is a diagram schematically illustrating dopant density within a sensor according to embodiments.
Figure 70A:
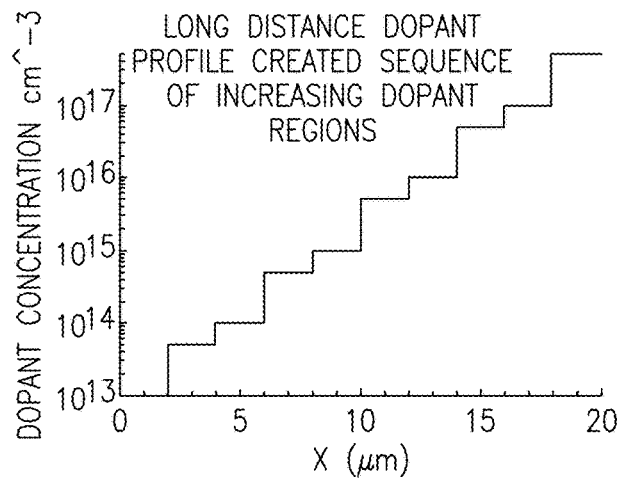
FIG. 70A schematically illustrates a graded (stepped) doping concentration profile as a function of distance within a sensor according to an embodiment.
Figure 70B:
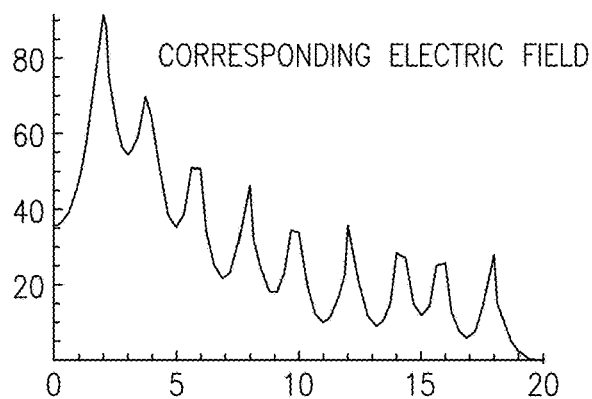
Figure 70C:
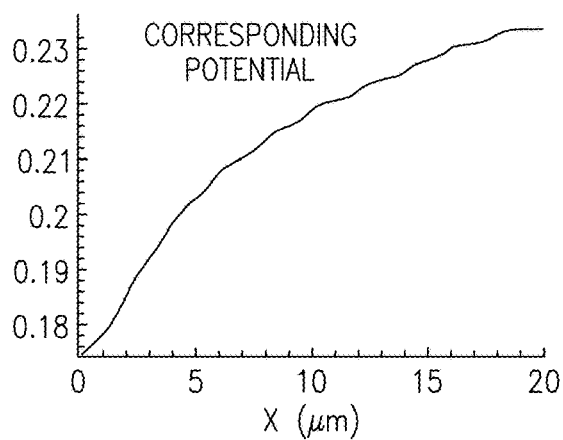

FIG. 69 is a cross section of a temperature wear-out monitor device constituting another embodiment of this disclosure. The temperature wear-out monitor device in this embodiment can work without an external voltage source. As before, an E-field is applied to move the diffused noble metal such as gold (or other non-noble metal monitor atoms) away from the first region 1020, and at a rate which is known and predictable. In this embodiment the E-field is provided by a graded doping profile within the second portion 1030. The second portion 1030 may be doped to form an extended PN junction or the second portion 1030 may be doped with a graded profile of a single polarity, i.e. N type or P type. The doping concentration of the one of the dopants is schematically illustrated in FIG. 69. For example, the concentration of a donor impurity, such as phosphorous, may be relatively low near the first region 1020 and relatively high in a volume designated 1070 which is distal from the first region 1020. By contrast, the concentration of an acceptor impurity such as boron may be relatively low in the region 1070 and relatively high in a region 1072 proximate the first region 1020. FIG. 70A is a graph showing the doping concentration with the end closest the first region 1020 having a doping concentration of approximately $10^{13}$ impurities per cm³ rising to approximately $10^{18}$ impurities per cm³ in a stepwise fashion over a distance of 20 microns. Such a doping profile can be achieved by masking the surface of the second region and then etching apertures in the mask where the concentration of apertures varies such that the mask is largely open or fully open at one end and mainly closed, i.e. with only a few apertures, at the other end, and which the aperture density varying there between. Once the mask is removed the substrate can be heat treated in order to diffuse the phosphorous away from the implantation sites in order to create a stepwise approximation to the linear graded profile which in turn gives rise to an electric fuel distribution as shown in FIG. 70B and a voltage potential across a device varying as a function of distance as shown in FIG. 70C.

Figure 71:
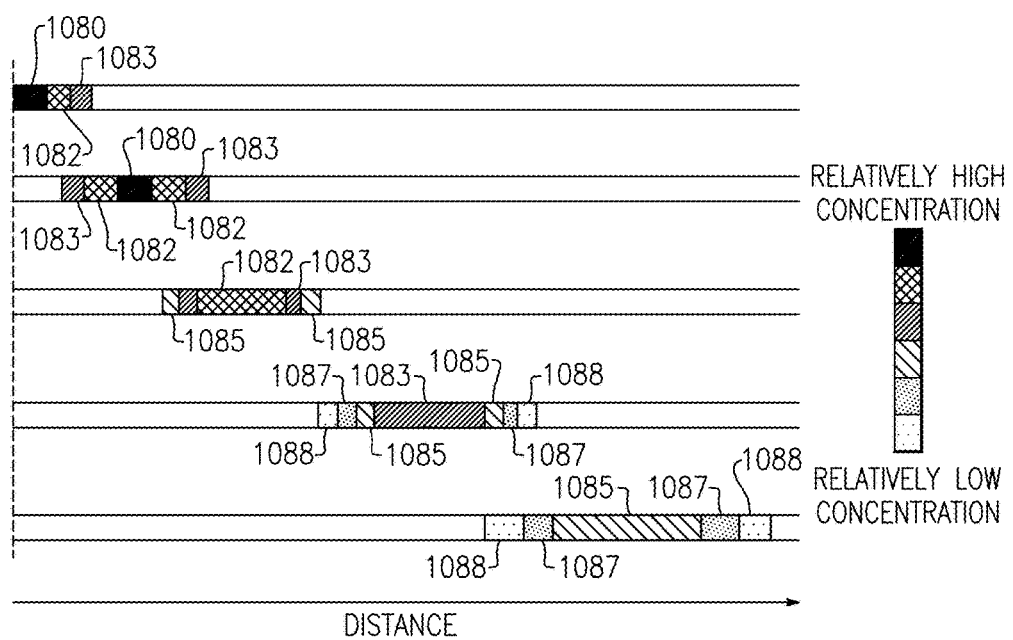
FIG. 71 schematically illustrates the migration of a diffused region of material as a function of time under the influence of the electric field.

FIG. 71 schematically illustrates how a "blob" of monitor atoms which has entered the second region 1030 progresses along the second region as a function of time under the influence of the electrostatic fields. The concentration of the diffused gold is shown over a plurality of snap shots T1 to T5 taken at different instances in time, for example one month apart, six months apart or one year apart as appropriate although longer or shorter periods are also possible depending on the voltage gradient acting along the second portion 1030. Because the gold has diffused into the second portion 1030 by way of the first portion 1020, the gold has a varying density profile. For diagrammatic simplicity, the density of the gold is represented by shaded areas in the diagram. Area 1080 represents a portion of a first high concentration and area 1082 represents an region of a second (reduced) concentration an area 1083 represents a third area of further reduced concentration. The E-field acts to migrate this region of material along the memory portion 1030, and in the diagram from left to right. Meanwhile, the gold will also still be subject to some diffusion. Thus the blocks 1080, 1082, and 1083 translate from left to right due to the action of the E-field and spread due to the action of diffusion. Thus at time T2 region 1080 has translated to a new position and is now bounded on either side by a region of reduced concentration 1082 and region of further reduced concentration 1083.

By the time T3 is reached the region 80 has diffused so much that gold at first concentration no longer exists. The concentration has dropped into the range represented by 1082 bounded by regions of reduced concentration 1083c and fourth (further reduced) concentration 1085. By the time T4 is reached concentration at the second level represented by a region 1082 no longer exists and instead we have region 1083 bounded by regions of the fourth concentration 1085, and regions of a fourth concentration 1087 and a sixth concentration 1088.

Figure 72:
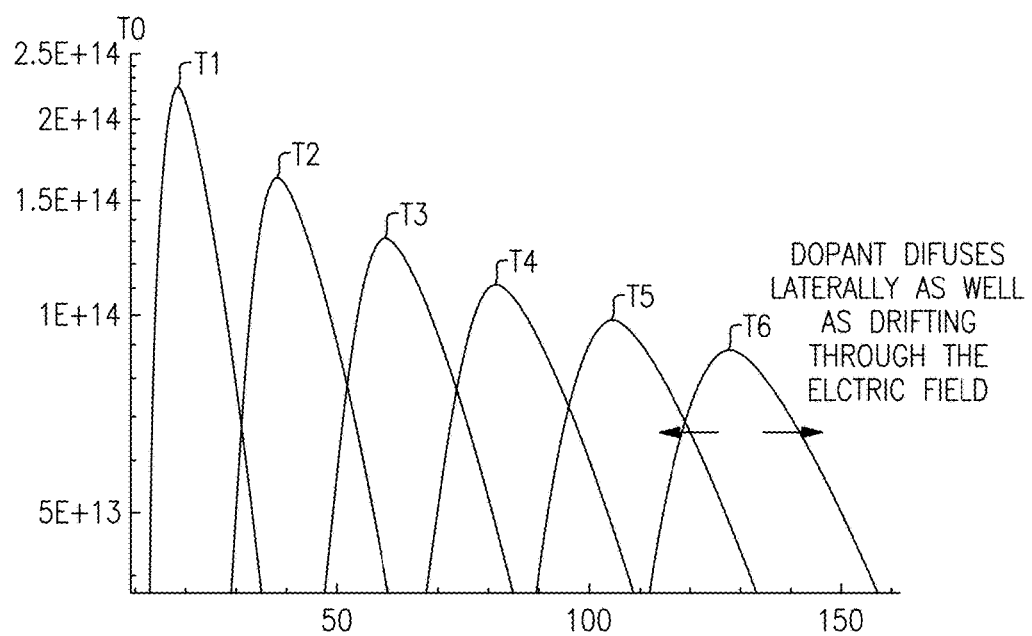
FIG. 72 is a graph showing the combined effects of diffusion and drifts.

By the time T5 is reached the block of impurity has diffused to become broader and is now comprised of regions of the fourth, fifth and sixth concentrations. Thus it is to be noted that as the monitor atoms drifts from left to right as a function of the E-field, it also broadens as a result of diffusion. FIG. 72 graphically represents the same information as FIG. 71, but now showing diffusion profiles against nominal center position as time progresses from T1 to T6, for a region of contact having been made at time T0.

As noted before, the effective initial concentration is a function of temperature and the actual doping concentration noted in the wear-out monitor device after a period of time can be regarded as a convolution of the various monitor atom concentrations as a result of changes in temperature at the interface between the gold and the semiconductor.

Having successfully demonstrated mechanisms for encoding the prevailing temperature into a spatially modulated doping profile within a portion of semiconductor which acts as both a wear-out monitor device and a memory, there is a need to be able to address and read data from the memory.

Figure 73:
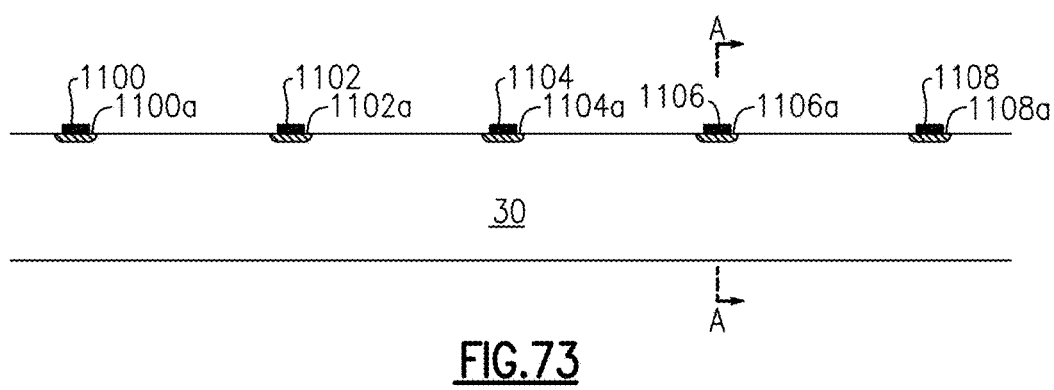
FIG. 73 is a cross section view of a read structure, according to embodiments.

FIG. 73 is a cross section to a first embodiment of an array read devices where a plurality of electrodes 1100, 1102, 1104, 1106 and 1108 are formed in a spaced apart manner within the second region 30 of the semiconductor. Although only five electrodes have been shown, fewer or more may be provided. In order to avoid setting up a Schottky barrier, each one of the electrodes 1100 to 1108 may be deposited over a small highly doped region 1100a to 1108a.

Each of the electrodes may be selected by a multiplexer, or each pair of electrodes may be selected by a multiplexer, to place it in contact with a measurement circuit such that a leakage current between adjacent electrodes can be measured or a leakage current between any selected one of the electrodes 1100 to 1108 and a further electrode or semiconductor region formed beneath the layer 1030 or to one side of the layer 1030 can also be determined.

Figure 74:
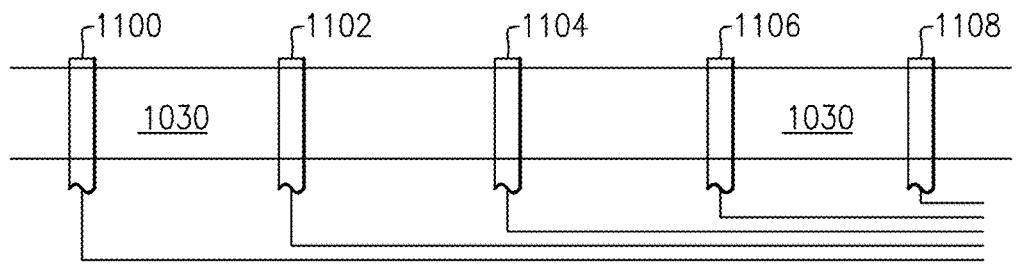
FIG. 74 is a plan view of the read structure of FIG. 17.

FIG. 74 shows the arrangement of FIG. 73 in a plan view.

Figure 75:
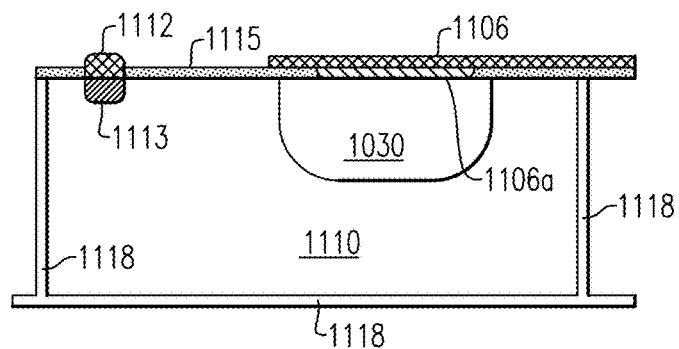
FIG. 75 is a cross section through the read structure of FIG. 17 along line A-A'.

FIG. 75 is a cross section through the device along the line A-A' of FIG. 73, where the second region 1030 has been doped to be an N-type region (either with or without a graded doping profile depending on whether the device is intended to be able to operate in an unpowered mode). The second region 1030 is formed as an elongate finger within a P-type well 1110. A contact 1112 is made to the P-type material 1110 by way of a highly doped region 1113. The surface of the semiconductor is covered by a passivation layer 1115, for example silicon dioxide, except where the contacts 1112 and 1116 are formed. The well may be bounded (if desired) by further doped regions so as to form reverse biased p-n junctions or as shown in FIG. 75 by insulating walls as is known in silicon on insulator fabrication techniques.

Figure 76:
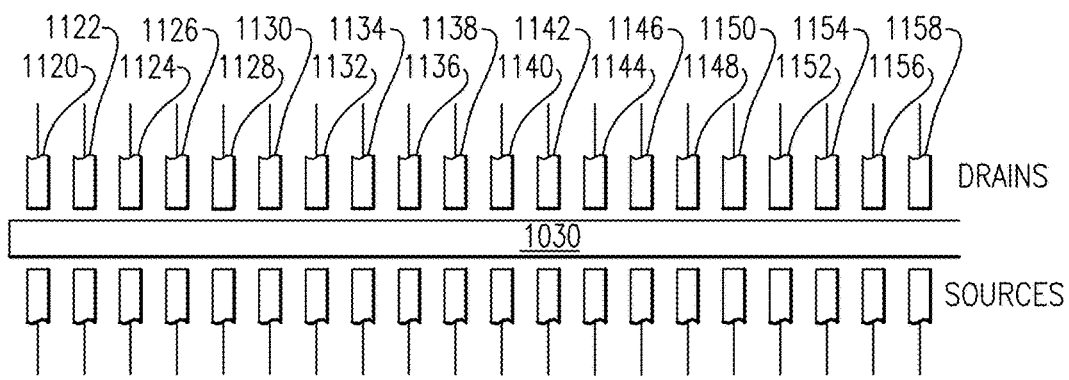
FIG. 76 is a plan view of an alternative read structure, according to embodiments.

In a further embodiment, as shown in FIG. 76, a plurality of transistors may be formed spatially along the length of the second region 1030. In this illustration transistors 1120, 1122, 1124, 1126, 1128, 1130, 1132, 1134, 1136, 1138, 1140, 1142, 1144, 1146, 1148, 1150, 1152, 1154, 1156 and 1158 are formed such that one of their active regions, for example their drains, are positioned on one side of the region semiconductor 1030 and another of their active regions, for example their sources, are positioned on the other side of the region 1030. The wear-out monitor device may be formed in a variety of sizes depending on the desired temporal resolution and period of use. Without limitation wear-out monitor devices may range from tens of microns to hundreds of microns in length.

The transistor construction may be that of a JFET or a MOSFET or similar. In a JFET construction the drain-source doping may extend beneath the second region 1030, and the second region may act as a gate. In a MOSFET construction the second region may be of the same semiconductor type as the drain and source regions so as to form a channel between the drain and source, and a further electrode may be provided over the second region 1030. In other embodiments the semiconductor around and including the second region 1030 may be doped so as to form bipolar junction transistors where the region 1030 may, for example, form an elongate base. Emitter regions may be provided adjacent or within selected portions of the region 1030 and contacts may be made to the emitter regions. A further implant adjacent the region 1030 can act as a collector. The collector region may be shared by the bipolar junction transistors or each transistor may be fabricated with its own collector.

During a reading, a reference voltage can be applied to the second region 1030, and then parameters of the transistors 1120 to 1158 may be determined, the parameters being a function of the doping in a channel portion for each one of the respective transistors. Parameters may include pinch-off voltage, leakage, gain, frequency response and so on.

Each of these parameters can be read but will actually also be a variable as a function of temperature of the die at the time the data is read on the devices. It is therefore desirable to include a further read structure which is positioned such that it cannot be influenced by diffusion of the monitor atoms. This can be achieved either by placing the read structure at the distal end of the second region 1030 at such a distance that diffusion of the monitor atoms is unlikely within the working lifetime of the device, within a region where the drift field inhibits monitor atoms interfering with the operation of the reference device or by fabricating the reference device in an isolated region of the semiconductor.

There may be instances where it is desired to modify the ability of the dopant material, e.g. gold, to diffuse into the semiconductor. For example, it may be desirable to inhibit diffusion if a temperature is below a first threshold where the results are largely relevant, or above a second temperature range where the gold diffuses too fast. Under such circumstances, it might be desired to use further wear-out monitor devices with further different doping materials.

For example, if it is desired to measure over a high temperature range, then an impurity or monitor atoms with a higher activation energy should be chosen. Silver has an activation energy in silicon of 1.6 eV making it suitable for use at higher temperatures.

For monitoring at temperatures of many hundreds of degrees platinum with an activation energy of 2.2 eV or aluminum with an activation energy of 3 eV may be suitable.

For lower temperatures, copper with an activation energy of 1.0 eV or sodium with an activation energy of 0.76 eV may be used. This list is not exhaustive and is given only by way of example.

Figure 77:
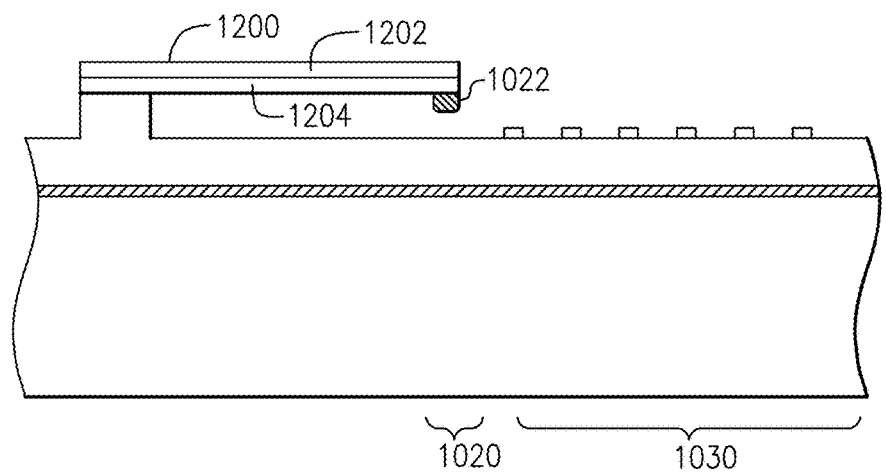
FIG. 77 shows a first arrangement for isolating the material that provides the solute from the first region, according to embodiments.

FIG. 77 schematically illustrates a wear-out monitor device arrangement where the dopant 1022 is held on a cantilever 1200. The cantilever may be formed by adjacent layers of dissimilar materials having dissimilar coefficients of thermal expansion. Thus the cantilever acts like a bi-metallic strip, tending to bend in one direction as it warms and in another direction as it cools. The choice of direction of bend is at the designer's discretion. Thus, the dopant material 1022 may be held away from the temperature wear-out monitor device during a first range of temperatures and forced into contact with the first region 1020 of the temperature wear-out monitor device over a second range of temperature. The contact can either be made as the temperature increases if the uppermost layer 1202 expands more than the lowermost layer 1204; or it may be lifted away as the temperature increases if the lowermost layer 1204 has a higher temperature coefficient of thermal expansion as the layer 1202. This, in conjunction with the electric field sweeping the dopant along the array, allows a more binary approach to temperature sensing to be adopted, with relatively high concentrations of the dopant indicating that the strip support the dopant 1022 into contact with the surface, and relatively low concentrations indicating that the dopant 1022 had been pulled away from contact with the surface of the semiconductor.

In some instances it may desired to inhibit recording or enable recording temperature after certain events, for example after first power up. Such an arrangement may be achieved by using a structure similar to that shown in FIG.

77 where the dopant 1222 is carried on a movable cantilever on an electrically controlled microelectronic mechanical system. Such MEMS systems, for example switches, are well known to the person skilled in the art.

Figure 78:
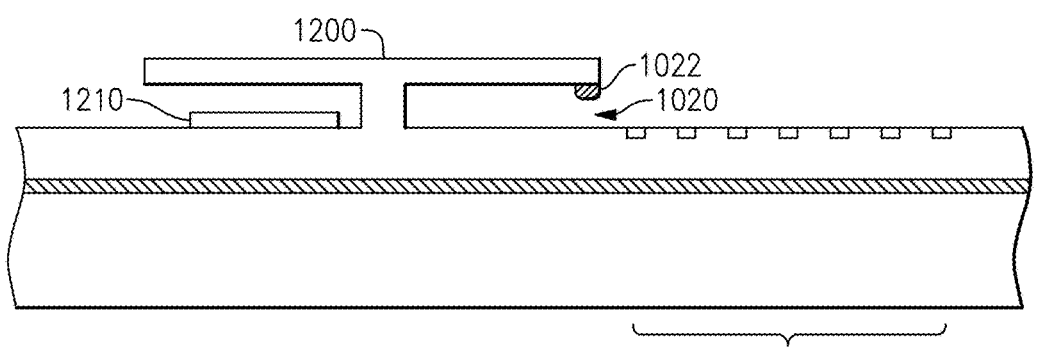
FIG. 78 shows a second arrangement for isolating the solute from the first region, according to embodiments.

For example, in the arrangement shown in FIG. 78, the cantilever may be naturally biased such that it contacts the dopant 1022 with the semiconductor material in the first region 1020. However, this contact can be broken by applying a voltage to the control electrode 1210 on an opposing side of the teeter-totter arrangement shown in FIG. 78, thereby lifting the dopant 1022 out of contact with the first region 1020. Thus the provision of a suitable voltage on the control contact 1210 may be used to pull the dopant 1022 out of contact with the first region 1020. Similarly, if a control electrode is formed on the other side of the switch opposing the electrode 1210, then the electrodes could be used to pull the dopant into contact with the region 1020.

Other mechanisms to move the block of monitor atom material 1022 into and/or out of contact with the semiconductor may also be used. For example mechanical force acting across a membrane exposed on one side to a fluid may be used to form a pressure wear-out monitor device to record over-pressure or under-pressure events. Furthermore if the contact footprint is profiled such that the contact area varies with pressure then the magnitude of the over-pressure event may be encoded within the monitor atom concentration.

Figure 79:
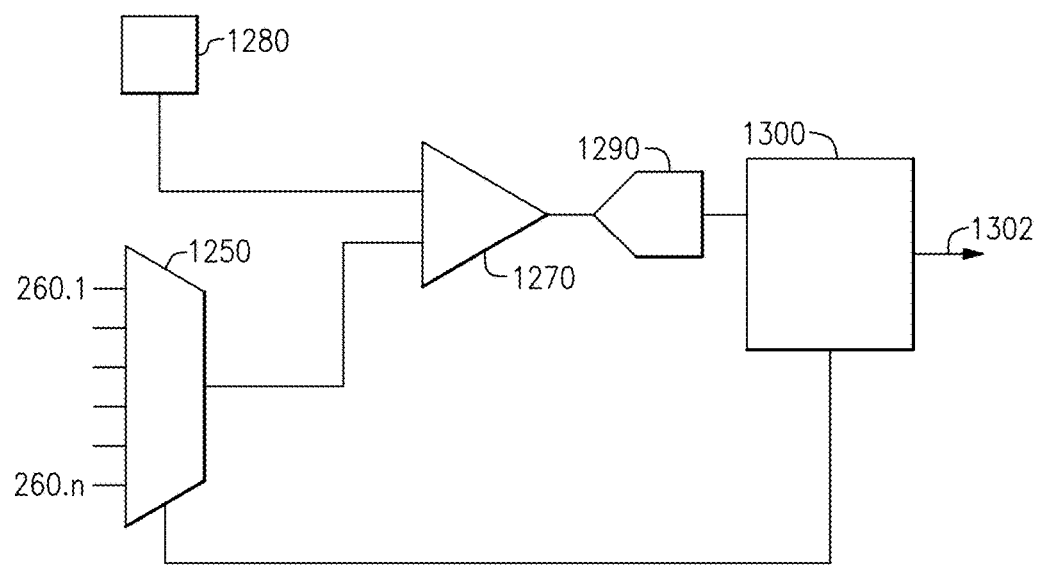
FIG. 79 is a schematic diagram of a data acquisition circuit for use with a sensor of the present disclosure, according to embodiments.

FIG. 79 schematically illustrates a data retrieval circuit which may be embedded on a die with the temperature wear-out monitor device described hereinbefore. A multiplexer 1250 is provided to select one of the plurality of inputs 1260.1 to 1260.$n$ which interact with the read structure. Thus, if the read structure is formed as a plurality of diode like structures then the inputs 1260.1 to 1260.$n$ select individual ones of the electrodes 844 shown in FIG. 84. If, however, the read structure is formed of the transistors, then the inputs 1260.1 to 1260.$n$ can select between individual ones of the transistors 1120 to 1158 shown in FIG. 76. An output of the multiplexer is provided to a first input of a difference amplifier 1270. A second input of a difference amplifier 1270 receives a reference signal from the reference signal generator 1280. The reference signal generator 1280 may be formed by an identical read device as used in the temperature wear-out monitor device, but where a source of the monitor atoms is not provided. The reference device 1280 is used to compensate for the temperature effects on the read circuit at the time of taking a reading. The difference signal output by the amplifier 1270 is digitized by a digital to analog converter 1290 and provided to a data processor 1300. The data processor 1300 may be implemented by a programmable data processor. Alternatively, it may be implemented as a combination of a state machine that controls the multiplexer 1250 and a lookup table in order to translate the output voltage per concentration. The data processor 1300 provides an output 1302. The output 1302 may be provided by way of a contacting or wireless communications link at the designer's choice. Other circuit configurations are possible, such as configuring the measurement components into Wheatstone bridge like circuits.

Figure 80:
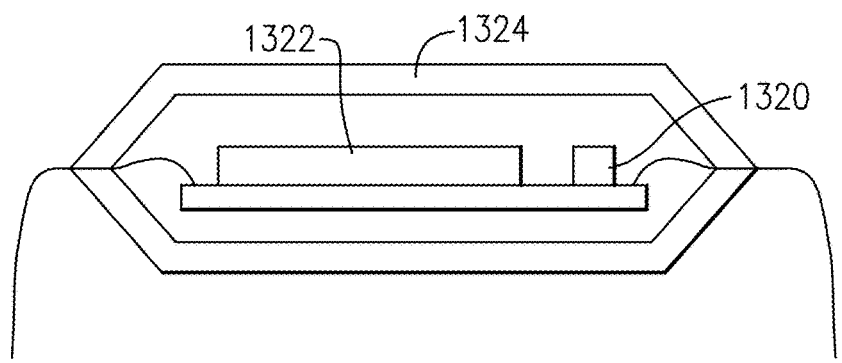
FIG. 80 shows a die carrying an embodiment of the present disclosure co-packaged with a functional circuit in a chip scale package, according to embodiments.

The circuits described herein may be implemented on a functional die. Alternatively, the circuits disclosed herein may be provided on a specialized die 1320 which is co-packaged with a die containing a functional circuit 1322 within a chip scale package 1324 as schematically illustrated in FIG. 80.

The arrangements described so far have been appropriate to a temperature wear-out monitor device. However, given that the rate of diffusion is also a function of concentration, then the teachings disclosed herein can also be applied to a concentration monitor.

Figure 81:
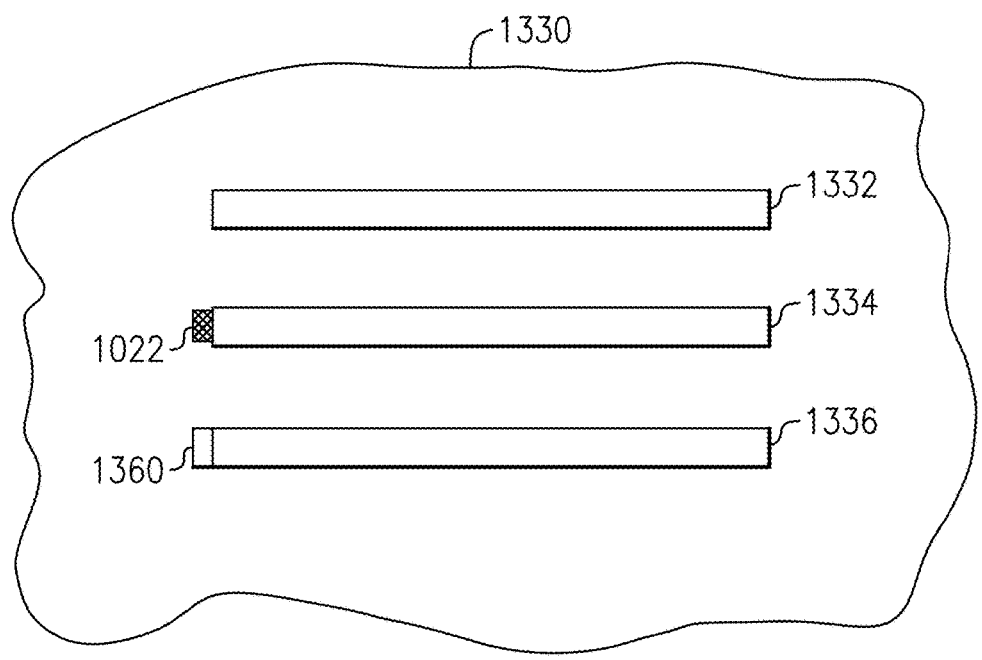
FIG. 81 is a plan view of a concentration sensor constituting an embodiment of this disclosure, according to embodiments.

FIG. 81 schematically illustrates a plan view of a concentration monitor in accordance with the teachings of the present disclosure. The concentration monitor, generally designated 1330 and shown in a plan view comprises two or three channels. A first channel 1332 that can be included is a temperature reference channel. A second channel 1334 that can be included is a temperature measurement channel and a third channel 1336 that can be included is a concentration measurement channel. The second channel 1334 is formed from one of the embodiments described hereinbefore. The first channel 1332 is similarly formed, but does not include the source of monitor atoms 1022. The concentration channel 1336 is formed much like the temperature channel 1334, but instead the gold 1022 is not applied and an aperture 1360 is formed such that second monitor atoms, or reagent, whose concentration has been measured can diffuse into the first region of the third channel 1336. Each of the channels includes measurement structures of the type described hereinbefore and is connected to a suitable data processing circuit. The temperature channel 1334 can be similar to the temperature wear-out monitor devices described with respect to various embodiments, e.g., with respect to FIGS. 66A/66B, and can include a first region and a second region, where the first region is adapted to be exposed to first monitor atoms and the second region is adapted to migrate the first monitor atoms away from the first region. When included, the temperature reference channel 1332 includes a third region corresponding to the second region of temperature channel 1334. When included, the concentration measurement channel 1336 includes a third region including the aperture 1360 to expose the second monitor atoms or reagent and a fourth region in contact with the third region and adapted to migrate the second monitor atoms or reagent along the fourth region.

Figure 82:
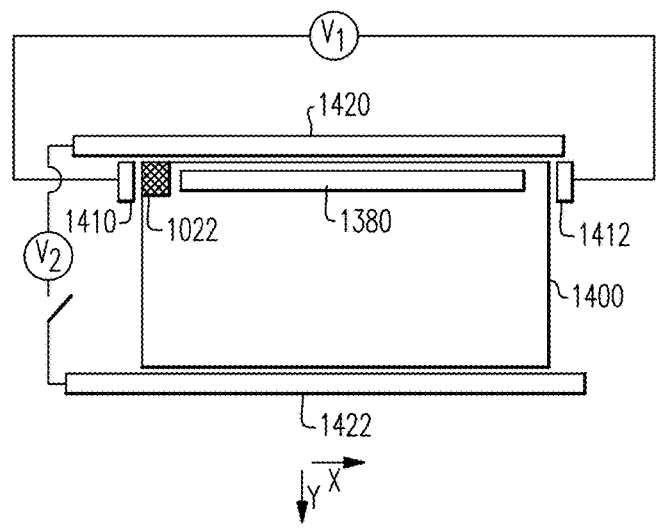
FIG. 82 shows an embodiment having a clear/reset function, according to embodiments.

In the arrangements shown and described hereinbefore the wear-out monitor device keeps a permanent record of the temperature concentration. This is achieved by causing the impurity atoms to drift from the impurity source along the body of the wear-out monitor device under the influence of an intrinsic electric field, or a built-in electric field, or of an externally applied electric field. The electric field is applied along a first direction. The provision of an electric field may also be used to periodically clear the wear-out monitor device by sweeping the impurity atoms away from the read structure. Such an arrangement is schematically illustrated in FIG. 82, where a source of monitor atoms 1022 and the read structure, designated 1380, are formed at the surface of a region of semiconductor 1400. In use, the monitor atoms is swept through the semiconductor in an X direction by an intrinsic electric field set up by the doping, or as shown here by potential difference V1 applied between electrodes 1410 and 1412. However, from time to time, a second voltage V2 applied between electrodes 1420 and 1422 may be used to sweep the impurity atoms in the Y direction. If V2 is much greater than V1 then it can be seen that the read structure 1380 can effectively be reset by applying the second voltage V2 to sweep the impurity atoms out of the measurement/read region 1380.

Figure 83:
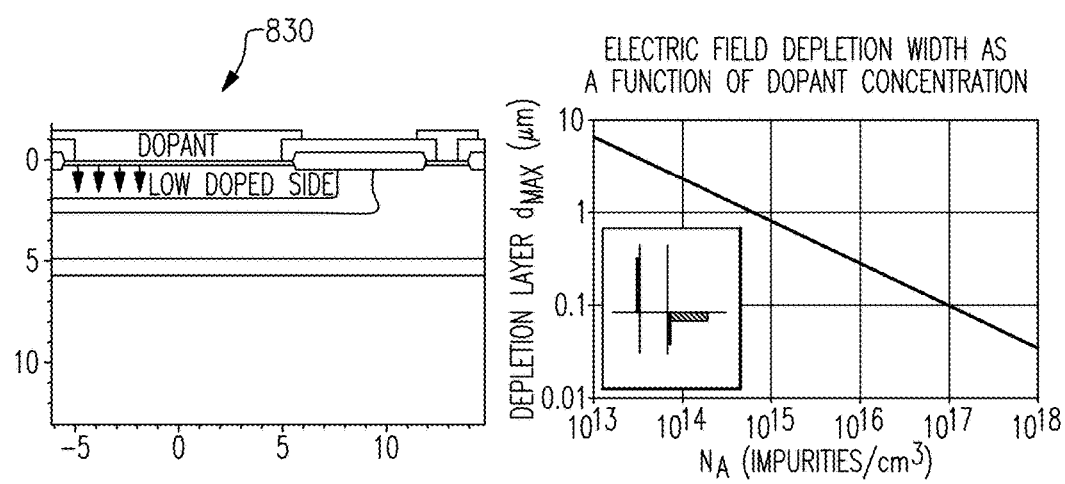
FIG. 83 illustrates a wear-out monitor device configured for time-resolved monitoring of wear-out of a core circuit, according to embodiments.

FIG. 83 illustrates a wear-out monitor device 840 configured for time-resolved monitoring of wear-out of a core circuit, according to embodiments. The illustrated device structure is similar to those described supra. It will be appreciated that a graph of depletion width versus dopant concentration such as the one illustrated can be utilized to tailor the relative width (depth) and/or sensitivity of the depletion region as a monitor region.

Figure 84:
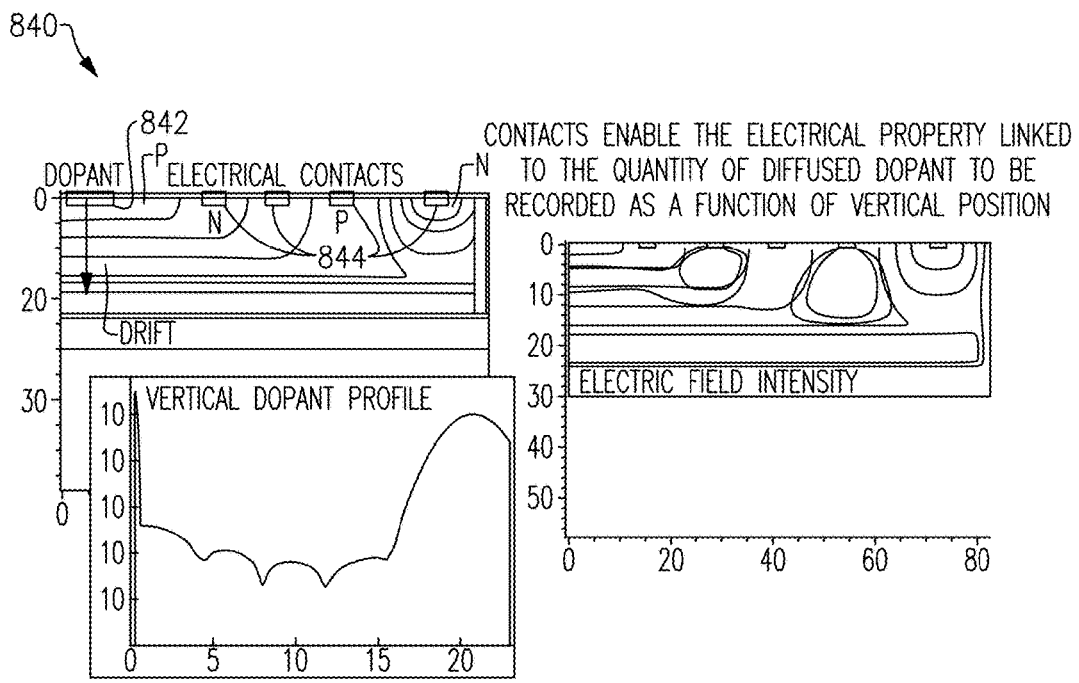
FIG. 84 illustrates a wear-out monitor device configured for time-resolved monitoring of wear-out of a core circuit, according to embodiments.

FIG. 84 illustrates a wear-out monitor device 840 configured for time-resolved monitoring of wear-out of a core circuit, according to embodiments. The illustrated device 840 includes a plurality of PN junctions regions in vertical and lateral directions, where one of the P regions has formed thereon a reservoir of diffusant or monitor atoms, and each of the P and N regions has formed thereon an electrode 844. As configured, the plurality of contacts allow an electrical property, e.g., leakage current, associated with the quantity of diffused diffusant atoms to be recorded as a function of vertical and/or horizontal position, which can in turn indicate a temporal history. In addition, as discussed in more detail below, by utilizing diffusant atoms that have a charge, the electrodes can be utilized to "fast forward" or "rewind" the movement of the diffusant atoms.

Figure 85:
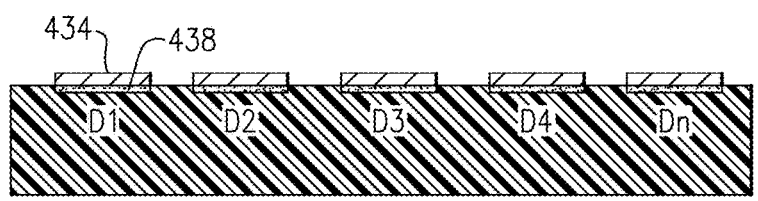
FIG. 85 illustrates a plurality of wear-out monitors, in which different ones of the wear-out monitor devices can be enabled and co-ordinated using a combination of different features described above, depending on the application, according to embodiments.

FIG. 85 illustrates a plurality of wear-out monitors, in which different ones of the wear-out monitor devices can be enabled and co-ordinated using a combination of different features described above, depending on the application. The wear-out monitors in FIG. 85 have barrier layers formed between the reservoir of monitor atoms and the underlying substrate. As illustrated and described supra, individual wear-out monitors can be initialized at different times by applying a stimulus, e.g., a voltage, to alter or eliminate the barrier layer of the individual wear-out monitor devices, thereby initializing the wear-out monitor devices. Wear-out monitor devices that are initialized are ready to diffuse the monitor atoms from the reservoirs into the substrate, and changes in electrical properties resulting therefrom can be measured.

Figure 86:
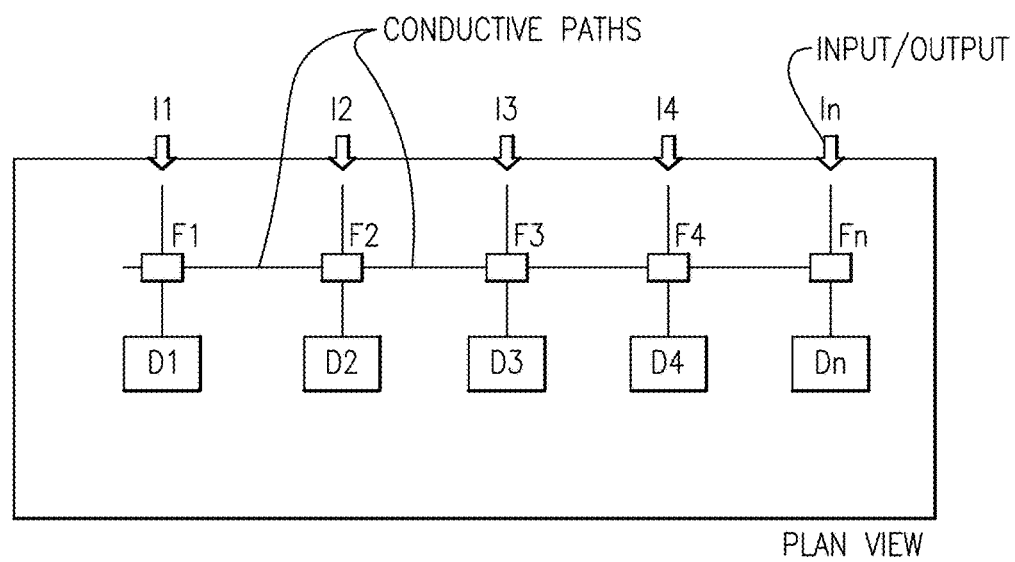
FIG. 86 illustrates a plurality of wear-out monitors arranges in an array, where accessing individual diffusion monitor devices can be co-ordinated by fuses, according to embodiments.

FIG. 86 illustrates a plurality of wear-out monitors arranges in an array, where accessing individual diffusion monitor devices can be co-ordinated by fuses. For example after a certain time period/operating life of a first wear-out monitor device D1, a first fuse F1 connected to the first wear-out monitor D1 may be blown, and subsequently a voltage is applied to a second wear-out monitor device D2 such that D2 is now the active monitor. Using an application specific multiplexing system the different inputs/outputs (I1 . . . In) can be co-ordinated (such that fuse blowing may not be desired) and electrical outputs effectively showing relative differences in the diffusion of the atoms from the different monitors may provide valuable information.

FIGS. 87-94 illustrate embodiments of a wear-out monitor device having a plurality of wear-out monitor devices or regions (e.g., D1, D2, . . . ) electrically connected to sensing circuitry configured for monitoring, e.g., time-resolved monitoring, of wear-out of a core circuit, according to embodiments.

Figure 87:
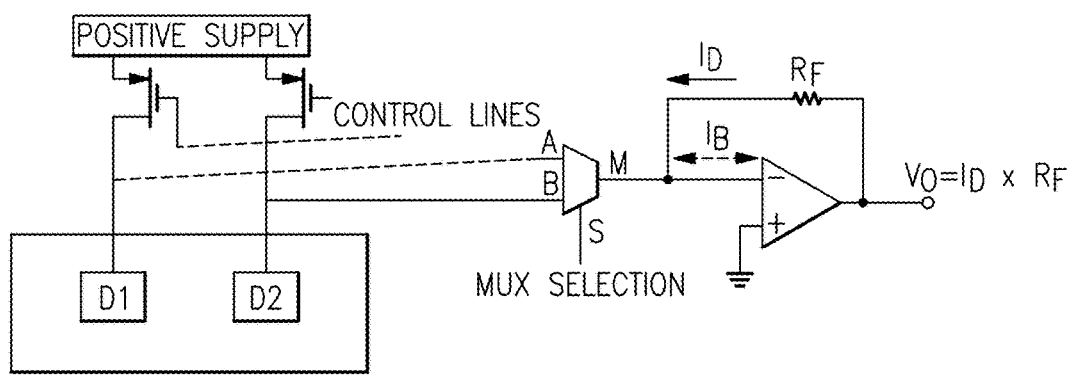
FIG. 87 illustrates an arrangement of wear-out monitors comprising a plurality of wear-out monitors or regions each connected to a transistor and a sensing circuitry for time-resolved monitoring, according to embodiments.

FIG. 87 illustrates an arrangement of wear-out monitors comprising a plurality of wear-out monitors or regions (D1, D2, . . . Dn) each connected to a transistor and a sensing circuitry for time-resolved monitoring, according to embodiments.

Figure 88:
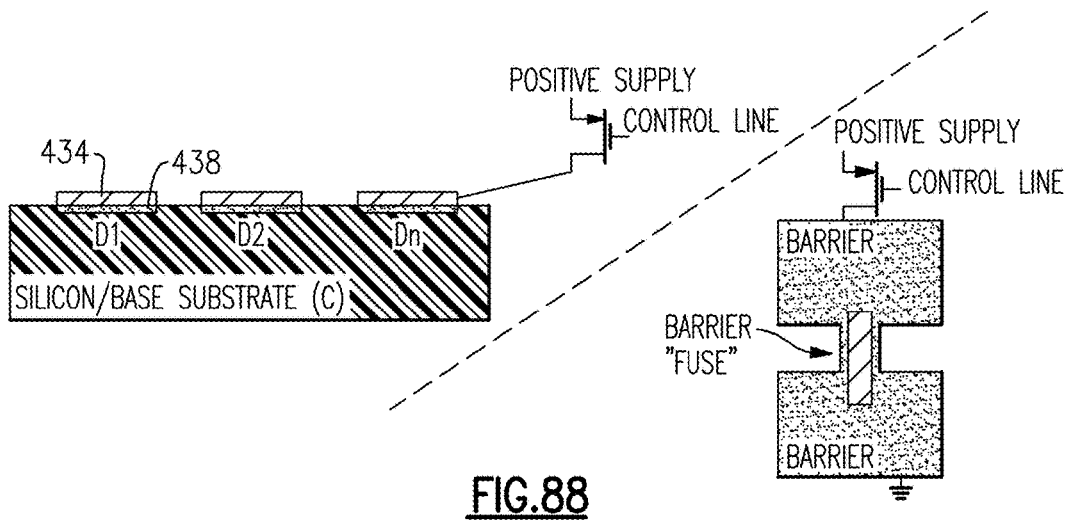
FIG. 88 illustrates a wear-out monitor comprising a plurality of reservoirs each comprising monitor atoms that are separated from a substrate by a barrier, according to embodiments.

FIG. 88 illustrates a wear-out monitor (cross sectional view on the left, plan view on the right) comprising a plurality of reservoirs 434 each comprising the monitor atoms that are separated from a substrate 62 by a barrier 438, according to embodiments. Similar to the wear-out device illustrated with respect to FIG. 43A, each of the reservoirs contain monitor atoms, e.g., Au, and each of the barriers 438 is formed of a material that can be eliminated or consumed when a sufficient electrical stimulus, e.g., voltage or current, is applied to initiate diffusion of the monitor atoms. Each of the barriers 438 can be connected to a transistor to provide the electrical stimulus. As illustrated in the plan view, the barrier 438 is configured as a thin film in areas where the reservoir or monitor atoms are disposed, such that high current applied to the barrier 438 forms an opening in the barrier 438 by, e.g., melting or electromigration, to initiate the diffusion.

FIGS. 89-94 illustrate wear-out monitors comprising a substrate (e.g., Si) having formed thereon a reservoir of monitor atoms (e.g., Au) and a plurality of electrodes (D1, D2, . . . Dn) for time-resolved monitoring, according to embodiments. As described elsewhere, each of D1, D2, . . . Dn may be formed on a PN junction formed in the substrate, in which the depletion region can serve as a monitor region.

Figure 89:
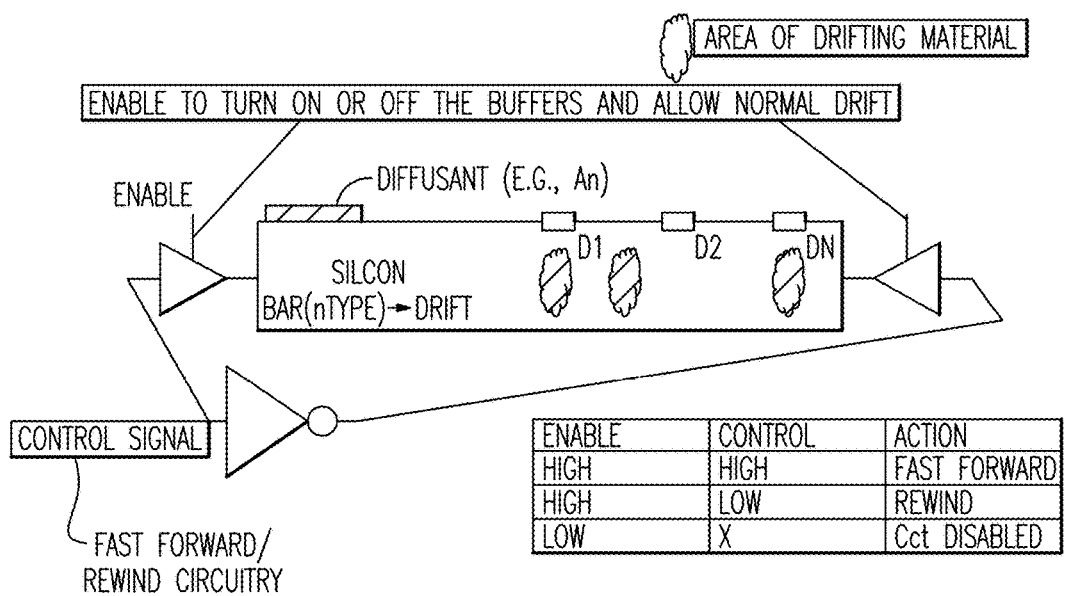
FIG. 89 illustrates wear-out monitor comprising a substrate having formed thereon a reservoir of monitor atoms and a plurality of electrodes for time-resolved monitoring, where the substrate is connected to a "fast forward" and/or a "rewind" circuitry for laterally diffusing the monitor atoms, according to embodiments.

FIG. 89 illustrates a substrate is connected to a "fast forward" and/or a "rewind" circuitry and configured to laterally diffuse the monitor atoms towards left or right by flowing current in the left or right directions depending on the charge state of the monitor atoms, once the monitor atoms have diffused into the substrate from the reservoir.

Figure 90:
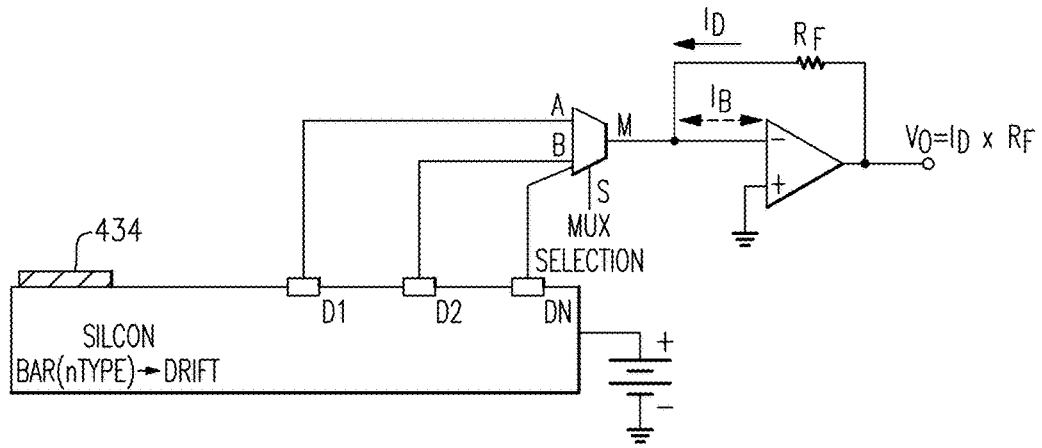
FIG. 90 illustrates wear-out monitor comprising a substrate having formed thereon a reservoir of monitor atoms and a plurality of electrodes for time-resolved monitoring, where the electrodes are connected to a reverse bias leakage multiplexed measurement circuitry, according to embodiments.

FIG. 90 illustrates the electrodes being connected to a reverse bias leakage multiplexed measurement circuitry, according to embodiments. In one implementation, when a positive is applied to an n+ region, e.g., +1V, the diode would be under a reverse bias would force about 0V on both positive and negative terminals.

Figure 91:
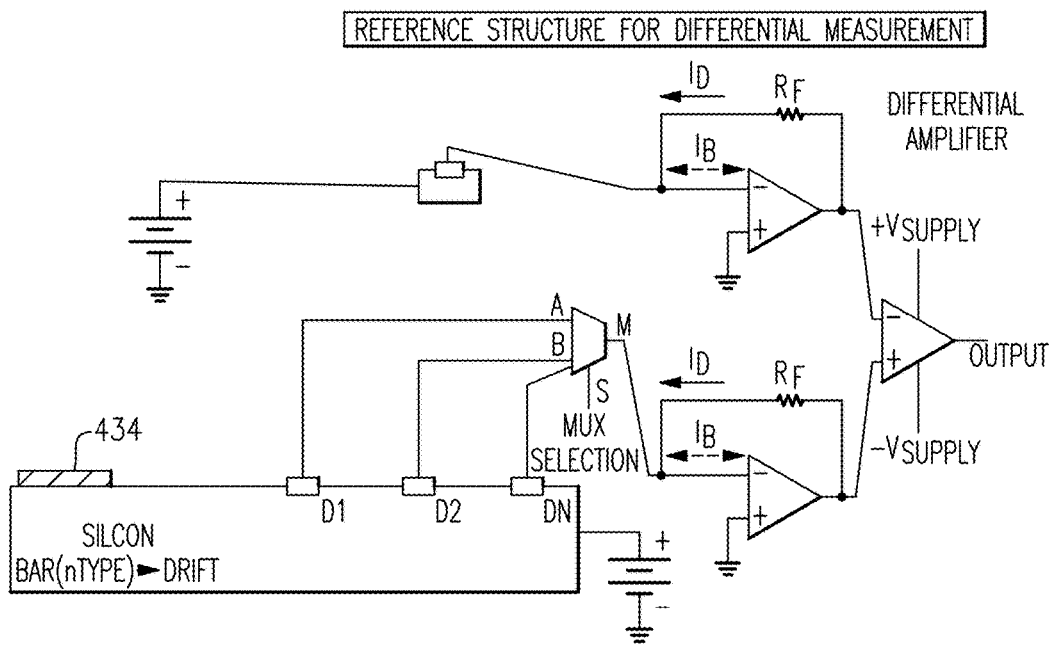
FIG. 91 illustrates the electrodes being connected to a reverse bias leakage multiplexed measurement circuitry comprising a reference structure for differential measurements, according to embodiments.

FIG. 91 illustrates the electrodes being connected to a reverse bias leakage multiplexed measurement circuitry comprising a reference structure for differential measurements, according to embodiments.

Figure 92:
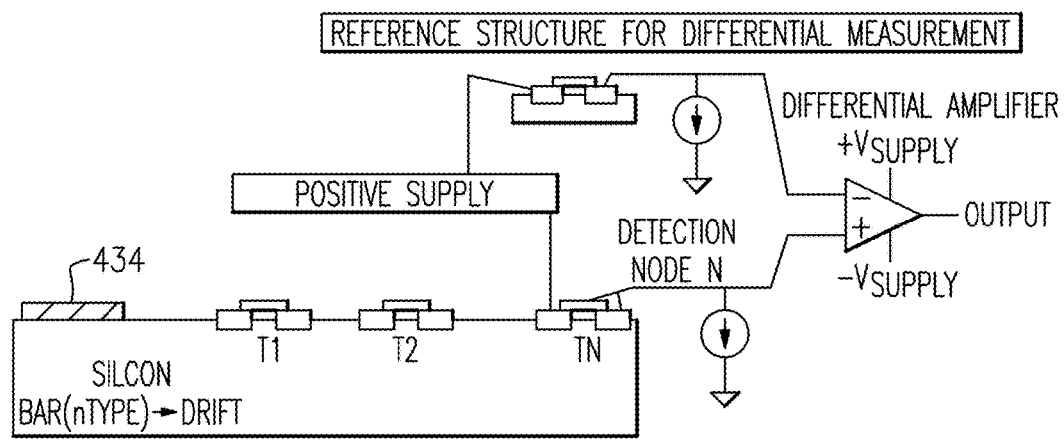

FIG. 92 illustrates a plurality of monitor MOS transistors T1, T2, . . . TN whose gates serve as the electrodes D1, D2, . . . Dn . . . The monitor MOS transistors as well as a reference transistor are connected to a differential amplifier for a differential measurement, according to embodiments. The circuitry is configured to measure, among other parameters, shifts in the MOS threshold voltages while the MOS transistors are turned on, whose shifts may result from diffusion of monitor atoms into the channels of the MOS transistors. In operation, when the threshold voltages of the MOS transistors shift, the voltage at the detection node changes accordingly. The measurement can be single ended or differential.

Figure 93:
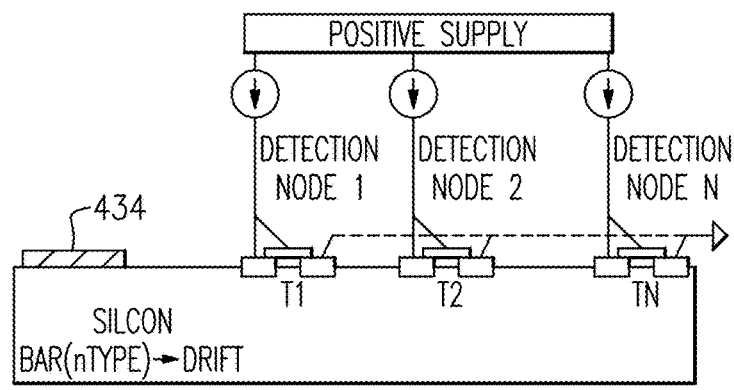

FIG. 93 illustrates a plurality of monitor MOS transistors T1, T2, . . . TN whose gates serve as the electrodes D1, D2, . . . Dn . . . The monitor MOS transistors are connected to current sources. The circuitry is configured to measure, among other parameters, leakage current through the channels while the MOS transistors are turned off. In operation, after the detection nodes are initially pulled high by the current sources, current leakage through the channels resulting from monitor atoms that may have diffused therein pulls the detection node low.

Figure 94:
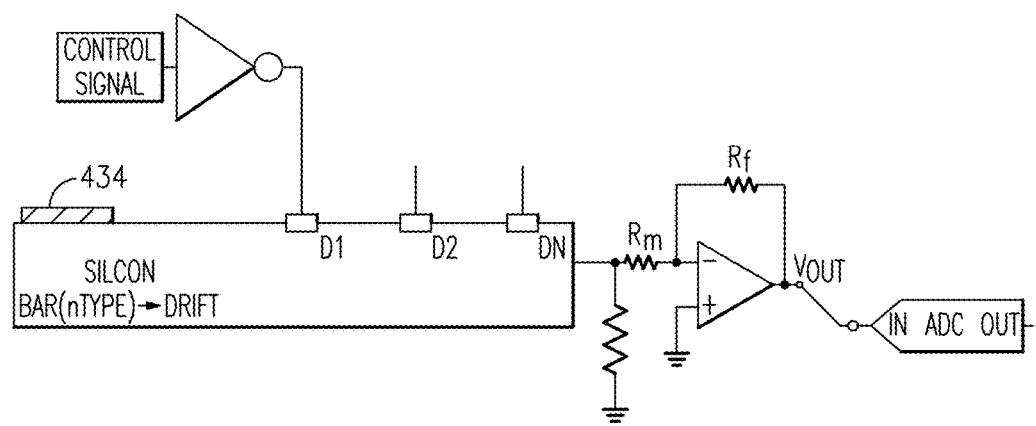

FIG. 94 illustrates a sensing circuit configured to measure reverse bias recovery current. The electrodes are configured to receive control signals for driving the diodes from forward to reverse bias by the inverter/buffer. When the diode is driven from forward to reverse bias, the voltage at the left of Rin is pulled approximately to GND. Because of the diode reverse recovery, the voltage at the left of Rin is pulled below GND. This signal is amplified and converted to measure the diode reverse recovery.

Figure 95A:
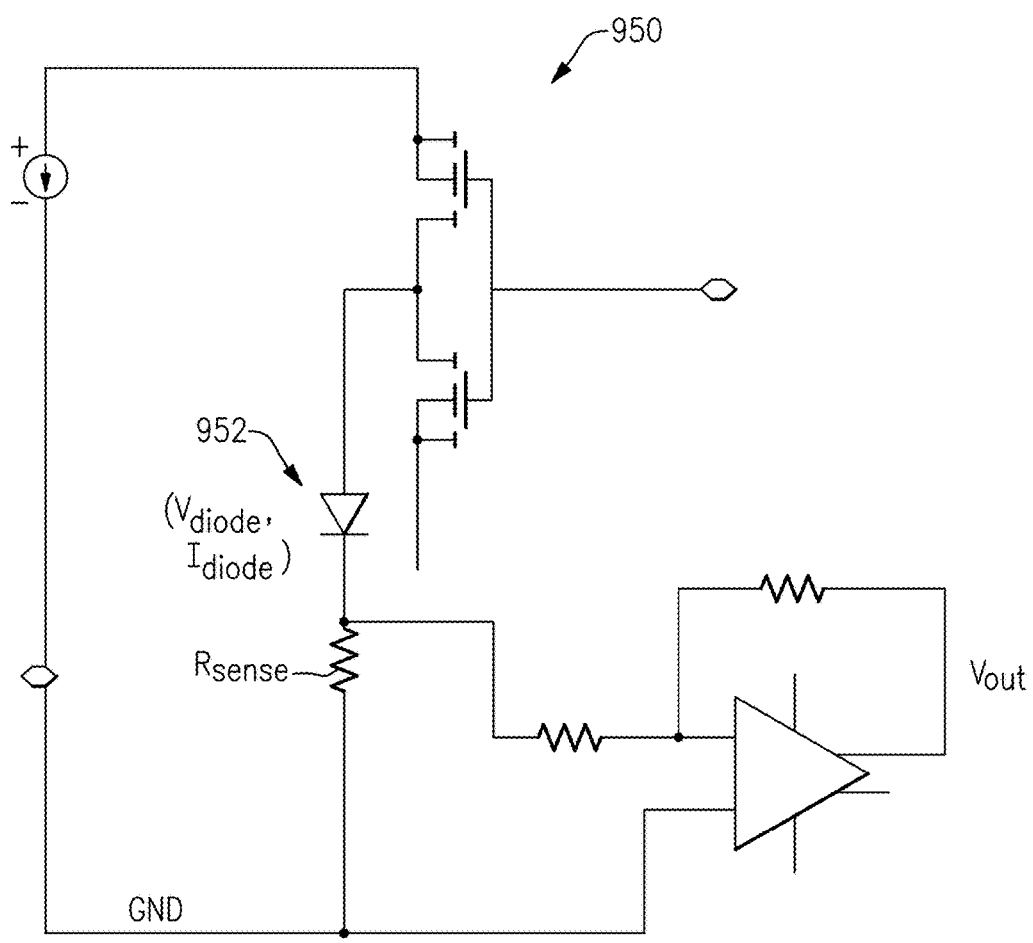

FIG. 95A illustrates a sensing circuit 950 configured to measure reverse bias recovery current comprising a monitor diode 952 and configured for monitoring wear-out of a core circuit, according to embodiments. It has been recognized that when switching from a conducting to a blocking state, a diode or a rectifier has stored charge that must first be discharged before the diode blocks reverse current. This discharge takes a finite amount of time known as the reverse recovery rime, or $t_{rr}$. During this time, diode current may flow in the reverse direction. The inventors have discovered that the reverse recovery time ($t_{rr}$) of such a diode is altered by impurities, e.g., gold, entering the PN junction of the diode as a result of wear-out stress. Based on this effect, the wear-out of the core circuit can be semi-quantitatively determined, according to embodiments. The illustrated circuit 950 is configured to switch the monitor the diode 952 from a forward biased configuration to a reverse biased configuration, and to measure the reverse recovery therefrom, to semi-quantitatively determine the amount, the type and/or the location of the impurities resulting from the wear-out stress.

Figure 95B:
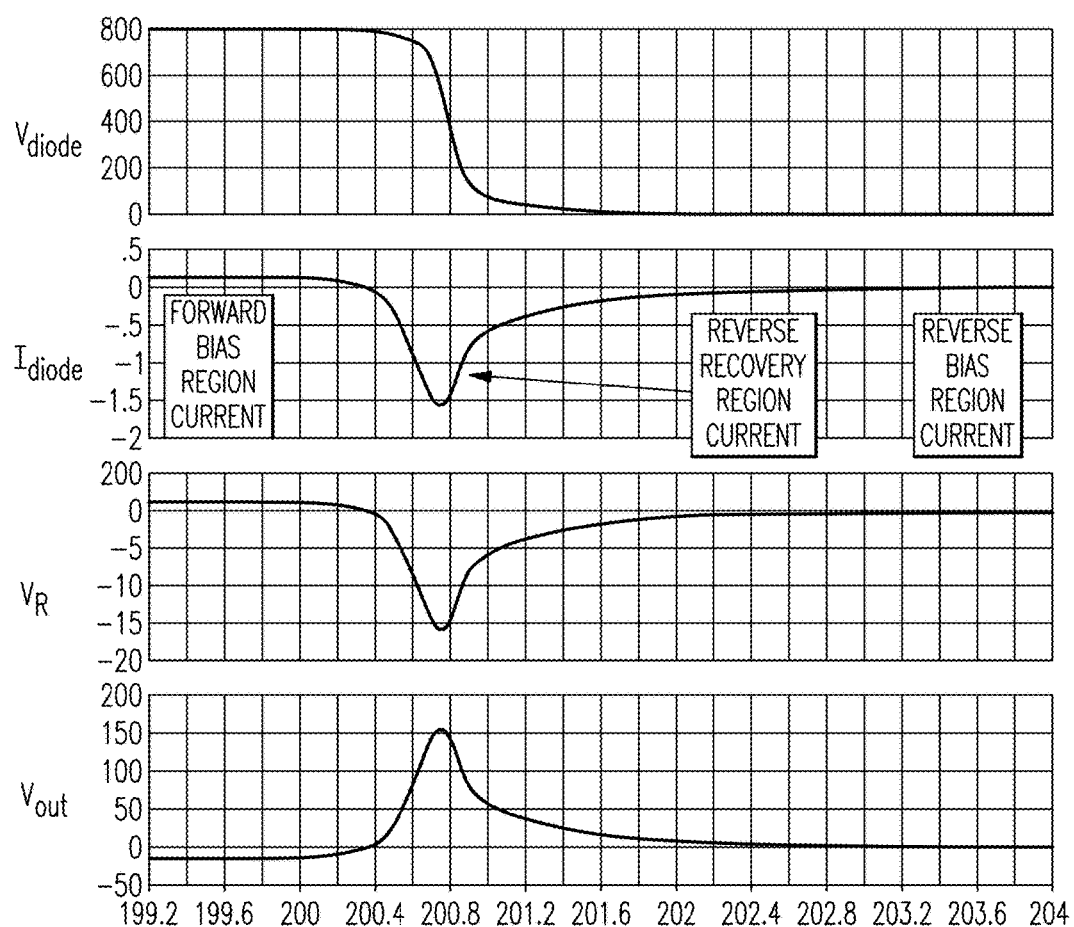
Figure 96A:
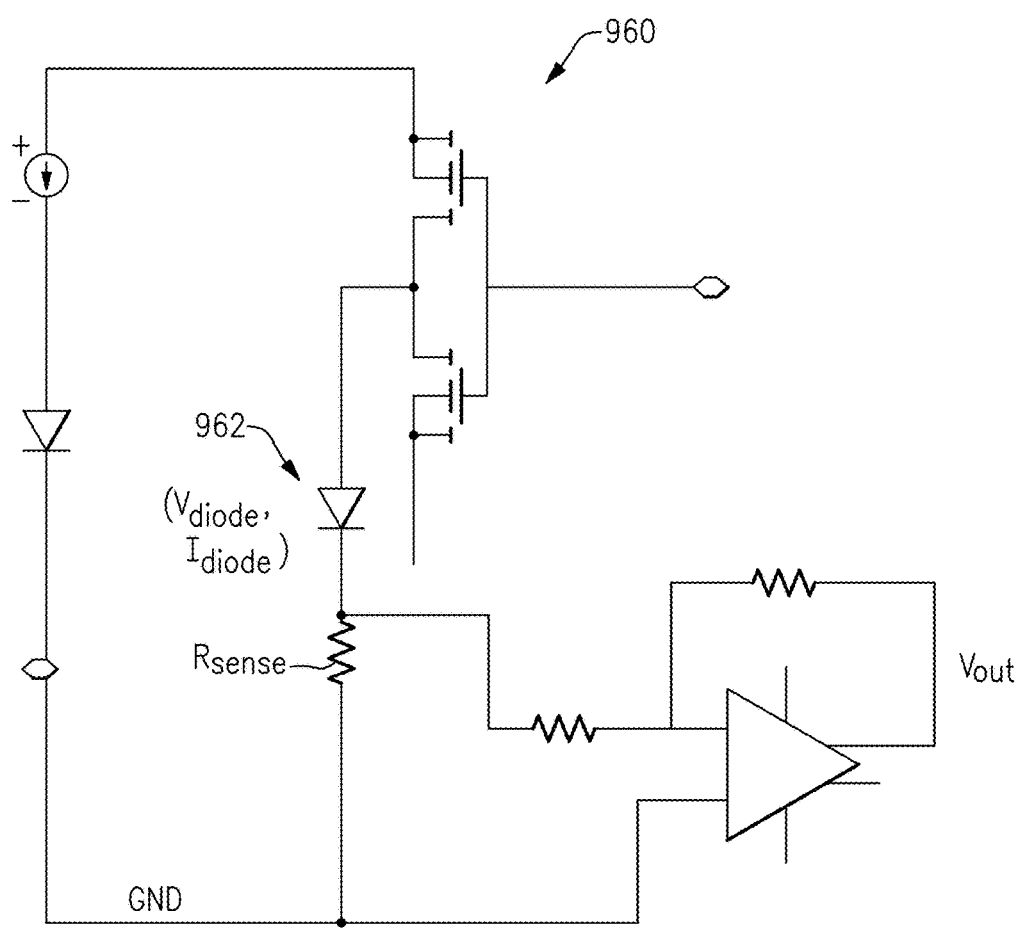

FIG. 95B illustrates current and voltages measured at different nodes of the sensing circuit 950 illustrated in FIG. 96A, as the monitor diode 952 is switched from a forward biased configuration to a reverse biased configuration. Illustrated four graphs from the top of page corresponds to a voltage at the inverter output which provides the switching voltage $V_{diode}$ across the diode 952, current $I_{diode}$ across the diode 952, voltage $V_{sense}$ across the sense resistor $R_{sense}$ serially connected to the diode 952 and the output voltage $V_{out}$ across the amplifier, as a function of time. As illustrated, the second graph from the top of page illustrates the current measured across the diode 952 as it transitions across different regions, including a forward bias region, a forward recovery region and a reverse bias region. A positive voltage output from an amplifier can be used to semi-quantitatively determine the wear-out of the core circuit.

FIG. 96A illustrates a reference circuit 960 comprising a reference diode 962, which does not have impurities diffused therein. The reference circuit 960 includes various circuit components that corresponds to the circuit components of the sensing circuit 950 illustrated above with respect to FIG. 95A, except, instead of the monitor diode 952 configured to monitor wear-out of a core circuit, the reference circuit 960 includes the reference diode 962. The reference diode 962 does not, for example, include monitor atoms that are configured to diffuse into the depletion region of the diode 962.

Figure 96B:
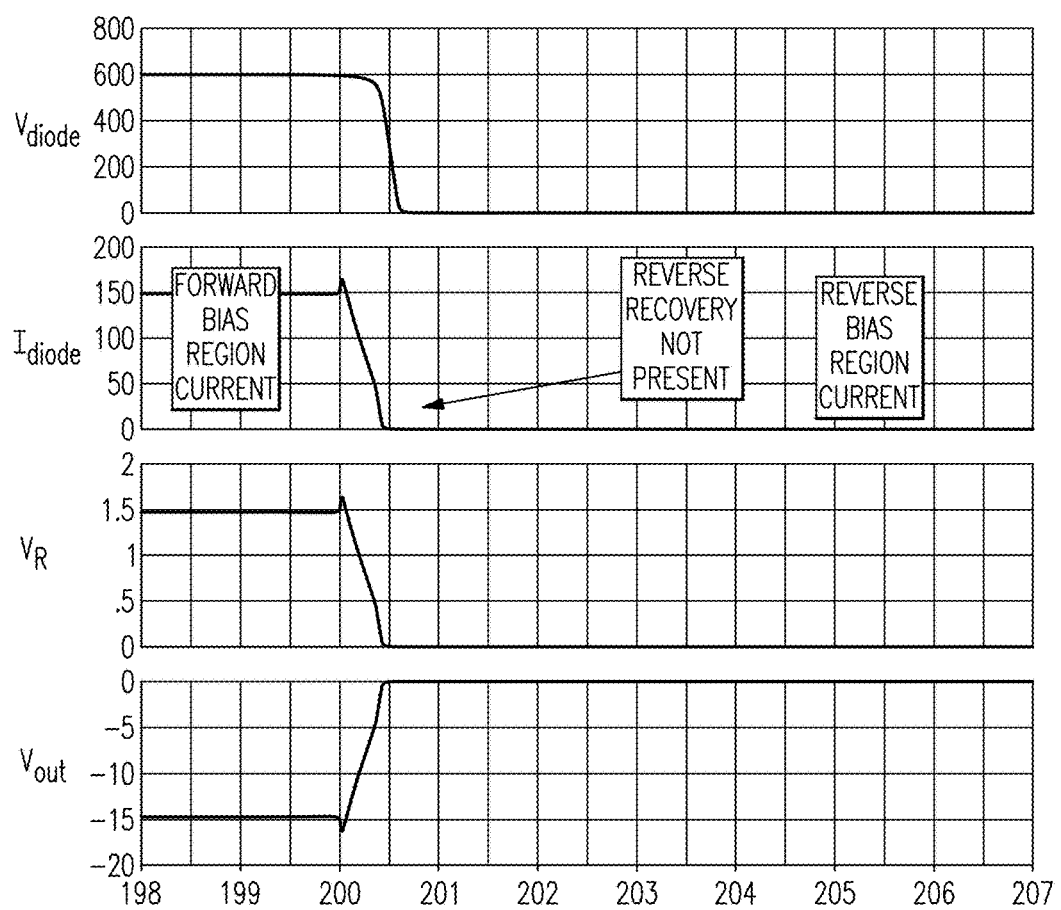

FIG. 96B illustrates current and voltages measured at different nodes of the reference circuit 960 illustrated in FIG. 96A, as the reference diode 962 is switched from a forward biased configuration to a reverse biased configuration. The four graphs illustrated in FIG. 96B corresponds to the four graphs illustrated with respect to the sensing circuit 950 in FIG. 95B. In particular, the second graph illustrates current across the reference diode 962 of FIG. 96A as it is switched from a forward biased configuration to a reverse biased configuration, using the sensing circuit 960 illustrated in FIG. 96A. As illustrated, a relatively smaller voltage output from an amplifier compared to the voltage output measured in FIG. 95B can be used as a reference to semi-quantitatively determine the wear-out of the core circuit.

Wear-Out Monitor Devices Configured for Reversing the Diffusion Direction of Monitor Atoms As described with respect to various embodiments above, the concentration of monitor atoms at certain location within a wear-out monitor device can be indicative of an integrated history of a wear-out stress. Because atomic diffusion can be driven by concentration gradient, without an opposing chemical potential, the net movement direction of the monitor atoms tends to be in the direction of decreasing concentration of the monitor atoms. As a result, for various configurations, the wear-out monitor device can be configured as "one-time use" devices. However, for some applications, it may be desirable to be able to "rewind" the movement of monitor atoms in a reverse direction after being subjected to a wear-out stress.

To address these and other needs, similar to various embodiments described above, a wear-out monitor device is configured such that the wear-out stress causes the monitor atoms to diffuse away from the reservoir and into the monitor region. Furthermore, the wear-out monitor device is configured such that the monitor atoms are adapted to have a charge state when diffused in the monitor region, and configured to apply an electric field to the monitor region such that, when the electric field is applied to the monitor region having the monitor atoms diffused therein, the electric field causes the monitor atoms to diffuse away from the monitor region and back into the reservoir. It will be appreciated that the direction of movement of the monitor atoms in these embodiments is in a direction of increasing concentration gradient. Thus, according to various embodiments, the wear-out monitor device is configured to apply the electric field having a magnitude such that, when the electric field is applied to the monitor region having the monitor atoms diffused therein, the electric field causes the monitor atoms to diffuse in the direction of increasing concentration gradient. These embodiments are described with respect to FIGS. 97 and 98.

FIG. 97 illustrates a cross-sectional view of a wear-out monitor device, similar to those illustrated with respect to FIGS. 56A and 63A, in operation, where the wear-out monitor device is configured such that electrical signatures based on interdiffusion of atoms can be utilized to measure wear-out of a core circuit, according to embodiments. FIG. 98 illustrates a cross-sectional view of the wear-out monitor device of FIG. 97 and a control and sensing circuitry connected to the device. In particular, the devices illustrated in FIGS. 97 and 98 comprise a plurality of regions, where each region is configured to be initialized using an external stimulus, and for monitoring, e.g., time-resolved monitoring, of wear-out of a core circuit, according to embodiments. After being initialized and being subjected to wear-out stress thereby allowing the monitor atoms to diffuse into respective monitor regions, because the monitor atoms are adapted to have a charge state when diffused in the monitor regions, by applying an electric field to the monitor regions having the monitor atoms diffused therein, the monitor atoms are caused to diffuse away from the monitor region and back into the reservoir.

Sensor Network Systems Based on Wear-Out Monitor Devices Configured for Controlled Initialization, for Time-Resolved Monitoring and for Reversing the Diffusion Direction of Monitor Atoms Some devices include a core circuit that has a predicted time and/or a predicted amount of usage that can lead to failure of the core circuit. The predicted time-to-fail and/or the predicted usage-to-fail are sometimes calculated and/or experimentally determined for a set of conditions, e.g., average conditions. For example, a mean time to failure may be calculated for electromigration-related failures can be based on a set of conditions including current density, temperature and activation energy. However, the actual time and/or usage of the core circuit are sometimes significantly different (e.g., below or above) from the time and/or usage conditions under which the failure is predicted, leading to unexpected failure or unnecessary replacement. Thus, there is a need to alert a user of the core circuit of an indication of wear-out that more closely represents the actual time or usage the core circuit has been subjected to. In the following, systems integrating various embodiments of the wear-out monitors & mission profile monitors are described, to address this and/or other needs.

According to various embodiments, a sensor network system includes a sensor node network. The sensor node network includes a plurality of sensor nodes, where each of the sensor nodes includes one or more wear-out monitor devices described above and an application processing unit. The one or more wear-out monitor devices are separated from and suitably arranged relative to a core circuit, and are configured to record an indication of wear-out of the core circuit, wherein the indication is associated with localized diffusion of a diffusant within the wear-out monitor device in response to a wear-out stress that causes the wear-out of the core circuit. The wear-out monitor devices are configured to record an indication of wear-out regardless of whether the wear-out monitor device of the sensor node is powered or unpowered. The sensor node network is communicatively coupled to a server or a hosted service to transmit the recorded indication thereto. The server or the hosted service is configured to communicate the indication of wear-out to a user and/or to provide an alarm signal indicating to replace a part.

There are many different application-specific systems that can be deployed with the wear-out monitors disclosed herein. In reference to FIG. 99, a system, e.g., a sensor network system for monitoring wear-out of a core circuit, is described.

The illustrated system of FIG. 99 includes one or more sensors. According to embodiments, the sensors may be arranged in a sensor node 1450. As described herein, one or more sensors arranged in a module may be referred to as a sensor node. In various embodiments, a sensor node 1450 can include one or more sensors configured for capturing data, e.g., in an unpowered package. The sensor node can additionally include an application processing unit (APU), which in turn includes one or more microprocessors, RAM, nonvolatile RAM (NVRAM), a hard disk, communications modules and/or a collection of physical interfaces. A sensor node additionally has one or more data access interfaces to enable the collection of captured data. These interfaces include, but are not limited to, GPIO pins, USB ports, parallel interfaces, RS232 connections, Ethernet ports or a radio for wireless transmission (RF, Wi-Fi, Bluetooth, etc.), among other ports or interfaces. As used herein, data that has been collected from a node via physical or wireless means is known as a data stream while in transit.

Installation and configuration of a sensor node can be performed, e.g., over a secured protocol to ensure the node can be securely and safely added to the sensor network. This ensures that all nodes can be trusted in a network and prevents unauthorized nodes from gaining access to the network.

Still referring to FIG. 99, data recordings or readings can be captured at each sensor node. In some applications, depending on the environment and data processing capabilities of a sensor node, data can be transformed into information at each sensor node. Information includes data that has been transformed using analytic data processing algorithms to determine enhanced or greater resolution of the data been captured. In some applications, depending on the network environment and processing capabilities of a sensor node, captured data can be secured using encryption or similar methods to prevent unauthorized access.

Still referring to FIG. 99, data/information captured at the one or more nodes is transferred or transmitted (depending on the capabilities of the sensor node) to an upstream system 1454. As described herein, an upstream system is a separate, independent piece of equipment that is not a sensor node but configured to store, process and make available all the data and/or information from a sensor network. The upstream system secures the data, depending on the capabilities of the sensor node, network environment and application needs of the system. The upstream system transforms the data into information, whose information can be used to address specific domain problems encountered by the application covered by the system.

Still referring FIG. 99, the sensor node of the illustrated system can have various configurations according to embodiments, as described below.

In some embodiments, the sensor node is configured under a zero power mode. In this mode, the sensor is configured to take readings and to store the readings without having to read from or store the readings to non-volatile random access memory (NVRAM), or with the continuous application of power.

In this mode, a microprocessor (MP) or NVRAM modules can be omitted. An interface can be provided to enable on-demand reading of each sensor node.

In some embodiments, the sensor node is configured under a continuous operation mode. In this mode, the sensors are continuously powered (e.g. via mains supply or battery), and is configured to take continuous readings from each sensor at a predetermined time interval. These readings are stored in NVRAM and can be later communicated to upstream systems using one or more interfaces.

In some embodiments the sensor node is configured under a mode in which the sensors are configured to be periodically waken up and to record latest readings. Under this mode, using an internal clock (via crystal or other), some NVRAM and some simple logic circuits the system are periodically waken-up from an ultra-low powered, deep sleep state and readings are taken from each sensor the readings are stored in NVRAM. These readings can be later communicated to upstream systems using one or more interfaces.

In some embodiments, the sensor node is configured under a mode in which the sensors are configured to be waken up to an interrupt event and to record latest readings. Under this mode, with the addition of a MP and some I/O circuits, the system could wake up to an interrupt event and take a reading from each sensor and store those readings in NVRAM. These readings can be later communicated to upstream systems using one or more interfaces.

For the various sensor node configurations, the NVRAM can be configured such that when NVRAM is approaching capacity, the sensor node can be configured to either stop recording readings or use a first in first out (FIFO) methodology to continuously record the readings.

For various sensor node configurations described above, the sensor node can be configured to sense instantaneous node operating conditions in addition to the one or more sensor readings, to analyze the data using on-board algorithm processors to perform computations for making informed decisions about the data, and to store the results of these computations (i.e. store information not data). For example, this information could be used in additional computations to refine the period of wakeup or configuration of interrupt controllers to better utilize power capacity or to ensure a critical event is captured.

The sensors and sensor nodes may be further arranged in a sensor network. As described herein, a collection of sensor nodes may be referred to as a sensor network. A sensor network can cover, e.g., a single piece of equipment, a room, building, facility or geographic region including the entire planet. In the following, various configurations of a sensor network is describe, according to embodiments.

FIG. 100 illustrates a sensor network 1501 is communicatively coupled to a an upstream system including a private server 1509 through a network transmission 1502. The network and upstream systems are private to the business/organization and information gathered from transforming the captured data in the sensor network is used for applications specific to that business/organization.

The data captured from the network can be secured at each node using encryption or similar and securely transmitted to the private server. All network transmission, over either physical or wireless medium can be performed securely. The data transmission can be secured using a protocol that ensures confidentiality (the data stream cannot be access by unauthorized persons), integrity (ensuring that the data stream cannot be tampered with or changed) and utilizing authentication (to ensure that we identify that users and/or systems are who they claim to be).

Examples of secured transmission protocols include secure sockets layer (SSL), hashed message authentication codes (HMAC) and public/private key exchange.

The upstream server includes a system controller 1504 that routes and separates command and control (CnC) instructions from data collection/processing instructions. CnC instructions include but are not limited to network configuration commands, new node installation/setup commands and network health management.

CnC instructions are routed to a node manager 1506. A node is configured to process and to handle all CnC instructions.

Data collection and processing instructions are routed to a processing engine 1505. The processing engine 1505 is configured to store data as appropriate, transform data into information using data analytical algorithms, store information as appropriate and raise events depending on the system application needs, configuration and the results of the data transformation into information.

An event manager 1510 is configured to handle all raised events in the system. Event handling can include but is not limited to user display updates, email notifications, upstream system interactions and sensor network CnC instructions (e.g. forced shutdown command).

All data and information is persisted to a backing store. A backing store can include but is not limited to data files or databases 1508 (both relational and non-relational). The data is stored utilizing a data schema. An example schema that includes a sensor node and data database tables are illustrated below with respect to TABLES 2 and 3 below.

TABLE 2

Nodes Table

Unique id for the node
Application type or function of the node
Geolocation details for the node if appropriate
Salts/encryption keys used to decrypt data and communicate with the node

TABLE 3

Data Table

The unique node identifier that captured the reading
The value captured
Timestamp of when the readings where transmitted or collected from the node TABLE 3-continued Data Table Depending on the node geolocation details on the node when the data was captured FIG. 101 illustrates a sensor network communicatively coupled to cloud hosted services, according to embodiments. Sensor network data can be collected and transmitted to a hosted service or services, sometimes referred to as cloud computing services. The cloud is configured to persist, analyze and transform the data into information and take action appropriate action on that information.

These hosted services can be private (a private network within a business or facility), hybrid (a combination of public internet accessible services and a private networks) or public (internet accessible services) depending on the application needs and sensor network deployment.

Example of a public cloud is where the hosted services are used to capture data from a range of customer's privately owned sensor networks. The cloud utilizes its scale and processing capabilities to infer anomalies or significant information from the transformed data that is of value to each customer.

Possible service deployments include but are not limited to the following models.

A software-as-a-service (SaaS) model where the software and algorithms are sold to customers who are free to deploy these services on the hosted service network of their choice.

A platform-as-a-service (PaaS) model where each customer retains ownership and control of their data but online hosted services are provided and made available for the storage and analysis of their data.

Still referring to FIG. 101, the cloud, hosted services utilize a load balancer 1501 to ensure and efficient distribution of sensor network data streams to upstream processing systems. The distribution is generally but not exclusively based on volume and current load of backend hosted system.

FIG. 102 illustrates a sensor network according to embodiments, in which the sensors are configured to collect data by communicating directly with a private server or hosted services. However, a more practical approach is to use a proxy server to collect the data/information readings from the sensor network and is responsible for transmitting that collected data to upstream systems.

In the illustrated embodiment of FIG. 102, a proxy server can utilize secured protocols to transmit the data streams to upstream systems.

In general, a proxy server 1605 can have high capacity storage available to collect and store the data from the sensor network. Depending on the capacity and real time criticality of captured data the proxy server can be configured with an appropriate interval for communicating the data to upstream systems.

Under some circumstances, a proxy server can utilize a short range wireless protocol 1604 (e.g., Bluetooth) to collect data from the sensor network.

Under some circumstances, each sensor node could be directly connected to the proxy server utilizing a physical connection 1603 (e.g., RS232) and data could be transmitted over this connection.

A sneakernet device 1612 can be used to collect the data from each node and upload to the proxy server. A sneakernet refers to the transfer of electronic information by physically moving storage media (e.g. USB flash drives) or a reader device with on board storage from the source to the destination rather than transmitting the information over a wired or wireless network.

Without limitation, according to various embodiments, integrated circuit devices comprising one or more wear-out monitor devices/sensors (WOS) that can be configured to be used as part of a sensor network system described herein include one or more of the following features.

As described above, WOSs can record a wear-out state regardless of whether the WOs be powered or un-powered, and can be activated by various wear-out stresses including pressure, gas, time, voltage and/or current. A system combines the status of the WOSs and enables a higher level system take decisions of the combined status. The WOS can be derived to vary are different rates or in the presence of a current/voltage etc.

The WOS can be enabled or disabled by use of a physical "gate material/substance".

The WOS can be implemented through the monitoring of two physical phenomena that occur due to the presence of a primary material/structure/sensor (e.g. Gold, diffuses into silicon crystal lattice and then free silicon atoms oxidize on the upper surface of the gold, both physical phenomena can be electrically measured and controlled)

The WOS can be implemented using one or more realizations to create more data points on the current state of the device under monitoring.

The WOS may be created using multiple layers of material or primary material plus another element/substance to enable the monitoring of multiple temperature ranges by a single sensor.

The current state of the WOS can be reversed/reset/cleared under control.

The physical implementation of the WOS can enable unique signatures to be read from the WOS on a device per device basis.

The physical implementation of the WOS can enable atom counting.

The physical implementation of the WOS can allow for the enabling or disabling of some or all connectivity to the WOS through physical changes to the material boundaries The physical implementation of the WOS can enable multiple read points for a single/multiple source element/material.

A WOS could be used to detect that a device/chip/module has only been soldered once A barrier material may be used around/about/in-way-off to control the normal spread of the solvent/solute.

The barrier can/may be for blowing to enable (electrical, photonic, chemical, physical stress, breakdown, decay, etc.), for non-blowing to enable, for evaporation to enable.

The WOS can enable an additional capacitor differential sensor through physical growth of material e.g. silicon dioxide. This would allow the single sensor to generate two separate data point on wear out.

In some embodiments, one or more WOSs are embedded in the package for a single/multiple die, including SOCs and SIPs.

In some embodiments, one or more WOSs are contained within the same physical module and or 3D-printed assembly. Examples of physical module include a PCB board or flexible-substrate with multiple integrated circuits, but could equally be a system with or without physical connections between each component, example a ribbon cable, flex, RF and or optical.

In these embodiments, the WOS can be electrically and physically integrated to be inside a physical module. In other embodiments, the WOS can be electrically integrated but physically disposed external to the physical module. When external to the physical module, the WOS can capture ambient conditions.

In addition, the module can be active or passive. When the module is passive, the module has no independent power source but is capable of being read by an external device with its own power. When the module is active, the WOS is configured to monitor when, e.g., only when, power/voltage/current is present.

In some embodiments, WOSs can be embedded in a 3D-printed structure, where interconnect is embedded into/on-to the 3D-printed structure. This approach can enable multiple WOSs to be distributed throughout a structure.

In some embodiments, one or more WOSs are encapsulated in a module/structure that will experience extreme environmental conditions, e.g., temperature ranges. In these embodiments, relatively more sensitive electronics are kept at a suitable distance away or isolated from the source of the extreme environmental conditions, e.g., temperature sources. The WOSs can be connected via a physical/optical/RF medium that enables the ability to take a reading from the sensor.

In some embodiments, one or more WOSs are stored in a module with the minimum electronics for remotely and/or wirelessly transmitting sensor readings either on demand or periodically.

Periodic data transfer can be made either through a powered sensor, or through harvested environmental energy (light, sun, temperature).

The remote module/structure can also be polled through RFID waves. Some remote communication methods can use a secure protocol.

The WOSs could be used as a "service life" meter, where after a given time the WOS flags to the system that the device has reached it maximum life and flags for replacement. This "service life" could be active or passive and could be for time, temperature, pressure, voltage, current, gas, etc.

FIG. 103 illustrates various physical and electrical connections that can be made to various wear-out monitor devices described supra, for integration into a sensor network system, according to embodiments. In particular, the illustrated wear-out monitor device is similar to the device illustrated with respect to FIG. 98. In particular, the illustrated devices comprises a plurality of regions, where each region is configured to be initialized using an external stimulus, and for monitoring, e.g., time-resolved monitoring, of wear-out of a core circuit, according to embodiments.

Examples of Sensor Network Systems Based on Wear-Out Monitor Devices

Example: System A

The inventors have recognized that it can be difficult to determine the active lifespan of a part comprising a core circuit when the part sits on a shelf in an inactive state for a relatively very long time. Knowing how long a part sat inactive before been used can be useful in failure analysis and general characterization of a part's lifetime performance and capability.

To address these and other needs, a sensor network system based on wear-out monitor devices according to embodiments is illustrated with respect to FIG. 1. In reference to FIG. 104, using multiple WOSs whereby one or more are based on materials that diffuse at room temperature we can take a reading when the part is first powered on and note that if a WOS shows a high level of diffusion then we know that the part has sat inactive for a long time before it was used. This is logged to non-volatile memory (NVM) or other persistent storage and can be used in precision analog circuit trimming and or post failure diagnostics, characterization or even to warn/indicate to the user the remaining lifetime and capabilities of the part. One or more of the sensors could be active.

A suitable cloud platform (cloud infrastructure that includes security, data processing and management technologies, across standard communication infrastructure) can be used to assist in failure diagnostics and or preventative-maintenance. As part of the sensor module registration process, significant attributes of the module such as unique-identifying-code, unique-identifying-profile of the WOS, diffusion levels of the WOS, can be recorded and reported on; and compared to the standard diffusion profile for the given device/module application space. This process could be available to users or restricted to a manufacturer's failure analysis organizations or a royalty based system protection division.

Once the sensor/module is registered, the manufacturer can provide an additional cloud service to help customers determine the operating conditions of the part, and expected lifetime remaining. For example an automotive device could flag final operation in x weeks/days/hours/minutes, giving the user a period of time to replace the device before it disables itself.

Thus, the System A can advantageously capture near full life history of a core circuit in a part during use, from calibration to failure analysis.

Example: System B

The inventors have recognized that the performance or accuracy of a WOS can be dependent on the material and operating temperature range of the part. It would be useful to capture and correlate out of band temperature events, for example, temperature spikes for a brief moment or long exposure to a temperature range below the activation level of the WOS material.

To address these and other needs, a system according to embodiments based on wear-out monitor devices include a combination of passive (WOS) and active sensors. Using the combination, additional readings can be made while the part is powered. These reading can be used in conjunction with the WOS reading to determine a more complete temperature profile of the system. In conjunction with a wake-up timer an actual profile could be captured and stored in NVM or communicated for external processing in a supervisor system and or a cloud infrastructure.

Thus, the System B can advantageously provide accurate temperature profile logging at a device level.

Example: System C

The inventors have recognized that data degradation can occur due to cosmic rays or particles, which can have serious consequences for systems that depend on non-ECC memory storage.

To address these and other needs, a system according to embodiments include memory chips with a WOS and detect a cosmic particle collision event due to a unique diffusion signature. This event could then be acted on by the system to either reset the system to a known good state or used a post failure analysis logging event.

The device registration process includes a system check to determine the initial state of the WOS and will flag any such events. Subsequent data synchronizations to the cloud servers can include a check for same events.

Thus, the System C can advantageously detect radiation-induced error (RIE).

Example: System D

The inventors have recognized that, it can be advantageous to detect die-cloning and or tampering and or other unauthorized access to a device and its internal system code.

To address these and other needs, a sensor network according to embodiments include a WOS configured to generate a unique source of entropy with a predictable diffusion progression based on the standard mission profile for the device. The system algorithm can detect if an attempt is made to inject a foreign decryption key to unlock system code or that a physical/electrical event (e.g. removing the cap of a device—large heat spike) has occurred that might indicate that someone is attempting to gain unauthorized access to the device. This information can be used to 'brick' the device or otherwise attempt to put the IP sensitive parts of the device beyond the reach of the attacker.

The combination of intrusion sensors and "bricking" a device can be a solution for IoT applications and embedded hardware solutions, as hacking organizations invest significant resources in gathering information on the device or devices they wish to attack. When possible, the hackers physically obtain target devices they wish to hack and attempt to reverse engineer the device and use it to test possible attacks.

Flagging potential hacks sometimes does not result in shutting off the device. In such applications where forcing a module shutdown can result in severe consequences (personnel health, machine health, security breaches), the preferred approach is to log an alert with the cloud platform. The cloud administrators can remotely deactivate the device.

Communicating with a hosted service, e.g., a cloud hosted service, can be through a variety of mechanisms, as described in FIGS. 105 and 106:

For more advanced triage purposes, geo-location hardware and monitoring can establish if the module was in the expected operating location, as described in FIG. 106:

Such use of technology can also be applied to internal failure analysis, where expensive processes and resources can be replaced by analyzing the cloud data. There is potential to sell this "intrusion detection" module and cloud service to customers with more expensive hardware or where it is preferred to conduct failure analysis in situ.

Thus, the System D can advantageously detect intrusions and protect device/customer IP.

Example: System E

The inventors have recognized that it can be advantageous to secure IoT modules in the cloud.

To address this and other needs, a system is configured such that, at any given time, the WOS records a unique diffusion amount and under normal operation the value can be within operating bands or rates of change. This value can be used to generate cryptographically signed code at boot time and algorithms can determine if firmware has been altered due to reverse engineering, de-soldering etc. More advanced solutions can combine the intrusion monitor with geo-location positioning.

Securing traffic to and from the device can be increased through an initial registration process with the cloud where intrusion module parameters are recorded. Future communications will include these variables as a salt for encrypting the channel. In effect, there will be a way to securely communicate with each module through its own diffusion fingerprint.

Thus, the System E can advantageously be configured such that device encryption becomes non-operational if operating life specifications are exceeded.

Example: System F

The inventors have recognized that some devices are provided by manufacturers with generic lifetime specifications. However, for these devices, no information may be available regarding how the customers utilize the devices and all returns are treated "equally" as we have no information on if the device reached its full lifetime. Thus, there is a need to provide information regarding how the customers have used a part having a core circuit before the part has reached its full lifetime.

To address this and other needs, a sensor network system according to embodiments comprise a WOS or combination of multiple WOSs and active life sensors, where the WOS(s) indicate specific operating lifetimes for a product. Once the lifetimes have exceeded, the device can become inoperable/shutdown. This could be invaluable for markets where quality of service (QOS) is a high priority, e.g., in automotive/industrial applications. The device could communicate it status (time to end of life) to a supervisor system or external to the likes of the cloud, creating a replacement device revenue stream and a cloud monitoring revenue stream.

CONCLUSION

In the embodiments described above, apparatus, systems, and methods for wear-out monitors are described in connection with particular embodiments. It will be understood, however, that the principles and advantages of the embodiments can be used for any other systems, apparatus, or methods with a need for monitoring wear-out. In the foregoing, it will be appreciated that any feature of any one of the embodiments can be combined and/or substituted with any other feature of any other one of the embodiments.

Aspects of this disclosure can be implemented in various electronic devices. Examples of the electronic devices can include, but are not limited to, consumer electronic products, parts of the consumer electronic products, electronic test equipment, cellular communications infrastructure such as a base station, etc. Examples of the electronic devices can include, but are not limited to, a mobile phone such as a smart phone, a wearable computing device such as a smart watch or an ear piece, a telephone, a television, a computer monitor, a computer, a modem, a hand-held computer, a laptop computer, a tablet computer, a personal digital assistant (PDA), a microwave, a refrigerator, a vehicular electronics system such as an automotive electronics system, a stereo system, a DVD player, a CD player, a digital music player such as an MP3 player, a radio, a camcorder, a camera such as a digital camera, a portable memory chip, a washer, a dryer, a washer/dryer, peripheral device, a clock, etc. Further, the electronic devices can include unfinished products.

Unless the context clearly requires otherwise, throughout the description and the claims, the words "comprise," "comprising," "include," "including" and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Likewise, the word "connected", as generally used herein, refers to two or more elements that may be either directly connected, or connected by way of one or more intermediate elements. Additionally, the words "herein," "above," "below," "infra," "supra," and words of similar import, when used in this application, shall refer to this application as a whole and not to any particular portions of this application. Where the context permits, words in the above Detailed Description using the singular or plural number may also include the plural or singular number, respectively. The word "or" in reference to a list of two or more items, that word covers all of the following interpretations of the word: any of the items in the list, all of the items in the list, and any combination of the items in the list.

Moreover, conditional language used herein, such as, among others, "can," "could," "might," "may," "e.g.," "for example," "such as" and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or whether these features, elements and/or states are included or are to be performed in any particular embodiment.

While certain embodiments have been described, these embodiments have been presented by way of example only, and are not intended to limit the scope of the disclosure. Indeed, the novel apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments. The various features and processes described above may be implemented independently of one another, or may be combined in various ways. All suitable combinations and subcombinations of features of this disclosure are intended to fall within the scope of this disclosure.

What is claimed is:

1. An integrated circuit device comprising a wear-out monitor device configured to record an indication of wear-out of a core circuit separated from the wear-out monitor device, the wear-out monitor device comprising a reservoir and a diffusion region, wherein the indication is associated with localized diffusion of a diffusant from the reservoir into the diffusion region in response to a wear-out stress that causes the wear-out of the core circuit.

2. The integrated circuit device of claim 1, wherein the reservoir is formed at a surface of a substrate, wherein the reservoir serves as a first electrode of the wear-out monitor device, and wherein the wear-out monitor device further comprises a second electrode formed at the surface and formed of a material different from the reservoir.

3. The integrated circuit device of claim 1, wherein the diffusant has a diffusion activation energy between 0.75 eV and 2.5 eV.

4. The integrated circuit device of claim 1, wherein the diffusant includes one or more elements selected from the group consisting of aluminum (Al), cobalt (Co), platinum (Pt), sulfur (S), nickel (Ni), silver (Ag), zinc (Zn), gold (Au), chromium (Cr), copper (Cu), iron (Fe), sodium (Na), and potassium (K).

5. The integrated circuit device of claim 1, further comprising a sensing circuit electrically connected to the wear-out monitor device and configured to detect an electrical property that changes in response to the localized diffusion of the diffusant.

6. The integrated circuit device of claim 1, further comprising a control circuit configured to apply a stimulus to activate the wear-out monitor prior to recording the indication of wear-out.

7. The integrated circuit device of claim 6, further comprising a physical barrier having an energy barrier for diffusion of the diffusant disposed between the reservoir and the diffusion region, wherein the physical barrier is configured such that the energy barrier is reduced in response to the stimulus to activate the wear-out monitor device.

8. The integrated circuit device of claim 1, wherein the wear-out monitor device comprises a plurality of monitor structures each configured to record an indication of wear-out of the core circuit.

9. The integrated circuit device of claim 8, wherein different ones of the monitor structures are configured to be activated by different stimuli prior to recording indications of wear-out of the core circuit.

10. The integrated circuit device of claim 1, wherein atoms of a substrate serve as the diffusant, such that the wear-out stress causes atoms of the substrate to diffuse from the substrate into a diffusion region in response to the wear-out stress.

11. The integrated circuit device of claim 1, wherein the wear-out monitor device is configured to apply an electric field to a diffusion region in a first direction, and wherein the diffusant has a charge state when diffused in the diffusion region such that, when the electric field is applied to the diffusion region having the diffusant diffused therein, the electric field causes the diffusant to further diffuse in the diffusion region in the first direction.

12. The integrated circuit device of claim 11, wherein the diffusion region and the reservoir are adjacently disposed in a second direction different than the first direction and configured such that the wear-out stress causes the diffusant to diffuse in the second direction.

13. The integrated circuit device of claim 12, wherein a plurality of conductive structures are formed on a surface of the diffusion region along the first direction and provide electrical access to the diffusion region at a plurality of locations.

14. The integrated circuit device of claim 1, wherein the wear-out monitor device is configured such that the wear-out stress causes the diffusant to diffuse away from the reservoir and into the diffusion region, wherein the diffusant has a charge state when diffused into the diffusion region, and wherein the wear-out monitor device is further configured to apply an electric field to the diffusion region such that, when the electric field is applied to the diffusion region having the diffusant diffused therein, the electric field causes the diffusant to diffuse toward the reservoir.

15. The integrated circuit device of claim 14, wherein the wear-out monitor device is configured to apply the electric field having a magnitude such that, when the electric field is applied to the diffusion region having the diffusant diffused therein, the electric field causes the diffusant to diffuse in a direction of increasing concentration gradient.

16. The integrated circuit device of claim 1, wherein the wear-out monitor device comprises a PN junction, and wherein the reservoir contacts one of a p-doped region or an n-doped region of the PN junction.

17. The integrated circuit device of claim 16, wherein the reservoir serves as an electrical contact for the one of the p-doped region or the n-doped region of the PN junction.

18. A method of monitoring wear-out of a core circuit of an integrated circuit device using a wear-out monitor device separated from the core circuit, the wear-out monitor device comprising a reservoir and a diffusion region, the method comprising:
  recording an indication of wear-out of the core circuit, wherein the indication is associated with localized diffusion of a diffusant from the reservoir into the diffusion region within the wear-out monitor device in response to a wear-out stress that causes the wear-out of the core circuit;
  detecting a property that changes in response to the localized diffusion of the diffusant; and
  reporting the property of the wear-out monitor device.

19. The method of claim 18, further comprising, prior to the recording, activating the wear-out monitor device by applying a stimulus to overcome an energy barrier.

20. The method of claim 18, further comprising applying an electric field to a diffusion region having the diffusant diffused therein to change a direction of diffusion of the diffusant in the diffusion region.

21. The method of claim 18, further comprising, prior to recording, subjecting the wear-out monitor device to the wear-out stress that causes the localized diffusion of the diffusant from the reservoir into the diffusion region.

22. The method of claim 21, further comprising, prior to subjecting the wear-out monitor device to the wear-out stress, activating the monitor device by applying a stimulus to overcome an energy barrier.

23. The method of claim 22, wherein applying the stimulus alters a physical barrier having the energy barrier and reduces the energy barrier.

24. The method of claim 21, further comprising, after subjecting the wear-out monitor device to the wear-out stress, applying an electric field to the diffusion region having the diffusant diffused therein in a first direction such that the electric field causes the diffusant to further diffuse in the first direction.

25. The method of claim 21, further comprising, after subjecting the wear-out monitor device to the wear-out stress which causes the diffusant to diffuse away from the reservoir and into the diffusion region, applying an electric field to the diffusion region having the diffusant diffused therein, such that the electric field causes the diffusant to diffuse toward the reservoir.

26. An integrated circuit device with wear-out monitoring of a core circuit in the integrated circuit device, the integrated circuit device comprising:
  means for recording an indication of wear-out of a core circuit, the core circuit separated from the means for recording, the means for recording comprising a reservoir and a diffusion region, wherein the indication is associated with localized diffusion of a diffusant from the reservoir into the diffusion region within the means for recording in response to a wear-out stress that causes the wear-out of the core circuit; and means for detecting the indication of wear-out of the core circuit, the means for detecting the indication of wear-out being in communication with the means for recording the indication of wear-out.

27. The integrated circuit device of claim 1, wherein the wear-out monitor device comprises a semiconductor substrate.

28. The integrated circuit device of claim 1, wherein the wear-out monitor device comprises an insulating substrate.

29. The integrated circuit device of claim 1, wherein the wear-out monitor device and the core circuit are integrated in a common substrate.

30. The integrated circuit device of claim 1, wherein the diffusant has a diffusion activation energy less than 3.0 eV.

31. The integrated circuit device of claim 26, wherein the means for recording is configured to be activated in response to a stimulus prior to causing the diffusant to diffuse from the reservoir into the diffusion region.

32. The integrated circuit device of claim 26, further comprising means for applying an electric field to the diffusion region in a first direction, and wherein the diffusant has a charge state when diffused in the diffusing region such that, when the electric field is applied to the diffusing region, the electric field causes the diffusant to further diffuse in the diffusing region in the first direction.

33. The integrated circuit device of claim 26, wherein the means for recording is configured such that the wear-out stress causes the diffusant to diffuse away from the reservoir and into the diffusion region, wherein the diffusant has a charge state when diffused into the diffusion region, and wherein the recording means is further configured to apply an electric field to the diffusion region such that, when the electric field is applied to the diffusion region, the electric field causes the diffusant to diffuse toward the reservoir.

34. The integrated circuit device of claim 26, wherein the reservoir is formed at a surface of a substrate, wherein the reservoir serves as a first electrode of the means for recording the indication of wear-out, and wherein the means for recording the indication of wear-out further comprises a second electrode formed at the surface and formed of a material different from the reservoir.

35. The integrated circuit device of claim 26, wherein the diffusant has a diffusion activation energy between 0.75 eV and 2.5 eV.

36. The integrated circuit device of claim 26, wherein atoms of a substrate serve as the diffusant, such that the wear-out stress causes atoms of the substrate to diffuse from the substrate into a diffusion region in response to the wear-out stress.

37. An integrated circuit device comprising a wear-out monitor device configured to record an indication of wear-out of a core circuit separated from the wear-out monitor device based on diffusion of a charged diffusant, wherein the wear-out monitor device comprises:

a reservoir comprising the charged diffusant; and a diffusion region in communication with the reservoir such that the wear-out stress causes the charged diffusant to diffuse from the reservoir into the diffusion region.

38. The integrated circuit device of claim 37, wherein the wear-out monitor device is configured to apply an electric field to the charged diffusant.

39. The integrated circuit device of claim 38, wherein the wear-out monitor device is configured to cause a change in a direction of diffusion of the charged diffusant by applying the electric field.

40. The integrated circuit device of claim 38, wherein the charged diffusant has a charge sign and the direction of the electric field is such that, upon application of the electric field, the charged diffusant diffuses in a direction of increasing concentration gradient of the charged diffusant.

41. The integrated circuit device of claim 38, wherein the wear-out monitor device comprises a PN junction and is configured to record the indication of wear-out based on localized diffusion of the charged diffusant in the PN junction.

42. The integrated circuit device of claim 38, wherein the wear-out monitor device further comprises a plurality of electrodes positioned at different distances from the reservoir, wherein the electrodes are configured to apply the electric field.

43. The integrated circuit device of claim 37, wherein the wear-out monitor device is configured to initiate the diffusion of the charged diffusant upon activation by a stimulus prior to recording the indication of wear-out.

* * * * *